US011952380B2

(12) United States Patent
Nair et al.

(10) Patent No.: US 11,952,380 B2
(45) Date of Patent: *Apr. 9, 2024

(54) SUBSTITUTED BICYCLIC HETEROCYCLIC COMPOUNDS AS PRMT5 INHIBITORS

(71) Applicant: LUPIN LIMITED, Mumbai (IN)

(72) Inventors: Prathap Sreedharan Nair, Pune (IN); Ganesh Bhausaheb Gudade, Pune (IN); Sachin Sethi, Pune (IN); Dipak Raychand Lagad, Pune (IN); Chetan Sanjay Pawar, Pune (IN); Mahadeo Bhaskar Tryambake, Pune (IN); Chaitanya Prabhakar Kulkarni, Pune (IN); Anil Kashiram Hajare, Pune (IN); Balasaheb Arjun Gore, Pune (IN); Sanjeev Anant Kulkarni, Pune (IN); Milind Dattatraya Sindkhedkar, Pune (IN); Venkata P. Palle, Pune (IN); Rajender Kumar Kamboj, Pune (IN)

(73) Assignee: LUPIN LIMITED, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 17/738,370

(22) Filed: May 6, 2022

(65) Prior Publication Data

US 2022/0267339 A1 Aug. 25, 2022

Related U.S. Application Data

(63) Continuation of application No. 16/772,959, filed as application No. PCT/IB2018/060015 on Dec. 13, 2018, now Pat. No. 11,459,330.

(30) Foreign Application Priority Data

| Dec. 13, 2017 | (IN) | ............................ 201721044886 |
| Jul. 2, 2018 | (IN) | ............................ 201821024634 |
| Oct. 23, 2018 | (IN) | ............................ 201821040029 |

(51) Int. Cl.
| A61K 31/519 | (2006.01) |
| A61K 31/53 | (2006.01) |
| A61P 35/00 | (2006.01) |
| C07D 471/04 | (2006.01) |
| C07D 487/04 | (2006.01) |
| C07D 519/00 | (2006.01) |

(52) U.S. Cl.
CPC ............ *C07D 487/04* (2013.01); *A61P 35/00* (2018.01); *C07D 471/04* (2013.01); *C07D 519/00* (2013.01)

(58) Field of Classification Search
CPC ........ A61K 31/519; A61K 31/53; A61P 35/00
See application file for complete search history.

(56) References Cited

U.S. PATENT DOCUMENTS

| 2012/0230951 A1 | 9/2012 | Alam et al. |
| 2014/0200216 A1 | 7/2014 | Li et al. |

FOREIGN PATENT DOCUMENTS

| WO | 2004009574 A1 | 1/2004 |
| WO | 2005016878 A2 | 2/2005 |
| WO | 2006091905 A1 | 8/2006 |
| WO | 2007141473 A1 | 12/2007 |
| WO | 2008107478 A1 | 9/2008 |
| WO | 2009112679 A1 | 9/2009 |
| WO | 2011077133 A2 | 6/2011 |
| WO | 2011079236 A1 | 6/2011 |
| WO | 2012002577 A1 | 1/2012 |
| WO | 2012037108 A1 | 3/2012 |
| WO | 2013028447 A1 | 2/2013 |
| WO | 2013185103 A1 | 12/2013 |
| WO | 2014008223 A2 | 1/2014 |
| WO | 2014100695 A1 | 6/2014 |
| WO | 2014100716 A1 | 6/2014 |
| WO | 2014100719 A2 | 6/2014 |
| WO | 2014100730 A1 | 6/2014 |
| WO | 2014100734 A1 | 6/2014 |
| WO | 2014128465 A1 | 8/2014 |
| WO | 2014145214 A2 | 9/2014 |
| WO | 2015054572 A1 | 4/2015 |
| WO | 2015177110 A1 | 11/2015 |
| WO | 2015198229 A1 | 12/2015 |
| WO | 2015200677 A2 | 12/2015 |
| WO | 2015200680 A2 | 12/2015 |
| WO | 2016022605 A1 | 2/2016 |
| WO | 2016034671 A1 | 3/2016 |
| WO | 2016034673 A1 | 3/2016 |
| WO | 2016034675 A1 | 3/2016 |
| WO | 2016038550 A1 | 3/2016 |
| WO | 2016135582 A1 | 9/2016 |

(Continued)

OTHER PUBLICATIONS

Alexander, E. P. et al. "Abstract 4786: Cellular localization of PRMT5 correlates with poor recurrent free survival in triplenegative breast cancer (TNBC)" (2015) Cancer Research 75(15): 1-2.
Emens, L. A. "Breast Cancer Immunotherapy: Facts and Hopes" (2017) Clinical Cancer Research 24(3): 511-520.
Brehmer, D. et al. "Abstract DDT02-04: A novel PRMT5 inhibitor with potent in vitro and in vivo activity in preclinical lung cancer models" (2017) Cancer Research 77(13): 1-3.
Tosh, D. K. et al. "Efficient, large-scale synthesis and preclinical studies of MRS5698, a highly selective A3 adenosine receptor agonist that protects against chronic neuropathic pain" (2015) Purinergic Signalling 11: 371-387.

(Continued)

*Primary Examiner* — Bruck Kifle
(74) *Attorney, Agent, or Firm* — Volpe Koenig

(57) ABSTRACT

The invention relates to substituted bicyclic heterocyclic compounds of formula (I), pharmaceutically acceptable salts thereof and pharmaceutical compositions for treating diseases, disorders or conditions associated with the overexpression of PRMT5 enzyme. The invention also relates to methods of treating diseases, disorders or conditions associated with the overexpression of PRMT5 enzyme.

20 Claims, No Drawings

(56) References Cited

FOREIGN PATENT DOCUMENTS

| WO | 2016145150 A3 | 9/2016 |
|---|---|---|
| WO | 2016178870 A1 | 11/2016 |
| WO | 2017032840 A1 | 3/2017 |
| WO | 2017087528 A1 | 5/2017 |

OTHER PUBLICATIONS

Doherty, E. M. et al. "Novel Vanilloid Receptor-1 Antagonists: 2. Structure-Activity Relationships of 4-Oxopyrimidines Leading to the Selection of a Clinical Candidate" (2007) Journal of Medicinal Chemistry 50(15): 3515-3527.

Smil, D. et al. "Discovery of a Dual PRMT5-PRMT7 Inhibitor" (2015) ACS Med. Chem. Lett. 6: 408-412.

Saha, K. et al. "Sulforaphane suppresses PRMT5/MEP50 function in epidermal squamous cell carcinoma leading to reduced tumor formation" (2017) Carcinogenesis 38(8): 827-836.

Stopa, N. et al. "The PRMT5 arginine methyltransferase: many roles in development, cancer and beyond" (2015) Cellular and Molecular Life Sciences 72(11): 2041-2059.

Chiang, K. et al. "PRMT5 Is a Critical Regulator of Breast Cancer Stem Cell Function via Histone Methylation and FOXP1 Expression" (2017) Cell Reports 21: 3498-3513.

Chen, X. et al. "PRMT5 Circular RNA Promotes Metastasis of Urothelial Carcinoma of the Bladder through Sponging miR-30c to Induce Epithelial-Mesenchymal Transition" (2018) Clinical Cancer Research 24(24): 6319-6330.

Kanda, M. et al."Protein arginine methyltransferase 5 is associated with malignant phenotype and peritoneal metastasis in gastric cancer" (2016) International Journal of Oncology 49: 1195-1202.

Jin, Y. et al. "Targeting methyltransferase PRMT5 eliminates leukemia stem cells in chronic myelogenous leukemia" (2016) J Clin Invest. 126(10): 3961-3980.

Tamiya, H. et al. "SHARPIN-mediated regulation of protein arginine methyltransferase 5 controls melanoma growth" (2018) J Clin Invest. 128(1): 517-530.

Bao, X. et al. "Overexpression of PRMT5 Promotes Tumor Cell Growth and Is Associated with Poor Disease Prognosis in Epithelial Ovarian Cancer" (2013) Journal of Histochemistry & Cytochemistry 61(3): 206-217.

Cinelli, M. A. et al. "Nitrile in the Hole: Discovery of a Small Auxiliary Pocket in Neuronal Nitric Oxide Synthase Leading to the Development of Potent and Selective 2-Aminoquinoline Inhibitors" (2017) J. Med. Chem. 60: 3958-3978.

Marquez, V. E. et al. "Total Synthesis of (-)-Neplanocin A" (1988) J. Org. Chem. 53: 5709-5714.

Cheng, D. et al. "Small Molecule Regulators of Protein Arginine Methyltransferases" (2004) The Journal of Biological Chemistry 279(23): 23892-23899.

Chung, J. et al. "Protein Arginine Methyltransferase 5 (PRMT5) Inhibition Induces Lymphoma Cell Death through Reactivation of the Retinoblastoma Tumor Suppressor Pathway and Polycomb Repressor Complex 2 (PRC2) Silencing" (2013) The Journal of Biological Chemistry 288(49): 35534-35547.

Kaushik, S. et al. "Genetic deletion or small molecule inhibition of the arginine methyltransferase PRMT5 exhibit anti-tumoral activity in mouse models of MLL-rearranged AML" (2018) Leukemia 32(2): 499-509.

Gullà, A. et al. "Protein Arginine Methyltransferase 5 (PRMT5) has prognostic relevance and is a druggable target in Multiple Myeloma" (2018) Leukemia 32(4): 996-1002.

Wang, L. et al. "Protein Arginine Methyltransferase 5 Suppresses the Transcription of the RB Family of Tumor Suppressors in Leukemia and Lymphoma Cells" (2008) Molecular and Cellular Biology 28(20): 6262-6277.

Park, J. H. et al. "Protein arginine methyltransferase 5 is a key regulator of the MYCN oncoprotein in neuroblastoma cells" (2015) Molecular Oncology 9(3): 617-627.

Chan-Penebre, E. et al. "A selective inhibitor of PRMT5 with in vivo and in vitro potency in MCL models" (2015) Nat Chem Biol 11(6): 432-437.

Yang, Y. and Bedford, M. T. "Protein arginine methyltransferases and cancer" (2013) Nature Reviews Cancer 13: 37-50.

Banasavadi-Siddegowda, Y. K. et al. "PRMT5-PTEN molecular pathway regulates senescence and self-renewal of primary glioblastoma neurosphere cells" (2017) Oncogene 36(2): 263-274.

Deng, X. et al. "Protein arginine methyltransferase 5 functions as an epigenetic activator of the androgen receptor to promote prostate cancer cell growth" (2017) Oncogene 36: 1223-1231.

Zhang, B. et al. "Arginine methyltransferase inhibitor-1 inhibits sarcoma viability in vitro and in vivo" (2018) Oncology Letters 16: 2161-2166.

Yang, D. et al. "Protein N-arginine methyltransferase 5 promotes the tumor progression and radioresistance of nasopharyngeal carcinoma" (2016) Oncology Reports 35: 1703-1710.

Jeon, J. Y. et al. "Protein arginine methyltransferase 5 is implicated in the aggressiveness of human hepatocellular carcinoma and controls the invasive activity of cancer cells" (2018) Oncology Reports 40: 536-544.

Kumar, B. et al. "Nuclear PRMT5, cyclin D1 and IL-6 are associated with poor outcome in oropharyngeal squamous cell carcinoma patients and is inversely associated with p16-status" (2017) Oncotarget 8(9): 14847-14859.

Zhang, B. et al. "Targeting protein arginine methyltransferase 5 inhibits colorectal cancer growth by decreasing arginine methylation of eIF4E and FGFR3" (2015) Oncotarget 6(26): 22799-22811.

Dong, S. H. et al. "Arginine methyltransferase inhibitor 1 exhibits antitumor effects against cervical cancer in vitro and in vivo" (2018) Pharmazie 73: 269-273.

Nicholas, C. et al. "PRMT5 Is Upregulated in Malignant and Metastatic Melanoma and Regulates Expression of MITF and p27Kip1" (2013) Plos One 8(9): e74710.

Kryukov, G. V. et al. "MTAP deletion confers enhanced dependency on the PRMT5 arginine methyltransferase in cancer cells" (2016) Science 351(6278): 1214-1219.

Gu, Z. et al. "Protein arginine methyltransferase 5 is essential for growth of lung cancer cells" (2012) Biochem. J. 446: 235-241.

Karkhanis, V. et al. "Versatility of PRMT5-induced methylation in growth control and development" (2011) Trends in Biochemical Sciences 36(12): 633-641.

Sheng, Y. et al. "Methylation of tumor suppressor gene CDH13 and SHP1 promoters and their epigenetic regulation by the UHRF1/PRMT5 complex in endometrial carcinoma" (2016) Gynecologic Oncology 140(1): 145-151.

Deng, L. et al. "Synthesis, activity and metabolic stability of non-ribose containing inhibitors of histone methyltransferase DOT1L" (2013) Med. Chem. Commun. 4(5): 822-826.

Chan-Penebre, E. et al. "A selective inhibitor of PRMT5 with in vivo and in vitro potency in MCL models." Nat Chem Biol. Jun. 2015;11(6):432-7. doi: 10.1038/nchembio.1810. Epub Apr. 27, 2015. PMID: 25915199.

Duncan K.W. et al. "Structure and Property Guided Design in the Identification of PRMT5 Tool Compound EPZ015666." ACS Med Chem Lett. Dec. 2, 2015;7(2):162-6. doi: 10.1021/acsmedchemlett. 5b00380. PMID: 26985292; PMCID: PMC4753547.

SUBSTITUTED BICYCLIC HETEROCYCLIC COMPOUNDS AS PRMT5 INHIBITORS

CROSS-REFERENCE TO RELATED APPLICATIONS

The present application is a continuation of U.S. application Ser. No. 16/772,959, which is a 35 USC § 371 national stage of International Application No. PCT/IB2018/060015, which was filed Dec. 13, 2018 and claimed the benefit of Indian Provisional Patent Application Nos. IN 201721044886 filed on Dec. 13, 2017, IN 201821040029 filed on Oct. 23, 2018, and IN 201821024634 filed on Jul. 2, 2018, all of which are incorporated herein by reference in their entirety for all purposes.

FIELD OF THE INVENTION

The invention relates to substituted bicyclic heterocyclic compounds of formula (I), pharmaceutically acceptable salts thereof and pharmaceutical compositions for treating diseases, disorders or conditions associated with the overexpression of PRMT5 enzyme. The invention also relates to methods of treating diseases, disorders or conditions associated with the overexpression of PRMT5 enzyme.

BACKGROUND TO THE INVENTION

Methylation of proteins is a common post-translational modification that affects the protein's activity and its interaction with other biological molecules. N-methylation typically occurs on the nitrogen atoms of arginine, lysine and histidine residues and there are different families of enzymes that catalyze the methylation reaction, each being specific to the amino acid residue that will be methylated.

A family of 9 enzymes, called Protein Arginine N-Methyl Transferases (PRMTs), are responsible for the methylation of the guanidinium group of arginine. The guanidinium group of arginine bears 2 terminal nitrogen atoms that undergo monomethylation or dimethylation. Depending on the type of dimethylation, the enzymes are further classified as type I or type II. Type I PRMTs catalyse the monomethylation or the asymmetric dimethylation whereas type II enzymes catalyse the symmetric dimethylation. Some of the substrates that undergo methylation are histones, Sm ribonucleoproteins, MRE11 and p53 binding protein 1.

The methylation of arginine side-chains has an important role to play in various cell functions that include transcription activation as well as transcription repression, mRNA translation, pre-mRNA splicing, protein trafficking and signal transduction. It also occurs on myriad substrates. The enzymatic activity of the PRMTs hence affects cellular processes like cell proliferation, repair of damaged DNA as well as cell cycle and cell death. It has been shown that PRMT enzyme-mediated hypermethylation leads to certain disease conditions like cancer (Nature Reviews Cancer 2013, 13, p37; Cellular and Molecular Life Sciences 2015, 72, p2041; Trends in Biochemical Sciences 2011, 36, p633).

At present, the most studied type II enzyme is PRMT5, which is conserved across the eukaryotic organisms. Overexpression of PRMT5 is linked with carcinogenesis and decreased patient survival in several human malignancies (Cell Mol Life Sci., 2015, 72, p2041). PRMT5 directly interacts with proteins often dysregulated or mutated in cancers, hence a putative oncogene (Mol Cell Biol, 2008, 28, p6262). PRMT5 mediated transcriptional repression of tumor suppressor genes like p53, RB-1, ST7, or upregulation of Cyclin D1, CDK4, CDK6, eLF4E, MITF, FGFR3 associate with the oncogenesis in both solid tumors and hemaological malignancies. PRMT5 is located in the nucleus as well as the cytoplasm and its overexpression has been linked to a wide range of cancers including, but not limited to, glioblastoma multiforme (Oncogene, 2017, 36, p263), prostate cancer (Oncogene, 2017, 36, p1223), and pancreatic cancer (Science, 2016, 351, p1214), mantle cell lymphoma (Nature Chemical Biology, 2015, 11, p432), non-Hodgkin's lymphomas and diffuse large B-cell lymphoma (Journal of Biological Chemistry, 2013, 288, p35534), acute myeloid leukemia (Leukemia, 2018, 32, p499), acute lymphoblastic leukemia (AACR; Cancer Research 2017; 77 (13 Suppl):Abstract nr 1128), multiple myeloma (Leukemia, 2018, 32, p996), non-small cell lung cancer (The Biochemical Journal, 2012, 446, p235), small cell lung cancer (AACR; Cancer Research 2017; 77(13 Suppl):Abstract nr DDT02-04), breast cancer (Cell Reports, 2017, 21, p3498), triple negative breast cancer (AACR; Cancer Res 2015; 75(15 Suppl):Abstract nr 4786), gastric cancer (International Journal of Oncology, 2016, 49, p1195), colorectal cancer (Oncotarget, 2015, 6, p22799), ovarian cancer (J Histochem Cytochem 2013, 61, p206), bladder cancer (Clinical Cancer Research, 2018, CCR-18-1270), hepatocellular cancer (Oncology Reports, 2018, 40, p536), melanoma (PLoS One, 2013, 8, e74710; J Clin Invest. 2018, 128, p517), sarcoma (Oncology Letters, 2018, 16, p2161), oropharyngeal squamous cell carcinoma (Oncotarget, 2017, 8, p14847), chronic myelogenous leukemia (J Clin Invest, 2016, 126, p3961), epidermal squamous cell carcinoma (Carcinogenesis, 2017, 38, p827), nasopharyngeal carcinoma (Oncology Reports, 2016, 35, p1703), neuroblastoma (Molecular Oncology, 2015, 9, p617), endometrial carcinoma (Gynecol Oncol., 2016, 140, p145), cervical cancer (Pharmazie, 2018, 73, p269). These findings have led to further research which show that inhibiting PRMT5 reduces cell proliferation (Molecular and Cellular Biology 2008, 28, p6262, The Journal of Biological Chemistry 2013, 288, p35534).

Inhibitors of arginine methyl transferases were first disclosed in 2004 by Cheng et al in the Journal of Biological Chemistry—Vol. 279 (23), p. 23892. Since then, various other compounds and substances having greater selectivity towards either type I or type II arginine methyl transferases have been disclosed. Other publications that disclose small molecules as inhibitors in relation to PRMT5 are: WO2011077133, WO2011079236, WO2014100695, WO2014100716, WO2014100719, WO2014100730, WO2014100734, WO2014128465, WO2014145214, WO2015200677, WO2015200680, WO2015198229, WO2016022605, WO2016034671, WO2016034673, WO2016034675, WO2016038550, WO2016135582, WO2016145150, WO2016178870, WO2017032840 and ACS Medicinal Chemistry Letters 2015, 6, p408.

SUMMARY OF THE INVENTION

In accordance with one aspect, the invention provides compound of general formula (I), a stereoisomer thereof, or a pharmaceutically acceptable salt thereof,

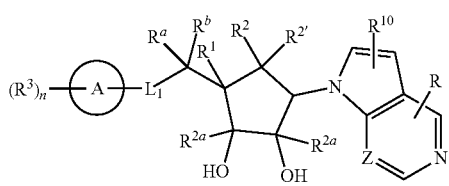

(I)

wherein, $L_1$ is selected from —$CR^aR^b$—, —$NR^a$—, S, and O;

Z=CH or N;

$R^a$ and $R^b$ are independently selected at each occurrence from hydrogen, substituted or unsubstituted alkyl, and substituted or unsubstituted cycloalkyl;

ring A is selected from,

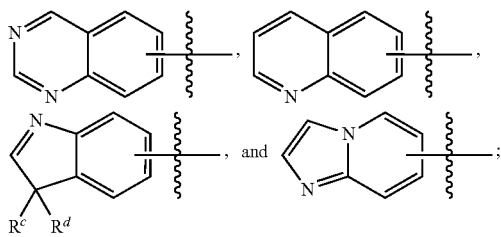

$R^c$ and $R^d$ are selected from substituted or unsubstituted alkyl or together with the carbon atoms to which they are attached form a $C_3$-$C_6$ cycloalkyl ring;

R is selected from —$NR^4R^5$, hydrogen, halogen, substituted or unsubstituted alkyl, substituted or unsubstituted alkoxy, substituted or unsubstituted heteroaryl and substituted or unsubstituted cycloalkyl;

$R^1$ and $R^2$ together with the carbon atoms to which they are attached form a bond in order to form a —C=C—; or $R^1$ and $R^2$ together with the carbon atoms to which they are attached form a cyclopropane ring;

$R^{2'}$ and $R^{2a}$ which may be same or different and are independently selected from hydrogen and substituted or unsubstituted alkyl;

$R^3$ is independently selected at each occurrence from halogen, cyano, nitro, substituted or unsubstituted alkyl, —$OR^6$, —$NR^7R^8$, substituted or unsubstituted cycloalkyl, —C(O)OH, —C(O)O-alkyl, —C(O)$R^9$, —C(O)$NR^7R^8$, —$NR^7C(O)R^9$, substituted or unsubstituted aryl, substituted or unsubstituted heteroaryl, and substituted or unsubstituted heterocyclyl;

$R^4$ and $R^5$ are independently selected from hydrogen, substituted or unsubstituted alkyl, and substituted or unsubstituted cycloalkyl;

$R^6$ is selected from hydrogen, substituted or unsubstituted alkyl, and substituted or unsubstituted cycloalkyl;

$R^7$ and $R^8$ are independently selected from hydrogen, substituted or unsubstituted alkyl, and substituted or unsubstituted cycloalkyl;

$R^9$ is selected from substituted or unsubstituted alkyl and substituted or unsubstituted cycloalkyl;

$R^{10}$ is selected from hydrogen, halogen, and substituted or unsubstituted alkyl;

'n' is an integer ranging from 0 to 4, both inclusive;

when an alkyl group is substituted, it is substituted with 1 to 4 substituents independently selected from oxo (=O), halogen, cyano, cycloalkyl, aryl, heteroaryl, heterocyclyl, —$OR^{7a}$, —C(=O)OH, —C(=O)O(alkyl), —$NR^{8a}R^{8b}$, —$NR^{8a}C(=O)R^{9a}$, and —C(=O)$NR^{8a}R^{8b}$;

when the heteroaryl group is substituted, it is substituted with 1 to 4 substituents independently selected from halogen, nitro, cyano, alkyl, haloalkyl, perhaloalkyl, cycloalkyl, heterocyclyl, aryl, heteroaryl, —$OR^{7a}$, —$NR^{8a}R^{8b}$, —$NR^{7a}C(=O)R^{9a}$, —C(=O)$R^{9a}$, —C(=O)$NR^{8a}R^{8b}$, —$SO_2$-alkyl, —C(=O)OH, and —C(=O)O-alkyl;

when the heterocycle group is substituted, it is substituted either on a ring carbon atom or on a ring hetero atom, and when it is substituted on a ring carbon atom, it is substituted with 1 to 4 substituents independently selected from oxo (=O), halogen, cyano, alkyl, cycloalkyl, perhaloalkyl, —$OR^{7a}$, —C(=O)$NR^{8a}R^{8b}$, —C(=O)OH, —C(=O)O-alkyl, —N(H)C(=O)(alkyl), —N(H)$R^{8a}$, and —N(alkyl)$_2$; and when the heterocycle group is substituted on a ring nitrogen, it is substituted with substituents independently selected from alkyl, cycloalkyl, aryl, heteroaryl, —$SO_2$(alkyl), —C(=O)$R^{9a}$, and —C(=O)O(alkyl); when the heterocycle group is substituted on a ring sulfur, it is substituted with 1 or 2 oxo (=O) group(s);

$R^{7a}$ is selected from hydrogen, alkyl, perhaloalkyl, and cycloalkyl;

$R^{8a}$ and $R^{8b}$ are each independently selected from hydrogen, alkyl, and cycloalkyl; and $R^{9a}$ is selected from alkyl and cycloalkyl.

The details of one or more embodiments of the invention set forth in below are only illustrative in nature and not intended to limit to the scope of the invention. Other features, objects and advantages of the inventions will be apparent from the description and claims.

According to one embodiment, the invention provides compounds having the structure of Formula (II), a stereoisomer thereof, or a pharmaceutically acceptable salt thereof,

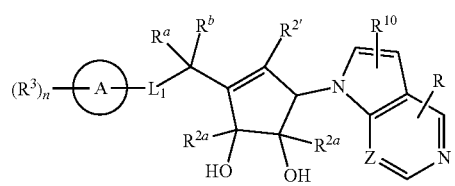

(II)

wherein,

Ring A, $L_1$, Z, $R^a$, $R^b$, $R^{2'}$, R, $R^{2a}$, $R^3$, $R^{10}$ and 'n' are as defined herein above.

According to another embodiment, the invention provides compounds having the structure of Formula (III), a stereoisomer thereof, or a pharmaceutically acceptable salt thereof,

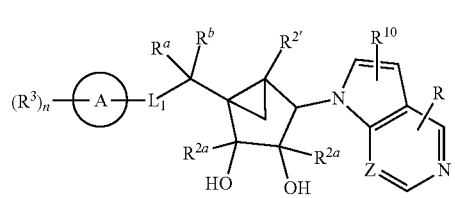

(III)

wherein,

Ring A, $L_1$, Z, $R^a$, $R^b$, $R^{2'}$, R, $R^{2a}$, $R^3$, $R^{10}$ and 'n' are as defined herein above.

According to one embodiment, the invention provides compounds having the structure of Formula (IV), a stereoisomer thereof, or a pharmaceutically acceptable salt thereof, (IV)

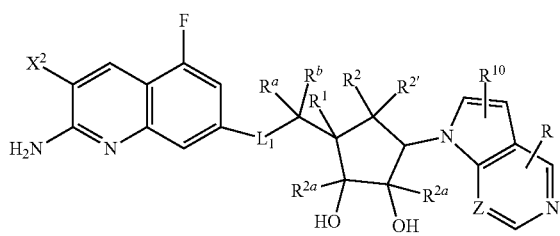

wherein, $X^2$ is Br or $C_1$;

$L_1$, $R^a$, $R^b$, $R^1$, $R^{2'}$, $R^2$, $R$, $R^{2a}$ and $R^{10}$ are as defined herein above.

In accordance with an embodiment of the invention, $R^c$ and $R^d$ are independently selected from substituted or unsubstituted alkyl or $R^c$ and $R^d$ together with the carbon atom to which they are attached form a cyclobutyl ring.

In certain embodiment, $R^c$ and $R^d$ are independently selected from methyl or $R^c$ and $R^d$ together with the carbon atom to which they are attached from a cyclobutyl ring.

In any of above embodiments, $R^a$ and $R^b$ are independently selected from hydrogen, methyl, and cyclopropyl.

In any of above embodiments, $R^3$ is selected from halogen, cyano, —$OR^6$, —$NR^7R^8$, substituted or unsubstituted alkyl, and substituted or unsubstituted aryl.

In certain embodiments, $R^3$ is independently selected from —F, Cl, Br, CN, —$NH_2$, —$NH(CH_3)$, —$NHCH(CH_3)_2$, —$CH_3$, cyclopropyl, —$CH(CH_3)_2$, —$CF_2CH_3$, —$OCH_3$,

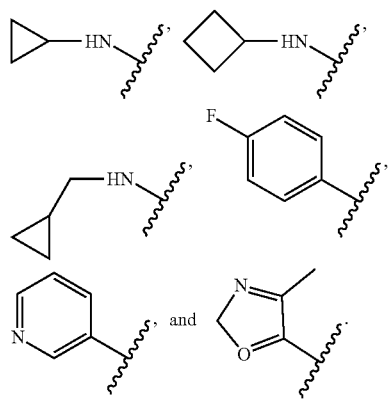

In any of above embodiments, $R^{2'}$ and $R^{2a}$ are independently selected from hydrogen and methyl.

In any of above embodiments, R is selected from hydrogen, halogen, —$NR^4R^5$, and substituted or unsubstituted alkyl, substituted or unsubstituted cycloalkyl and substituted or unsubstituted heteroaryl.

In certain embodiments, R is selected from hydrogen, —$NH_2$, methyl, Chloro, cyclopropyl, and

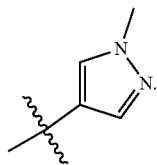 [SMILES: *c1cnn(C)c1]

In any of above embodiments, $R^4$ and $R^5$ are independently selected from hydrogen.

In any of above embodiments, $R^6$ is selected from substituted and unsubstituted alkyl.

In certain embodiments, $R^6$ is selected from methyl.

In any of above embodiments, $R^7$ and $R^8$ are independently selected from hydrogen, methyl, —$CH(CH_3)_2$, —$CH_2$-cyclopropyl, cyclopropyl, and cyclobutyl.

In any of above embodiments, $R^{10}$ is selected from hydrogen, —F, and methyl.

In any of above embodiments, n is selected from 1 to 3.

According to another embodiment, there are provided compounds having the structure of Formula (I) wherein Li is selected from —$CH_2$—, —$CH(CH_3)$—, —NH—, —$N(CH_3)$—S, and O;

According to another embodiment, there are provided compounds having the structure of Formula (I) wherein ring A is

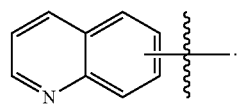

According to another embodiment, there are provided compounds having the structure of Formula (I) wherein ring A is

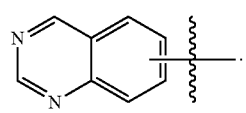

According to another embodiment, there are provided compounds having the structure of Formula (I) wherein ring A is

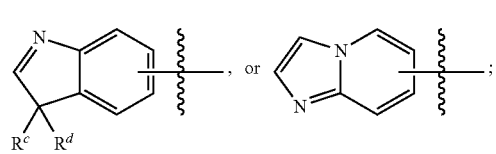

According to another embodiment, there are provided compounds having the structure of Formula (I), wherein ring A is selected from—

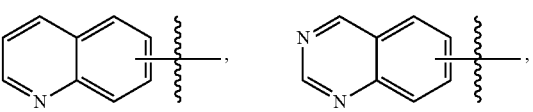

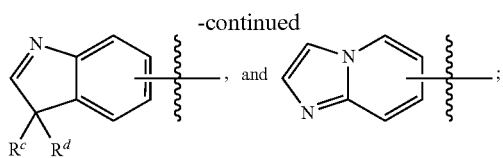

L1 is selected from —CH2-, —CH(CH3)-, —NH—, —N(CH3)-, S, and O; $R^3$ is selected from F, Cl, Br, CN, —NH$_2$, —NH(CH$_3$), —NHCH(CH$_3$)$_2$, —CH$_3$, cyclopropyl, —CH(CH$_3$)$_2$, —CF$_2$CH$_3$, —OCH$_3$, CF$_3$,

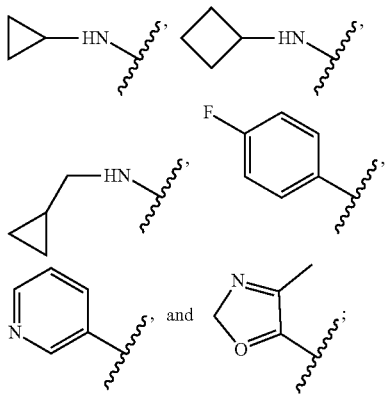

R is selected from hydrogen, —NH$_2$, Cl, —CH(CH$_3$)$_2$, methyl, ethyl, cyclopropyl and

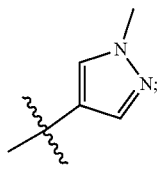 [SMILES: *c1cnn(C)c1]

$R^a$ and $R^b$ are independently selected from hydrogen, methyl, and cyclopropyl; $R^{2'}$ and $R^{2a}$ are independently selected from hydrogen and methyl; $R^{10}$ is selected from hydrogen, —F, and methyl.

The examples 1 to 84 given herein are representative compounds, which are only illustrative in nature and are not intended to limit to the scope of the invention.

It should be understood that formula (I) structurally encompasses all tautomers, stereoisomers and isotopes wherever applicable and pharmaceutically acceptable salts that may be contemplated from the chemical structures generally described herein.

According to one embodiment, there are provided compounds of formula (I) to (IV) wherein the compound is in the form of the free base or is a pharmaceutically acceptable salt thereof.

In another aspect of the invention, there are provided compounds of formula (I) to (IV) or a pharmaceutically acceptable salt thereof for treating the diseases, disorders, syndromes or conditions associated with PRMT5 enzyme.

In one embodiment of the present invention, there are provided compounds of formula (I) to (IV), or a pharmaceutically acceptable salt thereof for treating diseases, disorders, syndromes or conditions by inhibition of PRMT5 enzyme.

In another aspect of the invention, there are provided compounds of formula (I) to (IV) or a pharmaceutically acceptable salt thereof for use as a medicament.

In another aspect of the invention, there are provided compounds of formula (I) to (IV) or a pharmaceutically acceptable salt thereof for use in treating the diseases, disorders, syndromes or conditions associated with PRMT5.

In one embodiment of the present invention, there are provided compounds of formula (I) to (IV) or a pharmaceutically acceptable salt thereof for use in treating diseases, disorders, syndromes or conditions by the inhibition of PRMT5.

In another aspect of the invention, there is provided a method of inhibiting PRMT5 by using a compound selected from formula (I) to (IV) or a pharmaceutically acceptable salt thereof.

In another aspect of the invention, there is provided a method of treating diseases, disorders or conditions associated with PRMT5 by using a compound selected from formula (I) to (IV).

In another aspect of the present invention, a method of treating diseases, disorders or conditions is selected from glioblastoma multiforme, prostate cancer, and pancreatic cancer, mantle cell lymphoma, non-Hodgkin's lymphoma and diffuse large B-cell lymphoma, acute myeloid leukemia, acute lymphoblastic leukemia, multiple myeloma, non-small cell lung cancer, small cell lung cancer, breast cancer, triple negative breast cancer, gastric cancer, colorectal cancer, ovarian cancer, bladder cancer, hepatocellular cancer, melanoma, sarcoma, oropharyngeal squamous cell carcinoma, chronic myelogenous leukemia, epidermal squamous cell carcinoma, nasopharyngeal carcinoma, neuroblastoma, endometrial carcinoma, and cervical cancer by using a compound selected from formula (I) to (IV) is provided.

In another aspect of the invention, there is provided a use of a compound selected from formula (I) to (IV) or a pharmaceutically acceptable salt thereof, for the manufacture of a medicament for treating, the diseases, disorders or conditions associated with PRMT5.

In another aspect, the invention provides a pharmaceutical composition comprising at least one compound of formula (I) to (IV) or a pharmaceutically acceptable salt thereof and at least one pharmaceutically acceptable excipient.

In another aspect, the invention provides a pharmaceutical composition comprising a therapeutically effective amount of compound of formula (I) to (IV) or a pharmaceutically acceptable salt thereof, for use in treating, the diseases, disorders or conditions associated with PRMT5 by administering to the subject in need thereof.

In another aspect of the present invention, wherein the use of compounds of formula (I) to (IV) or a pharmaceutically acceptable salt thereof for the diseases, disorders, syndromes or conditions associated by inhibition of PRMT5 are selected from the group consisting of glioblastoma multiforme, prostate cancer, and pancreatic cancer, mantle cell lymphoma, non-Hodgkin's lymphomas and diffuse large B-cell lymphoma, acute myeloid leukemia, acute lymphoblastic leukemia, multiple myeloma, non-small cell lung cancer, small cell lung cancer, breast cancer, triple negative breast cancer, gastric cancer, colorectal cancer, ovarian cancer, bladder cancer, hepatocellular cancer, melanoma, sarcoma, oropharyngeal squamous cell carcinoma, chronic myelogenous leukemia, epidermal squamous cell carcinoma, nasopharyngeal carcinoma, neuroblastoma, endometrial carcinoma, and cervical cancer.

In another aspect, the invention provides a pharmaceutical composition comprising a therapeutically effective amount of compound of formula (I) to (IV) or a pharmaceutically acceptable salt thereof, for treating the diseases, disorders or conditions associated with PRMT5 by administering to the subject in need thereof.

In another embodiment of the invention the compounds, their stereoisomers or pharmaceutically acceptable salts thereof are:

(1S,2R,5R)-3-(2-(2-Amino-3-bromoquinolin-7-yl)ethyl)-5-(4-amino-7H pyrrolo[2,3-d]pyrimidin-7-yl)cyclopent-3-ene-1,2-diol (Compound-1);

(1S,2R,5R)-3-(2-(2-amino-3-chloroquinolin-7-yl)ethyl)-5-(4-amino-7H-pyrrolo[2,3-d]pyrimidin-7-yl)cyclopent-3-ene-1,2-diol (Compound-2);

(1S,2R,5R)-3-(2-(2-amino-3-bromoquinolin-7-yl)ethyl)-5-(4-amino-5-fluoro-7H-pyrrolo[2,3-d]pyrimidin-7-yl)cyclopent-3-ene-1,2-diol (Compound-3);

(1S,2R,5R)-5-(4-amino-7H-pyrrolo[2,3-d]pyrimidin-7-yl)-3-(((2-aminoquinolin-7-yl)thio)methyl)cyclopent-3-ene-1,2-diol (Compound-4);

(1S,2R,5R)-3-(((2-amino-3-chloroquinolin-7-yl)thio)methyl)-5-(4-amino-7H-pyrrolo[2,3-d]pyrimidin-7-yl)cyclopent-3-ene-1,2-diol (Compound-5);

(1S,2R,5R)-5-(4-amino-7H-pyrrolo[2,3-d]pyrimidin-7-yl)-3-(((2-aminoquinolin-7-yl)(methyl)amino)methyl)cyclopent-3-ene-1,2-diol (Compound-6);

(1S,2R,5R)-3-(1-(2-Amino-3-bromoquinolin-7-yl)propan-2-yl)-5-(4-amino-7H-pyrrolo[2,3-d]pyrimidin-7-yl)cyclopent-3-ene-1,2-diol (Compound-7a and 7b);

(1S,2R,5R)-5-(4-Amino-7H-pyrrolo[2,3-d]pyrimidin-7-yl)-3-(1-((2-(methylamino) quinolin-7-yl)oxy)ethyl)cyclopent-3-ene-1,2-diol (Compound-8a and 8b);

(1S,2R,5R)-3-(((2-amino-3-chloro-5-fluoroquinolin-7-yl)oxy)methyl)-5-(4-amino-7H-pyrrolo[2,3-d]pyrimidin-7-yl)-2-methylcyclopent-3-ene-1,2-diol (Compound-9);

(1S,2R,5R)-5-(4-amino-7H-pyrrolo[2,3-d]pyrimidin-7-yl)-3-(2-(2-(methylamino)quinolin-7-yl)ethyl)cyclopent-3-ene-1,2-diol (Compound-10);

(1S,2R,5R)-5-(4-amino-7H-pyrrolo[2,3-d]pyrimidin-7-yl)-3-(2-(3-methylimidazo[1,2-a]pyridin-7-yl)ethyl)cyclopent-3-ene-1,2-diol (Compound-11);

(1S,2R,5R)-3-(((2-amino-3-chloro-5-fluoroquinolin-7-yl)oxy)methyl)-5-4 amino-7H-pyrrolo[2,3-d]pyrimidin-7-yl)-4-methylcyclopent-3-ene-1,2-diol (Compound-12);

(1S,2R,5R)-3-(2-(2-amino-3-chloro-5-fluoroquinolin-7-yl)ethyl)-5-(4-methyl-7H-pyrrolo[2,3-d]pyrimidin-7-yl)cyclopent-3-ene-1,2-diol (Compound-13);

(1S,2R,5R)-3-(2-(2-amino-3-chloro-5-fluoroquinolin-7-yl)ethyl)-5-(4-methyl-1H-pyrrolo[3,2-c]pyridin-1-yl)cyclopent-3-ene-1,2-diol hydrochloride (Compound-14);

(1S,2R,5R)-3-(2-(2-Amino-3-chloro-5-fluoroquinolin-7-yl)ethyl)-5-(1H-pyrrolo[3,2-c]pyridin-1-yl)cyclopent-3-ene-1,2-diol (Compound-15);

(1S,2R,5R)-3-(2-(2-amino-3-chloro-5-fluoroquinolin-7-yl)ethyl)-5-(7H-pyrrolo[2,3-d]pyrimidin-7-yl)cyclopent-3-ene-1,2-diol (Compound-16);

(1S,2R,5R)-5-(4-amino-7H-pyrrolo[2,3-d]pyrimidin-7-yl)-3-(((2-aminoquinolin-7-yl)amino)methyl)cyclopent-3-ene-1,2-diol (Compound-17);

(1S,2R,5R)-3-(((2-amino-3-chloro-5-fluoroquinolin-7-yl)oxy)methyl)-5-(4-amino-7H-pyrrolo[2,3-d]pyrimidin-7-yl)cyclopent-3-ene-1,2-diol (Compound-18);

(1S,2R,5R)-5-(4-amino-7H-pyrrolo[2,3-d]pyrimidin-7-yl)-3-(((2-(methylamino)quinolin-7-yl)oxy)methyl)cyclopent-3-ene-1,2-diol (Compound-19);

(1S,2R,5R)-3-(1-((2-amino-3-chloro-5-fluoroquinolin-7-yl)oxy)ethyl)-5-(4-amino-7H-pyrrolo[2,3-d]pyrimidin-7-yl)cyclopent-3-ene-1,2-diol (Compound-20a and 20b);

(1S,2R,5R)-3-(2-(2-amino-3-chloroquinolin-7-yl)ethyl)-5-(4-methyl-7H-pyrrolo[2,3-d]pyrimidin-7-yl)cyclopent-3-ene-1,2-diol (Compound-21);

(1S,2R,5R)-5-(4-Amino-7H-pyrrolo[2,3-d]pyrimidin-7-yl)-3-(2-(2-(cyclobutylamino) quinolin-7-yl)ethyl)cyclopent-3-ene-1,2-diol (Compound-22);

(1S,2R,5R)-3-(2-(2-Amino-3-fluoroquinolin-7-yl)ethyl)-5-(4-amino-7H-pyrrolo[2,3-d]pyrimidin-7-yl)cyclopent-3-ene-1,2-diol (Compound-23);

(1S,2R,5R)-3-(2-(2-amino-3-chloro-5-fluoroquinolin-7-yl)ethyl)-5-(4-amino-7H-pyrrolo[2,3-d]pyrimidin-7-yl)cyclopent-3-ene-1,2-diol (Compound-24);

(1S,2R,5R)-3-(2-(2-amino-3-chloro-6-fluoroquinolin-7-yl)ethyl)-5-(4-amino-7H-pyrrolo[2,3-d]pyrimidin-7-yl)cyclopent-3-ene-1,2-diol (Compound-25);

(1S,2R,5R)-3-(2-(2-amino-3-chloro-8-fluoroquinolin-7-yl)ethyl)-5-(4-amino-7H-pyrrolo[2,3-d]pyrimidin-7-yl)cyclopent-3-ene-1,2-diol (Compound-26);

(1S,2R,5R)-3-(2-(2-amino-3,3-dimethyl-3H-indol-6-yl)ethyl)-5-(4-amino-7H-pyrrolo[2,3-d]pyrimidin-7-yl)cyclopent-3-ene-1,2-diol (Compound-27);

(1S,2R,5R)-5-(4-amino-7H-pyrrolo[2,3-d]pyrimidin-7-yl)-3-(2-(2'-aminospiro[cyclobutane-1,3'-indol]-6'-yl)ethyl)cyclopent-3-ene-1,2-diol (Compound-28);

(1S,2R,5R)-3-(2-(2-amino-3,5-dichloroquinolin-7-yl)ethyl)-5-(4-amino-7H-pyrrolo[2,3-d]pyrimidin-7-yl)cyclopent-3-ene-1,2-diol (Compound-29);

(1S,2R,5R)-3-(2-(2-amino-3-chloroquinolin-7-yl)ethyl)-5-(2-amino-7H-pyrrolo[2,3-d]pyrimidin-7-yl)cyclopent-3-ene-1,2-diol (Compound-30);

(1S,2R,5R)-3-(2-(2-amino-3-chloro-5-fluoroquinolin-7-yl)ethyl)-5-(4-isopropyl-7H-pyrrolo[2,3-d]pyrimidin-7-yl)cyclopent-3-ene-1,2-diol (Compound-31);

(1S,2R,5R)-3-(2-(2-amino-3-chloro-5-fluoroquinolin-7-yl)ethyl)-5-(4-(1-methyl-1H-pyrazol-4-yl)-7H-pyrrolo[2,3-d]pyrimidin-7-yl)cyclopent-3-ene-1,2-diol (Compound-32);

(1S,2R,5R)-3-(1-(2-amino-3-chloro-5-fluoroquinolin-7-yl)propan-2-yl)-5-(4-amino-7H-pyrrolo[2,3-d]pyrimidin-7-yl)cyclopent-3-ene-1,2-diol (Compound-33a and 33b);

(1S,2R,5R)-3-(1-(2-amino-3-chloroquinolin-7-yl)propan-2-yl)-5-(4-amino-7H-pyrrolo[2,3-d]pyrimidin-7-yl)cyclopent-3-ene-1,2-diol (Compound-34a and 34b);

(1S,2R,5R)-3-(1-(2-Amino-3-chloro-5-fluoroquinolin-7-yl)propan-2-yl)-5-(4-methyl-7H-pyrrolo[2,3-d]pyrimidin-7-yl)cyclopent-3-ene-1,2-diol (Compound-35a and 35b);

(1S,2R,5R)-3-(1-(2-amino-3-chloro-5-fluoroquinolin-7-yl)propan-2-yl)-2-methyl-5-(4-methyl-7H-pyrrolo[2,3-d]pyrimidin-7-yl)cyclopent-3-ene-1,2-diol (Compound-36a and 36b);

(1S,2R,5R)-3-(2-(2-amino-3-chloro-5-fluoroquinolin-7-yl)ethyl)-5-(4-amino-7H-pyrrolo[2,3-d]pyrimidin-7-yl)-2-methylcyclopent-3-ene-1,2-diol (Compound-37);

(1S,2R,5R)-3-(1-(2-amino-3-chloro-5-fluoroquinolin-7-yl)propan-2-yl)-5-(4-amino-7H-pyrrolo[2,3-d]pyrimidin-7-yl)-2-methylcyclopent-3-ene-1,2-diol (Compound-38);

(1S,2R,5R)-3-(2-(2-amino-3-chloro-5-fluoroquinolin-7-yl)ethyl)-2-methyl-5-(4-methyl-7H-pyrrolo[2,3-d]pyrimidin-7-yl)cyclopent-3-ene-1,2-diol (Compound-39);

(1S,2R,5R)-3-(2-(2-amino-3-chloro-5-fluoroquinolin-7-yl)ethyl)-5-(4-amino-7H-pyrrolo[2,3-d]pyrimidin-7-yl)-2-ethylcyclopent-3-ene-1,2-diol (Compound-40);

(1S,2R,5R)-3-(2-(2-amino-3-chloro-5-fluoroquinolin-7-yl)ethyl)-5-(4-ethyl-7H-pyrrolo[2,3-d]pyrimidin-7-yl)cyclopent-3-ene-1,2-diol (Compound-41);

(1S,2R,5R)-3-(2-(2-amino-3-chloro-5-fluoroquinolin-7-yl)ethyl)-5-(4-cyclopropyl-7H-pyrrolo[2,3-d]pyrimidin-7-yl)cyclopent-3-ene-1,2-diol (Compound-42);

(1S,2R,5R)-3-(2-(2-Amino-3-bromo-5-fluoroquinolin-7-yl)ethyl)-5-(4-amino-7H-pyrrolo[2,3-d]pyrimidin-7-yl)cyclopent-3-ene-1,2-diol (Compound-43);

(1S,2R,5R)-3-(2-(2-Amino-3-bromo-5-fluoroquinolin-7-yl)ethyl)-5-(4-methyl-7H-pyrrolo[2,3-d]pyrimidin-7-yl)cyclopent-3-ene-1,2-diol (Compound-44);

(1S,2R,5R)-3-(1-(2-Amino-3-bromo-5-fluoro quinolin-7-yl)propan-2-yl)-5-(4-amino-7H-pyrrolo[2,3-d]pyrimidin-7-yl)cyclopent-3-ene-1,2-diol (Compound-45a and 45b);

(1S,2R,5R)-3-(2-(2-Amino-6-fluoroquinolin-7-yl)ethyl)-5-(4-amino-7H-pyrrolo[2,3-d]pyrimidin-7-yl)cyclopent-3-ene-1,2-diol (Compound-46);

(1S,2R,5R)-3-(2-(2-amino-5-fluoroquinolin-7-yl)ethyl)-5-(4-amino-7H-pyrrolo[2,3-d]pyrimidin-7-yl)cyclopent-3-ene-1,2-diol (Compound-47);

(1R,2R,3S,4R,5S)-1-(2-(2-Amino-3-chloro-5-fluoroquinolin-7-yl)ethyl)-4-(4-amino-7H-pyrrolo[2,3-d]pyrimidin-7-yl)bicyclo[3.1.0]hexane-2,3-diol (Compound-48);

(1R,2R,3S,4R,5S)-4-(4-Amino-7H-pyrrolo[2,3-d]pyrimidin-7-yl)-1-(2-(2-(methylamino)quinolin-7-yl)ethyl)bicyclo [3.1.0] hexane-2,3-diol (Compound-49);

(1R,2R,3S,4R,5S)-4-(4-Amino-7H-pyrrolo[2,3-d]pyrimidin-7-yl)-1-(2-(2-(isopropylamino)quinolin-7-yl)ethyl)bicyclo [3.1.0] hexane-2,3-diol (Compound-50);

(1R,2R,3S,4R,5S)-4-(4-Amino-7H-pyrrolo[2,3-d]pyrimidin-7-yl)-1-(2-(2-(cyclobutylamino)quinolin-7-yl)ethyl)bicyclo [3.1.0] hexane-2,3-diol (Compound-51);

(1R,2R,3S,4R,5S)-4-(4-Amino-7H-pyrrolo[2,3-d]pyrimidin-7-yl)-1-(2-(2-((cyclopropylmethyl)amino) quinolin-7-yl) ethyl)bicyclo[3.1.0]hexane-2,3-diol (Compound-52);

(1R,2R,3S,4R,5S)-4-(4-Amino-7H-pyrrolo[2,3-d]pyrimidin-7-yl)-1-(2-(2-amino-8-fluoroquinolin-7-yl)ethyl)bicyclo [3.1.0] hexane-2,3-diol (Compound-53);

(1R,2R,3S,4R,5S)-1-(2-(2-Amino-3-methylquinolin-7-yl)ethyl)-4-(4-amino-7H-pyrrolo[2,3-d]pyrimidin-7-yl)bicyclo[3.1.0]hexane-2,3-diol (Compound-54);

(1R,2R,3S,4R,5S)-1-(2-(2-Amino-3-isopropyl quinolin-7-yl)ethyl)-4-(4-amino-7H-pyrrolo[2,3-d]pyrimidin-7-yl)bicyclo[3.1.0]hexane-2,3-diol (Compound-55);

(1R,2R,3S,4R,5S)-1-(2-(2-Amino-3-(1,1-difluoroethyl) quinolin-7-yl)ethyl)-4-(4-amino-7H-pyrrolo [2,3-d] pyrimidin-7-yl)bicyclo[3.1.0]hexane-2,3-diol (Compound-56);

(1R,2R,3S,4R,5S)-1-(2-(2-Amino-3-cyclopropylquinolin-7-yl)ethyl)-4-(4-amino-7H-pyrrolo[2,3-d]pyrimidin-7-yl)bicyclo[3.1.0]hexane-2,3-diol (Compound-57);

(1R,2R,3S,4R,5S)-1-(2-(2-Amino-3-methoxyquinolin-7-yl)ethyl)-4-(4-amino-7H-pyrrolo[2,3-d]pyrimidin-7-yl)bicyclo[3.1.0]hexane-2,3-diol (Compound-58);

2-amino-7-(2-((1R,2R,3S,4R,5S)-4-(4-Amino-7H-pyrrolo [2,3-d]pyrimidin-7-yl)-2,3-dihydroxybicyclo [3.1.0] hexan-1-yl)ethyl)quinoline-3-carbonitrile (Compound-59);

(1R,2R,3S,4R,5S)-1-(2-(2-Amino-3-fluoroquinolin-7-yl)ethyl)-4-(4-amino-7H-pyrrolo[2,3-d]pyrimidin-7-yl)bicyclo[3.1.0]hexane-2,3-diol (Compound-60);

(1R,2R,3S,4R,5S)-1-(2-(2-Amino-3-chloroquinolin-7-yl)ethyl)-4-(4-amino-7H-pyrrolo[2,3-d]pyrimidin-7-yl)bicyclo[3.1.0]hexane-2,3-diol (Compound-61);

(1R,2R,3S,4R,5S)-1-(2-(2-Amino-3-chloro-6-fluoroquinolin-7-yl)ethyl)-4-(4-amino-7H-pyrrolo[2,3-d]pyrimidin-7-yl) bicyclo [3.1.0]hexane-2,3-diol (Compound-62);

(1R,2R,3S,4R,5S)-1-(2-(2-Amino-3-chloro-8-fluoroquinolin-7-yl)ethyl)-4-(4-amino-7H-pyrrolo[2,3-d]pyrimidin-7-yl)bicyclo[3.1.0]hexane-2,3-diol (Compound-63);

(1R,2R,3S,4R,5S)-1-(2-(2-amino-3-bromo-6-fluoroquinolin-7-yl)ethyl)-4-(4-amino-7H-pyrrolo[2,3-d]pyrimidin-7-yl)bicyclo[3.1.0]hexane-2,3-diol (Compound-64);

(1R,2R,3S,4R,5S)-4-(4-Amino-7H-pyrrolo[2,3-d]pyrimidin-7-yl)-1-(2-(3-methylimidazo[1,2-a]pyridin-7-yl) ethyl) bicyclo[3.1.0]hexane-2,3-diol (Compound-65);

(1R,2R,3S,4R,5S)-1-(2-(2-Amino-3,3-dimethyl-3H-indol-6-yl)ethyl)-4-(4-amino-7H-pyrrolo[2,3-d]pyrimidin-7-yl) bicyclo[3.1.0]hexane-2,3-diol (Compound-66);

(1R,2R,3S,4R,5S)-1-(2-(2-Amino-3-chloro-5-fluoroquinolin-7-yl)ethyl)-4-(4-amino-6-methyl-7H-pyrrolo[2,3-d]pyrimidin-7-yl)bicyclo[3.1.0]hexane-2,3-diol (Compound-67);

(1R,2R,3S,4R,5S)-1-(2-(2-Amino-3-chloro-6-fluoroquinolin-7-yl)ethyl)-4-(4-amino-6-methyl-7H-pyrrolo[2,3-d]pyrimidin-7-yl)bicyclo[3.1.0]hexane-2,3-diol (Compound-68);

(1R,2R,3S,4R,5S)-1-(2-(2-amino-3-chloro-5-fluoroquinolin-7-yl)ethyl)-4-(4-methyl-7H-pyrrolo[2,3-d]pyrimidin-7-yl) bicyclo[3.1.0]hexane-2,3-diol (Compound-69);

(1R,2R,3S,4R,5S)-1-(2-(2-Amino-3-chloro-5-fluoroquinolin-7-yl)ethyl)-4-(7H-pyrrolo[2,3-d]pyrimidin-7-yl)bicyclo [3.1.0]hexane-2,3-diol (Compound-70);

(1R,2R,3S,4R,5S)-4-(4-Amino-7H-pyrrolo[2,3-d]pyrimidin-7-yl)-1-(2-(2'-aminospiro[cyclobutane-1,3'-indol]-6'-yl)ethyl)bicyclo[3.1.0]hexane-2,3-diol (Compound-71);

(1R,2R,3S,4R,5S)-1-(2-(2-Amino-3-bromo-5-fluoroquinolin-7-yl)ethyl)-4-(4-amino-7H-pyrrolo[2,3-d]pyrimidin-7-yl)bicyclo[3.1.0]hexane-2,3-diol (Compound-72);

(1R,2R,3S,4R,5S)-1-(2-(2-Amino-3-bromoquinolin-7-yl) ethyl)-4-(4-amino-7H-pyrrolo [2,3-d]pyrimidin-7-yl)bicyclo[3.1.0]hexane-2,3-diol (Compound-73);

(1R,2R,3S,4R,5S)-4-(4-Amino-7H-pyrrolo[2,3-d]pyrimidin-7-yl)-1-(2-(2-aminoquinolin-7-yl)ethyl)bicyclo [3.1.0]hexane-2,3-diol (Compound-74);

(1R,2R,3S,4R,5S)-4-(4-amino-7H-pyrrolo[2,3-d]pyrimidin-7-yl)-1-(2-(2-aminoquinazolin-7-yl)ethyl)bicyclo[3.1.0] hexane-2,3-diol (Compound-75);

(1S,2R,3S,4R,5S)-1-((S)-1-(2-Amino-3-bromoquinolin-7-yl)propan-2-yl)-4-(4-amino-7H-pyrrolo[2,3-d]pyrimidin-7-yl)bicyclo[3.1.0]hexane-2,3-diol (Compound-76a and 76b);

(1S,2R,3S,4R,5S)-1-((S)-2-(2-Amino-3-chloro-5-fluoroquinolin-7-yl)-1-cyclopropylethyl)-4-(4-amino-7H-pyrrolo [2,3-d]pyrimidin-7-yl)bicyclo[3.1.0]hexane-2,3-diol (Compound-77a and 77b);

(1S,2R,3S,4R,5S)-1-(1-(2-Amino-3-chloro-5-fluoroquinolin-7-yl)propan-2-yl)-4-(4-amino-7H-pyrrolo[2,3-d]pyrimidin-7-yl)bicyclo[3.1.0]hexane-2,3-diol (Compound-78a and 78b);

(1R,2R,3S,4R,5S)-4-(4-Amino-7H-pyrrolo[2,3-d]pyrimidin-7-yl)-1-(2-(2-aminoquinolin-7-yl)propyl) bicyclo [3.1.0]hexane-2,3-diol (Compound-79a and 79b);

(1R,2R,3S,4R,5S)-1-(((2-Amino-3-bromoquinolin-7-yl) oxy)methyl)-4-(4-amino-7H-pyrrolo[2,3-d]pyrimidin-7-yl)bicyclo[3.1.0]hexane-2,3-diol (Compound-80);

(1S,2R,3S,4R,5S)-4-(4-Amino-7H-pyrrolo[2,3-d]pyrimidin-7-yl)-1-(((2-aminoquinolin-7-yl)thio)methyl) bicyclo [3.1.0] hexane-2,3-diol (Compound-81);

(1R,2R,3S,4R,5S)-1-(2-(2-Amino-3-(4-fluorophenyl)quinolin-7-yl)ethyl)-4-(4-amino-7H-pyrrolo[2,3-d]pyrimidin-7-yl)bicyclo[3.1.0]hexane-2,3-diol (Compound-82);

(1R,2R,3S,4R,5S)-1-(2-(2-Amino-3-(pyridin-3-yl)quinolin-7-yl)ethyl)-4-(4-amino-7H-pyrrolo[2,3-d]pyrimidin-7-yl)bicyclo[3.1.0]hexane-2,3-diol (Compound-83); and (1R,2R,3S,4R,5S)-1-(2-(2-Amino-3-(3-methyl isoxazol-4-yl)quinolin-7-yl)ethyl)-4-(4-amino-7H-pyrrolo[2,3-d]pyrimidin-7-yl)bicyclo[3.1.0]hexane-2,3-diol (Compound-84).

In another embodiment of the invention the compounds, their stereoisomer thereof, or a pharmaceutically acceptable salt thereof, are selected from:

(1S,2R,5R)-3-(2-(2-Amino-3-bromoquinolin-7-yl)ethyl)-5-(4-amino-7H pyrrolo[2,3-d]pyrimidin-7-yl)cyclopent-3-ene-1,2-diol (Compound-1);

(1S,2R,5R)-3-(2-(2-amino-3-chloroquinolin-7-yl)ethyl)-5-(4-amino-7H-pyrrolo[2,3-d]pyrimidin-7-yl)cyclopent-3-ene-1,2-diol (Compound-2);

(1S,2R,5R)-3-(1-(2-Amino-3-bromoquinolin-7-yl)propan-2-yl)-5-(4-amino-7H-pyrrolo[2,3-d]pyrimidin-7-yl)cyclopent-3-ene-1,2-diol (Compound-7a and 7b);

(1S,2R,5R)-3-(((2-amino-3-chloro-5-fluoroquinolin-7-yl)oxy)methyl)-5-(4-amino-7H-pyrrolo[2,3-d]pyrimidin-7-yl)-2-methylcyclopent-3-ene-1,2-diol (Compound-9);

(1S,2R,5R)-3-(2-(2-amino-3-chloro-5-fluoroquinolin-7-yl)ethyl)-5-(4-methyl-7H-pyrrolo[2,3-d]pyrimidin-7-yl)cyclopent-3-ene-1,2-diol (Compound-13);

(1S,2R,5R)-3-(2-(2-amino-3-chloro-5-fluoroquinolin-7-yl)ethyl)-5-(4-methyl-1H-pyrrolo[3,2-c]pyridin-1-yl)cyclopent-3-ene-1,2-diol hydrochloride (Compound-14);

(1S,2R,5R)-3-(((2-amino-3-chloro-5-fluoroquinolin-7-yl)oxy)methyl)-5-(4-amino-7H-pyrrolo[2,3-d]pyrimidin-7-yl)cyclopent-3-ene-1,2-diol (Compound-18);

(1S,2R,5R)-3-(1-((2-amino-3-chloro-5-fluoroquinolin-7-yl)oxy)ethyl)-5-(4-amino-7H-pyrrolo[2,3-d]pyrimidin-7-yl)cyclopent-3-ene-1,2-diol (Compound-20a and 20b);

(1S,2R,5R)-3-(2-(2-amino-3-chloroquinolin-7-yl)ethyl)-5-(4-methyl-7H-pyrrolo[2,3-d]pyrimidin-7-yl)cyclopent-3-ene-1,2-diol (Compound-21);

(1S,2R,5R)-3-(2-(2-Amino-3-fluoroquinolin-7-yl)ethyl)-5-(4-amino-7H-pyrrolo[2,3-d]pyrimidin-7-yl)cyclopent-3-ene-1,2-diol (Compound-23);

(1S,2R,5R)-3-(2-(2-amino-3-chloro-5-fluoroquinolin-7-yl)ethyl)-5-(4-amino-7H-pyrrolo[2,3-d]pyrimidin-7-yl)cyclopent-3-ene-1,2-diol (Compound-24);

(1S,2R,5R)-3-(2-(2-amino-3-chloro-6-fluoroquinolin-7-yl)ethyl)-5-(4-amino-7H-pyrrolo[2,3-d]pyrimidin-7-yl)cyclopent-3-ene-1,2-diol (Compound-25);

(1S,2R,5R)-3-(2-(2-amino-3-chloro-8-fluoroquinolin-7-yl)ethyl)-5-(4-amino-7H-pyrrolo[2,3-d]pyrimidin-7-yl)cyclopent-3-ene-1,2-diol (Compound-26);

(1S,2R,5R)-3-(2-(2-amino-3,5-dichloroquinolin-7-yl)ethyl)-5-(4-amino-7H-pyrrolo[2,3-d]pyrimidin-7-yl)cyclopent-3-ene-1,2-diol (Compound-29);

(1S,2R,5R)-3-(2-(2-amino-3-chloro-5-fluoroquinolin-7-yl)ethyl)-5-(4-isopropyl-7H-pyrrolo[2,3-d]pyrimidin-7-yl)cyclopent-3-ene-1,2-diol (Compound-31);

(1S,2R,5R)-3-(2-(2-amino-3-chloro-5-fluoroquinolin-7-yl)ethyl)-5-(4-(1-methyl-1H-pyrazol-4-yl)-7H-pyrrolo[2,3-d]pyrimidin-7-yl)cyclopent-3-ene-1,2-diol (Compound-32);

(1S,2R,5R)-3-(1-(2-amino-3-chloro-5-fluoroquinolin-7-yl)propan-2-yl)-5-(4-amino-7H-pyrrolo[2,3-d]pyrimidin-7-yl)cyclopent-3-ene-1,2-diol (Compound-33a and 33b);

(1S,2R,5R)-3-(1-(2-amino-3-chloroquinolin-7-yl)propan-2-yl)-5-(4-amino-7H-pyrrolo[2,3-d]pyrimidin-7-yl)cyclopent-3-ene-1,2-diol (Compound-34a and 34b);

(1S,2R,5R)-3-(2-(2-amino-3-chloro-5-fluoroquinolin-7-yl)ethyl)-5-(4-amino-7H-pyrrolo[2,3-d]pyrimidin-7-yl)-2-methylcyclopent-3-ene-1,2-diol (Compound-37);

(1S,2R,5R)-3-(1-(2-amino-3-chloro-5-fluoroquinolin-7-yl)propan-2-yl)-5-(4-amino-7H-pyrrolo[2,3-d]pyrimidin-7-yl)-2-methylcyclopent-3-ene-1,2-diol (Compound-38);

(1S,2R,5R)-3-(2-(2-amino-3-chloro-5-fluoroquinolin-7-yl)ethyl)-5-(4-amino-7H-pyrrolo[2,3-d]pyrimidin-7-yl)-2-ethylcyclopent-3-ene-1,2-diol (Compound-40);

(1S,2R,5R)-3-(2-(2-amino-3-chloro-5-fluoroquinolin-7-yl)ethyl)-5-(4-ethyl-7H-pyrrolo[2,3-d]pyrimidin-7-yl)cyclopent-3-ene-1,2-diol (Compound-41);

(1S,2R,5R)-3-(2-(2-amino-3-chloro-5-fluoroquinolin-7-yl)ethyl)-5-(4-cyclopropyl-7H-pyrrolo[2,3-d]pyrimidin-7-yl)cyclopent-3-ene-1,2-diol (Compound-42);

(1S,2R,5R)-3-(2-(2-Amino-3-bromo-5-fluoroquinolin-7-yl)ethyl)-5-(4-amino-7H-pyrrolo[2,3-d]pyrimidin-7-yl)cyclopent-3-ene-1,2-diol (Compound-43);

(1S,2R,5R)-3-(2-(2-Amino-3-bromo-5-fluoroquinolin-7-yl)ethyl)-5-(4-methyl-7H-pyrrolo[2,3-d]pyrimidin-7-yl)cyclopent-3-ene-1,2-diol (Compound-44);

(1S,2R,5R)-3-(1-(2-Amino-3-bromo-5-fluoro quinolin-7-yl)propan-2-yl)-5-(4-amino-7H-pyrrolo[2,3-d]pyrimidin-7-yl)cyclopent-3-ene-1,2-diol (Compound-45a and 45b);

(1S,2R,5R)-3-(2-(2-Amino-6-fluoroquinolin-7-yl)ethyl)-5-(4-amino-7H-pyrrolo[2,3-d]pyrimidin-7-yl)cyclopent-3-ene-1,2-diol (Compound-46);

(1S,2R,5R)-3-(2-(2-amino-5-fluoroquinolin-7-yl)ethyl)-5-(4-amino-7H-pyrrolo[2,3-d]pyrimidin-7-yl)cyclopent-3-ene-1,2-diol (Compound-47);

(1R,2R,3S,4R,5S)-1-(2-(2-Amino-3-chloro-5-fluoroquinolin-7-yl)ethyl)-4-(4-amino-7H-pyrrolo[2,3-d]pyrimidin-7-yl)bicyclo[3.1.0]hexane-2,3-diol (Compound-48);

(1R,2R,3S,4R,5S)-1-(2-(2-Amino-3-methylquinolin-7-yl)ethyl)-4-(4-amino-7H-pyrrolo[2,3-d]pyrimidin-7-yl)bicyclo[3.1.0]hexane-2,3-diol (Compound-54);

(1R,2R,3S,4R,5S)-1-(2-(2-Amino-3-chloroquinolin-7-yl)ethyl)-4-(4-amino-7H-pyrrolo[2,3-d]pyrimidin-7-yl)bicyclo[3.1.0]hexane-2,3-diol (Compound-61);

(1R,2R,3S,4R,5S)-1-(2-(2-Amino-3-chloro-6-fluoroquinolin-7-yl)ethyl)-4-(4-amino-7H-pyrrolo[2,3-d]pyrimidin-7-yl) bicyclo[3.1.0]hexane-2,3-diol (Compound-62);

(1R,2R,3S,4R,5S)-1-(2-(2-amino-3-bromo-6-fluoroquinolin-7-yl)ethyl)-4-(4-amino-7H-pyrrolo[2,3-d]pyrimidin-7-yl)bicyclo[3.1.0]hexane-2,3-diol (Compound-64);

(1R,2R,3S,4R,5S)-1-(2-(2-Amino-3-bromo-5-fluoroquinolin-7-yl)ethyl)-4-(4-amino-7H-pyrrolo[2,3-d]pyrimidin-7-yl)bicyclo[3.1.0]hexane-2,3-diol (Compound-72); and (1R,2R,3S,4R,5S)-1-(2-(2-Amino-3-bromoquinolin-7-yl)ethyl)-4-(4-amino-7H-pyrrolo [2,3-d]pyrimidin-7-yl)bicyclo[3.1.0]hexane-2,3-diol (Compound-73).

In another embodiment of the invention the compounds, their stereoisomer thereof, or a pharmaceutically acceptable salt thereof, are selected from:

(1S,2R,5R)-3-(2-(2-amino-3-chloro-5-fluoroquinolin-7-yl)ethyl)-5-(4-methyl-7H-pyrrolo[2,3-d]pyrimidin-7-yl)cyclopent-3-ene-1,2-diol (Compound-13);

(1S,2R,5R)-3-(2-(2-amino-3-chloro-5-fluoroquinolin-7-yl)ethyl)-5-(4-amino-7H-pyrrolo[2,3-d]pyrimidin-7-yl)cyclopent-3-ene-1,2-diol (Compound-24);

(1S,2R,5R)-3-(1-(2-amino-3-chloro-5-fluoroquinolin-7-yl)propan-2-yl)-5-(4-amino-7H-pyrrolo[2,3-d]pyrimidin-7-yl)cyclopent-3-ene-1,2-diol (Compound-33a and 33b);

(1S,2R,5R)-3-(2-(2-amino-3-chloro-5-fluoroquinolin-7-yl)
ethyl)-5-(4-amino-7H-pyrrolo[2,3-d]pyrimidin-7-yl)-2-
methylcyclopent-3-ene-1,2-diol (Compound-37);

(1R,2R,3S,4R,5S)-1-(2-(2-Amino-3-chloro-5-fluoroquino-
lin-7-yl)ethyl)-4-(4-amino-7H-pyrrolo[2,3-d]pyrimidin-
7-yl)bicyclo[3.1.0]hexane-2,3-diol (Compound-48);

(1R,2R,3S,4R,5S)-1-(2-(2-Amino-3-chloro-6-fluoroquino-
lin-7-yl)ethyl)-4-(4-amino-7H-pyrrolo[2,3-d]pyrimidin-
7-yl) bicyclo[3.1.0]hexane-2,3-diol (Compound-62);

(1R,2R,3S,4R,5S)-1-(2-(2-Amino-3-bromoquinolin-7-yl)
ethyl)-4-(4-amino-7H-pyrrolo [2,3-d]pyrimidin-7-yl)bi-
cyclo[3.1.0]hexane-2,3-diol (Compound-73);

(1S,2R,5R)-3-(2-(2-Amino-3-bromoquinolin-7-yl)ethyl)-5-
(4-amino-7H pyrrolo[2,3-d]pyrimidin-7-yl)cyclopent-3-
ene-1,2-diol (Compound-1);

(1S,2R,5R)-3-(2-(2-amino-3-chloro-6-fluoroquinolin-7-yl)
ethyl)-5-(4-amino-7H-pyrrolo[2,3-d]pyrimidin-7-yl)cy-
clopent-3-ene-1,2-diol (Compound-25);

(1S,2R,5R)-3-(((2-amino-3-chloro-5-fluoroquinolin-7-yl)
oxy)methyl)-5-(4-amino-7H-pyrrolo[2,3-d]pyrimidin-7-
yl)cyclopent-3-ene-1,2-diol (Compound-18);

(1S,2R,5R)-3-(1-(2-amino-3-chloroquinolin-7-yl)propan-2-
yl)-5-(4-amino-7H-pyrrolo[2,3-d]pyrimidin-7-yl)cyclo-
pent-3-ene-1,2-diol (Compound-34a and 34b);

(1S,2R,5R)-3-(1-(2-amino-3-chloro-5-fluoroquinolin-7-yl)
propan-2-yl)-5-(4-amino-7H-pyrrolo[2,3-d]pyrimidin-7-
yl)-2-methylcyclopent-3-ene-1,2-diol (Compound-38);

(1R,2R,3S,4R,5S)-1-(2-(2-Amino-3-chloroquinolin-7-yl)
ethyl)-4-(4-amino-7H-pyrrolo[2,3-d]pyrimidin-7-yl)bi-
cyclo[3.1.0]hexane-2,3-diol (Compound-61);

(1S,2R,5R)-3-(2-(2-Amino-3-bromo-5-fluoroquinolin-7-yl)
ethyl)-5-(4-amino-7H-pyrrolo[2,3-d]pyrimidin-7-yl)cy-
clopent-3-ene-1,2-diol (Compound-43);

(1S,2R,5R)-3-(1-(2-Amino-3-bromo-5-fluoro quinolin-7-yl)
propan-2-yl)-5-(4-amino-7H-pyrrolo[2,3-d]pyrimidin-7-
yl)cyclopent-3-ene-1,2-diol (Compound-45a);

(1S,2R,5R)-3-(2-(2-Amino-3-bromo-5-fluoroquinolin-7-yl)
ethyl)-5-(4-methyl-7H-pyrrolo[2,3-d]pyrimidin-7-yl)cy-
clopent-3-ene-1,2-diol (Compound-44);

(1R,2R,3S,4R,5S)-1-(2-(2-Amino-3-bromo-5-fluoroquino-
lin-7-yl)ethyl)-4-(4-amino-7H-pyrrolo[2,3-d]pyrimidin-
7-yl)bicyclo[3.1.0]hexane-2,3-diol (Compound-72); and (1R,2R,3S,4R,5S)-1-(2-(2-amino-3-bromo-6-fluoroquino-
lin-7-yl)ethyl)-4-(4-amino-7H-pyrrolo[2,3-d]pyrimidin-
7-yl)bicyclo[3.1.0]hexane-2,3-diol (Compound-64).

DETAILED DESCRIPTION OF THE INVENTION

Definitions and Abbreviations

Unless otherwise stated, the following terms used in the specification and claims have the meanings given below.

For purposes of interpreting the specification, the following definitions will apply and whenever appropriate, terms used in the singular will also include the plural and vice versa.

The terms "halogen" or "halo" means fluorine, chlorine, bromine, or iodine.

The term "alkyl" refers to an alkane derived hydrocarbon radical that includes solely carbon and hydrogen atoms in the backbone, contains no unsaturation, has from one to six carbon atoms, and is attached to the remainder of the molecule by a single bond, for example ($C_1$-$C_6$)alkyl or ($C_1$-$C_4$)alkyl, representative groups include e.g., methyl, ethyl, n-propyl, 1-methylethyl (isopropyl), n-butyl, n-pentyl and the like. Unless set forth or recited to the contrary, all alkyl groups described or claimed herein may be straight chain or branched.

The term "alkenyl" refers to a hydrocarbon radical containing from 2 to 10 carbon atoms and including at least one carbon-carbon double bond. Non-limiting Examples of alkenyl groups include, for example ($C_2$-$C_6$)alkenyl, ($C_2$-$C_4$) alkenyl, ethenyl, 1-propenyl, 2-propenyl (allyl), iso-propenyl, 2-methyl-1-propenyl, 1-butenyl, 2-butenyl and the like. Unless set forth or recited to the contrary, all alkenyl groups described or claimed herein may be straight chain or branched.

The term "alkynyl" refers to a hydrocarbon radical containing 2 to 10 carbon atoms and including at least one carbon-carbon triple bond. Non-limiting Examples of alkynyl groups include, for example ($C_2$-$C_6$)alkynyl, ($C_2$-$C_4$) alkynyl, ethynyl, propynyl, butynyl and the like. Unless set forth or recited to the contrary, all alkynyl groups described or claimed herein may be straight chain or branched.

The term "haloalkyl" refers to an alkyl group as defined above that is substituted by one or more halogen atoms as defined above. For example ($C_1$-$C_6$)haloalkyl or ($C_1$-$C_4$) haloalkyl. Suitably, the haloalkyl may be monohaloalkyl, dihaloalkyl or polyhaloalkyl including perhaloalkyl. A monohaloalkyl can have one iodine, bromine, chlorine or fluorine atom. Dihaloalkyl and polyhaloalkyl groups can be substituted with two or more of the same halogen atoms or a combination of different halogen atoms. Suitably, a polyhaloalkyl is substituted with up to 12 halogen atoms. Non-limiting Examples of a haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl and the like. A perhaloalkyl refers to an alkyl having all hydrogen atoms replaced with halogen atoms. Unless set forth or recited to the contrary, all haloalkyl groups described or claimed herein may be straight chain or branched.

The term "alkoxy" denotes an alkyl group attached via an oxygen linkage to the rest of the molecule. Representative examples of such groups are —$OCH_3$ and —$OC_2H_5$. Unless set forth or recited to the contrary, all alkoxy groups described or claimed herein may be straight chain or branched.

The term "alkoxyalkyl" refers to an alkoxy group as defined above directly bonded to an alkyl group as defined above, e.g., —$CH_2$—O—$CH_3$, —$CH_2$—O—$CH_2CH_3$, —$CH_2CH_2$—O—$CH_3$ and the like.

The term "cycloalkyl" refers to a non-aromatic mono or multicyclic ring system having 3 to 12 carbon atoms, such as ($C_3$-$C_{10}$)cycloalkyl, ($C_3$-$C_6$)cycloalkyl, cyclopropyl, cyclobutyl, cyclopentyl, cyclohexyl and the like. Examples of multicyclic cycloalkyl groups include, but are not limited to, perhydronaphththyl, adamantyl and norbornyl groups, bridged cyclic groups or spirobicyclic groups, e.g., spiro(4, 4)non-2-yl and the like.

The term "aryl" refers to an aromatic radical having 6- to 14-carbon atoms, including monocyclic, bicyclic and tricyclic aromatic systems, such as phenyl, naphthyl, tetrahydronaphthyl, indanyl, and biphenyl and the like.

The term "heterocyclic ring" or "heterocyclyl ring" or "heterocyclyl", unless otherwise specified, refers to substituted or unsubstituted non-aromatic 3- to 15-membered ring which consists of carbon atoms and with one or more heteroatom(s) independently selected from N, O or S. The heterocyclic ring may be a mono-, bi- or tricyclic ring system, which may include fused, bridged or spiro ring systems and the nitrogen, carbon, oxygen or sulfur atoms in the heterocyclic ring may be optionally oxidized to various oxidation states. In addition, the nitrogen atom may be optionally quaternized, the heterocyclic ring or heterocyclyl may optionally contain one or more olefinic bond(S), and one or two carbon atoms(S) in the heterocyclic ring or heterocyclyl may be interrupted with —$CF_2$—, —C(O)—, —S(O)—, $S(O)_2$ etc. In addition heterocyclic ring may also be fused with aromatic ring. Non-limiting Examples of heterocyclic rings include azetidinyl, benzopyranyl, chromanyl, decahydroisoquinolyl, indolinyl, isoindolinyl, isochromanyl, isothiazolidinyl, isoxazolidinyl, morpholinyl, oxazolinyl, oxazolidinyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisoquinolyl, tetrahydrofuryl, tetrahydropyranyl, thiazolinyl, thiazolidinyl, thiamorpholinyl, thiamorpholinylsulfoxide, thiamorpholinylsulfoneindoline, benzodioxole, tetrahydroquinoline, tetrahydrobenzopyran and the like. The heterocyclic ring may be attached by any atom of the heterocyclic ring that results in the creation of a stable structure.

The term "heteroaryl" unless otherwise specified, refers to a substituted or unsubstituted 5- to 14-membered aromatic heterocyclic ring with one or more heteroatom(S) independently selected from N, O or S. The heteroaryl may be a mono-, bi- or tricyclic ring system. The heteroaryl ring may be attached by any atom of the heteroaryl ring that results in the creation of a stable structure. Non-limiting Examples of a heteroaryl ring include oxazolyl, isoxazolyl, imidazolyl, furyl, indolyl, isoindolyl, pyrrolyl, triazolyl, triazinyl, tetrazolyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl, phthalazinyl and the like.

The compounds of the present invention may have one or more chiral centers. The absolute stereochemistry at each chiral center may be 'R' or 'S'. The compounds of the invention include all diastereomers and enantiomers and mixtures thereof. Unless specifically mentioned otherwise, reference to one stereoisomer applies to any of the possible stereoisomers. Whenever the stereoisomeric composition is unspecified, it is to be understood that all possible stereoisomers are included.

The term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are non-superimposable mirror images of one another. The term "chiral center" refers to a carbon atom to which four different groups are attached. As used herein, the term "diastereomers" refers to stereoisomers which are not enantiomers. The terms "racemate" or "racemic mixture" refer to a mixture of equal parts of enantiomers.

A "tautomer" refers to a compound that undergoes rapid proton shifts from one atom of the compound to another atom of the compound. Some of the compounds described herein may exist as tautomers with different points of attachment of hydrogen. The individual tautomers as well as mixture thereof are encompassed with compounds of formula (I).

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; c) lessening the disease, disorder or condition or at least one of its clinical or subclinical symptoms or (d) relieving the disease, i.e., causing regression of the state, disorder or condition or at least one of its clinical or subclinical symptoms.

The term "inhibitor" refers to a molecule that binds to an enzyme to inhibit the activity of the said enzyme either partially or completely.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a disease, disorder or condition, is sufficient to cause the effect in the subject, which is the purpose of the administration. The "therapeutically effective amount" will vary depending on the compound, the disease and its severity and the age, weight, physical condition and responsiveness of the subject to be treated.

Pharmaceutically Acceptable Salts

The compounds of the invention may form salts with acid or base. The compounds of invention may be sufficiently basic or acidic to form stable nontoxic acid or base salts, administration of the compound as a pharmaceutically acceptable salt may be appropriate. Non-limiting Examples of pharmaceutically acceptable salts are inorganic, organic acid addition salts formed by addition of acids including hydrochloride salts. Non-limiting Examples of pharmaceutically acceptable salts are inorganic, organic base addition salts formed by addition of bases. The compounds of the invention may also form salts with amino acids. Pharmaceutically acceptable salts may be obtained using standard procedures well known in the art, for example by reacting sufficiently basic compound such as an amine with a suitable acid.

Screening of the compounds of invention for PRMT5 inhibitory activity can be achieved by using various in vitro and in vivo protocols mentioned herein below or methods known in the art.

Pharmaceutical Compositions

The invention relates to pharmaceutical compositions containing the compounds of the formula (I), or pharmaceutically acceptable salts thereof disclosed herein. In particular, pharmaceutical compositions containing a therapeutically effective amount of at least one compound of formula (I) described herein and at least one pharmaceutically acceptable excipient (such as a carrier or diluent). Preferably, the contemplated pharmaceutical compositions include the compound(s) described herein in an amount sufficient to inhibit PRMT5 to treat the diseases described herein when administered to a subject.

The subjects contemplated include, for example, a living cell and a mammal, including human. The compound of the invention may be associated with a pharmaceutically acceptable excipient (such as a carrier or a diluent) or be diluted by a carrier, or enclosed within a carrier which can be in the form of a capsule, sachet, paper or other container. The pharmaceutically acceptable excipient includes pharmaceutical agent that does not itself induce the production of antibodies harmful to the individual receiving the composition, and which may be administered without undue toxicity.

Examples of suitable carriers or excipients include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, salicylic acid, fatty acids, fatty acid amines, fatty acid monoglycerides and diglycerides, pentaerytritol fatty acid esters, polyoxyethylene, hydroxymethylcellulose and polyvinylpyrrolidone.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared by conventional techniques known in the art. For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for Example, in a sachet.

The pharmaceutical compositions may be in conventional forms, for example, capsules, tablets, caplets, orally disintegrating tablets, aerosols, solutions, suspensions or products for topical application.

The route of administration may be any route which effectively transports the active compound of the invention to the appropriate or desired site of action. Suitable routes of administration include, but are not limited to, oral, oral inhalation, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Solid oral formulations include, but are not limited to, tablets, caplets, capsules (soft or hard gelatin), orally disintegrating tablets, dragees (containing the active ingredient in powder or pellet form), troches and lozenges. Tablets, dragees, or capsules having talc and/or a carbohydrate carrier or binder or the like are particularly suitable for oral application. Liquid formulations include, but are not limited to, syrups, emulsions, suspensions, solutions, soft gelatin and sterile injectable liquids, such as aqueous or non-aqueous liquid suspensions or solutions. For parenteral application, particularly suitable are injectable solutions or suspensions, preferably aqueous solutions with the active compound dissolved in polyhydroxylated castor oil.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as pocketed tablets, capsules, and powders in vials or ampoules. Also, the unit dosage form can be a capsule, tablet, caplet, cachet, or lozenge itself, or it can be the appropriate number of any of these in packaged form.

For administration to subject patients, the total daily dose of the compounds of the invention depends, of course, on the mode of administration. For example, oral administration may require a higher total daily dose, than an intravenous (direct into blood). The quantity of active component in a unit dose preparation may be varied or adjusted from 0.1 mg to 1000 mg by oral administration and 1 µg to 5000 µg by inhalation according to the potency of the active component or mode of administration.

Those skilled in the relevant art can determine suitable doses of the compounds for use in treating the diseases and disorders described herein. Therapeutic doses are generally identified through a dose ranging study in subject based on preliminary evidence derived from the animal studies. Doses must be sufficient to result in a desired therapeutic benefit without causing unwanted side effects for the patient. For example, the daily dosage of the PRMT5 inhibitor can range from about 0.1 to about 30.0 mg/kg by oral administration. Mode of administration, dosage forms, suitable pharmaceutical excipients, diluents or carriers can also be well used and adjusted by those skilled in the art. All changes and modifications envisioned are within the scope of the invention.

Methods of Treatment

The invention provides compound of formula (I) and pharmaceutical compositions thereof as protein arginine methyl transferase-5 (PRMT5) inhibitors for treating the diseases, disorders or conditions associated with overexpression of PRMT5. The invention further provides a method of treating diseases, disorders or conditions associated with overexpression of PRMT5 in a subject in need thereof by administering to the subject a therapeutically effective amount of a compound or a pharmaceutical composition of the invention.

In another aspect, the invention relates to a method of treating diseases, disorders or conditions associated with the overexpression of PRMT5. In this method, a subject in need of such treatment is administered a therapeutically effective amount of a compound of formula (D) or a pharmaceutically acceptable salt thereof as described herein.

In one embodiment of the present invention, the diseases, disorders, or conditions associated with the overexpression of PRMT5 are cancer.

In another embodiment, the invention provides a method of treating cancers, particularly, glioblastoma multiforme, prostate cancer, pancreatic cancer, mantle cell lymphoma, non-Hodgkin's lymphomas and diffuse large B-cell lymphoma, acute myeloid leukemia, acute lymphoblastic leukemia, multiple myeloma, non-small cell lung cancer, small cell lung cancer, breast cancer, triple negative breast cancer, gastric cancer, colorectal cancer, ovarian cancer, bladder cancer, hepatocellular cancer, melanoma, sarcoma, oropharyngeal squamous cell carcinoma, chronic myelogenous leukemia, epidermal squamous cell carcinoma, nasopharyngeal carcinoma, neuroblastoma, endometrial carcinoma, and cervical cancer.

It is to be understood that the invention encompasses the compounds of formula (I) or pharmaceutically acceptable salts thereof for use in the treatment of a disease or disorder mentioned herein.

It is to be understood that the invention encompasses the compounds of formula (I) or pharmaceutically acceptable salts thereof in the manufacture of a medicament for treating a disease or disorder mentioned herein.

General Methods of Preparation

The compound of formula described herein may be prepared by techniques known in the art. In addition, the compound of formula described herein may be prepared by following the reaction sequence as depicted in Scheme-1 to Scheme-27. Further, in the following schemes, where specific bases, acids, reagents, solvents, coupling agents, etc., are mentioned, it is understood that other bases, acids, reagents, solvents, coupling agents etc., known in the art may also be used and are therefore included within the scope of the present invention. Variations in reaction conditions, for example, temperature and/or duration of the reaction, which may be used as known in the art, are also within the scope of the present invention. All the isomers of the compound of formula in described in these schemes, unless otherwise specified, are also encompassed within the scope of this invention.

Scheme-1

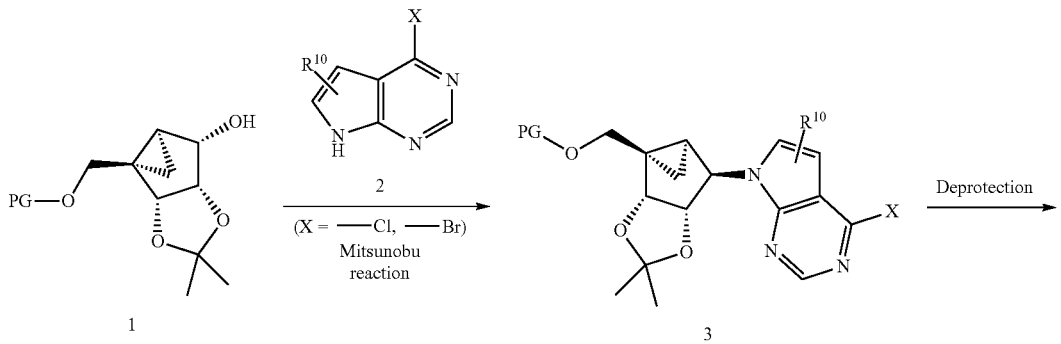

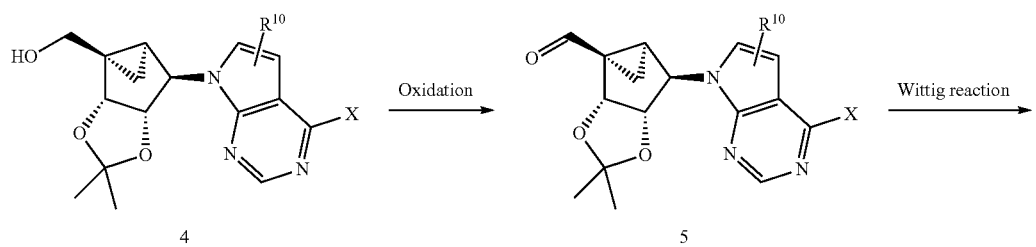

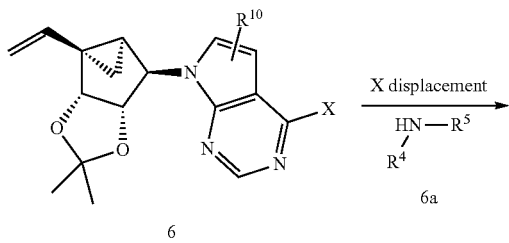

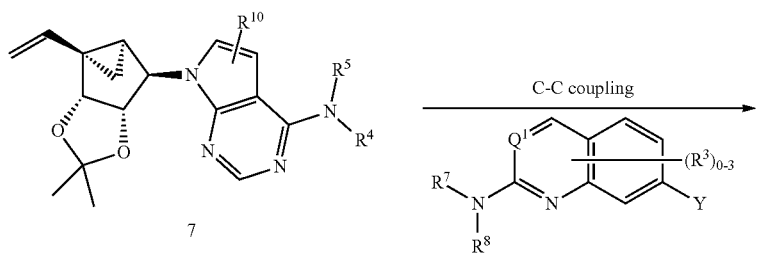

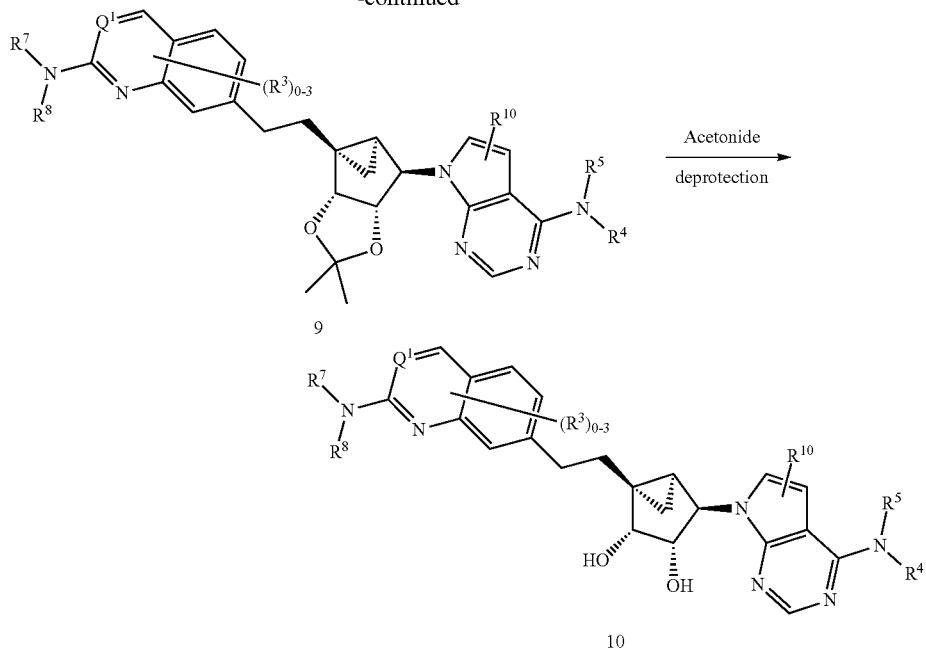

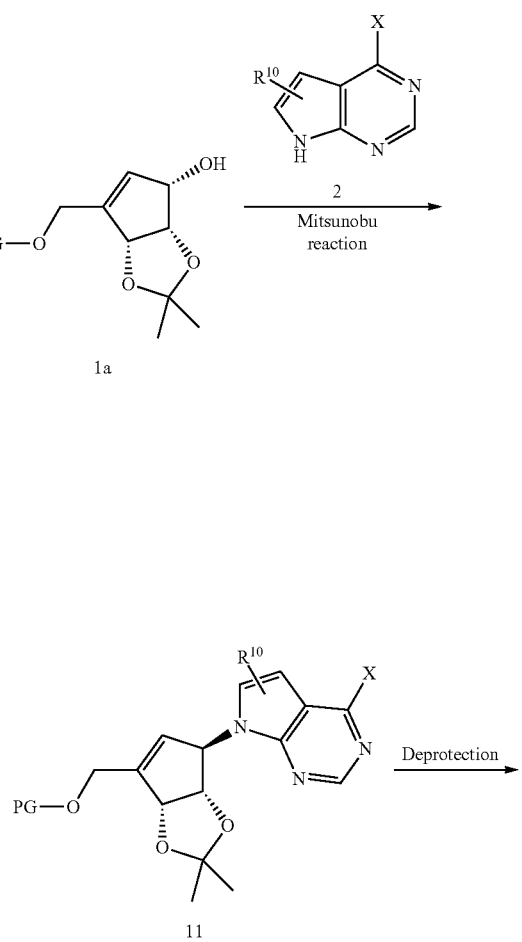

Scheme-1 illustrates the synthesis of compound of formula 10 (when $Q^1$ is N, CH or CX, where X can be Cl or Br). Compound of formula 1 (where PG=Protecting group), is prepared by following the procedure reported in Kenneth A. Jacobson et.al; Purinergic Signalling (2015) 11:371-387. Mitsunobu reaction of compound of formula 1 with compound of formula 2 (X=—Cl, —Br) using various azo dicarboxylate reagents such as but not limited to DEAD or DIAD in presence of phosphine such as but not limited to $PPh_a$ to form the compound of formula 3. Compound of formula 4 is formed upon treatment of compound of formula 3 with fluoride ions such as but not limited to TBAF. Oxidation of compound of formula 4 with oxidising agents such as but not limited to Dess-Martin periodinane can furnish the compound of formula 5. Reagents such as but not limited to methyltriphenylphosphonium bromide in presence of a base such as but not limited to KO$^t$Bu, NaO$^t$Bu, LiHMDS, NaHMDS, or KHMDS when treated with compound of formula 5 affords compound of formula 6. Compound of formula 6a (where $R^4$ and $R^5$ are defined herein above) upon treatment with compound of formula 6 affords compound of formula 7. Compound of formula 9 can be achieved by hydroboration of compound of formula 7 with suitable boranes such as but not limited to 9-BBN followed by addition of inorganic base such as but not limited to $K_3PO_4$ or $Cs_2CO_3$, in presence of Pd catalyst such as but not limited to Pd(dppf)$Cl_2$ or Pd(PPh$_3$)$_2$Cl$_2$ and compound of formula 8 (Y=—Br, —I, which can be prepared by following the procedure reported J. Med. Chem., 2017, 60 (9), 3958-3978). Acetonide deprotection of compound of formula 9 with acids such as but not limited to HCl or TFA affords compound of formula 10.

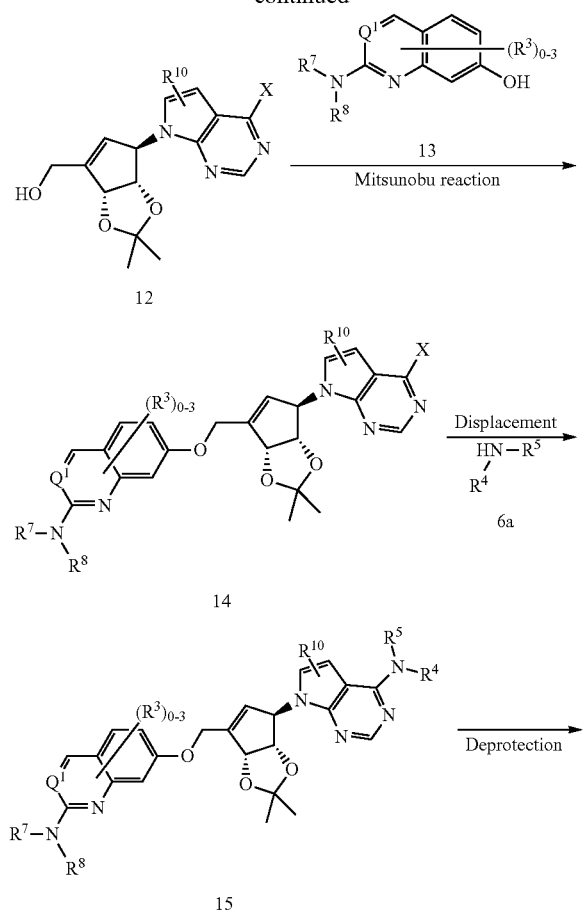

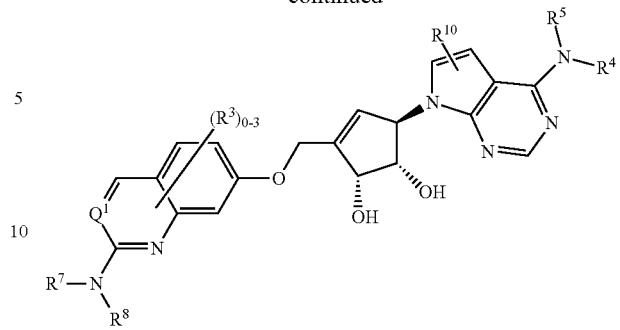

Scheme-2 illustrates the synthesis of compound of formula 16. This can be achieved by Mitsunobu reaction of compound of formula 1a, which is prepared by following the procedure reported in Kenneth A. Jacobson et.al; Purinergic Signalling (2015) 11:371-387, with compound of formula 2 using various azo dicarboxylate reagents such as but not limited to DIAD in presence of phosphine such as but not limited to $PPh_3$ to form the compound of formula 11, which can be further converted to compound of formula 12 upon treatment with fluoride ions such as but not limited to TBAF. Mitsunobu reaction of compound of formula 12 with compound of formula 13 (commercially available or synthesized as per known literature, where $Q^1$=C or N, $R^3$, $R^7$ and $R^8$ are defined herein above) using various azo dicarboxylate reagents such as but not limited to DIAD in presence of phosphine such as but not limited to $PPh_a$ affords the compound of formula 14. Compound of formula 6a upon treatment with compound of formula 14 affords compound of formula 15. Acetonide deprotection of compound of formula 15 with acids such as but not limited to HCl or TFA affords compound of formula 16.

Scheme-3

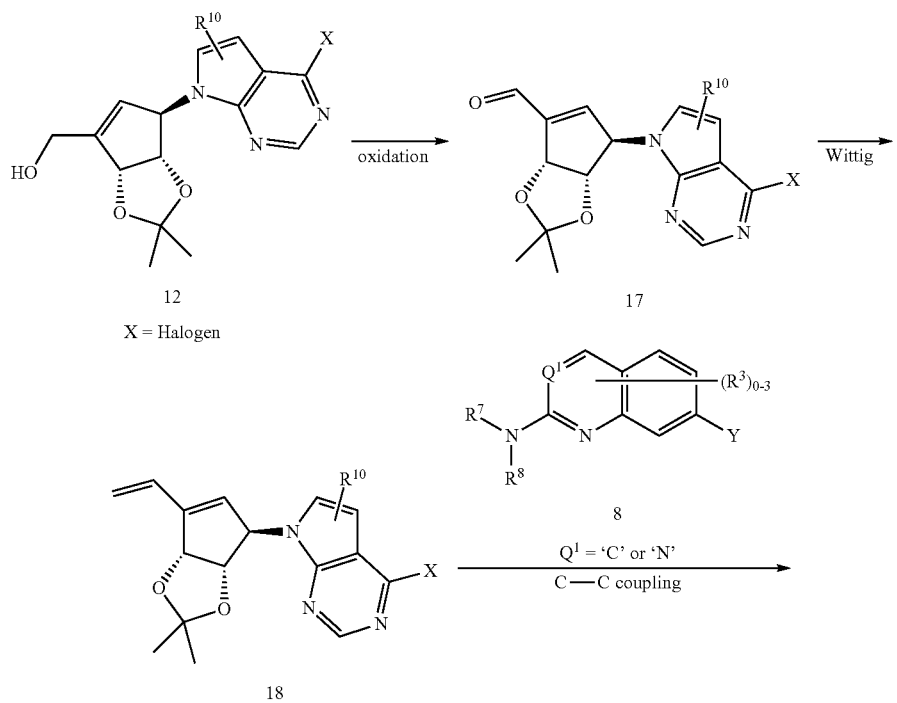

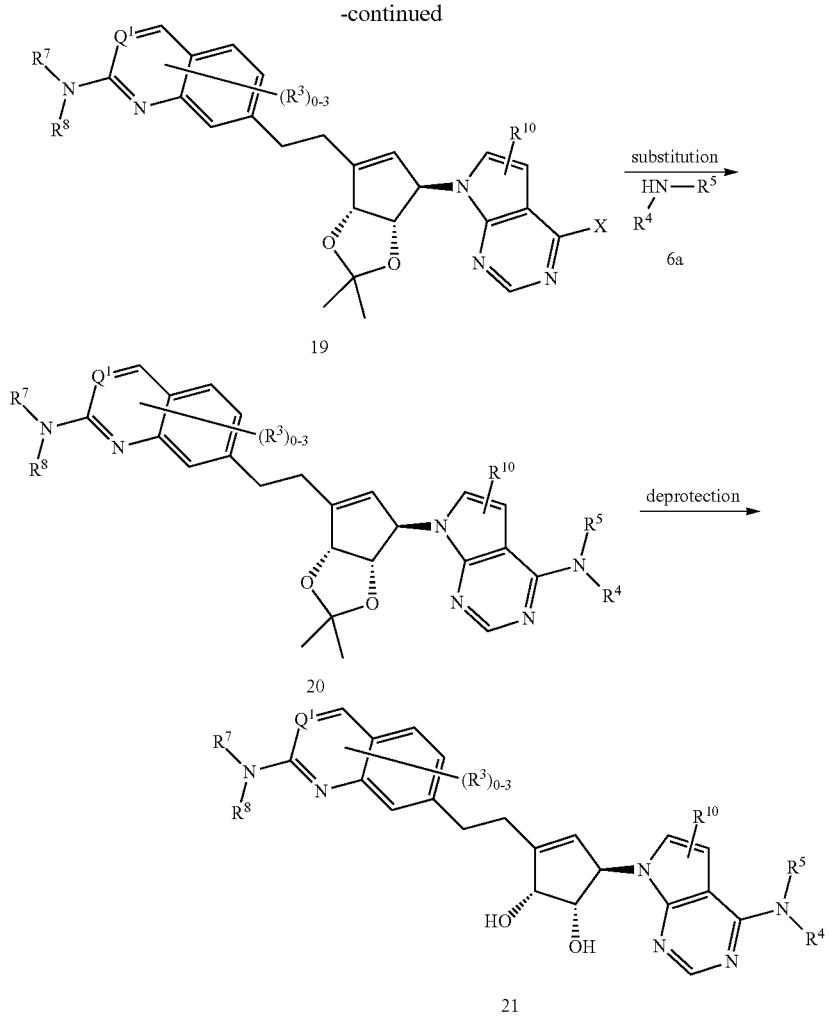

Scheme-3 illustrates the synthesis of compound of formula 21. Compound of formula 17 is formed upon treatment of compound of formula 12 with oxidising agents such as but not limited to Dess-Martin periodinane. Reagents such as but not limited to methyltriphenylphosphonium bromide in presence of a base such as but not limited to KO$^t$Bu, NaO$^t$Bu, LiHMDS, NaHMDS, or KHMDS when treated with compound of formula 17 affords compound of formula 18. Compound of formula 19 can be synthesized by hydroboration of compound of formula 18 with suitable boranes such as but not limited to 9-BBN followed by addition of inorganic base such as but not limited to tripotassium phosphate or Cs$_2$CO$_3$, in presence of Pd catalyst such as but not limited to Pd(dppf)Cl$_2$ or Pd(PPh$_3$)$_2$Cl$_2$ and compound of formula 8 (Y=—Br, —I), which was synthesized by following the procedure reported in WO2012002577 A1, followed by N-oxide formation, chlorination with phosphoroxychloride and nucleophilic substitution with PMB-NH$_2$ or J. Med. Chem, 2017, 60 (9), 3958-3978). Compound of formula 6a (where R$^4$ and R$^5$ are defined herein above) upon treatment with compound of formula 19 affords compound of formula 20. Acetonide deprotection of compound of formula 20 with acids such as but not limited to HCl or TFA affords compound of formula 21.

Scheme-4

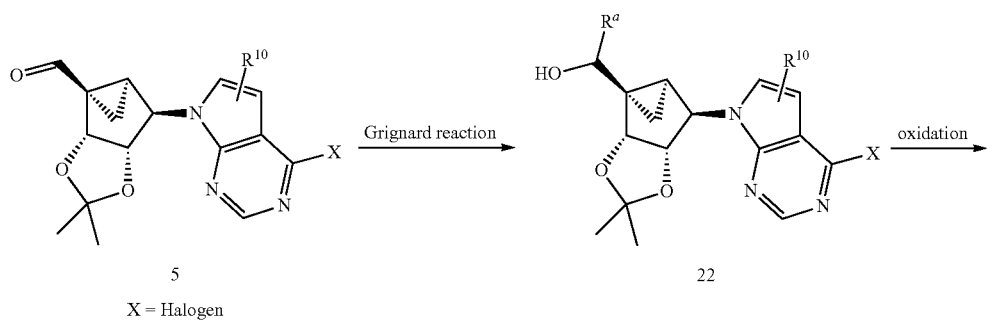

X = Halogen

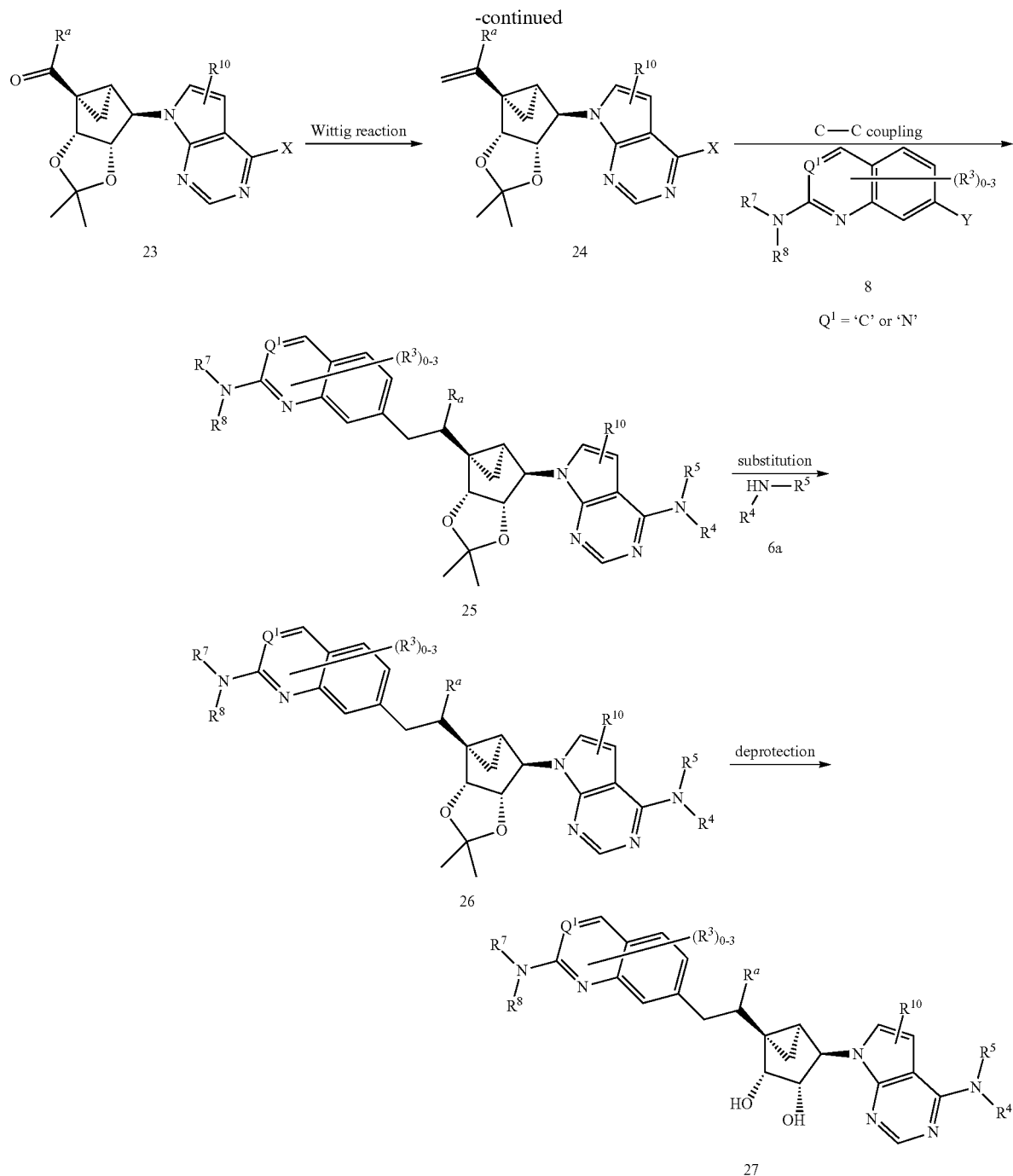

Scheme-4 illustrates the synthesis of compound of formula 27. Compound of formula 22 is formed upon treatment of compound of formula 5 with Grignard reagent such as but not limited to methylmagnesium bromide, ethylmagnesium bromide, cyclopropylmagnesium bromide etc. Compound of formula 22 on oxidation with oxidising agents such as but not limited to Dess-Martin periodinane gives compound of formula 23. Reagents such as but not limited to methyltriphenylphosphonium bromide in presence of base such as but not limited to KO$^t$Bu, NaO$^t$Bu, LiHMDS, NaHMDS, or KHMDS when treated with compound of formula 23 affords compound of formula 24. Compound of formula 25 can be achieved by hydroboration of compound of formula 24 with suitable boranes such as but not limited to 9-BBN followed by addition of inorganic base such as but not limited to tripotassium phosphate or $Cs_2CO_3$, in presence of Pd catalyst such as but not limited to Pd(dppf)$Cl_2$ or Pd(PPh$_3$)$_2Cl_2$ and compound of formula 8 (Y=—Br, —I), which was synthesized by following the procedure reported in WO2012002577 A1, followed by N-oxide formation, chlorination with Phosphoroxychloride, and nucleophilic substitution with PMB-$NH_2$ or J. Med. Chem, 2017, 60 (9), 3958-3978). Compound of formula 6a (where $R^4$ and $R^5$ are defined herein above) upon treatment with compound of formula 25 affords compound of formula 26. Acetonide deprotection of compound of formula 26 with acids such as but not limited to HCl or TFA affords compound of formula 27.
Scheme-5
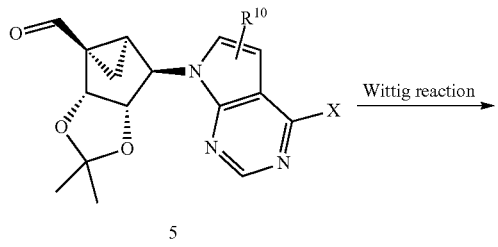
X = Halogen
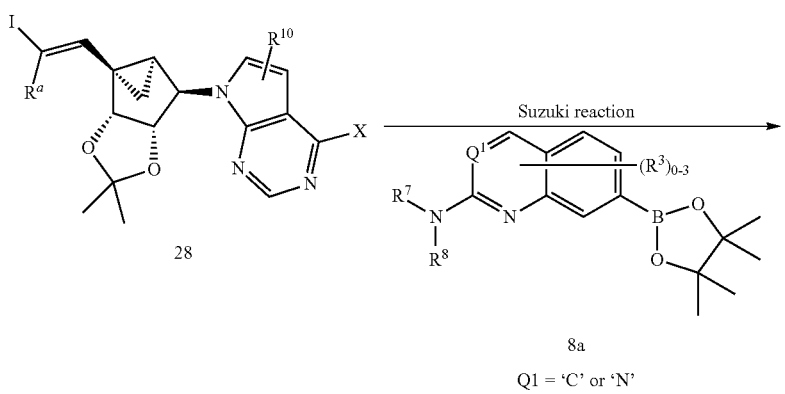
Q1 = 'C' or 'N'
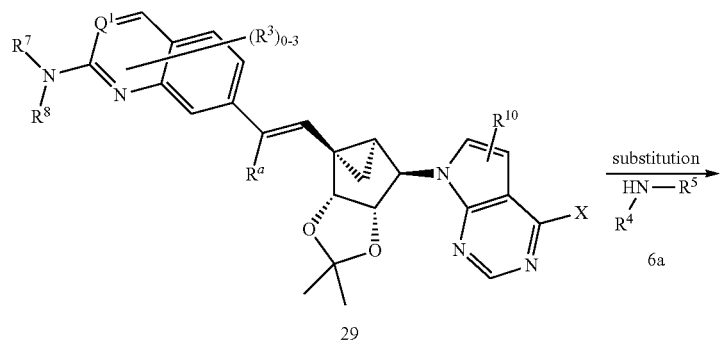
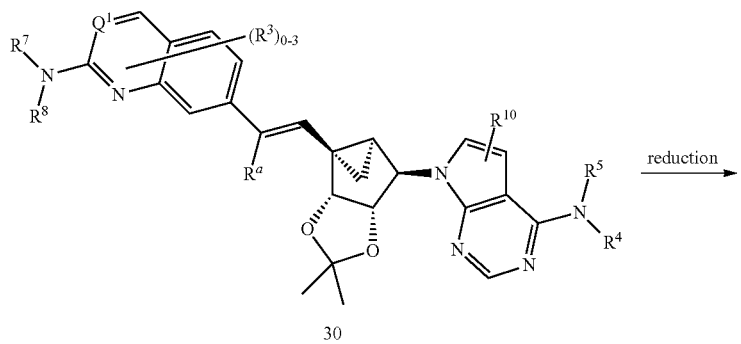

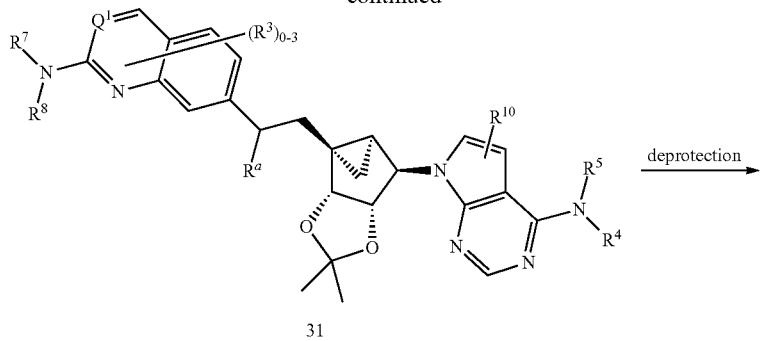

31

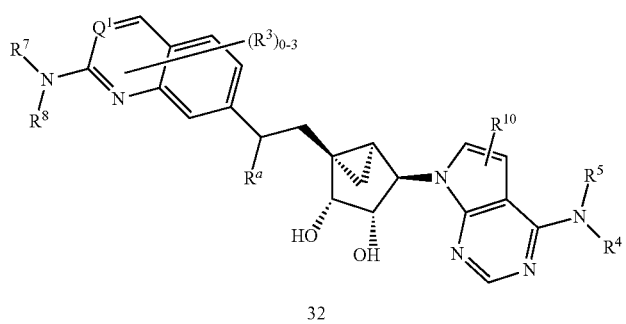

32

Scheme-5 illustrates the synthesis of compound of formula 32. Compound of formula 28 is formed upon treatment of compound of formula 5 with Wittig reagents such as but not limited to (1-iodoethyl) triphenylphosphonium bromide. Compound of formula 29 can be achieved by Suzuki coupling of compound of formula 28 with suitable inorganic base such as but not limited to tripotassium phosphate or $Cs_2CO_3$, in presence of Pd catalyst such as but not limited to $Pd(PPh_3)_4$, $Pd(dppf)Cl_2$ or $Pd(PPh_3)_2Cl_2$ and compound of formula 8a (Y = —Br, —I). Compound of formula 6a (where $R^4$ and $R^5$ are defined herein above) upon treatment with compound of formula 29 affords compound of formula 30. Hydrogenation of compound of formula 30 affords compound of formula 31. Acetonide deprotection of compound of formula 31 with acids such as but not limited to HCl or TFA affords compound of formula 32.

Scheme-6

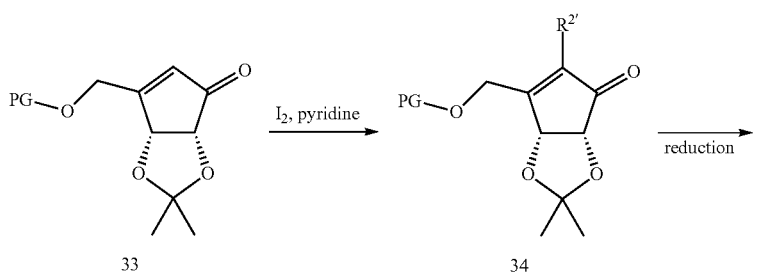

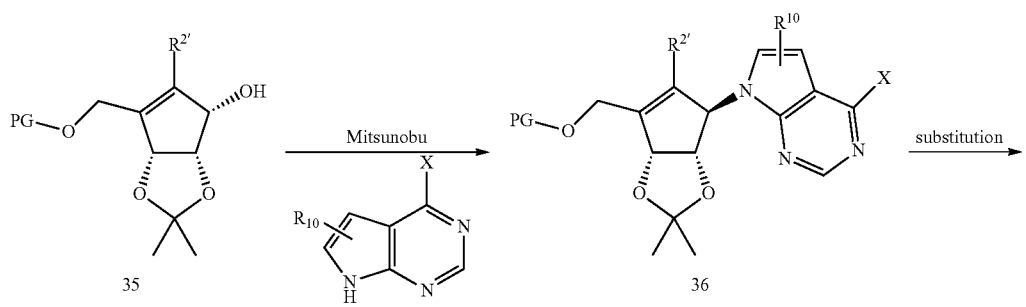

-continued
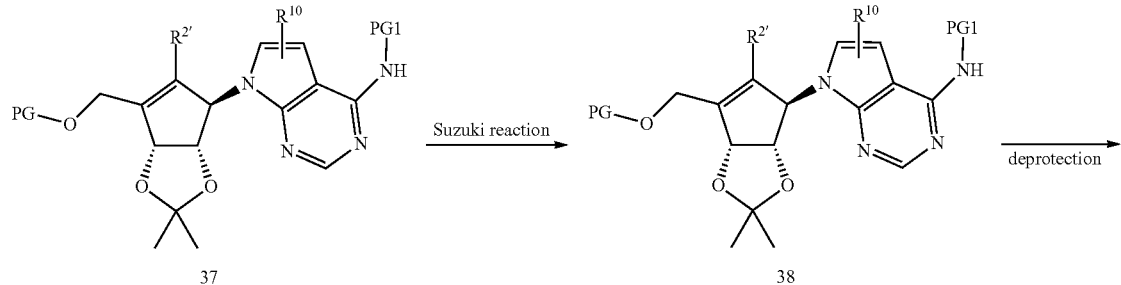
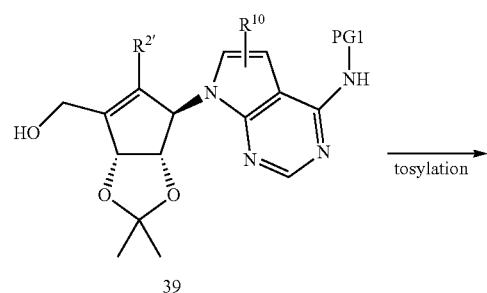
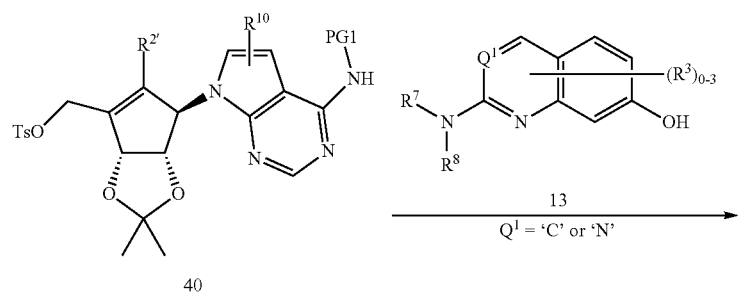
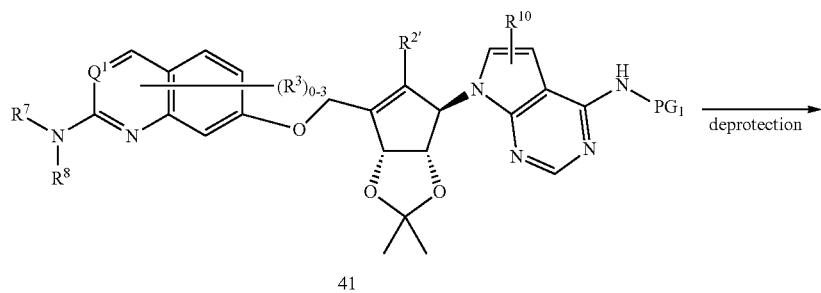
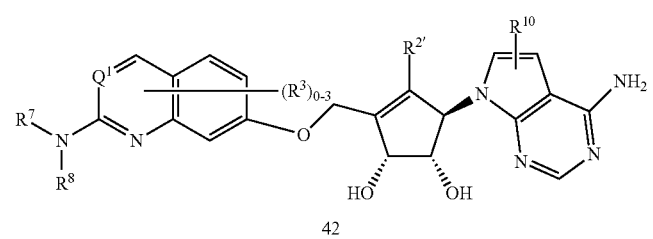

Compound of formula-33 (can be synthesized by following the protocol as mentioned in Med. Chem. Comm.; vol. 4; nb. 5; (2013); p. 822-826) upon treatment with iodine in presence of pyridine affords Compound of formula-34, which can be reduced by cerium chloride and sodium borohydride to get compound of formula-35. Mitsunobu reaction using compound of formula-2 with compound of formula-35 provides the compound of formula-36. Halogen of compound of formula-36 on substitution with PMB amine, followed by Suzuki reaction affords the compound of formula-38. TBDMS deprotection of compound of formula-38 followed by tosylation of compound of formula-39 provides compound of formula-40. The tosyl of compound of formula-40 is replaced with compound of formula-13 gives the compound of formula-41, which is further deprotected in acidic condition to get the final compound of formula-42.

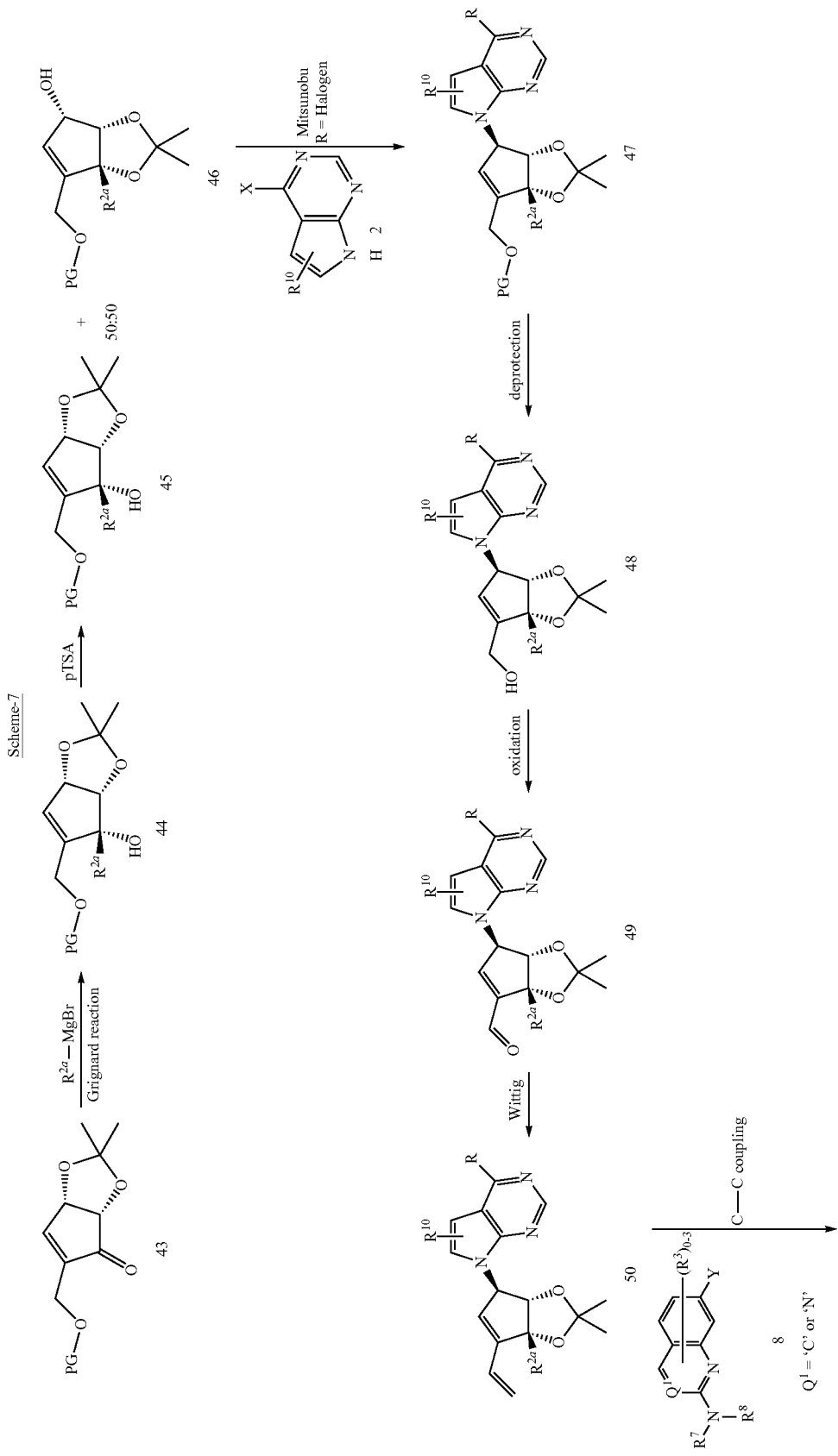

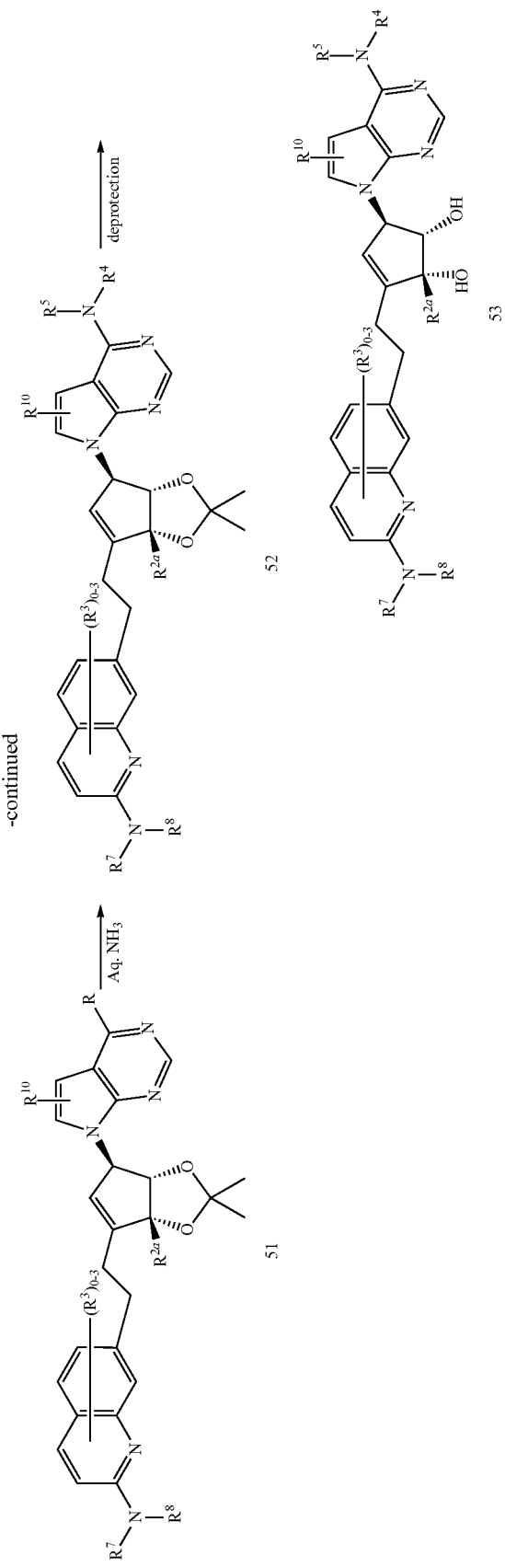

Reaction of compound of formula-43 [can be prepared by method reported in *J. Org. Chem.* 2014, 79, 8059-8066] with methyl magnesium bromide gives compound of formula-44, with only one stereoisomer with good yield. This when subjected to acetonide shuffling affords compound of formula-46. Mitsunobu reaction using compound of formula 2 with compound of formula-46 yields the compound of formula-47, which can be converted to compound of formula-48 on treating with TBAF. Compound of formula-48 can be oxidized with DMP to afford Compound of formula-49, which can undergo Witting reaction to give compound of formula-50. Compound of formula 51 can be achieved by hydroboration of compound of formula 50 with suitable boranes such as but not limited to 9-BBN followed by addition of inorganic base such as but not limited to $K_3PO_4$ or $Cs_2CO_3$, in presence of Pd catalyst such as but not limited to Pd(dppf)$Cl_2$ or Pd(PPh$_3$)$_2$$Cl_2$ and compound of formula 8. Compound of formula-51 on treating with aq. ammonia followed by treatment with trifluroacetic acid affords compound of formula-53.

Scheme-8

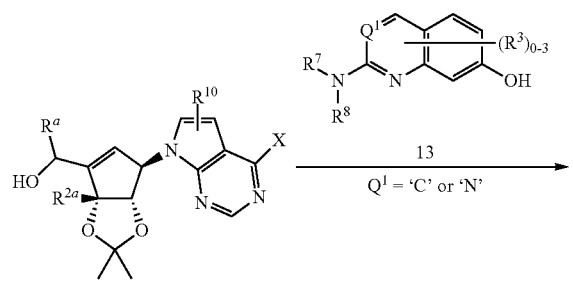

13

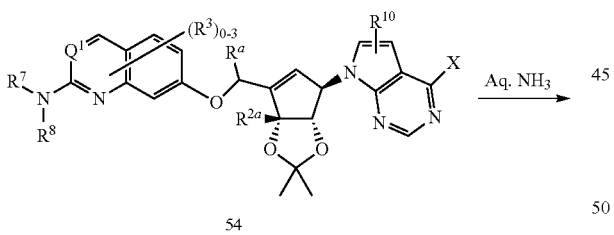

54

Aq. NH$_3$

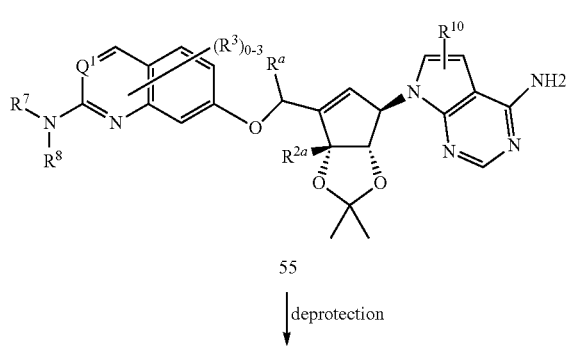

55 deprotection

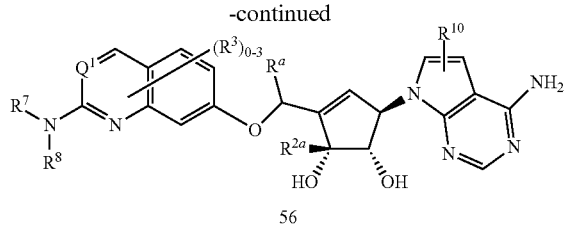

56

Compound of formula-48 (compound of formula 48a can be synthesized from 48 by oxidation and Grignard reaction) when condensed with compound of formula-13 using Mitsunobu reaction affords compound of formula-54, which can be reacted with ammonia followed by treatment with trifluoroacetic acid to provide a compound of formula 56.

Scheme-9

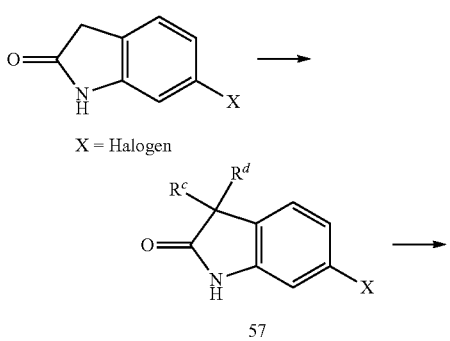

57

Rc and Rd together forms a carbocyclic ring

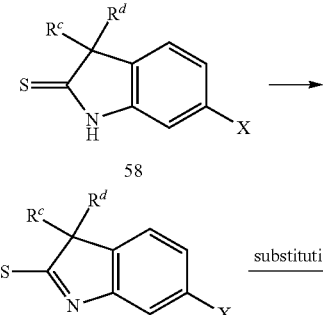

58

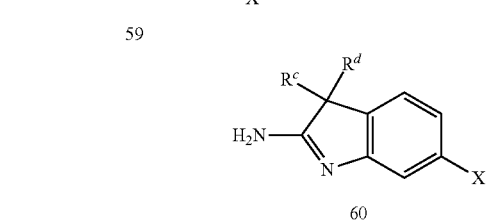

59 substitution

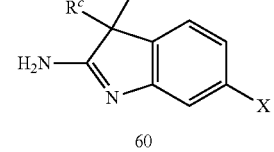

60

6-Halo-oxindole on treatment with a base, and methyl iodide or diiodopropane or appropriately substituted dihalide provides compound of formula-57. Compound of formula 57 when treated with Lawesson's reagent in hydrocarbon solvent such as but not limited to toluene at 100° C. for 3 h gives compound of formula-58, which is then treated with sodium hydride followed by methyl iodide in THF to yield compound of formula 59. Compound of formula 59 on treating with 7N ammonia in methanol at 100° C. for 16 h provides compound of formula-60.

Scheme-10

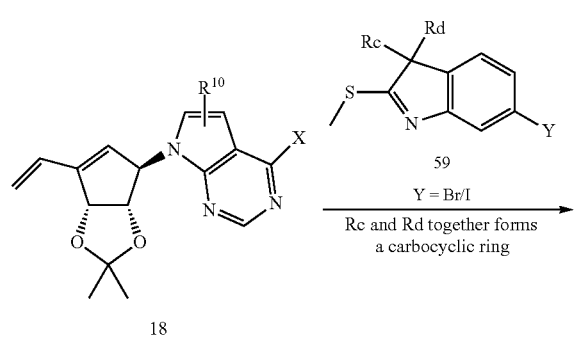

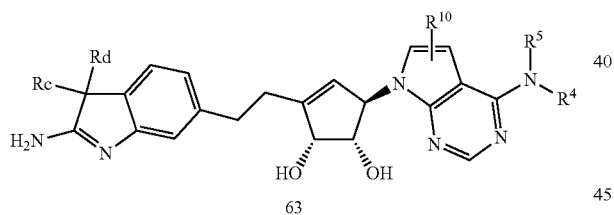

Hydroboration of compound of formula-18 with 9-BBN followed Suzuki coupling with compound of formula-59 in presence of Pd-118 or PdCl₂dppf in THF/H₂O at 50-70° C. for 5-16 h provide compound of formula-61, which is then treated with compound of formula-6a followed by TFA to give compound of formula 63.

Scheme-11

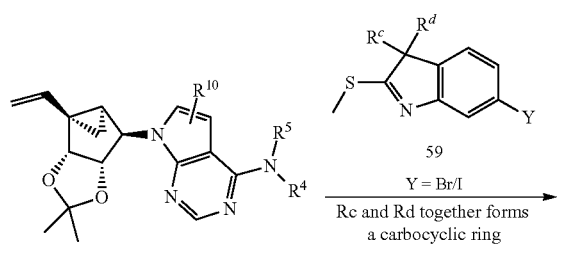

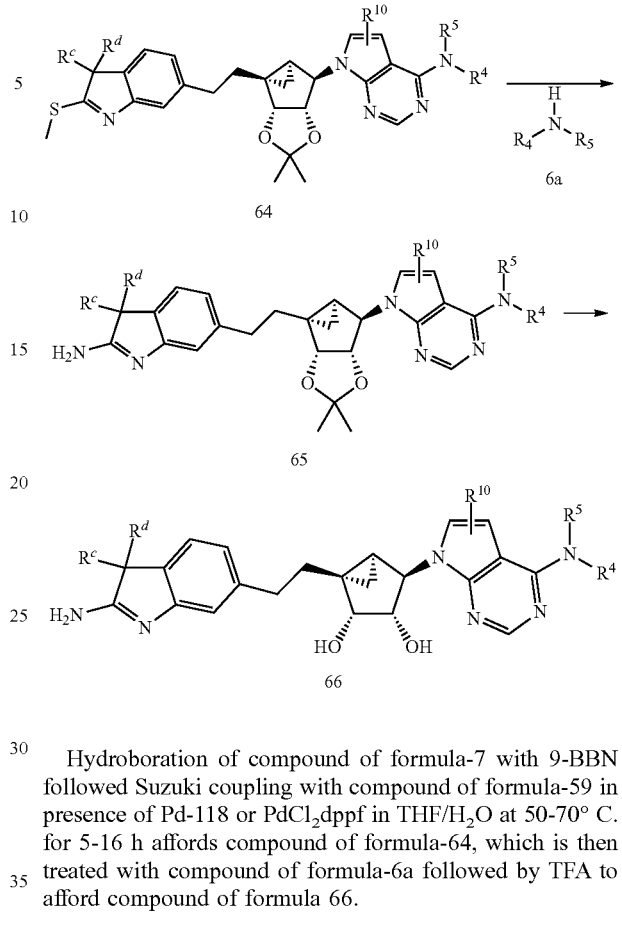

Hydroboration of compound of formula-7 with 9-BBN followed Suzuki coupling with compound of formula-59 in presence of Pd-118 or PdCl₂dppf in THF/H₂O at 50-70° C. for 5-16 h affords compound of formula-64, which is then treated with compound of formula-6a followed by TFA to afford compound of formula 66.

Scheme-12

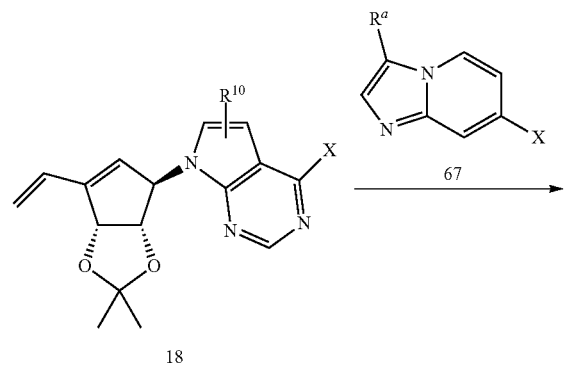

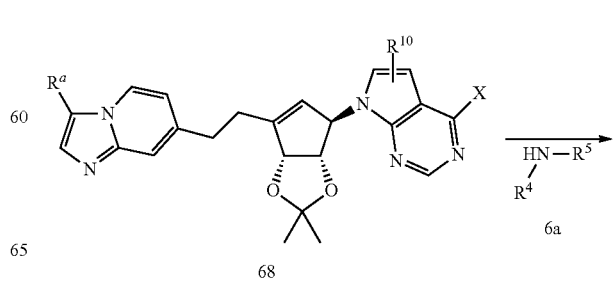

-continued

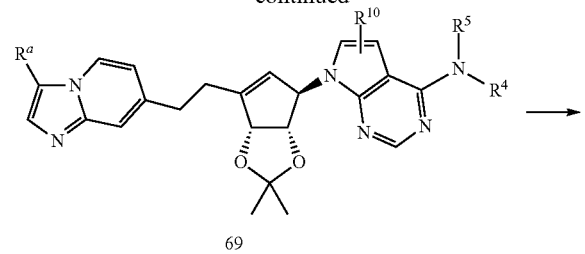

69

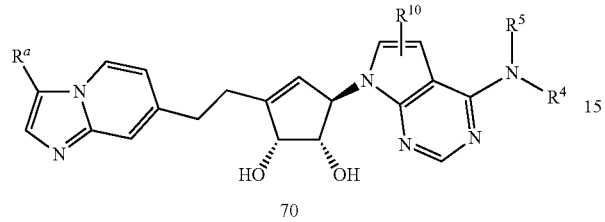

70

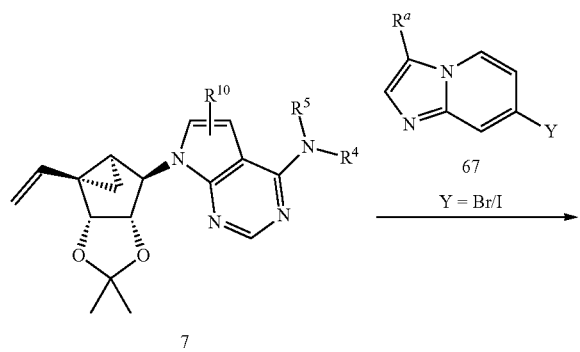

67  Y = Br/I

7

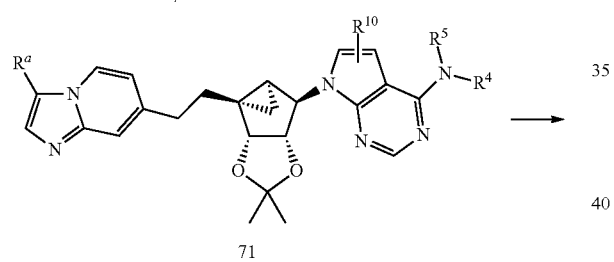

71

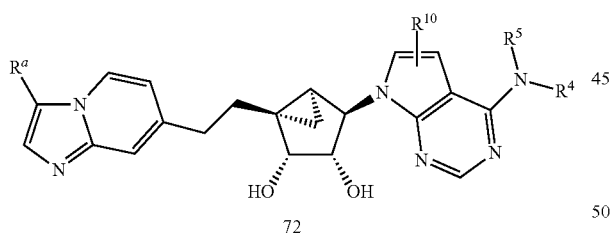

72

Scheme-13

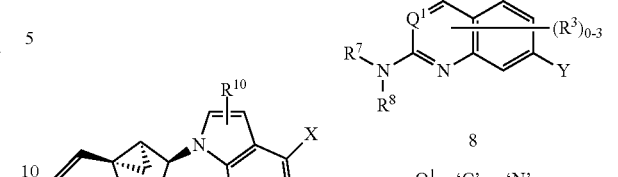

6   $Q^1 = $ 'C' or 'N'

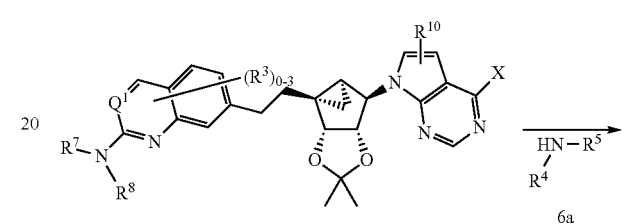

73

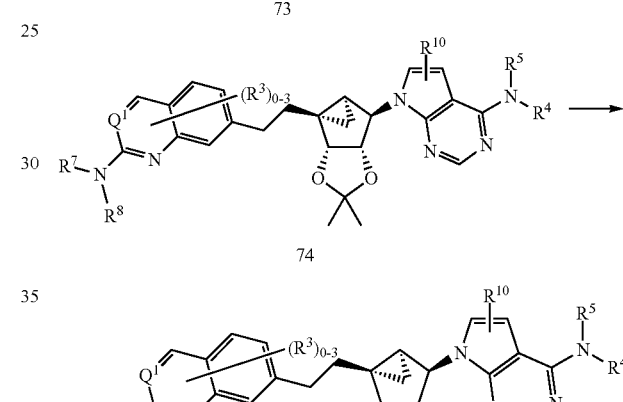

74

75

Hydroboration of compound of formula-6 with 9-BBN followed by Suzuki coupling of compound of formula 8 in presence of Pd-118 or PdCl$_2$dppf in THF/H$_2$O at 50-70° C. for 5-16 h affords compound of formula 73, which is when treated with compound of formula-6a followed by treatment with TFA affords compound of formula 75.

Hydroboration of compound of formula-18 with 9-BBN followed Suzuki coupling with compound of formula-67 in presence of Pd-118 in THF/H$_2$O at 50° C. for 5-16 h affords compound of formula-68, which is when treated with compound of formula-6a followed by TFA affords compound of formula-70. Hydroboration of compound of formula-7 with 9-BBN followed Suzuki coupling with compound of for-mula-67 in presence of Pd-118 or PdCl$_2$dppf in THF/H$_2$O at 50-70° C. for 5-16 h affords compound of formula-71, which is when treated with TFA affords compound of formula-72.

Scheme-14

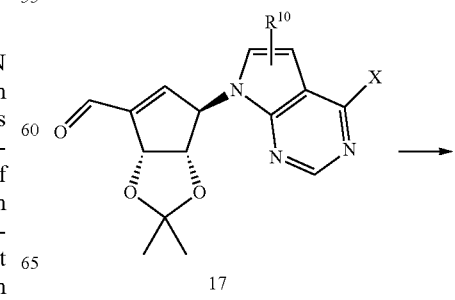

17

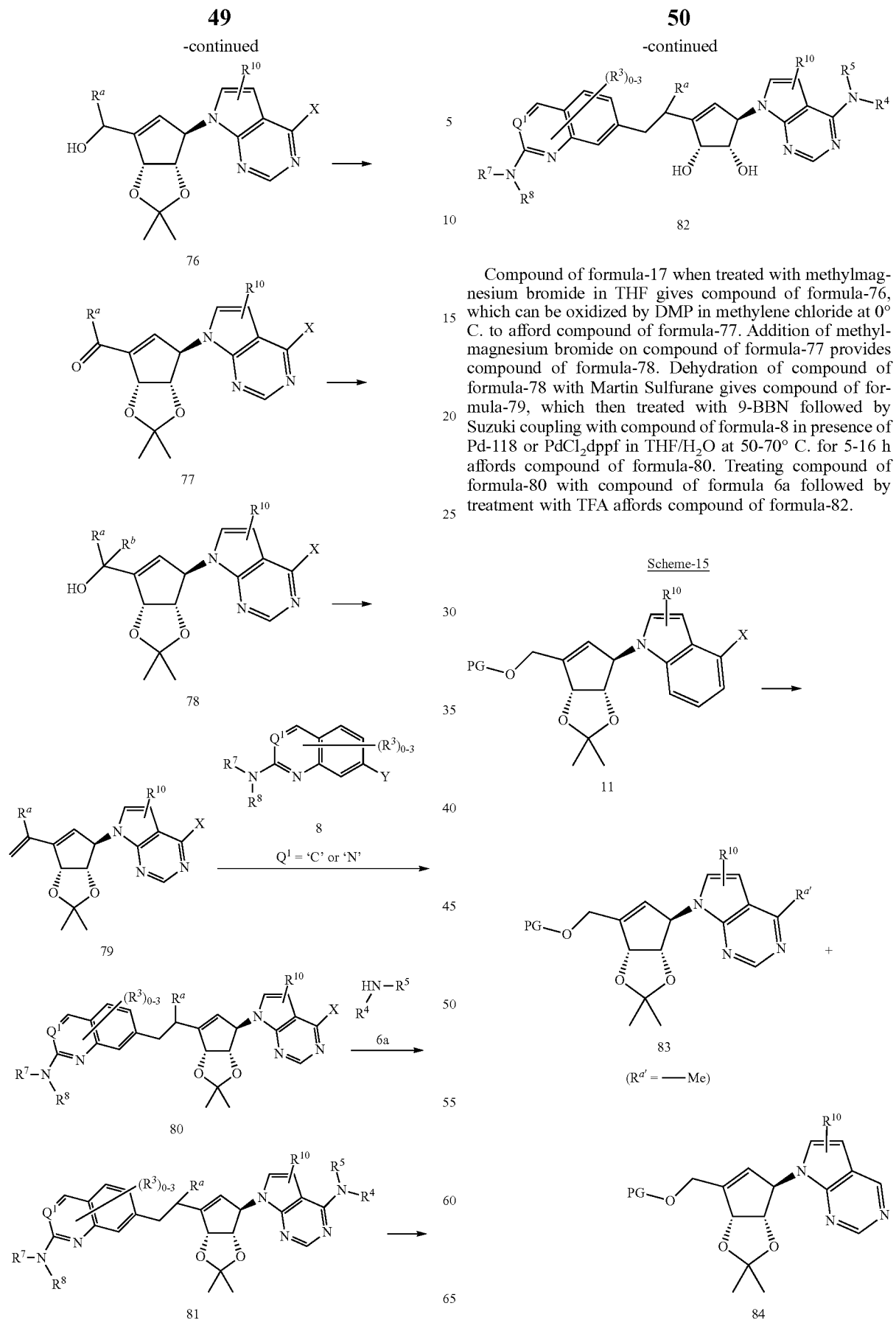

Compound of formula-17 when treated with methylmagnesium bromide in THF gives compound of formula-76, which can be oxidized by DMP in methylene chloride at 0° C. to afford compound of formula-77. Addition of methylmagnesium bromide on compound of formula-77 provides compound of formula-78. Dehydration of compound of formula-78 with Martin Sulfurane gives compound of formula-79, which then treated with 9-BBN followed by Suzuki coupling with compound of formula-8 in presence of Pd-118 or PdCl$_2$dppf in THF/H$_2$O at 50-70° C. for 5-16 h affords compound of formula-80. Treating compound of formula-80 with compound of formula 6a followed by treatment with TFA affords compound of formula-82.

Scheme-15

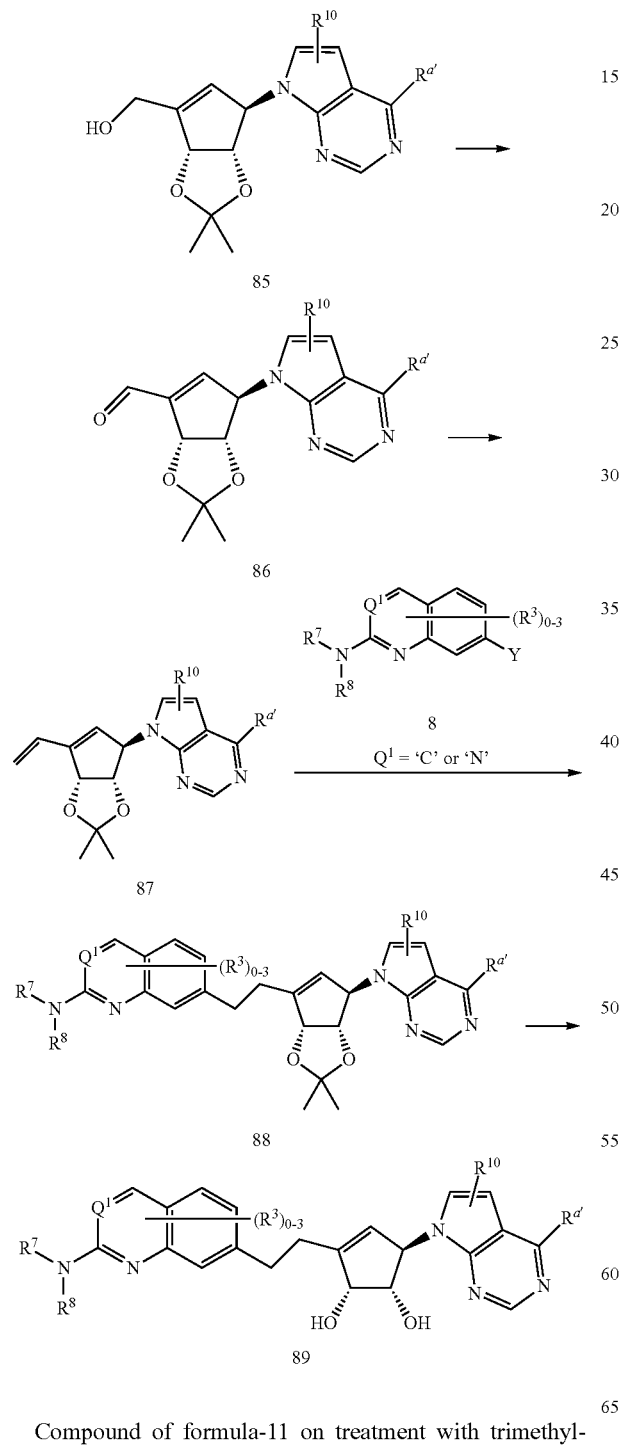

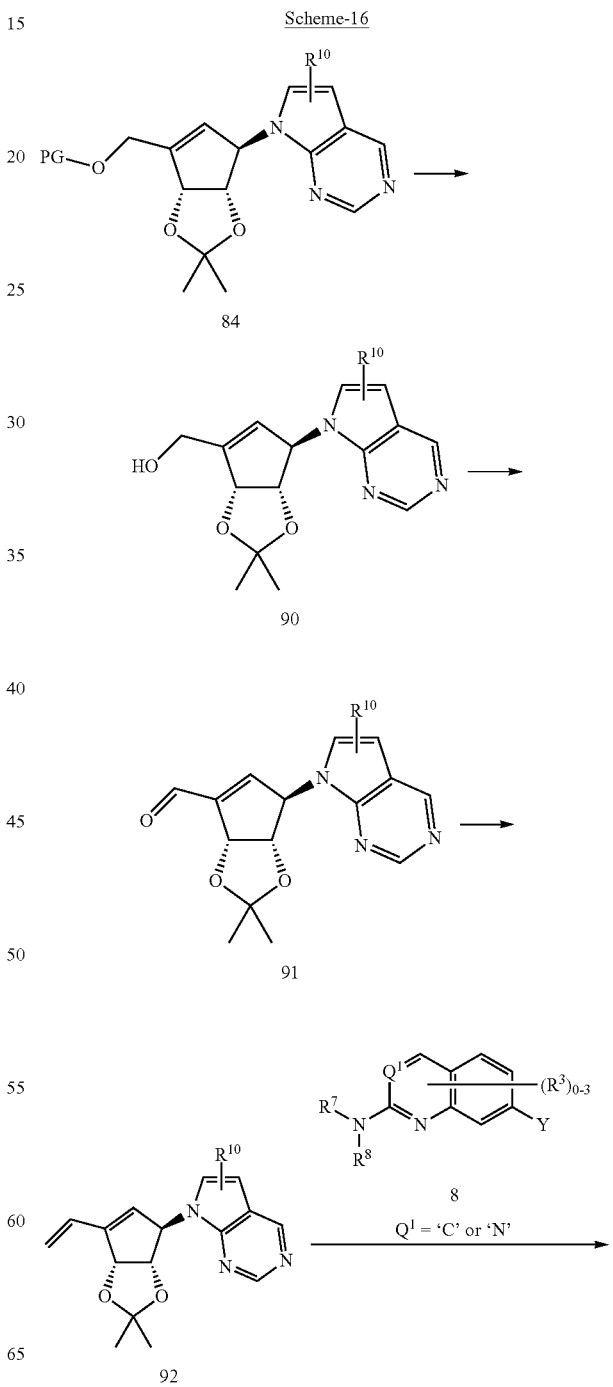

Compound of formula-11 on treatment with trimethylboroxine in presence of tripotassium phosphate, and Pd-118 or PdCl₂dppf gives mixture of compound of formula-83 and compound of formula-84. The PG of compound of formula-83 can be deprotected to afford compound of formula-85, which on oxidation with DMP gives compound of formula-86. Wittig reaction of compound of formula-86 provides compound of formula-87. Hydroboration of compound of formula-87 with 9-BBN followed by Suzuki coupling with compound of formula-8 in presence of Pd-118 or PdCl₂dppf in THF/H₂O at 50-70° C. for 5-16 h affords compound of formula-88, which when treated with TFA affords compound of formula-89.

Scheme-16

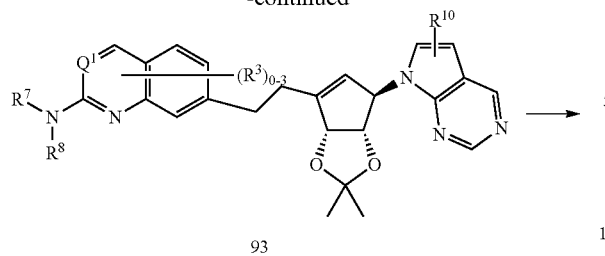

93

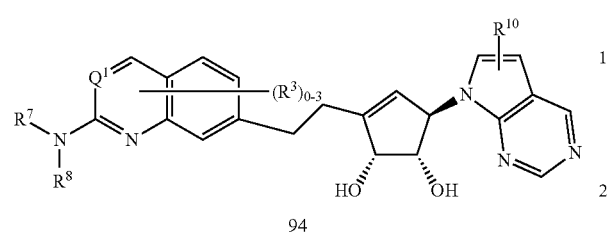

94

The protecting group of compound of formula-84 can be deprotected to afford compound of formula-90, which on oxidation with DMP gives compound of formula-91. Wittig reaction of compound of formula-91 provides compound of formula-92. Hydroboration of compound of formula-92 with 9-BBN followed by Suzuki coupling with compound of formula-8 in presence of Pd-118 or PdCl$_2$dppf in THF/H$_2$O at 50-70° C. for 5-16 h affords compound of formula-93, which is then treated with TFA to afford compound of formula 94.

Scheme-17

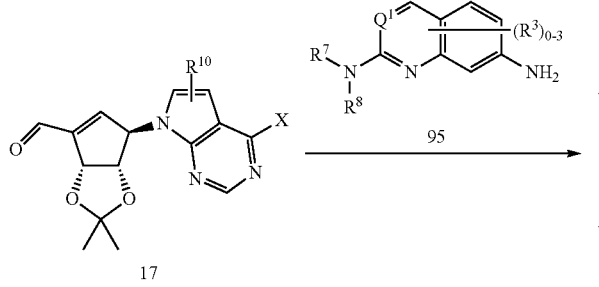

17

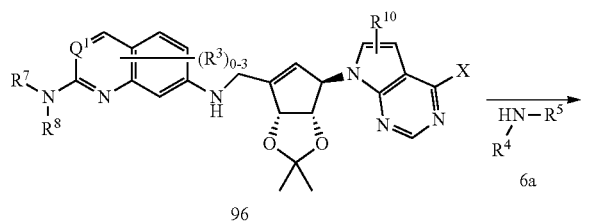

96

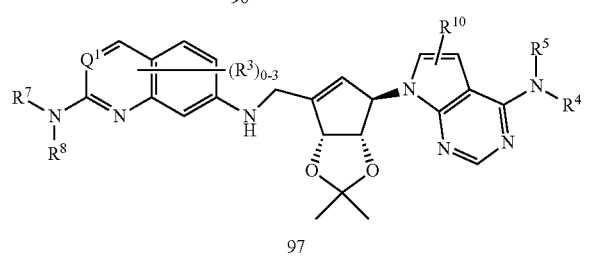

97

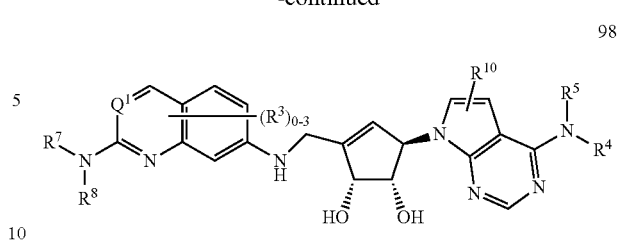

98

Reductive amination of compound of formula-17 with compound of formula-95 affords compound of formula-96, which is then treated with compound of formula-6a followed by treatment with TFA to afford compound of formula-98.

Scheme-18

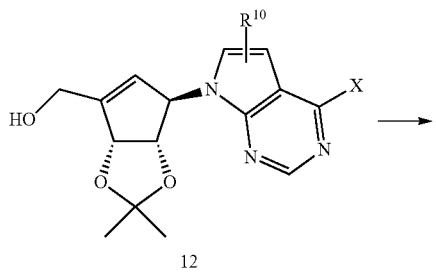

12

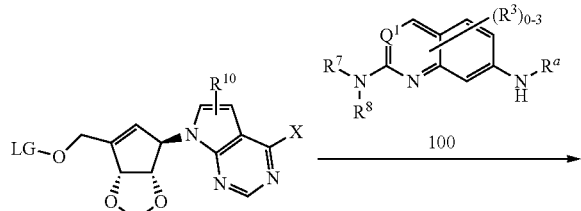

99

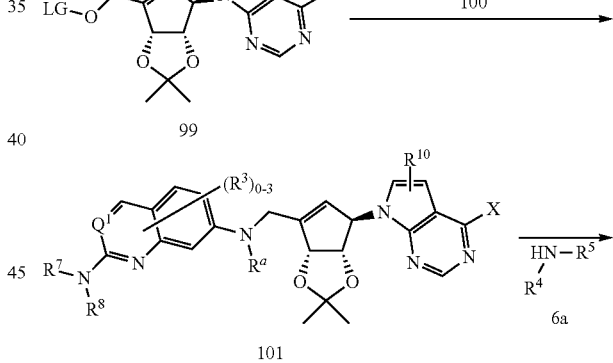

101

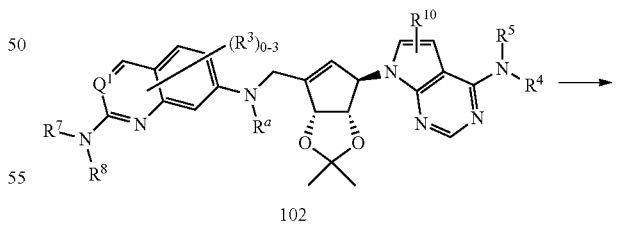

102

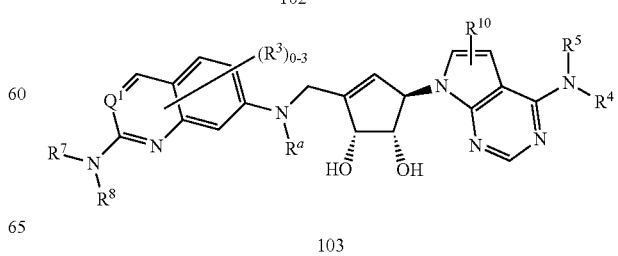

103

Compound of formula-12 is treated with TsCl/MsCl in presence of a base to give a compound of formula-99, which is then reacted with compound of formula-100 to yield compound of formula-101. Reaction of compound of formula-101 with compound of formula-6a followed by treatment with TFA affords compound of formula-103.

Scheme-19

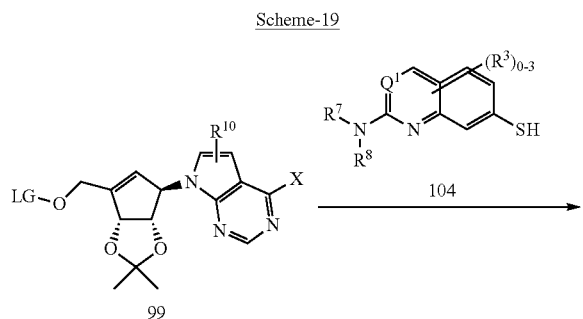

Scheme-20

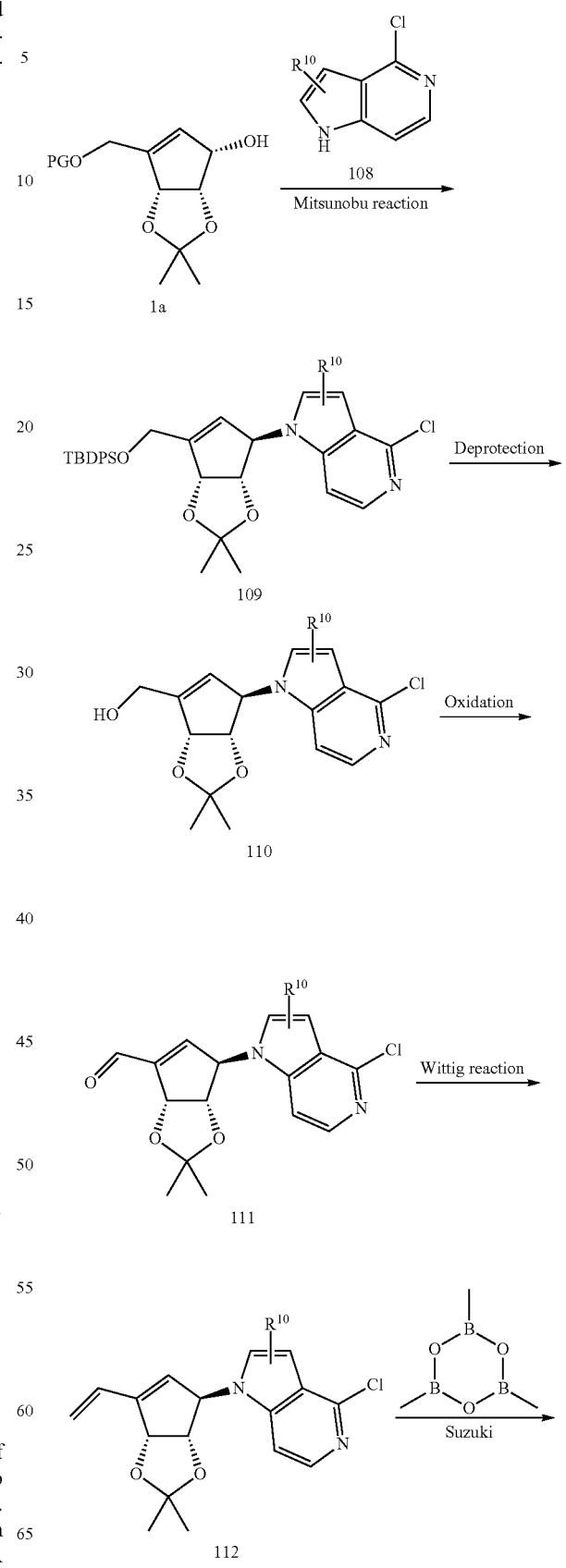

Compound of formula-99 is reacted with compound of formula-104 in presence of a base such as but not limited to cesium carbonate to afford a compound of formula-105. Substitution reaction of compound of formula-105 with compound of formula-6a followed by treatment with TFA affords compound of formula-107.

-continued

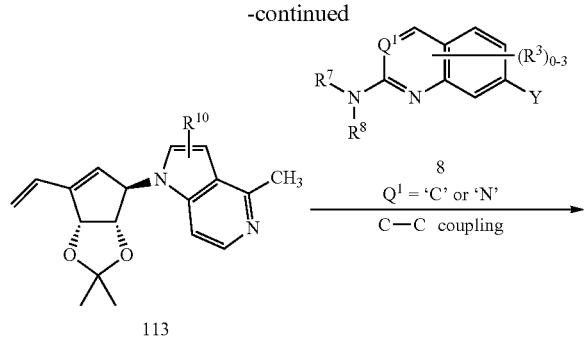

113

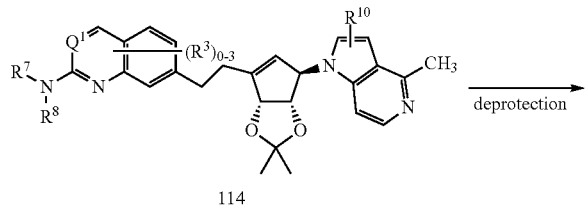

114

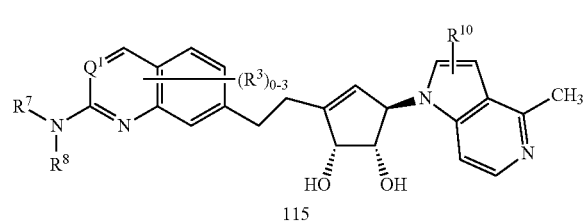

115

The compound of formula-109 can be synthesized by Mitsunobu reaction of compound of formula 1a with compound of formula 108 using various azo dicarboxylate reagents such as but not limited to DIAD in presence of phosphine such as but not limited to PPh₃. Compound of formula-109 can be further converted to compound of formula 110 upon treatment with fluoride ions such as but not limited to TBAF. Oxidation followed by Wittig reaction on compound of formula 110 gives compound of formula 112. The aromatic halogen of compound of formula 112 can be converted to alkyl groups such as a methyl group using Pd-118 or PdCl₂dppf with trimethylboroxine to afford compound of formula 113. Hydroboration of compound of formula-113 with 9-BBN followed by Suzuki coupling with compound of formula-8 in presence of Pd-118 or PdCl₂dppf in THF/H₂O at 50-70° C. for 5-16 h affords compound of formula-114, which when treated with TFA or HCl/MeOH affords compound of formula-115.

Scheme-21

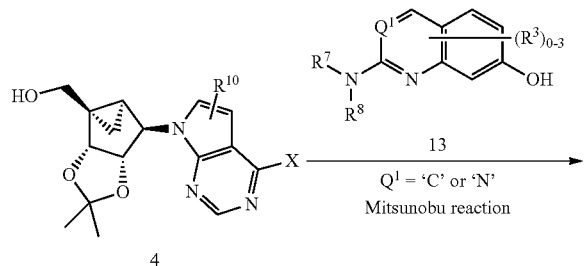

-continued

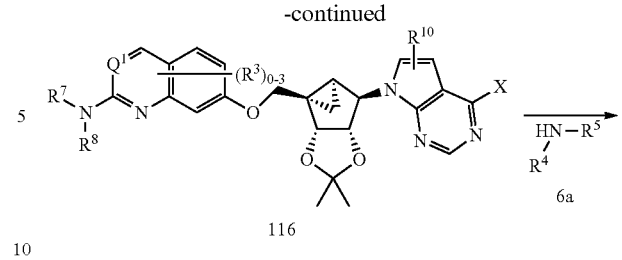

116

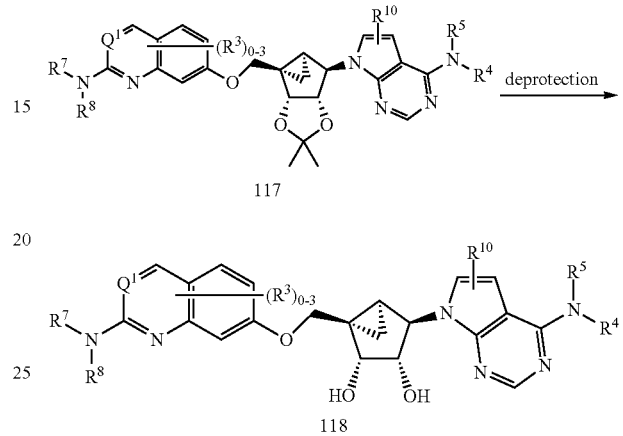

117

118

Mitsunobu reaction of compound of formula 4 (can be prepared from compound of formula 1 as described in scheme 1) with compound of formula 13 using various azo dicarboxylate reagents such as but not limited to DIAD in presence of phosphine such as but not limited to PPh₃ provides compound of formula 116. Compound of formula-116 on treating compound of formula 6a followed by treatment with trifluoroacetic acid affords compound of formula-118.

Scheme-22

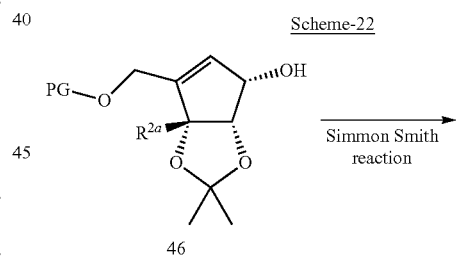

46

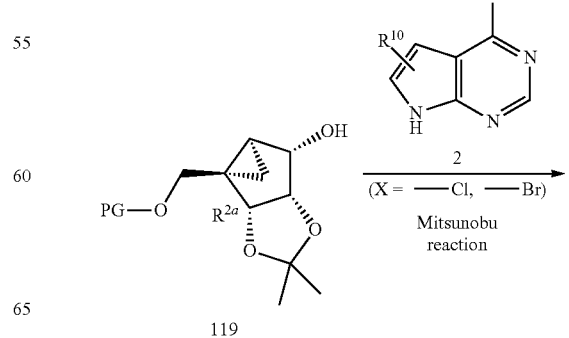

119

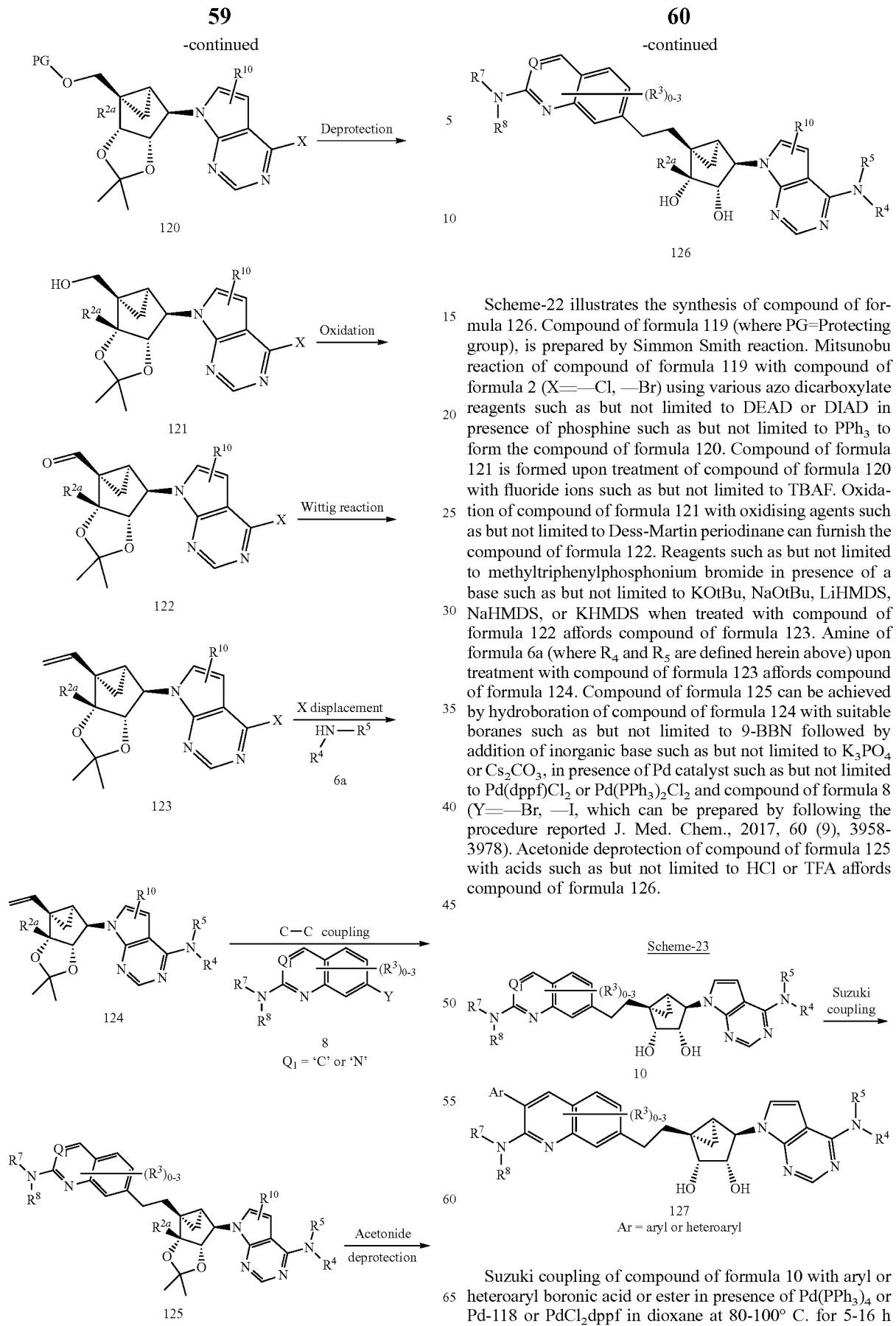

Scheme-22 illustrates the synthesis of compound of formula 126. Compound of formula 119 (where PG=Protecting group), is prepared by Simmon Smith reaction. Mitsunobu reaction of compound of formula 119 with compound of formula 2 (X=—Cl, —Br) using various azo dicarboxylate reagents such as but not limited to DEAD or DIAD in presence of phosphine such as but not limited to $PPh_3$ to form the compound of formula 120. Compound of formula 121 is formed upon treatment of compound of formula 120 with fluoride ions such as but not limited to TBAF. Oxidation of compound of formula 121 with oxidising agents such as but not limited to Dess-Martin periodinane can furnish the compound of formula 122. Reagents such as but not limited to methyltriphenylphosphonium bromide in presence of a base such as but not limited to KOtBu, NaOtBu, LiHMDS, NaHMDS, or KHMDS when treated with compound of formula 122 affords compound of formula 123. Amine of formula 6a (where $R_4$ and $R_5$ are defined herein above) upon treatment with compound of formula 123 affords compound of formula 124. Compound of formula 125 can be achieved by hydroboration of compound of formula 124 with suitable boranes such as but not limited to 9-BBN followed by addition of inorganic base such as but not limited to $K_3PO_4$ or $Cs_2CO_3$, in presence of Pd catalyst such as but not limited to $Pd(dppf)Cl_2$ or $Pd(PPh_3)_2Cl_2$ and compound of formula 8 (Y=—Br, —I, which can be prepared by following the procedure reported J. Med. Chem., 2017, 60 (9), 3958-3978). Acetonide deprotection of compound of formula 125 with acids such as but not limited to HCl or TFA affords compound of formula 126.

Suzuki coupling of compound of formula 10 with aryl or heteroaryl boronic acid or ester in presence of $Pd(PPh_3)_4$ or Pd-118 or $PdCl_2dppf$ in dioxane at 80-100° C. for 5-16 h affords compound of formula-127.

Scheme-24

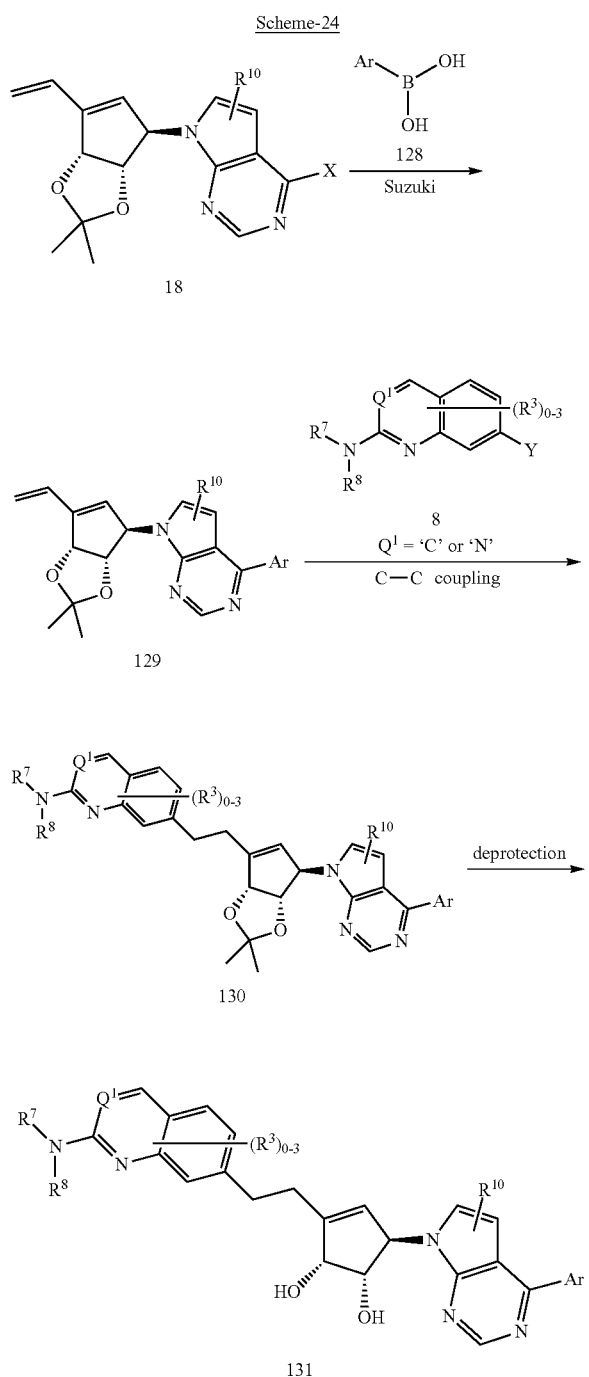

Scheme-25

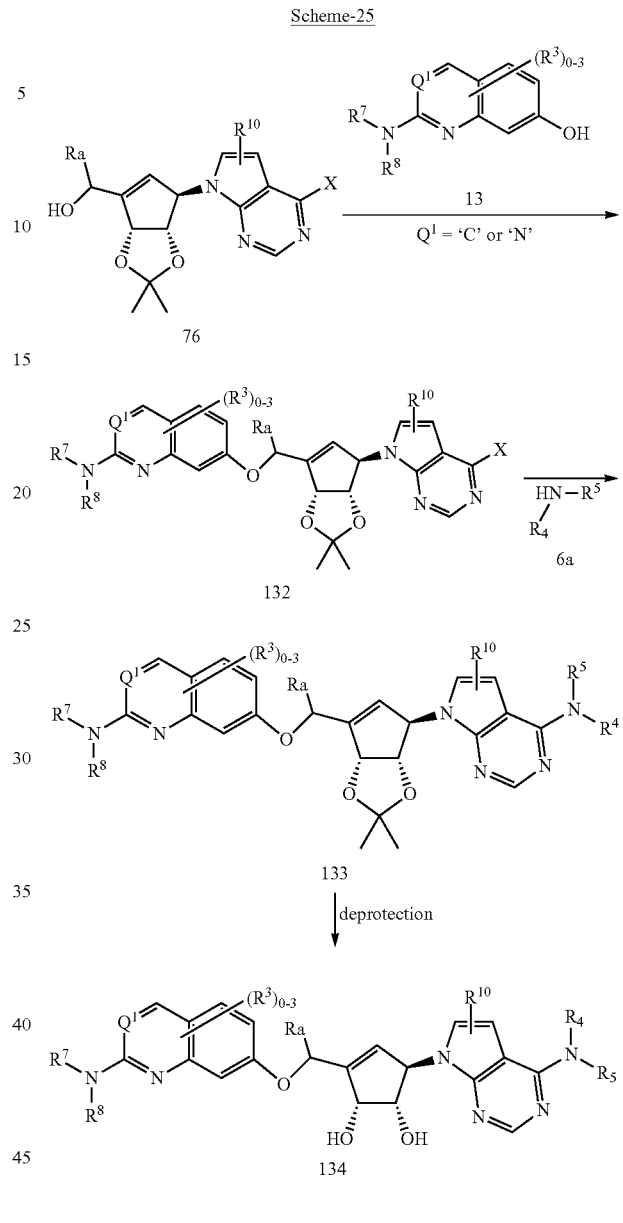

Compound of formula-76 when condensed with compound of formula-13 using Mitsunobu reaction affords compound of formula-132, which can be reacted with compound of formula-6a followed by treatment with trifluroacetic acid to provide a compound of formula-134.

Compound of formula-18 when treated with compound of formula-128 using Suzuki coupling affords compound of formula-129. Compound of formula 130 can be achieved by hydroboration of compound of formula 129 with suitable boranes such as but not limited to 9-BBN followed by addition of inorganic base such as but not limited to $K_3PO_4$ or $Cs_2CO_3$, in presence of Pd catalyst such as but not limited to $Pd(dppf)Cl_2$ or $Pd(PPh_3)_2Cl_2$ and compound of formula 8 (Y=—Br, —I, which can be prepared by following the procedure reported J. Med. Chem., 2017, 60 (9), 3958-3978). Acetonide deprotection of compound of formula 130 with acids such as but not limited to HCl or TFA affords compound of formula 131.

Scheme-26

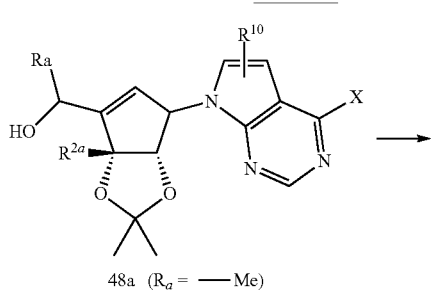

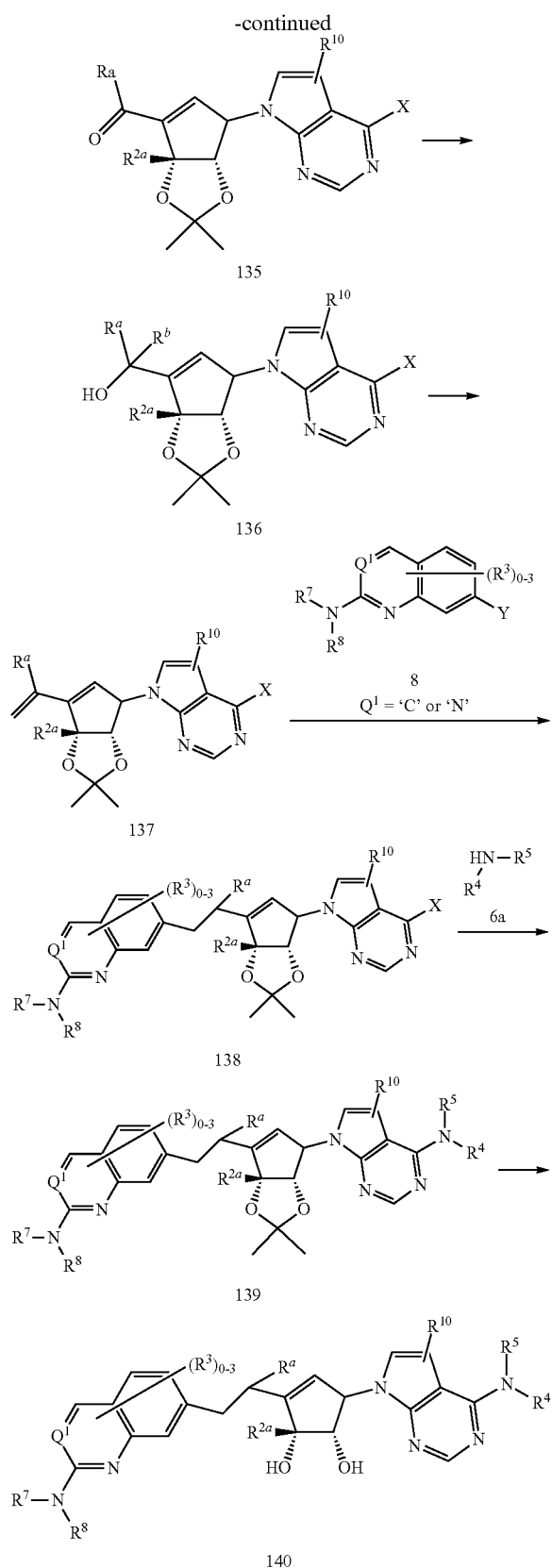

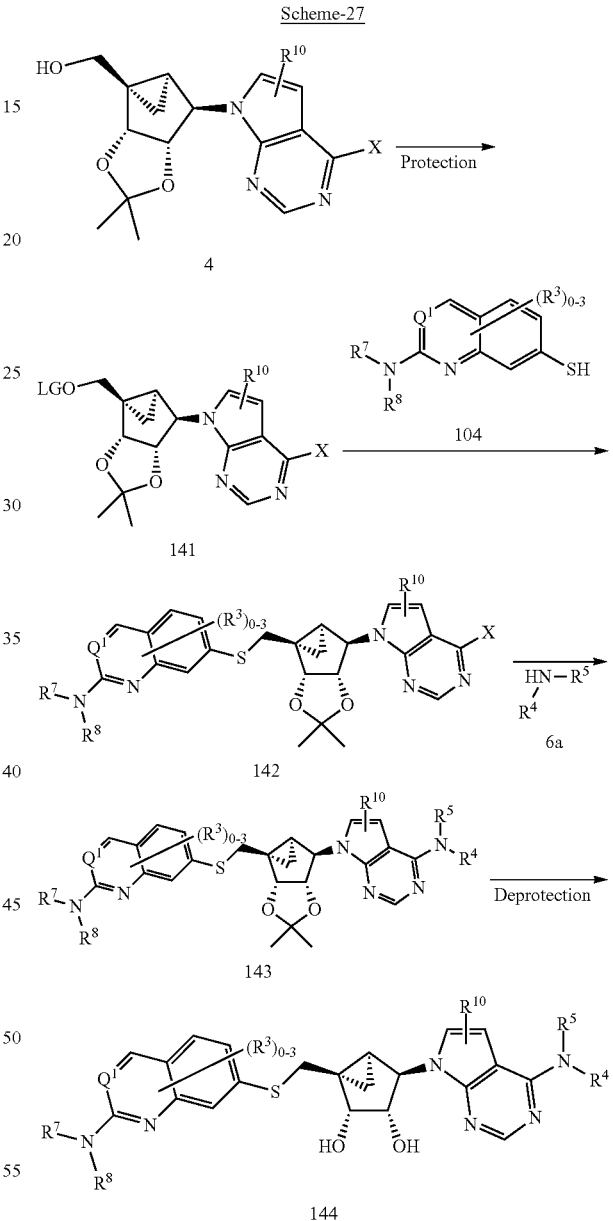

gives compound of formula-136. Dehydration of compound of formula-136 with Martin Sulfurane gives compound of formula-137, which then treated with 9-BBN followed by Suzuki coupling with compound of formula-8 in presence of Pd-118 or PdCl$_2$dppf in THF/H$_2$O at 50-70° C. for 5-16 h affords compound of formula-138. Treating compound of formula-138 with compound of formula 6a followed by treatment with TFA affords compound of formula-140.

Scheme-27

Compound of formula-48a when treated DMP in methylene chloride at 0° C. to afford compound of formula-135, which when react with methylmagnesium bromide in THF Compound of formula-4 is treated with TsCl/MsCl in presence of a base to give a compound of formula 141. Compound of formula-141 is reacted with compound of formula-104 in presence of a base such as but not limited to cesium carbonate to afford a compound of formula-142. Substitution reaction of compound of formula-142 with compound of formula-6a followed by treatment with TFA affords compound of formula-144.

Abbreviations

The following abbreviations may be used herein:
AcOH=Acetic acid
Aq.=aqueous
ca=about or approximately
$NH_4Cl$=Ammonium chloride
9-BBN=9-Borabicyclononane
BINAP=2,2'-Bis(diphenylphosphino)-1,1'-binaphthyl
Boc=tert-Butoxycarbonyl
t-Bu or tBu=tert-Butyl
$Cs_2CO_3$=Cesium Carbonate
$CHCl_3$=Chloroform
$CDCl_3$=Deuterated chloroform
DAST=Diethylaminosulphur trifluoride
dba=Dibenzylideneacetone
$CH_2Cl_2$ or DCM=Dichloromethane
DMP=Dess Martin Periodinane
DEAD=Diethyl azodicarboxylate
DIAD=Diisopropyl azodicarboxylate
DIPEA=Diisopropylethylamine
DMAP=4-Dimethylaminopyridine
DMF=N,N-Dimethylformamide
DMSO=Dimethylsulphoxide
DMSO-$d_6$=Deuterated dimethylsulphoxide
Et=ethyl
EtOH=Ethanol
EtOAc=Ethyl acetate
g=gram
$H_2O_2$=Hydrogen peroxide
$H_2SO_4$=Sulphuric acid
$K_2CO_3$=Potassium carbonate
KOH=Potassium hydroxide
$KO^tBu$=Potassium tert-butoxide
$K_3PO_4$=Potassium phosphate
KHMDS=Potassium bis(trimethylsilyl)amide
LDA=Lithium diisopropylamide
LHMDS=Lithium bis(trimethylsilyl)amide
LCMS=Liquid chromatography mass spectrometry
m-CPBA=meta-chloroperoxybenzoic acid
mg=milligram
Me=Methyl
MeOH=Methanol
MeOD=Deuterated methanol
MS=Molecular sieves
MsCl=Methanesulphonyl chloride
$MgSO_4$=Magnesium sulphate
NaH=Sodium hydride
NaOtBu=Sodium tert-butoxide
$NaHCO_3$=Sodium bicarbonate
$Na_2SO_4$=Sodium sulphate
$Na_2S_2O_3$=Sodium thiosulphate
$Na_2SO_3$=Sodium sulphite
NaHMDS=Sodium bis(trimethylsilyl)amide
NMP=N-Methyl-2-pyrrolidone
NBS=N-Bromosuccinimide
NCS=N-Chlorosuccinimide
NIS=N-Iodosuccinimide
NMO=N-Methylmorpholine-N-oxide
NMR=Nuclear magnetic resonance
Ph=phenyl
PDC=Pyridinium dichromate
$Pd(OAc)_2$=Palladium acetate
Pd/C=Palladium on carbon
Pd-118=[1,1'-Bis(di-tert-butylphosphino)ferrocene]dichloropalladium(II)
$Pd(PPh_3)_4$=Tetrakis(triphenylphosphine)palladium(0)
$POCl_3$=Phosphorous oxychloride
$PdCl_2$(dppf)=[1,1'-Bis(diphenylphosphino)ferrocene]dichloropalladium(II)
$Pd(PPh_3)_2Cl_2$=Bis(triphenylphosphine)palladium(II) dichloride
PCC=Pyridinium chlorochromate
PMB=p-Methoxybenzyl
PTSA=p-Toluenesulphonic acid
Rt=Retention time
rt=room temperature
Sat.=saturated
SFC=Supercritical fluid chromatography
TLC=Thin layer chromatography
TBAF=Tetrabutylammonium fluoride
TsCl=p-Toluenesulphonyl chloride
TBDMS=tert-Butyldimethylsilyl
TBDPS=tert-Butyldiphenylsilyl
$Et_3N$ or $NEt_3$ or TEA=Triethylamine
TFA=Trifluoroacetic acid
THF=Tetrahydrofuran
Ts=p-Toluenesulphonyl
p-TsOH=p-Toluenesulphonic acid

INTERMEDIATES

7-Bromoquinolin-2-amine

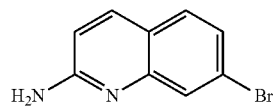 [SMILES: Nc1ccc2ccc(Br)cc2n1]

The title compound was prepared by following an analogous reaction protocol as described in Cinelli, Maris A et al, Journal of Medicinal Chemistry, 2017, vol. 60, #9, p. 3958-3978.

7-Bromo-N-(4-methoxybenzyl)quinolin-2-amine

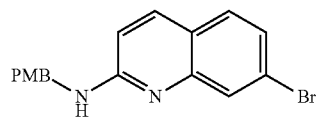

The title compound was prepared by following an analogous reaction protocol as described in Arnould, Jean-Claude et al, WO 2007/141473 A1.

7-Bromo-N-methylquinolin-2-amine

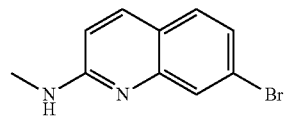

The title compound was prepared by following same reaction protocol as described in Arnould, Jean-Claude et al, WO 2007/141473 A1.

7-Bromo-N-isopropylquinolin-2-amine

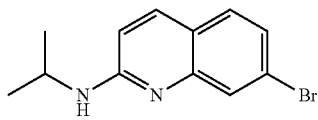

The title compound was prepared by following an analogous reaction protocol as described in Arnould, Jean-Claude et al, WO 2007/141473 A1.

7-Bromo-N-cyclobutylquinolin-2-amine

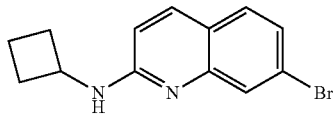 [SMILES: Brc1ccc2ccc(NC3CCC3)nc2c1]

The title compound was prepared by following an analogous reaction protocol as described in Arnould, Jean-Claude et al, WO 2007/141473 A1.

7-Bromo-N-(cyclopropylmethyl)quinolin-2-amine

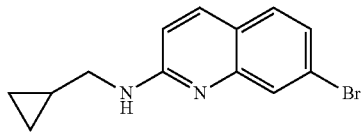 [SMILES: Brc1ccc2ccc(NCC3CC3)nc2c1]

The title compound was prepared by following analogous reaction protocol as described in Arnould, Jean-Claude et al, WO 2007/141473 A1.

7-Bromo-2-chloro-8-fluoroquinoline

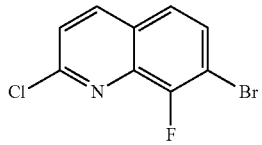 [SMILES: Fc1c(Br)ccc2ccc(Cl)nc12]

The title compound was prepared by following same reaction protocol as described in Aciro, Caroline et al, WO2013/185103 A1.

7-Bromo-2-chloro-3-isopropylquinoline

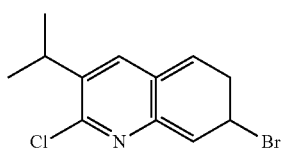

The title compound was prepared by following same reaction protocol as described in Vialard, Jorge Eduardo et al, WO2008/107478 A1; LCMS m/z=284.1, 286.1 (M+, M+2; 100%).

2-Amino-4-bromo-6-fluorobenzaldehyde

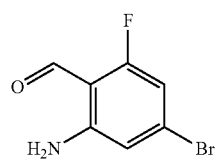 [SMILES: Nc1cc(Br)cc(F)c1C=O]

To a stirred solution of 4-bromo-2-fluoro-6-nitrobenzaldehyde (prepared by following same reaction protocol as described in Li, Liansheng et al, WO 2015/054572 A1; 4.15 g, 16.73 mmol) in ethanol (20 ml) & acetic acid (20 ml) was added iron powder (2.80 g, 50.2 mmol) at 0° C. and stirred the reaction mixture for 1 h. The reaction mixture was diluted with ethyl acetate (70 ml) and netralized with aq. sat. NaHCO$_3$ (100 ml). The resulting emulsion was filtered through celite. Layers were separated, organic layer was washed with brine (100 ml) and dried over anhydrous Na$_2$SO$_4$. The organic layer was filtered and concentrated in vacuo to afford (3.36 g, 92%) as a light green solid which was used for next step without purification. $^1$H NMR (400 MHz, DMSO-d$_6$) δ 10.10 (s, 1H), 7.78-7.54 (m, 2H), 6.84 (t, J=1.5 Hz, 1H), 6.64 (dd, J=11.1, 1.8 Hz, 1H).

1-Chloro-5-iodo-2-methyl-3-nitrobenzene

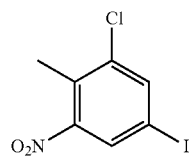

A solution of iodine (10.43 g, 41.1 mmol), potassium iodate (1.247 g, 5.83 mmol) in conc. H$_2$SO$_4$ (51.4 g, 525 mmol) was added to a solution of 1-chloro-2-methyl-3-nitrobenzene (5 g, 29.1 mmol) in conc. H$_2$SO$_4$ (51.4 g, 525 mmol) at 25° C. The resulting mixture was stirred at 25° C. for 6 h. The reaction mixture was added slowly onto crushed ice and extracted the product with ethyl acetate (75 ml). The organic layer was washed with aq.sat.NaHCO$_3$ (75 ml), aq.sat.Na$_2$S$_2$O$_3$ (75 ml) and brine (75 ml) successively. Dried the organic layer over anhydrous Na$_2$SO$_4$, filtered and concentrated in vacuo to give 9 g of crude compound. This residue was purified by combiflash (R$_f$200, Teledyne/Isco) instrument onto a Redisep® R$_f$ column with elution of petroleum ether to afford the title compound (8.5 g, 98%) as a pale yellow oil. $^1$H NMR (400 MHz, Chloroform-d) δ 8.02 (d, J=1.4 Hz, 1H), 7.96 (d, J=1.7 Hz, 1H), 2.50 (s, 3H).

2-(Bromomethyl)-1-chloro-5-iodo-3-nitrobenzene

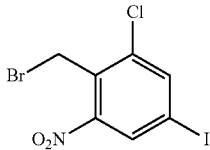 [SMILES: O=[N+]([O-])c1cc(I)cc(Cl)c1CBr]

To a stirred solution of 1-chloro-5-iodo-2-methyl-3-nitrobenzene (27.5 g, 92 mmol) in CCl$_4$ (280 ml) was added NBS (19.74 g, 111 mmol) and benzoyl peroxide (2.99 g, 9.24 mmol) at 25° C. The resulting mixture was stirred at 80° C. for 15 h. The solvent was evaporated in vacuo and this residue was purified by combiflash (R$_f$200, Teledyne/Isco) instrument onto a Redisep® R$_f$ column with gradient elution of (0 to 1%) of ethyl acetate in petroleum ether to afford the title compound (12g, 34.5%) as an off-white solid. $^1$H NMR (400 MHz, DMSO-d$_6$) δ 8.37-8.33 (m, 2H), 4.72 (s, 2H).

2-Chloro-4-iodo-6-nitrobenzaldehyde

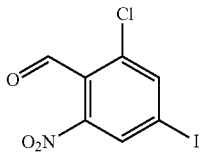

To a stirred solution of 2-(bromomethyl)-1-chloro-5-iodo-3-nitrobenzene (12 g, 31.9 mmol) in acetonitrile (150 ml) was added 4-methylmorpholine-N-oxide (9.19 g, 78 mmol) and molecular sieves 4 A° (30 g) at 25° C. The resulting mixture was stirred at 25° C. for 1.5 h. Water (75 ml) was added, pH was adjusted to 6 by adding 1N HCl. Extracted the product with ethyl acetate (75 ml). Layers were separated, organic layer was washed with brine (20 ml) and dried over anhydrous Na$_2$SO$_4$. The organic layer was filtered and concentrated in vacuo to give 16.5 g of crude compound. This residue was purified by combiflash (R$_f$200, Teledyne/Isco) instrument onto a Redisep® R$_f$ column with gradient elution (0 to 4%) of ethyl acetate in petroleum ether to afford the title compound (7 g, 70.5%) as an off-white solid. $^1$H NMR (400 MHz, DMSO-d$_6$) δ 10.22 (s, 1H), 8.46 (s, 2H).

2-Amino-6-chloro-4-iodobenzaldehyde

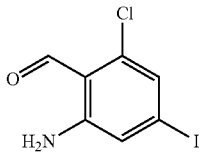 [SMILES: Nc1cc(I)cc(Cl)c1C=O]

The title compound was prepared by following an analogous reaction protocol as described in the preparation of 2-amino-4-bromo-6-fluorobenzaldehyde. $^1$H NMR (400 MHz, DMSO-d$_6$) δ 10.26 (s, 1H), 7.80-7.55 (m, 2H), 7.23 (d, J=1.4 Hz, 1H), 6.99 (d, J=1.5 Hz, 1H).

1-Fluoro-2-iodo-5-methyl-4-nitrobenzene

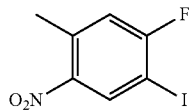

To a stirred solution of 2-fluoro-4-methyl-5-nitroaniline (2.0 g, 11.75 mmol) in conc.HCl (6.15 ml, 73.8 mmol) was added a solution of sodium nitrite (0.884 g, 12.81 mmol) in water (4 ml) in a dropwise manner at 0° C. After stirring for 15 mins, the mixture was filtered through a cotton pad and slowly poured into a stirred solution of potassium iodide (6.83 g, 41.1 mmol) in water (25 ml) at 0° C. The resulting mixture was stirred at 25° C. for 16 h. The reaction mixture was diluted with ethyl acetate (20 ml) and washed with 10% aq.NaOH (50 ml), aq.sat.NaHCO$_3$ (50 ml) successively. Layers were separated, organic layer was washed with brine (50 ml) and was dried over anhydrous Na$_2$SO$_4$. The organic layer was filtered and concentrated in vacuo to give 3.1 g of crude compound. This residue was purified by combiflash (R$_f$200, Teledyne/Isco) instrument onto a Redisep® R$_f$ column with petroleum ether as a eluent to afford the title compound (1.7 g, 51.5%) of the title compound as an off-white solid. $^1$H NMR (400 MHz, Chloroform-d) δ 8.45 (d, J=5.7 Hz, 1H), 7.06 (d, 1H), 2.62 (d, J=0.7 Hz, 3H); GCMS m/z=281.03 (M+, 50%).

1-(Bromomethyl)-5-fluoro-4-iodo-2-nitrobenzene

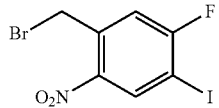

The title compound was prepared by following an analogous reaction protocol as described in the preparation of 2-(bromomethyl)-1-chloro-5-iodo-3-nitrobenzene. $^1$H NMR (400 MHz, Chloroform-d) δ 8.53 (d, J=5.6 Hz, 1H), 7.31 (d, J=7.8 Hz, 1H), 4.80 (s, 2H).

5-Fluoro-4-iodo-2-nitrobenzaldehyde

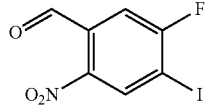

The title compound was prepared by following an analogous reaction protocol as described in the preparation of 2-chloro-4-iodo-6-nitrobenzaldehyde. $^1$H NMR (400 MHz, Chloroform-d) δ 10.42 (d, J=2.3 Hz, 1H), 8.62 (d, J=5.1 Hz, 1H), 7.60 (d, J=7.2 Hz, 1H).

2-Amino-5-fluoro-4-iodobenzaldehyde

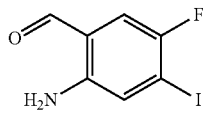

The title compound was prepared by following an analogous reaction protocol as described in the preparation of 2-amino-4-bromo-6-fluorobenzaldehyde. $^1$H NMR (400 MHz, Chloroform-d) δ 9.78 (d, J=0.6 Hz, 1H), 7.17-7.13 (m, 2H), 5.98 (s, 2H).

7-Bromo-3-cyclopropylquinoline

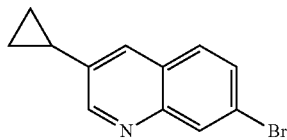 [SMILES: Brc1ccc2cc(C3CC3)cnc2c1]

To a stirred mixture of 2-amino-4-bromobenzaldehyde (2 g, 10.00 mmol) and 2-cyclopropylacetaldehyde (0.841 g, 10.00 mmol) in absolute ethanol (12 ml) was added a solution of KOH (0.191 g, 3.40 mmol) in ethanol (12 ml) in a dropwise manner under N$_2$ atmosphere. The resulting mixture was stirred at 95° C. for 5 h. The volatiles were evaporated in vacuo and the residue was dissolved in dichloromethane (60 ml) and washed with water (40 ml). Layers were separated, organic layer was washed with brine (50 ml) and dried over anhydrous Na$_2$SO$_4$. The organic layer was filtered and concentrated in vacuo to give 2.5 g of crude compound. This residue was purified by combiflash (R$_f$200, Teledyne/Isco) instrument onto a Redisep® R$_f$ column with gradient elution (0 to 6%) of ethyl acetate in petroleum ether to afford 7-bromo-3-cyclopropylquinoline (1 g, 40.3%) as a pale yellow solid. $^1$H NMR (400 MHz, DMSO-d$_6$) δ 8.80 (d, J=2.3 Hz, 1H), 8.17 (d, J=2.1 Hz, 1H), 8.00 (d, J=2.4 Hz, 1H), 7.89-7.80 (m, 1H), 7.70 (dd, J=8.8, 2.1 Hz, 1H), 2.15 (tt, J=8.1, 5.1 Hz, 1H), 1.14-1.03 (m, 2H), 0.95-0.81 (m, 2H); LCMS m/z=247.83, 249.83 (M+, M+2, 100%).

7-Bromo-3-(1,1-difluoroethyl)quinoline

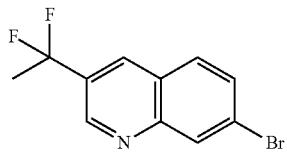

A mixture of 1-(7-bromoquinolin-3-yl)ethan-1-one (synthesized by following same reaction protocol as described in Alam, Muzaffar et al, US20120230951 A1; 2.4 g, 9.60 mmol) in diethylaminosulfur trifluoride (2.5 ml, 18.92 mmol) was stirred at 70° C. for 16 h. The resulting mixture was slowly poured into aq. sat. sodium bicarbonate (50 ml) and extracted with dichloromethane (50 ml). Layers were separated, organic layer was washed with brine (20 ml) and dried over anhydrous Na$_2$SO$_4$. The organic layer was filtered and concentrated in vacuo to give 3.2 g of crude compound. This residue was purified by combiflash (R$_f$200, Teledyne/Isco) instrument onto a Redisep® R$_f$ column with gradient elution (0 to 30%) of ethyl acetate in petroleum ether to afford the title compound (1.7 g, 65.1%) as a pale yellow solid. $^1$H NMR (400 MHz, DMSO-d$_6$) δ 9.13 (d, J=2.4 Hz, 1H), 8.71 (s, 1H), 8.34 (d, J=2.1 Hz, 1H), 8.11 (d, J=8.7 Hz, 1H), 7.88 (dd, J=8.7, 2.0 Hz, 1H), 2.14 (t, J=19.2 Hz, 3H), LCMS m/z=271.90, 273.90 (M+1; 100%).

7-Bromo-3-chloro-8-fluoroquinoline

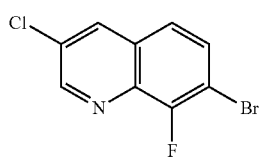 [SMILES: Fc1c(Br)ccc2cc(Cl)cnc12]

To a stirred solution of 7-bromo-8-fluoroquinoline (synthesized by following same reaction protocol as described in Ghergurovich, Jonathan Michael et al, WO2013028447 A1, 3.4 g, 15.04 mmol) in DMF (10 ml) was added N-chlorosuccinimide (4.02 g, 30.1 mmol) at 25° C. The reaction mixture was stirred at 100° C. for 16 h. The reaction mixture was cooled to 25° C. and poured onto ice cold water (100 ml) and stirred for 30 minutes. The precipitate was collected by filtration and washed with water. The precipitate was dried in vacuo to afford the title compound (2 g, 51%) as an off-white solid. $^1$H NMR (400 MHz, Chloroform-d) δ 8.90 (d, J=2.3 Hz, 1H), 8.18 (t, J=1.9 Hz, 1H), 7.72 (dd, J=8.9, 6.1 Hz, 1H), 7.48 (dd, J=8.8, 1.5 Hz, 1H); LCMS m/z=261.71 (M+; 100%).

7-Bromo-3-chloro-5-fluoroquinoline

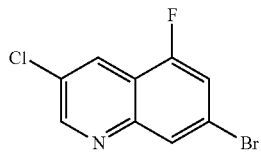 [SMILES: Fc1cc(Br)cc2ncc(Cl)cc12]

To a stirred solution of 2-amino-4-bromo-6-fluorobenzaldehyde (3.36 g, 15.41 mmol) in toluene (35 ml) was added 2-chloro-1,1-dimethoxyethane (2.304 g, 18.49 mmol) followed by p-toluene sulfonic acid monohydrate (2.93 g, 15.41 mmol) at 25° C. The resulting mixture was stirred at 110° C. using Dean Stark apparatus for 4 h under N$_2$ atmosphere. The reaction mixture was diluted with ethyl acetate (100 ml) and basified with aq.sat.NaHCO$_3$ (75 ml). Layers were separated, organic layer was washed with brine (20 ml) and dried over anhydrous Na$_2$SO$_4$. The organic layer was filtered and concentrated in vacuo to give 1.1 g of crude compound. This residue was purified by combiflash (R$_f$200, Teledyne/Isco) instrument onto a Redisep® R$_f$ column with gradient elution (0 to 2%) of ethyl acetate in petroleum ether to afford the title compound (1.64 g, 40.9%) as a light green solid. ¹H NMR (400 MHz, Chloroform-d) δ 8.88 (d, J=2.4 Hz, 1H), 8.38 (d, J=2.4 Hz, 1H), 8.15 (s, 1H), 7.45 (ddd, J=9.0, 3.5, 1.8 Hz, 1H); LCMS m/z=261.76 (M+1, 100%).

Intermediates in table-1 were synthesized by following an analogous reaction protocol as was used for the preparation of 7-bromo-3-chloro-5-fluoroquinoline using the appropriate starting materials.

TABLE-1

| Intermediate's Structure | Starting materials used | ¹H NMR and LCMS data |
|---|---|---|
| 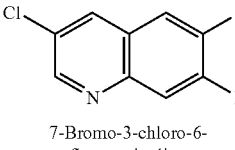<br>7-Bromo-3-chloro-6-fluoroquinoline | 2-Amino-4-bromo-5-fluorobenzaldehyde, which was synthesized as per US2014/200216 A1. | ¹H NMR (400 MHz, Chloroform-d) δ 8.81 (s, 1H), 8.43-8.38 (m, 1H), 8.12-8.08 (m, 1H), 7.47 (d, J = 8.4 Hz, 1H); LCMS m/z = 261.83 (M + 1; 100%). |
| 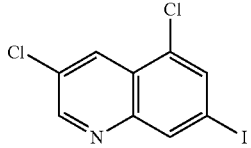<br>3,5-Dichloro-7-iodoquinoline | 2-Amino-6-chloro-4-iodobenzaldehyde | ¹H NMR (400 MHz, Chloroform-d) δ 8.85 (d, J = 2.3 Hz, 1H), 8.50 (dd, J = 2.3, 0.9 Hz, 1H), 8.48-8.45 (m, 1H), 7.96 (d, J = 1.6 Hz, 1H). |
| 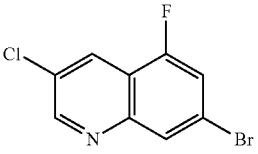<br>3,7-Dibromo-5-fluoroquinoline | 2-Amino-4-bromo-6-fluorobenzaldehyde | Crude was taken as such for the next step |
| <br>3-Bromo-6-fluoro-7-iodoquinoline | 2-Amino-5-fluoro-4-iodobenzaldehyde | ¹H NMR (400 MHz, Chloroform-d) δ 8.88 (d, J = 2.2 Hz, 1H), 8.61 (d, J = 6.0 Hz, 1H), 8.27 (d, J = 2.3 Hz, 1H), 7.39 (d, J = 7.8 Hz, 1H); LCMS m/z = 351.03, 353.03 (M − 1, M + 1, 60%). |

7-Bromo-3-chloro-5-fluoroquinoline 1-oxide

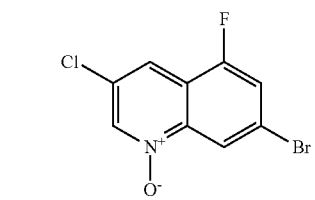 [SMILES: [O-][n+]1cc(Cl)cc2c(F)cc(Br)cc21]

A mixture of 7-bromo-3-chloro-5-fluoroquinoline (1.64 g, 6.30 mmol) and m-CPBA (2.90 g, 12.59 mmol) in CHCl₃ (30 ml) was heated at 50° C. for 16 h. The reaction mixture was diluted with chloroform (50 ml) and washed with aq.sat.

Na$_2$SO$_3$ (50 ml) followed by aq.sat.NaHCO$_3$ (50 ml). Layers were separated, organic layer was washed with brine (50 ml) and dried over anhydrous Na$_2$SO$_4$. The organic layer was filtered and concentrated in vacuo to give 1.35 g of crude compound. This residue was purified by combiflash (R$_f$200, Teledyne/Isco instrument onto a Redisep® R$_f$ column with gradient elution (0 to 20%) of ethyl acetate in petroleum ether to afford the title compound (542 mg, 31.1%) as a light brown solid. $^1$H NMR (400 MHz, DMSO-d$_6$) δ 8.97 (d, J=1.8 Hz, 1H), 8.46 (s, 1H), 8.17-8.10 (m, 1H), 8.03 (dd, J=9.5, 1.9 Hz, 1H); LCMS m/z=275.83, 277.83 (M+, M+2; 100%). Intermediates in table-2 were synthesized by following an analogous reaction protocol as was used for the preparation of 7-bromo-3-chloro-5-fluoroquinoline 1-oxide using the appropriate starting materials.

TABLE-2

| Intermediate's Structure | Starting materials used | $^1$H NMR and LCMS data |
| --- | --- | --- |
| 7-Bromo-3-methylquinoline 1-oxide | 7-Bromo-3-methylquinoline | $^1$H NMR (400 MHz, DMSO-d6) δ 8.60 (dd, J = 12.2, 1.7 Hz, 2H), 7.97 (d, J = 8.7 Hz, 1H), 7.85 (dd, J = 8.7, 2.0 Hz, 1H), 7.77 (q, J = 1.1 Hz, 1H), 2.40 (d, J = 1.0 Hz, 3H); LCMS m/z = 237.9, 239.9 (M+, M + 2, 100%). |
| 7-Bromo-3-cyclopropylquinoline 1-oxide | 7-Bromo-3-cyclopropylquinoline | $^1$H NMR (400 MHz, DMSO-d6) δ 8.58 (dd, J = 13.9, 1.7 Hz, 2H), 7.93 (d, J = 8.7 Hz, 1H), 7.84 (dd, J = 8.7, 2.1 Hz, 1H), 7.66 (s, 1H), 2.08 (tt, J = 8.4, 5.0 Hz, 1H), 1.12-1.04 (m, 2H), 0.95-0.87 (m, 2H); LCMS m/z = 263.83, 265.83 (M+, M + 2, 100%). |
| 7-Bromo-3-(1,1-difluoroethyl) quinoline 1-oxide | 7-Bromo-3-(1,1-difluoroethyl)quinoline | LCMS m/z = 289.96 (M + 1; 100%). |
| 7-Bromo-3-methoxyquinoline 1-oxide | 7-Bromo-3-methoxy quinoline, which was synthesized as per Adams, Nicholas David et al., WO2014/008223 A1. | Crude was taken as such for the next step |
| 7-Bromo-3-chloro-6-fluoroquinoline 1-oxide | 7-Bromo-3-chloro-6-fluoroquinoline | $^1$H NMR (400 MHz, DMSO-d6) δ 8.87 (d, J = 1.8 Hz, 1H), 8.75 (d, J = 6.6 Hz, 1H), 8.14-8.03 (m, 2H); LCMS m/z = 275.77 (M + 1; 60%). |

TABLE-2-continued

| Intermediate's Structure | Starting materials used | ¹H NMR and LCMS data |
|---|---|---|
| 7-Bromo-3-chloro-8-fluoroquinoline 1-oxide | 7-Bromo-3-chloro-8-fluoroquinoline | ¹H NMR (400 MHz, DMSO-d6) δ 8.78 (d, J = 1.5 Hz, 1H), 8.17 (s, 1H), 7.99 (dd, J = 8.8, 5.7 Hz, 1H), 7.80 (dd, J = 8.8, 1.6 Hz, 1H); LCMS m/z = 277.83 (M + 1; 100%). |
| 3,5-Dichloro-7-iodoquinoline 1-oxide | 3,5-Dichloro-7-iodoquinoline | ¹H NMR (400 MHz, DMSO-d6) δ 8.95 (d, J = 1.7 Hz, 1H), 8.80 (t, J = 1.3 Hz, 1H), 8.33 (d, J = 1.6 Hz, 1H), 8.08 (t, J = 1.3 Hz, 1H). |
| 3,7-Dibromo-5-fluoroquinoline 1-oxide | 3,7-Dibromo-5-fluoroquinoline | LCMS m/z = 322.0 (M + 1; 100%). |
| 3-Bromo-6-fluoro-7-iodoquinoline 1-oxide | 3-Bromo-6-fluoro-7-iodoquinoline | ¹H NMR (400 MHz, DMSO-d6) δ 8.91 (d, J = 6.0 Hz, 1H), 8.87 (d, J = 1.5 Hz, 1H), 8.22 (t, J = 1.1 Hz, 1H), 7.92 (d, J = 8.3 Hz, 1H). |

7-Bromo-2,3-dichloro-5-fluoroquinoline

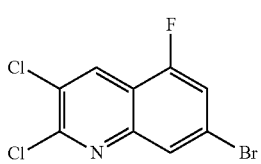 [SMILES: Fc1cc(Br)cc2nc(Cl)c(Cl)cc12]

To a stirred solution of 7-bromo-3-chloro-5-fluoroquinoline 1-oxide (542 mg, 1.960 mmol) in CHCl₃ (10 ml) was added POCl₃ (1.867 ml, 20.03 mmol) at 25° C. The resulting mixture was stirred at 65° C. for 2 h under N₂ atmosphere. The reaction mixture was poured onto ice cold water (50 ml), carefully basified with solid NaHCO₃ and extracted the product with dichloromethane (50 ml). Layers were separated, organic layer was washed with brine (50 ml) and was dried over anhydrous Na₂SO₄. The organic layer was filtered and concentrated in vacuo to give 1.2 g of crude compound. This residue was purified by combiflash (R/200, Teledyne/Isco) instrument onto a Redisep® R/ column with gradient elution (0 to 10%) of ethyl acetate in petroleum ether to afford the title compound (410 mg, 70.9%) as a white solid. ¹H NMR (400 MHz, Chloroform-d) δ 8.49-8.43 (m, 1H), 8.04 (dt, J=1.9, 1.0 Hz, 1H), 7.45 (dd, J=8.9, 1.7 Hz, 1H); LCMS m/z=296.19 (M+1; 100%).

Intermediates in table-3 were synthesized by following an analogous reaction protocol as was used for the preparation of 7-bromo-2,3-dichloro-5-fluoroquinoline using the appropriate starting materials.

TABLE-3

| Intermediate's Structure | Starting materials used | $^1$H NMR and LCMS data |
|---|---|---|
| 7-Bromo-2-chloro-3-methylquinoline | 7-Bromo-3-methylquinoline 1-oxide | $^1$H NMR (400 MHz, DMSO-d6) δ 8.04 (t, J = 1.0 Hz, 1H), 8.17 (d, J = 2.0 Hz, 1H), 7.94 (d, J = 8.7 Hz, 1H), 7.78 (dd, J = 8.7, 2.0 Hz, 1H), 2.48 (d, J = 1.0 Hz, 3H); LCMS m/z 256, 258 (M+, M + 2, 100%). |
| 7-Bromo-2-chloro-3-cyclopropyl quinoline | 7-Bromo-3-cyclopropylquinoline 1-oxide | $^1$H NMR (400 MHz, DMSO-d6) δ 8.16 (d, J = 3.0 Hz, 2H), 7.92 (d, J = 8.7 Hz, 1H), 7.77 (dd, J = 8.7, 2.0 Hz, 1H), 2.21 (tt, J = 8.4, 5.3 Hz, 1H), 1.10 (dt, J = 8.5, 3.2 Hz, 2H), 0.92-0.81 (m, 2H); LCMS m/z 281.90, 283.90 (M+, M + 2, 100%). |
| 7-Bromo-2-chloro-3-(1,1-difluoro ethyl)quinoline | 7-Bromo-3-(1,1-difluoroethyl)quinoline 1-oxide | LCMS m/z = 306, 308 (M+, M + 2; 100%). |
| 7-Bromo-2-chloro-3-methoxy quinoline | 7-Bromo-3-methoxyquinoline 1-oxide | LCMS m/z = 271.69, 273.69 |
| 7-Bromo-2,3-dichloro-6-fluoro quinoline | 7-Bromo-3-chloro-6-fluoroquinoline 1-oxide | $^1$H NMR (400 MHz, Chloroform-d) δ 8.31 (d, J = 6.3 Hz, 1H), 8.23-8.18 (m, 1H), 7.48 (d, J = 8.2 Hz, 1H). |
| 7-Bromo-2,3-dichloro-8-fluoro quinoline | 7-Bromo-3-chloro-8-fluoroquinoline 1-oxide | $^1$H NMR (400 MHz, DMSO-d6) δ 8.94 (d, J = 1.6 Hz, 1H), 7.97 (dd, J = 8.9, 6.3 Hz, 1H), 7.83 (dd, J = 8.9, 1.3 Hz, 1H), LCMS m/z = 295.65 (M + 1; 100%). |

TABLE-3-continued

| Intermediate's Structure | Starting materials used | ¹H NMR and LCMS data |
|---|---|---|
| 2,3,5-Trichloro-7-iodoquinoline | 3,5-Dichloro-7-iodoquinoline 1-oxide | ¹H NMR (400 MHz, Chloroform-d) δ 8.59 (d, J = 0.8 Hz, 1H), 8.38 (dd, J = 1.6, 0.8 Hz, 1H), 7.96 (d, J = 1.5 Hz, 1H). |
| 3,7-Dibromo-2-chloro-5-fluoro quinoline | 3,7-Dibromo-5-fluoroquinoline 1-oxide | Crude was taken as such for the next step |
| 3-Bromo-2-chloro-6-fluoro-7-iodoquinoline | 3-Bromo-6-fluoro-7-iodoquinoline 1-oxide | ¹H NMR (400 MHz, Chloroform-d) δ 8.54 (dd, J = 5.9, 0.7 Hz, 1H), 8.38 (s, 1H), 7.40 (d, J = 7.6 Hz, 1H). |

7-Bromo-3-chloro-5-fluoroquinolin-2-amine

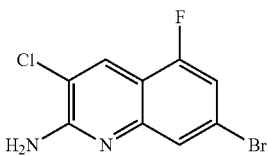

A mixture of 7-bromo-2,3-dichloro-5-fluoroquinoline (410 mg, 1.390 mmol), aqueous ammonia (9.74 ml, 250 mmol) in dioxane (10 ml) was heated at 120° C. in a steel bomb for 24 h. The reaction mixture was diluted with ethyl acetate (20 ml) and washed with water (20 ml). Layers were separated, organic layer was washed with brine (20 ml) and dried over anhydrous $Na_2SO_4$. The organic layer was filtered and concentrated in vacuo to give 1.15 g of crude compound. This residue was purified by combiflash ($R_f$200, Teledyne/Isco) instrument onto a Redisep® $R_f$ column with gradient elution (0 to 30%) of ethyl acetate in petroleum ether to afford the title compound (297 mg, 78%) as a white solid. ¹H NMR (400 MHz, DMSO-d₆) δ 8.23 (s, 1H), 7.51 (d, J=1.9 Hz, 1H), 7.32 (dd, J=9.5, 1.9 Hz, 1H), 7.25 (s, 2H); LCMS m/z=276.83 (M+1; 100%).

Intermediates in table-4 were synthesized by following an analogous reaction protocol as was used for the preparation of 7-bromo-3-chloro-5-fluoroquinolin-2-amine using the appropriate starting materials.

TABLE-4

| Intermediate's Structure | Starting materials used | ¹H NMR and LCMS data |
|---|---|---|
| 7-Bromo-8-fluoroquinolin-2-amine | 7-Bromo-2-chloro-8-fluoroquinoline | ¹H NMR (400 MHz, DMSO-d6) δ 7.95 (dd, J = 8.9, 1.8 Hz, 1H), 7.42 (dd, J = 8.7, 1.4 Hz, 1H), 7.35-7.27 (m, 1H), 6.93 (s, 2H), 6.88-6.79 (m, 1H); LCMS m/z = 240.8 (M+; 100%) |

TABLE-4-continued

| Intermediate's Structure | Starting materials used | ¹H NMR and LCMS data |
|---|---|---|
| 7-Bromo-3-methylquinolin-2-amine | 7-Bromo-2-chloro-3-methylquinoline | ¹H NMR (400 MHz, DMSO-d6) δ 7.75 (t, J = 1.0 Hz, 1H), 7.60 (d, J = 2.0 Hz, 1H), 7.54 (d, J = 8.4 Hz, 1H), 7.25 (dd, J = 8.5, 2.0 Hz, 1H), 6.51 (s, 2H), 2.19 (d, J = 1.1 Hz, 3H); LCMS m/z = 237, 239 (M+, M + 2, 100%). |
| 7-Bromo-3-isopropylquinolin-2-amine | 7-Bromo-2-chloro-3-isopropyl quinoline | LCMS m/z = 265.1, 267.1 (M+, M + 2; 100%). |
| 7-Bromo-3-cyclopropylquinolin-2-amine | 7-Bromo-2-chloro-3-cyclopropyl quinoline | ¹H NMR (400 MHz, DMSO-d6) δ 7.63 (s, 1H), 7.59 (d, J = 2.0 Hz, 1H), 7.55 (d, J = 8.5 Hz, 1H), 7.24 (dd, J = 8.5, 2.0 Hz, 1H), 6.65 (s, 2H), 1.80 (tdd, J = 8.2, 4.6, 2.9 Hz, 1H), 1.01-0.92 (m, 2H), 0.69-0.62 (m, 2H); LCMS m/z = 262.83, 264.83 (M+, M + 2, 100%). |
| 7-Bromo-3-(1,1-difluoroethyl)quinolin-2-amine | 7-Bromo-2-chloro-3-(1,1-difluoroethyl)quinoline | LCMS m/z = 287.96 (M + 1, 100%). |
| 7-Bromo-3-methoxyquinolin-2-amine | 7-Bromo-2-chloro-3-methoxyquinoline | LCMS m/z = 253, 255 (M+, M + 2; 100%). |
| 7-Bromo-3-chloro-6-fluoroquinolin-2-amine | 7-Bromo-2,3-dichloro-6-fluoro quinoline | ¹H NMR (400 MHz, DMSO-d6) δ 8.23 (s, 1H), 7.79 (d, J = 6.7 Hz, 1H), 7.67 (dd, J = 9.3, 2.0 Hz, 1H), 6.97 (s, 2H); LCMS m/z = 276.83 (M + 1; 100%). |
| 7-Bromo-3-chloro-8-fluoroquinolin-2-amine | 7-Bromo-2,3-dichloro-8-fluoro quinoline | ¹H NMR (400 MHz, DMSO-d6) δ 8.32 (d, J = 1.7 Hz, 1H), 7.30 (s, 2H), 7.35-7.16 (m, 2H), LCMS m/z = 276.86 (M + 1; 100%). |

TABLE-4-continued

| Intermediate's Structure | Starting materials used | ¹H NMR and LCMS data |
|---|---|---|
| 3,5-Dichloro-7-iodoquinolin-2-amine | 2,3,5-Trichloro-7-iodoquinoline | ¹H NMR (400 MHz, DMSO-d6) δ 8.22 (s, 1H), 7.94-7.81 (m, 1H), 7.67 (d, J = 1.6 Hz, 1H), 7.24 (s, 2H). |
| 3,7-Dibromo-5-fluoroquinolin-2-amine | 3,7-Dibromo-2-chloro-5-fluoro quinoline | ¹H NMR (400 MHz, DMSO-d6) δ 8.39 (d, J = 0.7 Hz, 1H), 7.50 (d, J = 1.7 Hz, 1H), 7.31 (dd, J = 9.5, 1.8 Hz, 1H), 7.14 (s, 2H); LCMS m/z = 318.96, 320.34, 322.34 (M − 1, M+, M + 2; 100%). |
| 3-Bromo-6-fluoro-7-iodoquinolin-2-amine | 3-Bromo-2-chloro-6-fluoro-7-iodoquinoline | ¹H NMR (400 MHz, DMSO-d6) δ 8.39 (s, 1H), 7.97 (d, J = 5.9 Hz, 1H), 7.55 (d, J = 8.5 Hz, 1H), 6.82 (s, 2H). |

7-Bromo-3-chloro-5-fluoro-N-(4-methoxybenzyl)quinolin-2-amine

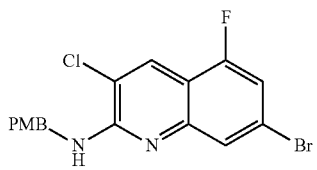

The title compound was prepared by following an analogous reaction protocol as described in Banka, Anna Lindsey et al, WO2012/037108 A1 using appropriate starting materials. ¹H NMR (400 MHz, DMSO-d6) δ 8.22 (d, J=0.8 Hz, 1H), 7.96 (t, J=6.1 Hz, 1H), 7.58 (dd, J=1.8, 1.0 Hz, 1H), 7.39-7.28 (m, 3H), 6.91-6.82 (m, 2H), 4.62 (d, J=6.1 Hz, 2H), 3.71 (s, 3H); LCMS m/z=397 (M+1; 100%).

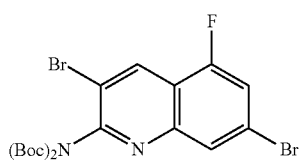

A mixture of 3,7-dibromo-5-fluoroquinolin-2-amine (2.05 g, 6.41 mmol), Et₃N (2.68 ml, 19.22 mmol), DMAP (0.078 g, 0.641 mmol) and Boc anhydride (3.12 ml, 13.45 mmol) in THF (25 ml) was stirred at 25° C. for 16 h. The reaction mixture was diluted with ethyl acetate (20 ml) and washed with water (20 ml). Layers were separated, organic layer was washed with brine (20 ml) and dried over anhydrous Na₂SO₄. The organic layer was filtered and concentrated in vacuo to give 3.9 g of crude compound. This residue was purified by combiflash (R$_f$200, Teledyne/Isco) instrument onto a Redisep® R$_f$ column with gradient elution (0 to 5%) of ethyl acetate in petroleum ether to afford the di-boc compound (2.5 g, 75%) as an off-white solid. ¹H NMR (400 MHz, Chloroform-d) δ 8.65 (d, J=0.8 Hz, 1H), 8.08 (q, J=1.2 Hz, 1H), 7.46 (dd, J=8.9, 1.7 Hz, 1H), 1.42 (s, 18H).

2-Amino-7-bromoquinoline-3-carbonitrile

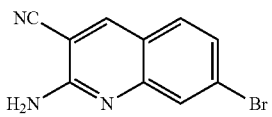

A mixture of 2-amino-4-bromobenzaldehyde (0.448 g, 2.240 mmol), malononitrile (0.222 g, 3.36 mmol) and piperidine (0.111 ml, 1.120 mmol) in ethanol (10 ml) was stirred at 100° C. for 16 h. The volatiles were evaporated in vacuo and the residue was purified by combiflash (R$_f$200, Teledyne/Isco) instrument onto a Redisep® R$_f$ column with gradient elution (0 to 10%) of ethyl acetate in petroleum ether to afford the title compound (0.343 g, 61.7%) as an off-white solid. ¹H NMR (400 MHz, DMSO-d₆) δ 8.71 (s, 1H), 7.74-7.65 (m, 2H), 7.42 (dd, J=8.6, 2.0 Hz, 1H), 7.20 (s, 2H); LCMS m/z=248, 250 (M+, M+2, 100%).

7-Bromo-N-(4-methoxybenzyl)quinazolin-2-amine

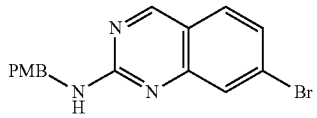

The title compound was prepared by following an analogous reaction protocol as described in L₁, Liansheng et al, WO2017/087528 A1; LCMS m/z=344.1 (M+, 100%).

7-Bromo-3-fluoroquinolin-2-amine

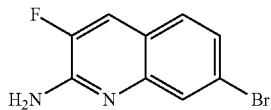

The title compound was prepared by an following analogous reaction protocol as described in Banka, Anna Lindsey et al, WO2012/037108 A1.

7-Bromo-3-chloroquinolin-2-amine

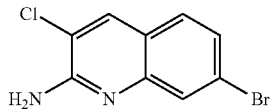

The title compound was prepared by following an analogous reaction protocol as described in Banka, Anna Lindsey et al, WO2012/037108 A1.

7-Bromo-3-chloro-N-(4-methoxybenzyl)quinolin-2-amine

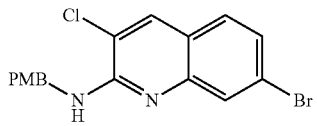

The title compound was prepared by following an analogous reaction protocol as described in Banka, Anna Lindsey et al, WO2012/037108 A1.

7-Bromo-3-chloro-N,N-bis(4-methoxybenzyl)quinolin-2-amine

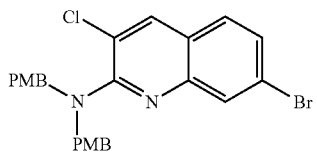

To a stirred suspension of 7-bromo-3-chloroquinolin-2-amine (2.0 g, 7.77 mmol) in DMF (20 ml) was added NaH (0.932 g, 23.30 mmol) at 0° C. The resulting mixture was stirred at 0° C. for 15 min. Then 1-(chloromethyl)-4-methoxybenzene (3.65 g, 23.30 mmol) was added dropwise under N₂ atmosphere. The reaction mixture was then stirred for 16 h at 25° C. The reaction mixture was poured into ice water (150 mL) and extracted with ethyl acetate (150 ml). Layers were separated, organic layer was washed with brine (100 ml) and dried over anhydrous Na₂SO₄. The organic layer was filtered and concentrated in vacuo to give 3.87 g of crude compound. This residue was purified by combiflash (R$_f$200, Teledyne/Isco) instrument onto a Redisep® R$_f$ column with gradient elution (0 to 30%) of ethyl acetate in petroleum ether to afford the title compound (2.2 g, 56.9%) as an off-white solid. 1H NMR (400 MHz, DMSO-d6) δ 8.45 (s, 1H), 7.89 (d, J=1.9 Hz, 1H), 7.77 (d, J=8.6 Hz, 1H), 7.56 (dd, J=8.6, 2.0 Hz, 1H), 7.31-7.22 (m, 4H), 6.93-6.82 (m, 4H), 4.54 (s, 4H), 3.70 (s, 6H); LCMS m/z=498.97 (M+1; 100%).

3-Bromo-7-iodo-N-(4-methoxybenzyl)quinolin-2-amine

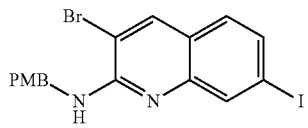

The title compound was prepared by following an analogous reaction protocol as described in Banka, Anna Lindsey et al, WO2012/037108 A1.

6-Bromo-3,3-dimethylindoline-2-thione

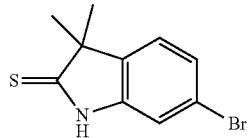

The suspension of 6-bromo-3,3-dimethylindolin-2-one (3.5 g, 14.58 mmol), which was synthesized by following an analogous reaction protocol as was reported in WO2015/177110, A1 and Lawesson's reagent (7.66 g, 18.95 mmol) in toluene (15 ml) was heated at 100° C. for 3 h under N₂ atmosphere. Solvent was evaporated in vacuo and this residue was purified by combiflash (R$_f$200, Teledyne/Isco) instrument onto a Redisep® R$_f$ column with gradient elution (0-20%) of ethyl acetate in petroleum ether to afford the title compound (3.3 g, 88%) as an off-white solid. ¹H NMR (400 MHz, DMSO-d₆) δ 12.67 (s, 1H), 7.40 (d, J=7.9 Hz, 1H), 7.31 (dd, J=7.9, 1.8 Hz, 1H), 7.15 (d, J=1.7 Hz, 1H), 1.30 (s, 6H); LCMS m/z=256.89 (M+1; 30%).

6-Bromo-3,3-dimethyl-2-(methylthio)-3H-indole

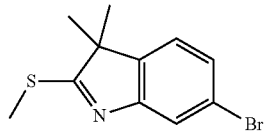

To a stirred suspension of 6-bromo-3,3-dimethylindoline-2-thione (3 g, 11.71 mmol) in THF (40 ml) was added NaH (0.703 g, 17.57 mmol) at 0° C. The resulting mixture was stirred for 15 min at 0° C. Methyl iodide (1.098 ml, 17.57 mmol) was added and stirred the reaction mixture for 1 h at 0° C. under N₂ atmosphere. The reaction mixture was diluted with ethyl acetate (50 ml) and washed with water (50 ml). Layers were separated, organic layer was washed with brine (50 ml) and dried over anhydrous sodium sulphate. The organic layer was filtered and concentrated in vacuo to give 3.5 g of crude compound. This residue was purified by combiflash (R$_f$200, Teledyne/Isco) instrument onto a Redisep® R$_f$ column with gradient elution (0-5%) of ethyl acetate in petroleum ether to afford the title compound (3.1 g, 98%) as a white solid. ¹H NMR (400 MHz, DMSO-d₆) δ 7.60 (d, J=1.7 Hz, 1H), 7.41 (d, J=7.9 Hz, 1H), 7.32 (dd, J=7.9, 1.8 Hz, 1H), 2.60 (s, 3H), 1.29 (s, 6H); LCMS m/z=269.90 (M+; 40%).

6'-Bromospiro[cyclobutane-1,3'-indoline]-2'-thione

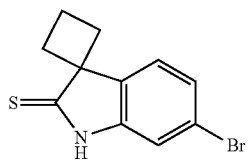 [SMILES: S=C1Nc2cc(Br)ccc2C12CCC2]

The title compound was prepared by following an analogous reaction protocol as was described in the preparation of 6-bromo-3,3-dimethylindoline-2-thione. LCMS m/z=267.65 (M+; 20%).

6'-Bromo-2'-(methylthio)spiro[cyclobutane-1,3'-indole]

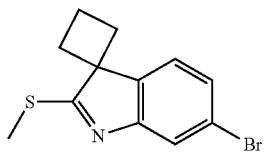

The title compound was prepared by following an analogous reaction protocol as was described in the preparation of 6-bromo-3,3-dimethyl-2-(methylthio)-3H-indole. ¹H NMR (400 MHz, Chloroform-d) δ 7.63 (d, J=1.7 Hz, 1H), 7.44 (d, J=7.9 Hz, 1H), 7.32 (dd, J=7.9, 1.7 Hz, 1H), 2.73 (s, 3H), 2.61-2.46 (m, 4H), 2.37-2.30 (m, 2H); LCMS m/z=281.78, 283.78 (M+, M+2; 100%).

6'-Bromospiro[cyclobutane-1,3'-indol]-2'-amine

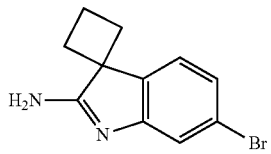 [SMILES: NC1=Nc2cc(Br)ccc2C12CCC2]

To stirred solution of 6'-bromo-2'-(methylthio)spiro[cyclobutane-1,3'-indole] (1.2 g, 4.25 mmol) in 7N ammonia in methanol (15 ml, 371 mmol) was heated at 100° C. for 16 h. Solvent was evaporated in vacuo and this residue was purified by combiflash (R$_f$200, Teledyne/Isco) instrument onto a Redisep® R$_f$ column with gradient elution (0-10%) of methanol in dichloromethane to afford the title compound (650 mg, 60.9%) as white solid. ¹H NMR (400 MHz, DMSO-d₆) δ 7.69 (s, 2H), 7.46 (d, J=8.2 Hz, 1H), 7.01 (h, J=1.8 Hz, 2H), 2.63-2.53 (m, 2H), 2.43-2.30 (m, 1H), 2.23-2.09 (m, 3H); LCMS m/z=250.87 (M+; 100%).

7-Bromo-3-methylimidazo[1,2-a]pyridine

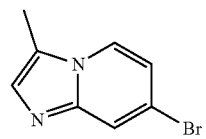

The title compound was prepared by following an analogous reaction protocol as was described in Dubois., Laurent et al, WO 2009/112679 A1.

2-(Methylamino)quinolin-7-ol

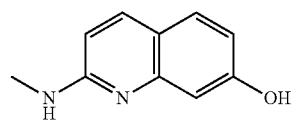

The title compound was prepared by following an analogous reaction protocol as was described in Doherty, Elizabeth M. et.al, Journal of Medicinal Chemistry, 2007, vol. 50, #15, p. 3515-3527.

3-Bromo-N-(4-methoxybenzyl)-7-(4,4,5,5-tetramethyl-1,3,2-dioxaborolan-2-yl)quinolin-2-amine

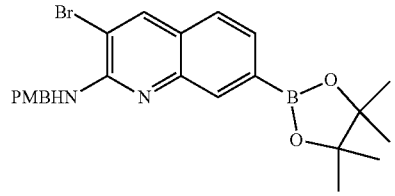

A mixture of 3-bromo-7-iodo-N-(4-methoxybenzyl)quinolin-2-amine (1.5 g, 3.20 mmol), bispinacolotodiboron (0.974 g, 3.84 mmol), [1,1'-bis(diphenylphosphino) ferrocene] dichloropalladium(II), complex with dichloromethane (0.261 g, 0.320 mmol) and potassium acetate (0.533 g, 5.44 mmol)) in DMSO (50 ml) was heated at 80° C. for 15 min in a preheated oil bath. The reaction mixture was allowed to cool to 25° C., diluted with ethyl acetate (50 ml) and poured onto ice-cold water (100 ml). Layers were separated, organic layer was washed with brine (50 ml) and dried over anhydrous sodium sulphate. The organic layer was filtered and concentrated in vacuo to give 2.5 g of crude compound. This residue was purified by combiflash (R$_f$200, Teledyne/Isco) instrument onto a Redisep® R$_f$ column with gradient elution (0-7%) of ethyl acetate in petroleum ether to afford the title compound (1.35 g, 90%) as an off-white solid. $^1$H NMR (400 MHz, DMSO-d$_6$) δ 8.42 (d, J=0.7 Hz, 1H), 7.86 (d, J=1.1 Hz, 1H), 7.65 (d, J=7.9 Hz, 1H), 7.43 (dd, J=7.9, 1.1 Hz, 1H), 7.40-7.32 (m, 3H), 6.99-6.74 (m, 2H), 4.62 (d, J=6.0 Hz, 2H), 3.71 (s, 3H), 1.32 (s, 12H); LCMS m/z=468.89 (M+; 100%).

3-Bromo-2-((4-methoxybenzyl)amino)quinolin-7-ol

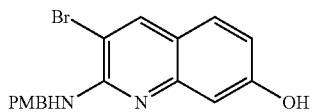

To a stirred solution of 3-bromo-N-(4-methoxybenzyl)-7-(4,4,5,5-tetramethyl-1,3,2-dioxaborolan-2-yl)quinolin-2-amine (0.35 g, 0.746 mmol) in THF (20 ml) was added AcOH (0.064 ml, 1.119 mmol) dropwise at 0° C. and stirred for 1 h. Aq. H$_2$O$_2$ (0.5 ml, 1.492 mmol) was added slowly at 0° C. The resulting mixture was stirred at 25° C. for 5 h. The reaction mixture was diluted with ethyl acetate (20 ml) and washed with aq.sat.Na$_2$SO$_3$ (20 ml). Layers were separated, organic layer was washed with brine (20 ml) and dried over anhydrous sodium sulphate. The organic layer was filtered and concentrated in vacuo to give 0.41 g of crude compound. This residue was purified by combiflash (R$_f$200, Teledyne/Isco) instrument onto a Redisep® R$_f$ column with gradient elution (0-25%) of ethyl acetate in petroleum ether to afford the title compound (0.13 g, 48.5%) as an off-white solid. LCMS m/z=359.22 (M+; 100%).

3-Chloro-5-fluoro-N-(4-methoxybenzyl)-7-(4,4,5,5-tetramethyl-1,3,2-dioxaborolan-2-yl)quinolin-2-amine

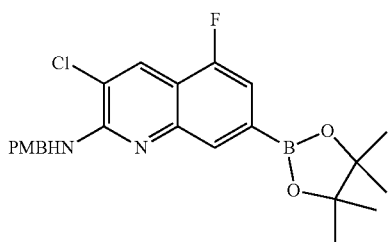

The title compound was synthesized by following an analogous reaction protocol as was described in the preparation of 3-bromo-N-(4-methoxybenzyl)-7-(4,4,5,5-tetramethyl-1,3,2-dioxaborolan-2-yl)quinolin-2-amine. $^1$H NMR (400 MHz, Chloroform-d) δ 1H NMR (400 MHz, Chloroform-d) δ 8.17 (d, J=0.9 Hz, 1H), 8.07 (s, 1H), 7.41-7.36 (m, 2H), 7.29 (dd, J=10.0, 0.8 Hz, 1H), 6.94-6.89 (m, 2H), 5.69 (s, 1H), 4.77 (d, J=5.4 Hz, 2H), 3.83 (s, 3H), 1.29 (s, 12H); LCMS m/z=443.05 (M+; 100%).

3-Chloro-5-fluoro-2-((4-methoxybenzyl)amino)quinolin-7-ol

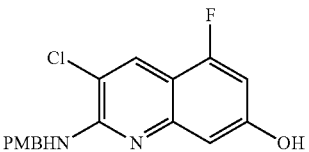

The title compound was synthesized by following an analogous reaction protocol as was described in the preparation of 3-bromo-2-((4-methoxybenzyl)amino)quinolin-7-ol. $^1$H NMR (400 MHz, DMSO-d6) δ 10.19 (d, J=1.0 Hz, 1H), 8.02 (s, 1H), 7.55 (t, J=6.2 Hz, 1H), 7.43-7.28 (m, 2H), 6.91-6.82 (m, 2H), 6.67 (d, J=2.1 Hz, 1H), 6.57 (dd, J=11.7, 2.2 Hz, 1H), 4.60 (d, J=6.0 Hz, 2H), 3.71 (s, 3H); LCMS m/z=333.15, 335.15 (M+, M+2; 30%).

N2-(4-Methoxybenzyl)quinoline-2,7-diamine

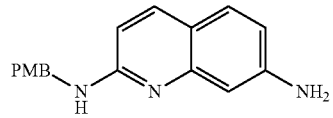

A mixture of 7-bromo-N-(4-methoxybenzyl)quinolin-2-amine (0.6 g, 1.748 mmol), copper(I) iodide (0.033 g, 0.175 mmol), and N1,N1-dimethylethane-1,2-diamine (0.171 ml, 1.748 mmol) in AMMONIA (0.757 ml, 35.0 mmol) and DMSO (1 ml) at 130° C. for 15 h. The resulting suspension was cooled to 25° C. and saturated aqueous sodium sulphate solution (5 mL) was added. The resulting mixture was extracted with ethyl acetate (20 ml×3). The organic layer was separated, dried over MgSO4, filtered and concentrated. This residue was purified by combiflash (R$_f$200, Teledyne/Isco) instrument onto a Redisep® R$_f$ column with gradient elution (0-5%) of methanol in dichloromethane to afford the title compound (0.18 g, 36.9%) as a brown solid. $^1$H NMR (400 MHz, DMSO-d$_6$) δ 7.55 (d, J=8.7 Hz, 1H), 7.34-7.29 (m, 2H), 7.25 (d, J=8.4 Hz, 1H), 7.07 (t, J=5.8 Hz, 1H), 6.91-6.83 (m, 2H), 6.56 (d, J=2.2 Hz, 1H), 6.52 (dd, J=8.4, 2.2 Hz, 1H), 6.40 (d, J=8.7 Hz, 1H), 5.32 (s, 2H), 4.49 (d, J=5.8 Hz, 2H), 3.72 (s, 3H); LCMS m/z=280.2 (M+1, 100%).

N2-(4-Methoxybenzyl)-N7-methylquinoline-2,7-diamine

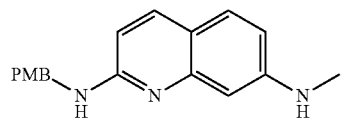

A mixture of 7-bromo-N-(4-methoxybenzyl)quinolin-2-amine (0.5 g, 1.457 mmol), methanamine (7.54 ml, 7.28 mmol) and copper (0.046 g, 0.728 mmol) was stirred at 110° C. in a sealed tube for 12 h. The reaction mixture was diluted with ethyl acetate (20 ml) and washed with water (20 ml).

The organic layer was separated, dried over MgSO4, filtered and concentrated. This residue was purified by combiflash (R<sub>f</sub>200, Teledyne/Isco) instrument onto a Redisep® R<sub>f</sub> column with gradient elution (0-5%) of methanol in dichloromethane to afford the title compound (0.4 g, 94%) as a brown liquid. LCMS m/z=294.09 (M+1; 100%).

S-(2-((4-Methoxybenzyl)amino)quinolin-7-yl) ethanethioate

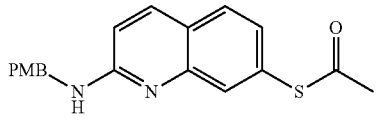

To a stirred solution of 7-bromo-N-(4-methoxybenzyl) quinolin-2-amine (2 g, 5.83 mmol), potassium thioacetate (1.331 g, 11.65 mmol), DIEA (2.035 ml, 11.65 mmol) and xantphos (0.337 g, 0.583 mmol) in 1,4-dioxane (20 ml) was added Pd$_2$(dba)$_3$ (0.534 g, 0.583 mmol) at 25° C. under N$_2$ atmosphere. The resulting mixture was stirred at 110° C. for 1.5 h under microwave condition. The reaction mixture was diluted with ethyl acetate (20 ml) and washed with water (20 ml). The organic layer was separated, dried over MgSO4, filtered and concentrated. This residue was purified by combiflash (R<sub>f</sub>200, Teledyne/Isco) instrument onto a Redisep® R<sub>f</sub> column with gradient elution (0-20%) of ethyl acetate in petroleum ether to afford the title compound (0.67 g, 34%) as an off-white solid. $^1$H NMR (400 MHz, Chloroform-d) δ 7.87-7.80 (m, 2H), 7.63 (d, J=8.3 Hz, 1H), 7.39-7.32 (m, 2H), 7.28-7.23 (m, 1H), 6.95-6.87 (m, 2H), 6.67 (d, J=9.0 Hz, 1H), 5.21 (s, 1H), 4.67 (d, J=5.4 Hz, 2H), 3.82 (s, 3H), 2.47 (s, 3H); LCMS m/z=339.22 (M+1; 100%).

2-((4-Methoxybenzyl)amino)quinoline-7-thiol

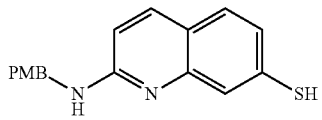

To a stirred solution of S-(2-((4-methoxybenzyl)amino) quinolin-7-yl) ethanethioate (0.67 g, 1.98 mmol) in 20 mL of ethanol was added KOH (0.33 g, 5.94 mmol) at 25° C. The resulting mixture was stirred at 25° C. for 1 h. The reaction mixture was quenched with sat.aqueous NH$_4$Cl (20 ml) and extracted with ethyl acetate (20 ml). The organic layer was separated, dried over MgSO4, filtered and concentrated in vacuo to give the title compound (0.56 g, 95%) as a brown solid. 1H NMR (400 MHz, Chloroform-d) δ 7.77 (d, J=8.9 Hz, 1H), 7.64 (d, J=1.8 Hz, 1H), 7.46 (d, J=8.3 Hz, 1H), 7.37-7.32 (m, 2H), 7.10 (dd, J=8.3, 1.9 Hz, 1H), 6.93-6.87 (m, 2H), 6.58 (d, J=8.9 Hz, 1H), 5.58 (s, 1H), 4.64 (d, J=5.3 Hz, 2H), 3.82 (s, 3H); LCMS m/z=297.09 (M+; 100%).

S-(2-(Bis(4-methoxybenzyl)amino)-3-chloroquinolin-7-yl) ethanethioate

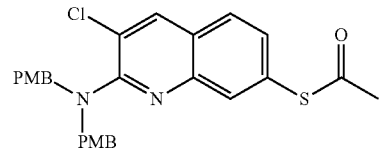

The title compound was synthesized by following an analogous reaction protocol as was described in the preparation of S-(2-((4-methoxybenzyl)amino)quinolin-7-yl) ethanethioate. LCMS m/z=493.30 (M+; 100%).

2-(Bis(4-methoxybenzyl)amino)-3-chloroquinoline-7-thiol

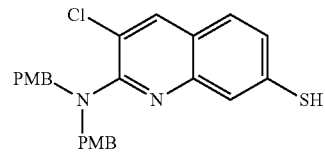

To a solution of solution of S-(2-(bis(4-methoxybenzyl) amino)-3-chloroquinolin-7-yl) ethanethioate (300 mg, 0.608 mmol) in ethanol (9 ml) was added KOH (51.2 mg, 0.913 mmol) at 25° C. The mixture was heated at 50° C. for 2 h. The reaction solution was allowed to cool to 25° C., adjusted pH to 4 with HCl (1N) and concentrated in vacuo to get 0.4 g of crude compound, which was triturated with diethyl ether (20 ml) to get the title compound (200 mg, 72.9%) as an off-white solid. LCMS m/z=450.42 (M+; 100%).

((3aR,6R,6aS)-6-(4-Chloro-7H-pyrrolo[2,3-d]pyrimidin-7-yl)-2,2-dimethyl-6,6a-dihydro-3aH-cyclopenta[d][1,3]dioxol-4-yl)methanol

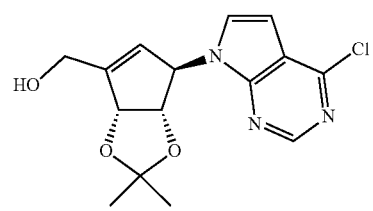

The title compound was prepared by following the same reaction protocol as was described in Kenneth A. Jacobson et.al; Purinergic Signalling (2015) 11:371-387.

((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)methyl 4-methylbenzenesulfonate

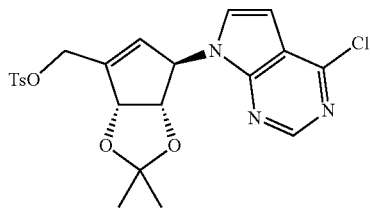 [SMILES: Cc1ccc(S(=O)(=O)OCC2=C[C@@H](n3ccc4c(Cl)ncnc43)[C@@H]3OC(C)(C)O[C@H]23)cc1]

To a stirred solution of ((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)methanol (0.5 g, 1.554 mmol) in dichloromethane (10 ml) was added TEA (0.651 ml, 4.66 mmol), DMAP (0.038 g, 0.311 mmol), followed by a slow addition of p-TsCl (0.355 g, 1.865 mmol) at 0° C. and stirred for 10 mins. The resulting mixture was stirred at 25° C. for 2 h. The reaction mixture was diluted with ethyl acetate (20 ml) and washed with water (20 ml). The organic layer was separated, dried over MgSO4, filtered and concentrated in vacuo to give 0.71 g of crude compound. This residue was purified by combiflash (R$_f$200, Teledyne/Isco) instrument onto a Redisep® R$_f$ column with gradient elution (0-10%) of ethyl acetate in petroleum ether to afford the title compound (0.282 g, 38.1%) as a pale yellow liquid. $^1$H NMR (400 MHz, Chloroform-d) δ 8.69 (t, J=2.8 Hz, 1H), 7.89-7.81 (m, 2H), 7.42-7.34 (m, 2H), 7.12 (s, 1H), 6.64 (d, J=3.8 Hz, 1H), 5.86 (d, J=12.4 Hz, 2H), 5.36 (d, J=5.6 Hz, 1H), 4.90-4.77 (m, 2H), 4.63 (t, J=4.5 Hz, 1H), 2.52-2.45 (m, 3H), 1.45 (s, 3H), 1.34 (s, 3H); LCMS m/z=476.17 (M+; 100%).

(3aS,4R,6aR)-4-(4-Chloro-7H-pyrrolo[2,3-d]pyrimidin-7-yl)-2,2-dimethyl-3a,6a-dihydro-4H-cyclopenta[d][1,3]dioxole-6-carbaldehyde

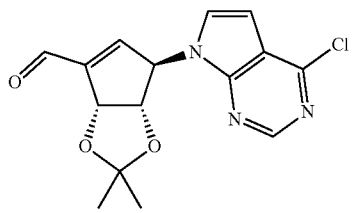 [SMILES: CC1(C)O[C@@H]2[C@H](O1)C(C=O)=C[C@H]2n1ccc2c(Cl)ncnc21]

To a stirred solution of ((3aS,4R,6aR)-4-(4-Chloro-7H-pyrrolo[2,3-d]pyrimidin-7-yl)-2,2-dimethyl-3a,6a-dihydro-4H-cyclopenta[d][1,3]dioxol-6-yl)methanol (2.50 g, 7.77 mmol) in CH$_2$Cl$_2$ (40 ml) at 0° C., was added Dess-Martin Periodinane (3.95 g, 9.32 mmol) portion-wise and stirred for 1 h. The reaction mixture was diluted with dichloromethane (50 ml) and washed with water (50 ml). The organic layer was separated, dried over MgSO4, filtered and concentrated in vacuo to give 2.71 g of crude compound. This residue was purified by combiflash (R$_f$200, Teledyne/Isco) instrument onto a Redisep® R$_f$ column with gradient elution (0-30%) of ethyl acetate in petroleum ether to afford the title compound (2.32 g, 93%) as a colorless oil. $^1$H NMR (400 MHz, Chloroform-d) δ 10.00 (s, 1H), 8.67 (s, 1H), 7.12 (d, J=3.6 Hz, 1H), 6.78 (dd, J=2.6, 0.9 Hz, 1H), 6.69 (d, J=3.7 Hz, 1H), 5.97 (dt, J=2.8, 1.4 Hz, 1H), 5.76 (dd, J=5.9, 1.5 Hz, 1H), 4.88 (dt, J=5.9, 1.1 Hz, 1H), 1.54 (s, 3H), 1.40 (s, 3H); LCMS m/z=320.2 (M+1, 100%).

4-Chloro-7-((3aS,4R,6aR)-2,2-dimethyl-6-vinyl-3a,6a-dihydro-4H-cyclopenta[d][1,3] dioxol-4-yl)-7H-pyrrolo[2,3-d]pyrimidine

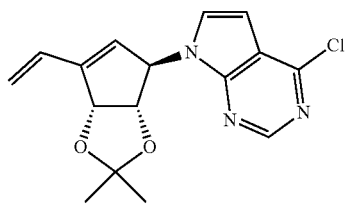

To a cooled suspension of methyl(triphenyl)phosphonium bromide (5.03 g, 14.07 mmol) in THF (30 mL) at 0° C., was added 1M KHMDS in THF (14.07 mL, 14.07 mmol) slowly and stirred for 5 min. The reaction mixture was allowed to warm to 25° C. and stirred for 10 min. Cooled the reaction mixture to 0° C. and slowly added a solution of (3aS,4R,6aR)-4-(4-Chloro-7H-pyrrolo[2,3-d]pyrimidin-7-yl)-2,2-dimethyl-3a,6a-dihydro-4H-cyclopenta [d][1,3]dioxole-6-carbaldehyde (1.8 g, 5.63 mmol) in THF (1 ml). Stirred the reaction mixture at 25° C. for 10 min. The reaction mixture was quenched with sat.aqueous NH$_4$Cl (50 ml) and extracted with ethyl acetate (50 ml). The organic layer was separated, dried over Na$_2$SO$_4$, filtered and concentrated in vacuo to give 2.1 g of crude compound. This residue was purified by combiflash (R$_f$200, Teledyne/Isco) instrument onto a Redisep® R$_f$ column with gradient elution (0-7%) of ethyl acetate in petroleum ether to afford the title compound (0.81 g, 45.3%) as an off-white solid. $^1$H NMR (400 MHz, Chloroform-d) δ 8.72 (s, 1H), 7.11 (d, J=3.6 Hz, 1H), 6.66-6.57 (m, 2H), 5.94 (d, J=2.6 Hz, 1H), 5.81-5.75 (m, 2H), 5.57 (dd, J=6.0, 1.5 Hz, 1H), 5.49 (d, J=10.9 Hz, 1H), 4.66 (dt, J=6.0, 1.0 Hz, 1H), 1.52 (s, 3H), 1.40 (s, 3H); LCMS m/z=318.09 (M+1, 100%).

7-((3aS,4R,6aR)-2,2-Dimethyl-6-vinyl-4,6a-dihydro-3aH-cyclopenta [d][1,3]dioxol-4-yl)-4-ethyl-7H-pyrrolo[2,3-d]pyrimidine

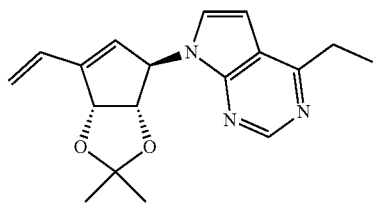 [SMILES: C=CC1=C[C@@H](n2ccc3c(CC)ncnc32)[C@@H]2OC(C)(C)O[C@H]12]

To a stirred solution of 4-chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine (500 mg, 1.573 mmol) in THF (1 ml) and NMP (0.2 ml) was added ferric acetylacetonate (55.6 mg, 0.157 mmol) at 25° C. 2M Ethylmagnesium chloride in THF (1.573 ml, 3.15 mmol) was added dropwise and the reaction mixture was stirred for 4 h.

The reaction mixture was quenched with sat.aqueous NH₄Cl (10 ml) and extracted with ethyl acetate (10 ml). The organic layer was separated, dried over Na₂SO₄, filtered and concentrated in vacuo to give 0.6 g of crude compound. This residue was purified by combiflash (R₂200, Teledyne/Isco) instrument onto a Redisep® R₂ column with gradient elution (0-90%) of ethyl acetate in petroleum ether to afford the title compound (0.28 g, 57.1%) as an off-white solid. ¹H NMR (400 MHz, DMSO-d6) δ 8.71 (s, 1H), 7.35 (d, J=3.6 Hz, 1H), 6.73 (d, J=3.6 Hz, 1H), 6.60 (dd, J=17.7, 10.8 Hz, 1H), 5.88 (d, J=2.7 Hz, 1H), 5.83-5.74 (m, 1H), 5.66-5.56 (m, 2H), 5.45-5.37 (m, 1H), 4.67 (dd, J=6.0, 1.1 Hz, 1H), 2.99 (q, J=7.6 Hz, 2H), 1.40 (s, 3H), 1.30 (s, 6H); LCMS m/z=312.21 (M+1, 100%).

7-((3aS,4R,6aR)-2,2-Dimethyl-6-vinyl-4,6a-dihydro-3aH-cyclopenta[d] [1,3]dioxol-4-yl)-4-isopropyl-7H-pyrrolo[2,3-d]pyrimidine

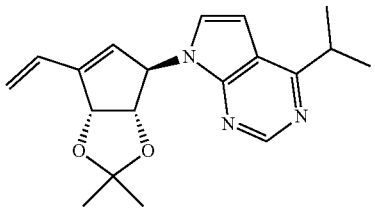 [SMILES: C=CC1=C[C@@H](n2ccc3c(C(C)C)ncnc32)[C@@H]2OC(C)(C)O[C@H]12]

A solution of 4-chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine (1 g, 3.15 mmol), 2M isopropyl magnesium bromide in THF (5.51 ml, 11.01 mmol) and PdCl₂(dppf) (0.230 g, 0.315 mmol) in toluene (10 ml) was heated at 100° C. for 30 min. After completion of the reaction, the reaction mixture was quenched with methanol and concentrated. This residue was purified by combiflash (R₂200, Teledyne/Isco) instrument onto a Redisep® R₂ column with gradient elution (0-2%) of methanol in dichloromethane to afford the title compound (150 mg, 14.65%) as an off-white solid. ¹H NMR (400 MHz, Chloroform-d) δ 8.98 (s, 1H), 7.48 (d, J=4.0 Hz, 1H), 7.11 (t, J=1.6 Hz, 1H), 6.86 (d, J=4.0 Hz, 1H), 3.98 (dt, J=2.5, 1.2 Hz, 2H), 3.50-3.43 (m, 1H), 2.66 (s, 1H), 2.20 (d, J=2.4 Hz, 1H), 2.00 (dd, J=7.2, 1.0 Hz, 2H), 1.44 (dd, J=6.9, 3.1 Hz, 6H), 1.28 (s, 6H).

4-Cyclopropyl-7-((3aS,4R,6aR)-2,2-dimethyl-6-vinyl-3a,6a-dihydro-4H-cyclopenta[d] [1,3]dioxol-4-yl)-7H-pyrrolo[2,3-d]pyrimidine

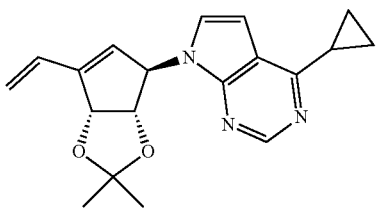 [SMILES: C=CC1=C[C@@H](n2ccc3c(C4CC4)ncnc32)[C@@H]2OC(C)(C)O[C@H]12]

The title compound was synthesized by following an analogous reaction protocol as was described in the preparation of 7-((3aS,4R,6aR)-2,2-dimethyl-6-vinyl-4,6a-dihydro-3aH-cyclopenta [d][1,3]dioxol-4-yl)-4-ethyl-7H-pyrrolo[2,3-d]pyrimidine. LCMS m/z=323.90 (M+; 100%).

1-((3aS,4R,6aR)-4-(4-Chloro-7H-pyrrolo[2,3-d]pyrimidin-7-yl)-2,2-dimethyl-3a,6a-dihydro-4H-cyclopenta[d][1,3]dioxol-6-yl)ethan-1-ol

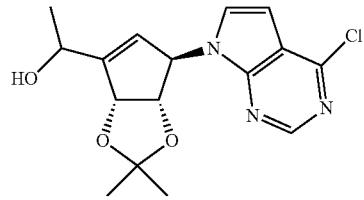 [SMILES: CC(O)C1=C[C@@H](n2ccc3c(Cl)ncnc32)[C@@H]2OC(C)(C)O[C@H]12]

To a stirred solution of (3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxole-6-carbaldehyde (2.30 g, 7.19 mmol) in THF (120 ml) at −78° C., was added methylmagnesium bromide (4.80 ml, 14.39 mmol) and the reaction mixture was stirred at same temperature for 3 h. The reaction mixture was quenched with a sat. aqueous NH₄Cl (50 ml) and extracted with ethyl acetate (50 ml). Layers were separated, the organic layer was washed with brine (50 ml) and dried over anhydrous sodium sulphate. The organic layer was filtered and concentrated in vacuo to give 2.2 g of crude compound and this crude residue was purified by combiflash (R₂200, Teledyne/Isco) instrument onto a Redisep® R₂ column with gradient elution (0 to 20%) of ethyl acetate in petroleum ether to afford the title compound (1.82 g, 75%) as a off-white solid. ¹H NMR (400 MHz, Chloroform-d) δ 8.70 (s, 1H), 7.11 (d, J=3.7 Hz, 1H), 6.63 (d, J=3.7 Hz, 1H), 5.88-5.81 (m, 1H), 5.80-5.71 (m, 1H), 5.59-5.45 (m, 1H), 4.76-4.64 (m, 2H), 1.59-1.49 (m, 6H), 1.38 (d, J=1.0 Hz, 3H), 1.32-1.23 (m, 1H); LCMS m/z=336.2 (M+; 100%).

1-((3aS,4R,6aR)-4-(4-Chloro-7H-pyrrolo[2,3-d]pyrimidin-7-yl)-2,2-dimethyl-3a,6a-dihydro-4H-cyclopenta[d][1,3]dioxol-6-yl)ethan-1-one

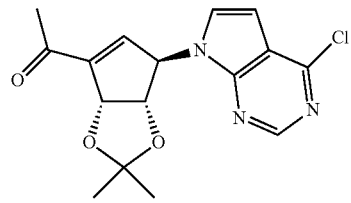 [SMILES: CC(=O)C1=C[C@@H](n2ccc3c(Cl)ncnc32)[C@@H]2OC(C)(C)O[C@H]12]

To a stirred solution of 1-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethan-1-ol (4.75 g, 14.15 mmol) in dichloromethane (45 ml) at 0° C., was added Dess-Martin Periodinane (7.20 g, 16.97 mmol) portion-wise and stirred for 30 min. Water (50 ml) was added and filtered the reaction mixture through a celite bed, washed with dichloromethane (25 ml×2). Separated the layers and the organic layer was washed with brine (50 ml), dried over anhydrous sodium sulphate and concentrated in vacuo to give 4.8 g crude compound. This crude residue was purified by combiflash (R₂200, Teledyne/Isco) instrument onto a Redisep® R$_f$ column with gradient elution (0 to 50%) of ethyl acetate in petroleum ether to afford the title compound (3.8 g, 80%) as an off-white solid. $^1$H NMR (400 MHz, Chloroform-d) δ 8.68 (s, 1H), 7.10 (d, J=3.7 Hz, 1H), 6.68 (d, J=3.6 Hz, 1H), 6.63 (dt, J=2.7, 0.7 Hz, 1H), 5.96 (dt, J=2.8, 1.5 Hz, 1H), 5.75 (dd, J=5.9, 1.6 Hz, 1H), 4.82 (dt, J=5.9, 1.1 Hz, 1H), 2.47 (s, 3H), 1.52 (s, 3H), 1.39 (s, 3H); LCMS m/z=334.09 (M+; 100%).

2-((3aS,4R,6aR)-4-(4-Chloro-7H-pyrrolo[2,3-d]pyrimidin-7-yl)-2,2-dimethyl-3a,6a-dihydro-4H-cyclopenta[d][1,3]dioxol-6-yl)propan-2-ol

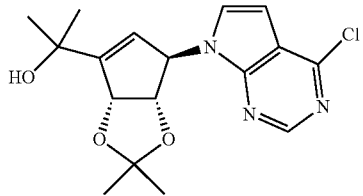 [SMILES: CC1(C)O[C@@H]2[C@H](O1)C(C(C)(C)O)=C[C@H]2n1ccc2c(Cl)ncnc21]

To a stirred solution of 1-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethan-1-one (1.0 g, 3.00 mmol)) in THF (10 ml) at −20° C., was added dropwise methyl magnesium bromide (1.498 ml, 4.49 mmol) and stirred the reaction mixture for 30 min at the same temperature. The reaction mixture was quenched with a sat. aqueous NH$_4$Cl (50 ml) and extracted with ethyl acetate (50 ml). Layers were separated, the organic layer was washed with brine (50 ml) and dried over anhydrous sodium sulphate. The organic layer was filtered and concentrated in vacuo to give 1.5 g of crude compound and this crude residue was purified by combiflash (R$_f$200, Teledyne/Isco) instrument onto a Redisep® R$_f$ column with gradient elution (0 to 30%) of ethyl acetate in petroleum ether to afford the title compound (850 mg, 81%) as an off-white solid. $^1$H NMR (400 MHz, Chloroform-d) δ 8.69 (s, 1H), 7.09 (d, J=3.6 Hz, 1H), 6.71-6.60 (m, 1H), 5.82 (s, 1H), 5.78-5.69 (m, 1H), 5.65-5.58 (m, 1H), 4.69 (dt, J=5.8, 1.0 Hz, 1H), 1.59-1.53 (m, 9H), 1.38 (s, 3H); LCMS m/z=350.2 (M+; 100%).

4-Chloro-7-((3aS,4R,6aR)-2,2-dimethyl-6-(prop-1-en-2-yl)-3a,6a-dihydro-4H-cyclopenta[d][1,3]dioxol-4-yl)-7H-pyrrolo[2,3-d]pyrimidine

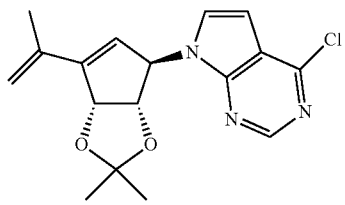 [SMILES: C=C(C)C1=C[C@@H](n2ccc3c(Cl)ncnc32)[C@@H]2OC(C)(C)O[C@H]12]

To a stirred solution of 2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)propan-2-ol (8.2 g, 23.44 mmol) in dichloromethane (80 ml) at 0° C. was added Martin's Sulfurane (17.34 g, 25.8 mmol) and the stirred the reaction mixture for 45 min at 25° C. The reaction mixture was quenched with an sat.aq. sodium bicarbonate (100 ml), extracted with dichloromethane (100 ml). Layers were separated, the organic layer was washed with brine (50 ml) and was dried over anhydrous sodium sulphate. The organic layer was filtered and concentrated in vacuo to give 8.5 g of crude compound. This crude residue was purified by combiflash (Rf200, Teledyne/Isco) instrument onto a Redisep® Rf column with gradient elution (0 to 30%) of ethyl acetate in petroleum ether to afford the title compound (4.2 g, 54.0%) as an off-white solid. $^1$H NMR (400 MHz, Chloroform-d) δ 8.71 (s, 1H), 7.11 (d, J=3.6 Hz, 1H), 6.63 (d, J=3.6 Hz, 1H), 6.00-5.94 (m, 1H), 5.76 (d, J=2.7 Hz, 1H), 5.62-5.52 (m, 2H), 5.33 (d, J=1.7 Hz, 1H), 4.67 (dt, J=6.0, 1.0 Hz, 1H), 2.03 (t, J=1.0 Hz, 3H), 1.52 (s, 3H), 1.40 (s, 3H); LCMS m/z=332.28 (M+; 100%).

7-((3aS,4R,6aR)-2,2-Dimethyl-6-(prop-1-en-2-yl)-4,6a-dihydro-3aH-cyclo penta[d][1,3] dioxol-4-yl)-4-methyl-7H-pyrrolo[2,3-d]pyrimidine

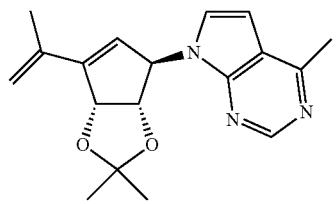 [SMILES: C=C(C)C1=C[C@@H](n2ccc3c(C)ncnc32)[C@@H]2OC(C)(C)O[C@H]12]

To a degassed solution of 4-chloro-7-((3aS,4R,6aR)-2,2-dimethyl-6-(prop-1-en-2-yl)-3a,6a-dihydro-4H-cyclopenta[d][1,3]dioxol-4-yl)-7H-pyrrolo[2,3-d]pyrimidine (1.000 g, 3.01 mmol) in dioxane (10 ml) and water (1 ml), was added potassium phosphate, tribasic (1.575 g, 9.04 mmol), dichloro[1,1'-bis(di-t-butylphosphino)ferrocene]palladium (II) (0.196 g, 0.301 mmol) and 2,4,6-trimethyl-1,3,5,2,4,6-trioxatriborinane (4.21 ml, 30.1 mmol) at 25° C. The resulting mixture was stirred at 100° C. for 50 min under microwave condition. Solvent was removed and the crude residue was purified by combiflash (Rf200, Teledyne/Isco) instrument onto a Redisep® Rf column with gradient elution (0 to 50%) of ethyl acetate in petroleum ether to afford the title compound (0.84 g, 90%) as an off-white solid. LCMS m/z=312.28 (M+1; 100%).

7-((3aS,4R,6aR)-6-(((tert-Butyldiphenylsilyl)oxy) methyl)-2,2-dimethyl-3a,6a-dihydro-4H-cyclopenta[d][1,3]dioxol-4-yl)-4-methyl-7H-pyrrolo[2,3-d]pyrimidine (A)

7-((3aS,4R,6aR)-6-(((tert-Butyldiphenylsilyl)oxy) methyl)-2,2-dimethyl-3a,6a-dihydro-4H-cyclopenta[d][1,3]dioxol-4-yl)-7H-pyrrolo[2,3-d]pyrimidine (B)

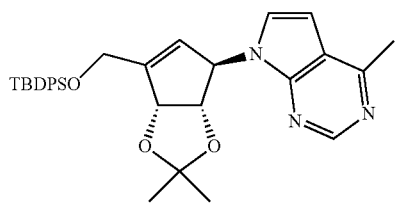

A

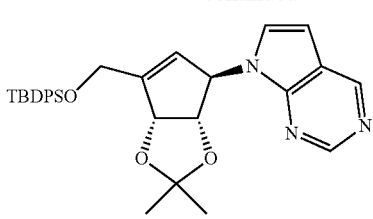

To a degassed solution of 7-((3aS,4R,6aR)-6-(((tert-butyldiphenylsilyl)oxy)methyl)-2,2-dimethyl-3a,6a-dihydro-4H-cyclopenta[d][1,3]dioxol-4-yl)-4-chloro-7H-pyrrolo[2,3-d]pyrimidine (5 g, 8.93 mmol) in dioxane (80 ml) and water (10 ml), was added potassium phosphate tribasic (4.66 g, 26.8 mmol), dichloro[1,1'-bis(di-t-butylphosphino) ferrocene]palladium(II) (0.582 g, 0.893 mmol) and 2,4,6-trimethyl-1,3,5,2,4,6-trioxatriborinane (12.48 ml, 89 mmol) at 25° C. The reaction mixture was heated at 80° C. for 8 h. The reaction mixture was diluted with ethyl acetate (50 ml) and washed with water (50 ml). Layers were separated and the organic layer was washed with brine (50 ml) and dried over anhydrous sodium sulphate. The organic layer was filtered and concentrated in vacuo to give 4.3 g of crude compound. This crude residue was purified by combiflash (Rf200, Teledyne/Isco) instrument onto a Redisep® Rf column with gradient elution (0 to 20%) of ethyl acetate in petroleum ether to afford the title compound, A (3.2 g, 66%) and B (0.75 g, 15.98%) as an off-white solids. $^1$H NMR of A (400 MHz, Chloroform-d) δ 8.83 (s, 1H), 7.71 (tt, J=6.6, 1.5 Hz, 4H), 7.48-7.37 (m, 6H), 6.91 (d, J=3.6 Hz, 1H), 6.57 (d, J=3.6 Hz, 1H), 5.88 (s, 2H), 5.25 (d, J=5.7 Hz, 1H), 4.60 (d, J=5.7 Hz, 1H), 4.55-4.45 (m, 2H), 2.77 (s, 3H), 1.45 (s, 3H), 1.32 (s, 3H), 1.11 (s, 9H); LCMS m/z=540.4 (M+1; 100%); $^1$H NMR of B (400 MHz, Chloroform-d) δ 7.71 (tt, J=6.6, 1.5 Hz, 4H), 7.53-7.35 (m, 6H), 6.98 (d, J=3.6 Hz, 1H), 6.57 (d, J=3.6 Hz, 1H), 5.90 (d, J=14.5 Hz, 2H), 5.26 (d, J=5.7 Hz, 1H), 4.61 (d, J=5.7 Hz, 1H), 4.51 (d, J=9.3 Hz, 2H), 1.46 (s, 3H), 1.33 (s, 3H), 1.28 (s, 2H), 1.11 (s, 9H); LCMS m/z=526.44 (M+1; 100%).

((3aS,4R,6aR)-2,2-dimethyl-4-(4-methyl-7H-pyrrolo[2,3-d]pyrimidin-7-yl)-3a,6a-dihydro-4H-cyclopenta[d][1,3]dioxol-6-yl)methanol

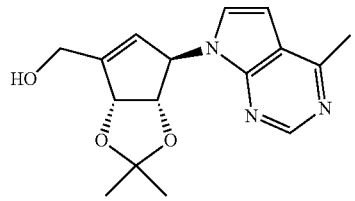 [SMILES: Cc1ncnc2c1ccn2[C@@H]1C=C(CO)[C@H]2OC(C)(C)O[C@H]21]

To a stirred solution of 7-((3aS,4R,6aR)-6-(((tert-butyldiphenylsilyl)oxy)methyl)-2,2-dimethyl-3a,6a-dihydro-4H-cyclopenta[d][1,3]dioxol-4-yl)-4-methyl-7H-pyrrolo[2,3-d]pyrimidine (3.20 g, 5.93 mmol) in THF (20 ml), was slowly added TBAF (8.89 ml, 8.89 mmol) at 25° C. and stirred the reaction mixture at 25° C. for 15 h. Volatiles were removed in vacuo and the crude residue was purified by combiflash (R$_f$200, Teledyne/Isco) instrument onto a Redisep® R$_f$ column with gradient elution (0 to 100%) of ethyl acetate in petroleum ether to afford the title compound (1.5 g, 84%) as an off-white solid. 1H NMR (400 MHz, Chloroform-d) δ 8.81 (s, 1H), 7.06 (d, J=3.6 Hz, 1H), 6.55 (d, J=3.6 Hz, 1H), 5.90-5.78 (m, 2H), 5.41 (ddd, J=5.8, 1.7, 0.9 Hz, 1H), 4.65 (dt, J=5.8, 0.9 Hz, 1H), 4.56-4.42 (m, 2H), 3.35 (d, J=8.2 Hz, 1H), 2.74 (s, 3H), 1.53 (s, 3H), 1.37 (s, 3H); LCMS m/z=302.21 (M+1; 100%).

(3aS,4R,6aR)-2,2-Dimethyl-4-(4-methyl-7H-pyrrolo[2,3-d]pyrimidin-7-yl)-3a,6a-dihydro-4H-cyclopenta[d][1,3]dioxole-6-carbaldehyde

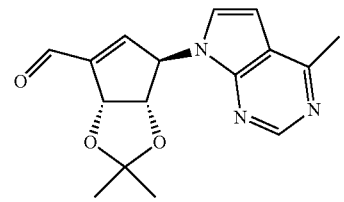 [SMILES: Cc1ncnc2c1ccn2[C@@H]1C=C(C=O)[C@H]2OC(C)(C)O[C@H]21]

To a stirred solution of 7-((3aS,4R,6aR)-6-(((tert-Butyldiphenylsilyl)oxy)methyl)-2,2-dimethyl-3a,6a-dihydro-4H-cyclopenta[d][1,3]dioxol-4-yl)-7H-pyrrolo[2,3-d]pyrimidine (1.50 g, 4.98 mmol) in dichloromethane (100 ml) at 0° C., was added Dess-Martin Periodinane (2.53 g, 5.97 mmol) portion-wise and stirred for 1 h. The reaction mixture was diluted with methylene chloride (50 ml) and washed with water (50 ml). Layers were separated, the organic layer was washed with brine (50 ml) and dried over anhydrous sodium sulphate. The organic layer was filtered and concentrated in vacuo to give a crude compound and this crude residue was purified by combiflash (Rf200, Teledyne/Isco) instrument onto a Redisep® Rf column with gradient elution (0 to 30%) of ethyl acetate in petroleum ether to afford the title compound (0.95 g, 63.8%) as an off-white solid. $^1$H NMR (400 MHz, Chloroform-d) δ 10.00 (s, 1H), 8.80 (s, 1H), 7.02 (d, J=3.6 Hz, 1H), 6.82-6.76 (m, 1H), 6.63 (d, J=3.6 Hz, 1H), 6.00 (dt, J=2.7, 1.4 Hz, 1H), 5.76 (dd, J=5.9, 1.5 Hz, 1H), 4.87 (dt, J=5.9, 1.1 Hz, 1H), 2.77 (s, 3H), 1.53 (s, 3H), 1.38 (s, 3H); LCMS m/z=300.15 (M+1; 100%)

7-((3aS,4R,6aR)-2,2-Dimethyl-6-vinyl-3a,6a-dihydro-4H-cyclopenta[d] [1,3]dioxol-4-yl)-4-methyl-7H-pyrrolo[2,3-d]pyrimidine

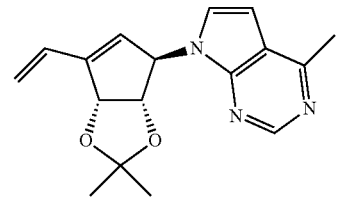 [SMILES: C=CC1=C[C@@H](n2ccc3c(C)ncnc32)[C@@H]2OC(C)(C)O[C@H]12]

The title compound was synthesized by following an analogous reaction protocol as was described in the preparation of 4-chloro-7-((3aS,4R,6aR)-2,2-dimethyl-6-vinyl-3a,6a-dihydro-4H-cyclopenta[d][1,3] dioxol-4-yl)-7H-pyrrolo[2,3-d]pyrimidine. $^1$H NMR (400 MHz, Chloroform-d) δ 8.83 (s, 1H), 7.01 (d, J=3.6 Hz, 1H), 6.68-6.53 (m, 2H), 5.95 (d, J=2.5 Hz, 1H), 5.80-5.71 (m, 2H), 5.56 (dd, J=6.0, 1.4 Hz, 1H), 5.47 (d, J=10.8 Hz, 1H), 4.65 (d, J=5.8 Hz, 1H), 2.75 (s, 3H), 1.52 (s, 3H), 1.40 (s, 3H); LCMS m/z=298.5 (M+1; 100%).

((3aS,4R,6aR)-2,2-Dimethyl-4-(7H-pyrrolo[2,3-d]
pyrimidin-7-yl)-3a,6a-dihydro-4H-cyclopenta[d][1,
3]dioxol-6-yl)methanol

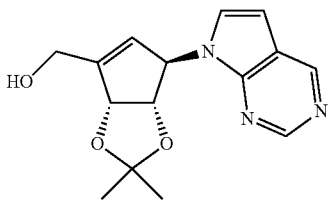 [SMILES: CC1(C)O[C@@H]2[C@H](O1)C(CO)=C[C@H]2n1ccc2cncnc21]

The title compound was synthesized by following an analogous reaction protocol as was described in the preparation of 7-((3aS,4R,6aR)-6-(((tert-butyldiphenylsilyl)oxy) methyl)-2,2-dimethyl-3a,6a-dihydro-4H-cyclopenta[d][1,3] dioxol-4-yl)-7H-pyrrolo[2,3-d]pyrimidine. LCMS m/z=287.90 (M+; 100%).

(3aS,4R,6aR)-2,2-Dimethyl-4-(7H-pyrrolo[2,3-d]
pyrimidin-7-yl)-3a,6a-dihydro-4H-cyclopenta[d][1,
3]dioxole-6-carbaldehyde

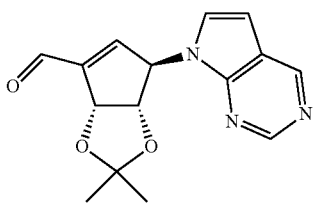 [SMILES: CC1(C)O[C@@H]2[C@H](O1)C(C=O)=C[C@H]2n1ccc2cncnc21]

The title compound was synthesized by following an analogous reaction protocol as was described in the preparation of (3aS,4R,6aR)-2,2-Dimethyl-4-(4-methyl-7H-pyrrolo[2,3-d]pyrimidin-7-yl)-3a,6a-dihydro-4H-cyclopenta[d][1,3]dioxole-6-carbaldehyde. $^1$H NMR (400 MHz, Chloroform-d) δ 10.01 (s, 1H), 9.04 (s, 1H), 8.93 (s, 1H), 7.11 (d, J=3.6 Hz, 1H), 6.83-6.77 (m, 1H), 6.67 (d, J=3.7 Hz, 1H), 6.03 (dt, J=2.8, 1.4 Hz, 1H), 5.77 (dd, J=5.9, 1.5 Hz, 1H), 4.89 (dt, J=6.0, 1.2 Hz, 1H), 1.54 (s, 3H), 1.41 (s, 3H); LCMS m/z=286.09 (M+; 100%).

7-((3aS,4R,6aR)-2,2-Dimethyl-6-vinyl-3a,6a-di-
hydro-4H-cyclopenta[d][1,3]dioxol-4-yl)-7H-pyrrolo
[2,3-d]pyrimidine

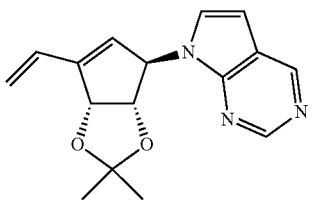 [SMILES: C=CC1=C[C@@H](n2ccc3cncnc32)[C@@H]2OC(C)(C)O[C@H]12]

The title compound was synthesized by following an analogous reaction protocol as was described in the preparation of 4-chloro-7-((3aS,4R,6aR)-2,2-dimethyl-6-vinyl-3a,6a-dihydro-4H-cyclopenta[d][1,3] dioxol-4-yl)-7H-pyrrolo[2,3-d]pyrimidine. $^1$H NMR (400 MHz, Chloroform-d) δ 8.97 (d, J=15.8 Hz, 2H), 7.09 (d, J=3.7 Hz, 1H), 6.68-6.56 (m, 2H), 5.98 (d, J=2.7 Hz, 1H), 5.82-5.72 (m, 2H), 5.60-5.54 (m, 1H), 5.52-5.44 (m, 1H), 4.66 (dt, J=5.8, 1.0 Hz, 1H), 1.52 (s, 3H), 1.40 (s, 3H); LCMS m/z=284.04 (M+1; 100%).

7-((3aS,4R,6aR)-6-(((tert-Butyldiphenylsilyl)oxy)
methyl)-2,2-dimethyl-4,6a-dihydro-3aH-cyclopenta
[d][1,3]dioxol-4-yl)-4-chloro-5-fluoro-7H-pyrrolo[2,
3-d] pyrimidine

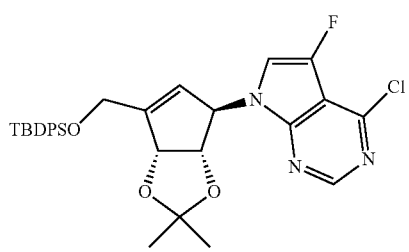

To a stirred solution of (3aS,4S,6aR)-6-(((tert-butyldiphenylsilyl)oxy)methyl)-2,2-dimethyl-3a,6a-dihydro-4H-cyclopenta[d][1,3]dioxol-4-ol (3.5 g, 8.24 mmol) in THF (50 ml) was added 4-chloro-5-fluoro-7H-pyrrolo[2,3-d]pyrimidine (3.54 g, 20.61 mmol, which was synthesized by following the same reaction protocol as was described in WO2005/16878, A2), triphenylphosphine (5.40 g, 20.61 mmol), DIAD (4.01 ml, 20.61 mmol) at 0° C. and stirred for 30 min. The resulting reaction mixture was stirred at 25° C. for 16 h. Volatiles were removed in vacuo and the crude residue was purified by combiflash (Rf200, Teledyne/Isco) instrument onto a Redisep® Rf column with gradient elution (0 to 10%) of ethyl acetate in petroleum ether to afford the title compound (2.7 g, 56.7%) as an off-white solid. LCMS m/z=577.94 (M+; 100%).

((3aR,6R,6aS)-6-(4-Chloro-5-fluoro-7H-pyrrolo[2,3-
d]pyrimidin-7-yl)-2,2-dimethyl-6,6a-dihydro-3aH-
cyclopenta[d][1,3]dioxol-4-yl)methanol

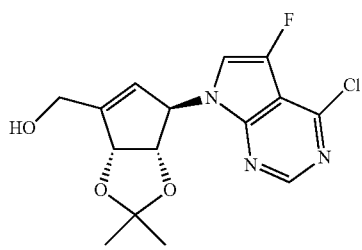 [SMILES: CC1(C)O[C@@H]2[C@H](O1)C(CO)=C[C@H]2n1cc(F)c2c(Cl)ncnc21]

The title compound was synthesized by following an analogous reaction protocol as was described in the preparation of 7-((3aS,4R,6aR)-6-(((tert-butyldiphenylsilyl)oxy) methyl)-2,2-dimethyl-3a,6a-dihydro-4H-cyclopenta[d][1,3] dioxol-4-yl)-7H-pyrrolo[2,3-d]pyrimidine. LCMS m/z=340.03 (M+; 100%).

(3aR,6R,6aS)-6-(4-Chloro-5-fluoro-7H-pyrrolo[2,3-d]pyrimidin-7-yl)-2,2-dimethyl-6,6a-dihydro-3aH-cyclopenta[d][1,3]dioxole-4-carbaldehyde

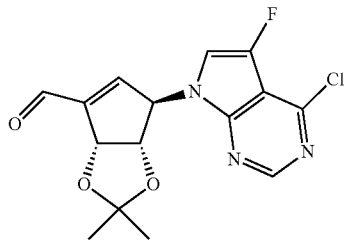 [SMILES: CC1(C)O[C@@H]2[C@H](O1)C(C=O)=C[C@H]2n1cc(F)c2c(Cl)ncnc21]

The title compound was synthesized by following an analogous reaction protocol as was described in the preparation of (3aS,4R,6aR)-2,2-Dimethyl-4-(4-methyl-7H-pyrrolo[2,3-d]pyrimidin-7-yl)-3a,6a-dihydro-4H-cyclopenta[d][1,3]dioxole-6-carbaldehyde. $^1$H NMR (400 MHz, DMSO-d6) δ 9.90 (s, 1H), 8.73 (s, 1H), 7.80 (d, J=2.0 Hz, 1H), 7.10-7.03 (m, 1H), 6.01 (dq, J=2.7, 1.4 Hz, 1H), 5.57 (dd, J=6.0, 1.5 Hz, 1H), 4.80 (dt, J=6.0, 1.2 Hz, 1H), 1.39 (s, 3H), 1.28 (s, 3H); LCMS m/z=338.03 (M+; 100%).

4-Chloro-7-((3aS,4R,6aR)-2,2-dimethyl-6-vinyl-4,6a-dihydro-3aH-cyclopenta[d][1,3]dioxol-4-yl)-5-fluoro-7H-pyrrolo[2,3-d]pyrimidine

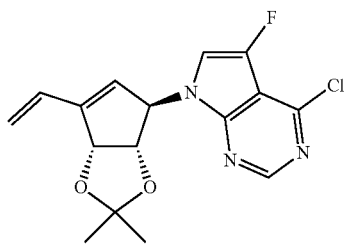 [SMILES: C=CC1=C[C@@H](n2cc(F)c3c(Cl)ncnc32)[C@@H]2OC(C)(C)O[C@H]12]

The title compound was synthesized by following an analogous reaction protocol as was described in the preparation of 4-chloro-7-((3aS,4R,6aR)-2,2-dimethyl-6-vinyl-3a,6a-dihydro-4H-cyclopenta[d][1,3] dioxol-4-yl)-7H-pyrrolo[2,3-d]pyrimidine. $^1$H NMR (400 MHz, DMSO-d$_6$) δ 8.71 (s, 1H), 7.66 (d, J=2.0 Hz, 1H), 6.66-6.52 (m, 1H), 5.90-5.78 (m, 2H), 5.67-5.55 (m, 2H), 5.47-5.36 (m, 1H), 4.71 (d, J=6.0 Hz, 1H), 1.38 (s, 3H), 1.31 (s, 3H); LCMS m/z=336.03 (M+; 100%).

7-((3aS,4R,6aR)-6-((((tert-Butyldiphenylsilyl)oxy)methyl)-2,2-dimethyl-4,6a-dihydro-3aH-cyclopenta[d][1,3]dioxol-4-yl)-2-chloro-7H-pyrrolo[2,3-d]pyrimidine

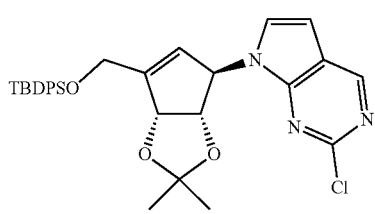

To a stirred solution of (3aS,4S,6aR)-6-(((tert-Butyldiphenylsilyl)oxy)methyl)-2,2-dimethyl-3a,6a-dihydro-4H-cyclopenta[d][1,3]dioxol-4-ol (1.2 g, 2.83 mmol) in THF (15 ml) was added 2-chloro-7H-pyrrolo[2,3-d]pyrimidine (0.738 g, 4.80 mmol), triphenylphosphine (2.59 g, 9.89 mmol) and DIAD (1.923 ml, 9.89 mmol) slowly at 0° C. and stirred for 5 mins. The reaction mixture was brought to 25° C. and stirred for 1 h. Volatiles were removed in vacuo and the crude residue was purified by combiflash (Rf200, Teledyne/Isco) instrument onto a Redisep® Rf column with gradient elution (0 to 15%) of ethyl acetate in petroleum ether to afford the title compound (1.1 g, 69.5%) as an off-white solid. $^1$H NMR (400 MHz, Chloroform-d) δ 8.84 (s, 1H), 7.70 (ddt, J=6.6, 5.0, 1.5 Hz, 4H), 7.50-7.34 (m, 6H), 6.94 (d, J=3.6 Hz, 1H), 6.59 (d, J=3.6 Hz, 1H), 5.84 (dt, J=19.8, 2.2 Hz, 2H), 5.30 (d, J=5.7 Hz, 1H), 4.63 (d, J=5.6 Hz, 1H), 4.57-4.42 (m, 2H), 1.43 (s, 3H), 1.33 (s, 3H), 1.10 (s, 9H); LCMS m/z=560.3 (M+; 100).

((3aR,6R,6aS)-6-(2-Chloro-7H-pyrrolo[2,3-d]pyrimidin-7-yl)-2,2-dimethyl-6,6a-dihydro-3aH-cyclopenta[d][1,3]dioxol-4-yl)methanol

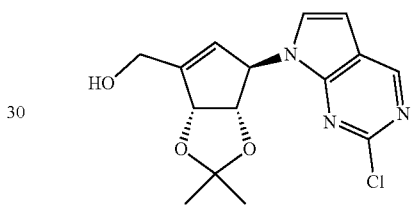

To a stirred solution of 7-((3aS,4R,6aR)-6-(((tert-butyldiphenylsilyl)oxy)methyl)-2,2-dimethyl-3a,6a-dihydro-4H-cyclopenta[d][1,3]dioxol-4-yl)-2-chloro-7H-pyrrolo[2,3-d]pyrimidine (500 mg, 0.893 mmol) in THF (5 ml) at 0° C., was added TBAF (1.250 ml, 1.250 mmol) slowly and stirred the reaction mixture at the same temperature for 10 min. The reaction mixture was brought to 25° C. and stirred for 30 mins. Volatiles were removed in vacuo and the crude residue was purified by combiflash (Rf200, Teledyne/Isco) instrument onto a Redisep® Rf column with gradient elution (0 to 40%) of ethyl acetate in petroleum ether to afford the title compound (0.27 g, 94%) as a colourless oil. $^1$H NMR (400 MHz, Chloroform-d) δ 8.81 (s, 1H), 7.28 (s, 1H), 7.08 (d, J=3.7 Hz, 1H), 6.57 (d, J=3.7 Hz, 1H), 5.92-5.62 (m, 2H), 5.47 (d, J=5.7 Hz, 1H), 4.69 (dt, J=5.6, 0.9 Hz, 1H), 4.59-4.37 (m, 2H), 1.52 (s, 3H), 1.38 (s, 3H); LCMS m/z=321.09 (M+; 100).

(3aR,6R,6aS)-6-(2-Chloro-7H-pyrrolo[2,3-d]pyrimidin-7-yl)-2,2-dimethyl-6,6a-dihydro-3aH-cyclopenta[d][1,3]dioxole-4-carbaldehyde

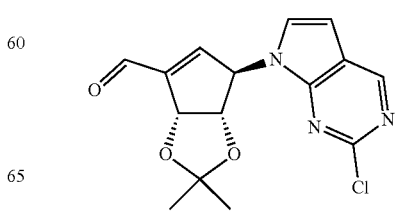

The title compound was synthesized by following an analogous reaction protocol as was described in the preparation of (3aS,4R,6aR)-2,2-Dimethyl-4-(4-methyl-7H-pyrrolo[2,3-d]pyrimidin-7-yl)-3a,6a-dihydro-4H-cyclopenta[d][1,3]dioxole-6-carbaldehyde. ¹H NMR (400 MHz, Chloroform-d) δ 9.99 (s, 1H), 8.86 (s, 1H), 7.04 (d, J=3.7 Hz, 1H), 6.75 (dd, J=2.6, 0.9 Hz, 1H), 6.65 (d, J=3.7 Hz, 1H), 6.00 (dt, J=2.7, 1.4 Hz, 1H), 5.77 (dd, J=5.9, 1.5 Hz, 1H), 4.88 (dd, J=5.9, 1.2 Hz, 1H), 1.53 (s, 3H), 1.40 (s, 3H); LCMS m/z=319.90 (M+; 100).

2-Chloro-7-((3aS,4R,6aR)-2,2-dimethyl-6-vinyl-4,6a-dihydro-3aH-cyclopenta[d][1,3]dioxol-4-yl)-7H-pyrrolo[2,3-d]pyrimidine

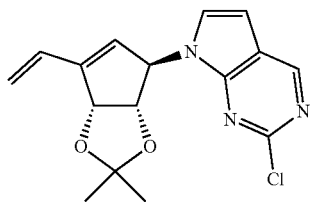 [SMILES: C=CC1=C[C@@H](n2ccc3cnc(Cl)nc32)[C@@H]2OC(C)(C)O[C@H]12]

The title compound was synthesized by following an analogous reaction protocol as was described in the preparation of 4-chloro-7-((3aS,4R,6aR)-2,2-dimethyl-6-vinyl-3a,6a-dihydro-4H-cyclopenta[d][1,3] dioxol-4-yl)-7H-pyrrolo[2,3-d]pyrimidine. ¹H NMR (400 MHz, Chloroform-d) δ 8.82 (s, 1H), 7.03 (d, J=3.6 Hz, 1H), 6.64-6.53 (m, 2H), 5.93 (d, J=2.6 Hz, 1H), 5.81-5.69 (m, 2H), 5.60 (dd, J=5.8, 1.4 Hz, 1H), 5.53-5.44 (m, 1H), 4.68 (dd, J=5.8, 1.1 Hz, 1H), 1.45 (s, 6H); LCMS m/z=318.15 (M+; 100).

1-((3aS,4R,6aR)-6-(((tert-Butyldiphenylsilyl)oxy)methyl)-2,2-dimethyl-4,6a-dihydro-3aH-cyclopenta[d][1,3]dioxol-4-yl)-4-chloro-1H-pyrrolo[3,2-c]pyridine

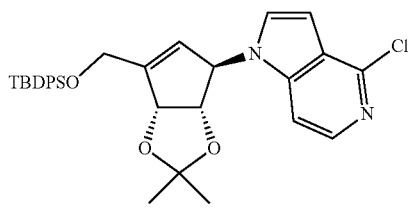

To a stirred solution of (3aS,4S,6aR)-6-(((tert-butyldiphenylsilyl)oxy)methyl)-2,2-dimethyl-3a,6a-dihydro-4H-cyclopenta[d][1,3]dioxol-4-ol (0.5 g, 1.178 mmol) in THF (7 ml) at 0° C. was added 4-chloro-1H-pyrrolo[3,2-c]pyridine (0.305 g, 2.002 mmol), triphenylphosphine (1.081 g, 4.12 mmol) and DIAD (0.801 ml, 4.12 mmol) slowly and stirred for 5 min. The reaction mixture was stirred at 25° C. for 16 h. Volatiles were removed in vacuo and the crude residue was purified by combiflash (Rf200, Teledyne/Isco) instrument onto a Redisep® Rf column with gradient elution (0 to 10%) of ethyl acetate in petroleum ether to afford the title compound (0.3 g, 45.6%) as an off-white solid. LCMS m/z=559.23 (M+; 100).

((3aR,6R,6aS)-6-(4-Chloro-1H-pyrrolo[3,2-c]pyridin-1-yl)-2,2-dimethyl-6,6a-dihydro-3aH-cyclopenta[d][1,3]dioxol-4-yl)methanol

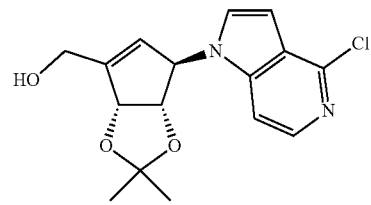

To a stirred solution of 1-((3aS,4R,6aR)-6-(((tert-butyldiphenylsilyl)oxy)methyl)-2,2-dimethyl-3a,6a-dihydro-4H-cyclopenta[d][1,3]dioxol-4-yl)-4-chloro-1H-pyrrolo[3,2-c]pyridine (1.3 g, 2.325 mmol) in THF (13 ml) was added TBAF (3.25 ml, 3.25 mmol) at 0° C. and stirred for 5 mins. The reaction mixture was brought to 25° C. and stirred for 1 h. Volatiles were removed in vacuo and the crude residue was purified by combiflash (Rf200, Teledyne/Isco) instrument onto a Redisep® Rf column with gradient elution (0 to 45%) of ethyl acetate in petroleum ether to afford the title compound (0.5 g, 67%) as an off-white solid. LCMS m/z=319.71 (M-1; 100).

(3aR,6R,6aS)-6-(4-Chloro-1H-pyrrolo[3,2-c]pyridin-1-yl)-2,2-dimethyl-6,6a-dihydro-3aH-cyclopenta[d][1,3]dioxole-4-carbaldehyde

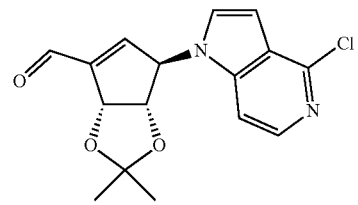 [SMILES: CC1(C)O[C@@H]2[C@H](O1)C(C=O)=C[C@H]2n1ccc2c(Cl)nccc21]

The title compound was synthesized by following an analogous reaction protocol as was described in the preparation of (3aS,4R,6aR)-2,2-Dimethyl-4-(4-methyl-7H-pyrrolo[2,3-d]pyrimidin-7-yl)-3a,6a-dihydro-4H-cyclopenta[d][1,3]dioxole-6-carbaldehyde. ¹H NMR (400 MHz, Chloroform-d) δ 10.05 (s, 1H), 8.19 (d, J=5.8 Hz, 1H), 7.34 (dd, J=5.9, 0.9 Hz, 1H), 6.99 (d, J=3.3 Hz, 1H), 6.94-6.89 (m, 1H), 6.74 (dd, J=3.3, 0.9 Hz, 1H), 5.73-5.58 (m, 2H), 4.67 (dt, J=5.9, 1.2 Hz, 1H), 1.55 (s, 3H), 1.39 (s, 3H); LCMS m/z=319.05 (M+; 100).

4-Chloro-1-((3aS,4R,6aR)-2,2-dimethyl-6-vinyl-4,6a-dihydro-3aH-cyclopenta[d][1,3] dioxol-4-yl)-1H-pyrrolo[3,2-c]pyridine

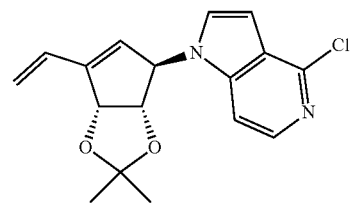 [SMILES: C=CC1=C[C@@H](n2ccc3c(Cl)nccc32)[C@@H]2OC(C)(C)O[C@H]12]

The title compound was synthesized by following an analogous reaction protocol as was described in the preparation of 4-chloro-7-((3aS,4R,6aR)-2,2-dimethyl-6-vinyl-3a,6a-dihydro-4H-cyclopenta[d][1,3] dioxol-4-yl)-7H-pyrrolo[2,3-d]pyrimidine. ¹H NMR (400 MHz, Chloroform-d) δ 8.14 (d, J=5.8 Hz, 1H), 7.37 (dd, J=5.9, 0.9 Hz, 1H), 7.06 (d, J=3.3 Hz, 1H), 6.70-6.59 (m, 2H), 5.91-5.72 (m, 2H), 5.55-5.48 (m, 3H), 4.59-4.47 (m, 1H), 1.53 (s, 3H), 1.40 (s, 3H); LCMS m/z=317.15 (M+; 100).

1-((3aS,4R,6aR)-2,2-Dimethyl-6-vinyl-3a,6a-dihydro-4H-cyclopenta[d][1,3]dioxol-4-yl)-4-methyl-1H-pyrrolo[3,2-c]pyridine

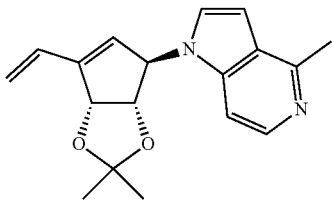 [SMILES: C=CC1=C[C@@H](n2ccc3c(C)nccc32)[C@@H]2OC(C)(C)O[C@H]12]

The title compound was synthesized by following an analogous reaction protocol as was described in the preparation of 7-((3aS,4R,6aR)-2,2-dimethyl-6-(prop-1-en-2-yl)-4,6a-dihydro-3aH-cyclo penta[d][1,3] dioxol-4-yl)-4-methyl-7H-pyrrolo[2,3-d]pyrimidine.

LCMS m/z=297.21 (M+; 100). Des chloro compound i.e. 1-((3aS,4R,6aR)-2,2-dimethyl-6-vinyl-3a,6a-dihydro-4H-cyclopenta[d][1,3]dioxol-4-yl)-1H-pyrrolo[3,2-c]pyridine was also formed, which was separated after Suzuki coupling step (Table-6) by reverse phase preparative HPLC.

(3aR,6aR)-6-(((tert-Butyldiphenylsilyl)oxy)methyl)-5-iodo-2,2-dimethyl-3a,6a-dihydro-4H-cyclopenta[d][1,3]dioxol-4-one

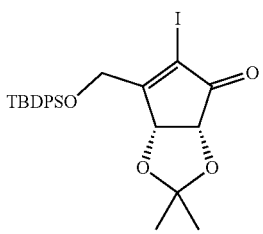

To a stirred solution of (3aR,6aR)-6-(((tert-butyldiphenylsilyl)oxy)methyl)-2,2-dimethyl-3a,6a-dihydro-4H-cyclopenta[d][1,3]dioxol-4-one (20 g, 47.3 mmol) and iodine (14.41 g, 56.8 mmol) in dichloromethane (250 ml), was added pyridine (3.45 ml, 42.6 mmol) under nitrogen atmosphere at 0° C. and stirred at 25° C. for 4 h. The reaction mixture was diluted with methylene chloride (100 ml) and washed with a saturated aqueous sodium thiosulfate (100 ml). Layers were separated, the organic layer was washed with brine (100 ml) and dried over anhydrous sodium sulphate. The organic layer was filtered and concentrated in vacuo to give 18 g of crude compound. This crude residue was purified by combiflash (Rf200, Teledyne/Isco) instrument onto a Redisep® Rf column with gradient elution (0 to 20%) of ethyl acetate in petroleum ether to afford the title compound (15 g, 57.8%) as a colorless oil. ¹H NMR (400 MHz, Chloroform-d) δ 7.74 (ddt, J=17.2, 6.5, 1.6 Hz, 4H), 7.58-7.36 (m, 6H), 5.19 (d, J=5.8 Hz, 1H), 4.79 (t, J=5.6 Hz, 1H), 4.53-4.33 (m, 2H), 1.45 (s, 3H), 1.35 (s, 3H), 1.08 (s, 9H).

(3aS,4R,6aR)-6-(((tert-Butyldiphenylsilyl)oxy) methyl)-5-iodo-2,2-dimethyl-3a,6a-dihydro-4H-cyclopenta[d][1,3]dioxol-4-ol

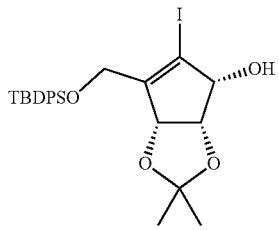

To a stirred solution of (3aR,6aR)-6-(((tert-butyldiphenylsilyl)oxy)methyl)-5-iodo-2,2-dimethyl-3a,6a-dihydro-4H-cyclopenta[d][1,3]dioxol-4-one (13.7 g, 24.98 mmol) in methanol (130 ml), was added cerium (III) chloride heptahydrate (10.24 g, 27.5 mmol) at 0° C. and the reaction mixture was stirred for 30 min. Sodium borohydride (0.992 g, 26.2 mmol) was added portion-wise and the resulting mixture was stirred at 0° C. for 2 h under N₂ atmosphere. The reaction mass was quenched with water (150 ml) and extracted with ethyl acetate (150 ml×2). The combined organic layer was washed with brine (100 ml), dried over sodium sulfate & concentrated to give 8.5 g of crude compound. This residue was purified by combiflash (Rf200, Teledyne/Isco) instrument onto a Redisep® Rf column with gradient elution (0 to 20%) of ethyl acetate in petroleum ether to afford the title compound (6 g, 43.6%) as a colorless oil. ¹H NMR (400 MHz, Chloroform-d) δ 7.84-7.62 (m, 4H), 7.48-7.39 (m, 6H), 5.19 (d, J=5.8 Hz, 1H), 4.86-4.71 (m, 1H), 4.46-4.31 (m, 3H), 2.84 (d, J=10.3 Hz, 1H), 1.45 (s, 3H), 1.38-1.33 (s, 3H), 1.08 (s 9H).

7-((3aS,4S,6aR)-6-(((tert-Butyldiphenylsilyl)oxy) methyl)-5-iodo-2,2-dimethyl-3a,6a-dihydro-4H-cyclopenta[d][1,3]dioxol-4-yl)-4-chloro-7H-pyrrolo[2,3-d]pyrimidine

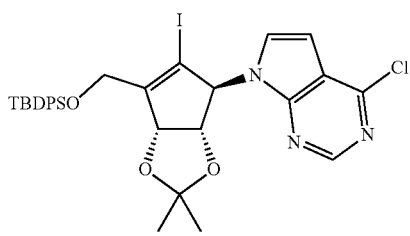

The title compound was synthesized by following an analogous reaction protocol as was described in the preparation of 1-((3aS,4R,6aR)-6-(((tert-butyldiphenylsilyl)oxy) methyl)-2,2-dimethyl-4,6a-dihydro-3aH-cyclopenta[d][1,3] dioxol-4-yl)-4-chloro-1H-pyrrolo[3,2-c] pyridine. ¹H NMR (400 MHz, Chloroform-d) δ 8.64 (s, 1H), 7.75 (ddt, J=20.3, 6.8, 1.5 Hz, 4H), 7.53-7.31 (m, 6H), 6.96 (d, J=3.7 Hz, 1H), 6.67 (d, J=3.6 Hz, 1H), 5.74-5.62 (m, 2H), 4.86-4.80 (m, 1H), 4.54-4.42 (m, 2H), 1.48 (s, 3H), 1.42 (s, 3H), 1.13 (s, 9H). LCMS m/z=686.33 (M+; 100).

7-((3aS,4S,6aR)-6-(((tert-Butyldiphenylsilyl)oxy) methyl)-5-iodo-2,2-dimethyl-3a,6a-dihydro-4H-cyclopenta[d][1,3]dioxol-4-yl)-N-(4-methoxybenzyl)-7H-pyrrolo[2,3-d]pyrimidin-4-amine

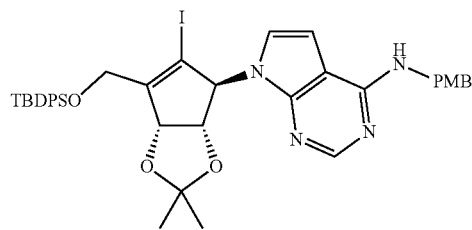

A mixture of 7-((3aS,4S,6aR)-6-(((tert-butyldiphenylsilyl)oxy)methyl)-5-iodo-2,2-dimethyl-3a,6a-dihydro-4H-cyclopenta[d][1,3]dioxol-4-yl)-4-chloro-7H-pyrrolo[2,3-d]pyrimidine (1.7 g, 2.478 mmol) and (4-methoxyphenyl) methanamine (3.40 g, 24.78 mmol) in ethanol (1.7 ml) was refluxed for 4 h. The reaction mixture was quenched with water (150 ml) and extracted with ethyl acetate (150 ml). The combined organic layer was washed with brine (100 ml), dried over sodium sulfate and concentrated to give 8.5 g of crude compound. This residue was purified by combiflash (Rf200, Teledyne/Isco) instrument onto a Redisep® Rf column with gradient elution (0 to 40%) of ethyl acetate in petroleum ether to afford the title compound (1.8 g, 92%) as an off white solid. $^1$H NMR (400 MHz, Chloroform-d) δ 8.37 (d, J=6.4 Hz, 1H), 7.76 (ddt, J=19.4, 6.8, 1.4 Hz, 4H), 7.52-7.32 (m, 8H), 7.00-6.88 (m, 2H), 6.67 (d, J=3.7 Hz, 1H), 6.42 (d, J=3.6 Hz, 1H), 5.71 (s, 1H), 5.61 (d, J=6.2 Hz, 1H), 4.80 (dd, J=12.7, 5.8 Hz, 3H), 4.60-4.37 (m, 2H), 3.84 (s, 3H), 3.77 (s, 1H), 1.46 (s, 3H), 1.41 (s, 3H), 1.13 (s, 9H); LCMS m/z=786.41 (M+; 100).

7-((3aS,4R,6aR)-6-(((tert-Butyldiphenylsilyl)oxy) methyl)-2,2,5-trimethyl-3a,6a-dihydro-4H-cyclopenta[d][1,3]dioxol-4-yl)-N-(4-methoxybenzyl)-7H-pyrrolo[2,3-d]pyrimidin-4-amine

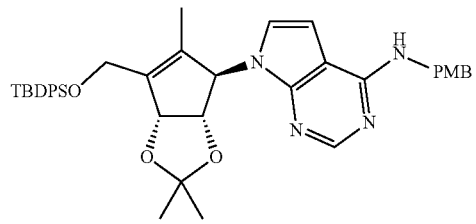

A mixture of 7-((3aS,4S,6aR)-6-(((tert-butyldiphenylsilyl)oxy)methyl)-5-iodo-2,2-dimethyl-3a,6a-dihydro-4H-cyclopenta[d][1,3]dioxol-4-yl)-N-(4-methoxybenzyl)-7H-rrolo[2,3-d] pyrimidin-4-amine (3.2 g, 4.07 mmol), 2,4,6-trimethyl-1,3,5,2,4,6-trioxatriborinane (1.021 g, 8.13 mmol) and potassium Carbonate (2.53 g, 18.30 mmol) in DMF (10 ml) was purged with nitrogen for 10 min in a seal tube. Pd(PPh$_3$)$_4$ (0.470 g, 0.407 mmol) was added to reaction mixture and stirred at 80° C. for 8 h. The reaction mixture was diluted with water (50 ml) and extracted with ethyl acetate (50 ml×2). The combined organic layer was washed with brine (50 ml), dried over sodium sulfate, concentrated in vacuo to give 3.1 g of crude compound. This residue was purified by combiflash (Rf200, Teledyne/Isco) instrument onto a Redisep® Rf column with gradient elution (0 to 40%) of ethyl acetate in petroleum ether to afford the title compound (2.7 g, 98%) as an off-white solid. LCMS m/z=675.60 (M+; 100).

((3aS,4R,6aR)-4-(4-((4-Methoxybenzyl)amino)-7H-pyrrolo[2,3-d]pyrimidin-7-yl)-2,2,5-trimethyl-3a,6a-dihydro-4H-cyclopenta[d][1,3]dioxol-6-yl)methanol

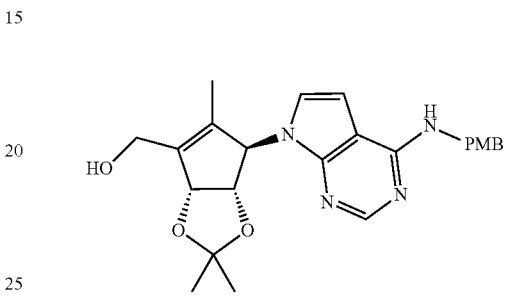

To a stirred solution of 7-((3aS,4R,6aR)-6-(((tert-butyldiphenylsilyl)oxy)methyl)-2,2,5-trimethyl-3a,6a-dihydro-4H-cyclopenta[d][1,3]dioxol-4-yl)-N-(4-methoxybenzyl)-7H-pyrrolo [2,3-d]pyrimidin-4-amine (2.7 g, 4.00 mmol) in THF (40 ml) at 0° C., was added TBAF (4.80 ml, 4.80 mmol) slowly and stirred for 2 h at 25° C. The reaction mixture was diluted with water (50 ml) and extracted with ethyl acetate (50 ml×2). The combined organic layer was washed with brine (50 ml), dried over sodium sulfate, filtered and concentrated in vacuo to give 2.2 g of crude compound. This residue was purified by combiflash (R$_f$200, Teledyne/Isco) instrument onto a Redisep® R$_f$ column with gradient elution (0 to 100%) of ethyl acetate in petroleum ether to afford the title compound (1.7 g, 97%) as a colorless oil. $^1$H NMR (400 MHz, Chloroform-d) δ 7.69 (ddd, J=12.0, 8.3, 1.4 Hz, 1H), 7.62-7.41 (m, 1H), 7.41-7.30 (m, 2H), 6.99-6.80 (m, 2H), 6.70 (d, J=3.6 Hz, 1H), 6.35 (d, J=3.5 Hz, 1H), 5.67 (s, 1H), 5.51 (d, J=5.9 Hz, 1H), 4.79 (d, J=5.5 Hz, 2H), 4.60 (dd, J=5.9, 0.9 Hz, 1H), 4.45 (s, 2H), 3.83 (s, 3H), 1.61 (t, J=1.1 Hz, 3H), 1.51 (s, 3H), 1.37 (s, 3H). LCMS m/z=437.17 (M+, 100%).

((3aS,4R,6aR)-4-(4-((4-Methoxybenzyl)amino)-7H-pyrrolo[2,3-d]pyrimidin-7-yl)-2,2,5-trimethyl-3a,6a-dihydro-4H-cyclopenta[d][1,3]dioxol-6-yl)methyl 4-methylbenzeneulfonate

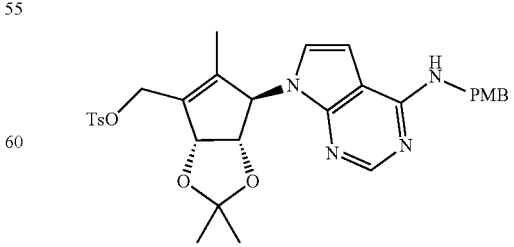

To a mixture of ((3aS,4R,6aR)-4-(4-((4-methoxybenzyl) amino)-7H-pyrrolo[2,3-d]pyrimidin-7-yl)-2,2,5-trimethyl- 3a,6a-dihydro-4H-cyclopenta[d][1,3]dioxol-6-yl)methanol (100 mg, 0.229 mmol), DMAP (5.60 mg, 0.046 mmol) and TEA (0.096 ml, 0.687 mmol) in CH₂Cl₂ (10 ml) at 0° C., was added a solution of p-toluene sulphonyl chloride (65.5 mg, 0.344 mmol) in CH₂Cl₂ (1 ml) and stirred for 1 h at 25° C. The reaction mixture was diluted with water (5 ml) and extracted with ethyl acetate (10 ml×2). The combined organic layer was washed with brine (10 ml), dried over sodium sulfate, filtered and concentrated in vacuo to give 0.2 g of crude compound. This residue was purified by combiflash (Rf200, Teledyne/Isco) instrument onto a Redisep® Rf column with gradient elution (0 to 40%) of ethyl acetate in petroleum ether to afford the title compound (0.08 g, 59.1%) as a colorless oil. Obtained product was used as such for next step without characterization.

(3aS,4R,6aS)-5-(((tert-Butyldiphenylsilyl)oxy)methyl)-2,2,4-trimethyl-3a,6a-dihydro-4H-cyclopenta[d][1,3]dioxol-4-ol

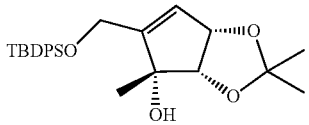

To a stirred solution of (3aS,6aS)-5-(((tert-butyldiphenylsilyl)oxy)methyl)-2,2-dimethyl-3a,6a-dihydro-4H-cyclopenta[d][1,3]dioxol-4-one (10.0 g, 23.66 mmol) [synthesized by following the same reaction protocol as was described in J. Org. Chem. 2014, 79, 8059-8066] in THF (100 ml), was added 3M methyl magnesium bromide in THF (11.85 ml, 35.5 mmol) at 0° C. The reaction mixture was stirred at 0° C. for 1 h. The reaction mixture was quenched with a saturated aqueous ammonium chloride (100 ml) and extracted with ethyl acetate (200 ml×2). The combined organic layer was washed with brine (50 ml), dried over sodium sulfate, filtered and concentrated in vacuo to give 9.8 g of crude compound. This residue was purified by combiflash (Rf200, Teledyne/Isco) instrument onto a Redisep® Rf column with gradient elution (0 to 20%) of ethyl acetate in petroleum ether to afford the title compound (8.50 g, 82%) as a colorless oil. $^1$H NMR (400 MHz, Chloroform-d) δ 7.72-7.67 (m, 4H), 7.47-7.37 (m, 6H), 5.84 (q, J=2.0 Hz, 1H), 5.11-5.00 (m, 1H), 4.46-4.28 (m, 3H), 3.51 (s, 1H), 1.47 (s, 3H), 1.42 (s, 3H), 1.26 (s, 3H), 1.09 (s, 9H).

(3aS,4S,6aR)-6-(((tert-Butyldiphenylsilyl)oxy)methyl)-2,2,6a-trimethyl-3a,6a-dihydro-4H-cyclopenta[d][1,3]dioxol-4-ol

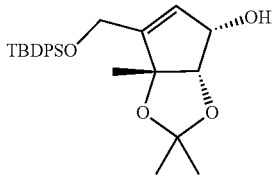

To a stirred solution of (3aS,4R,6aS)-5-(((tert-butyldiphenylsilyl)oxy)methyl)-2,2,4-trimethyl-3a,6a-dihydro-4H-cyclopenta[d][1,3]dioxol-4-ol (8.0 g, 18.24 mmol) in anhydrous acetone (80 ml), was added p-TsOH·H₂O (0.69 g, 3.65 mmol) at 25° C. and stirred for 18 h. TLC showed 50% conversion. The reaction mixture was then concentrated in vacuo, diluted with methylene chloride (100 ml) and washed with saturated NaHCO₃ (50 ml). Layers were separated, the organic layer was washed with brine (50 ml) and dried over anhydrous sodium sulphate. The organic layer was filtered and concentrated in vacuo to give 4.5 g of crude compound. This residue was purified by combiflash (Rf200, Teledyne/Isco) instrument onto a Redisep® Rf column with gradient elution (0 to 30%) of ethyl acetate in petroleum ether to afford the title compound (3.5 g, 43%) as an oil. $^1$H NMR (400 MHz, Chloroform-d) δ 7.74-7.65 (m, 4H), 7.48-7.35 (m, 6H), 5.81 (p, J=1.6 Hz, 1H), 4.62-4.55 (m, 1H), 4.44-4.24 (m, 3H), 1.39 (s, 3H), 1.34 (s, 3H), 1.29 (s, 3H), 1.10 (s, 9H).

7-((3aS,4R,6aR)-6-(((tert-Butyldiphenylsilyl)oxy)methyl)-2,2,6a-trimethyl-3a,6a-dihydro-4H-cyclopenta[d][1,3]dioxol-4-yl)-4-chloro-7H-pyrrolo[2,3-d]pyrimidine

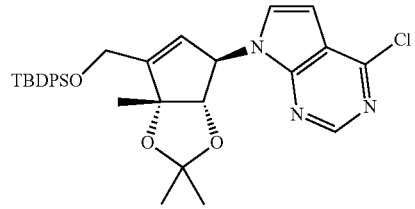

The title compound was synthesized by following an analogous reaction protocol as was described in the preparation of 1-((3aS,4R,6aR)-6-(((tert-butyldiphenylsilyl)oxy)methyl)-2,2-dimethyl-4,6a-dihydro-3aH-cyclopenta[d][1,3]dioxol-4-yl)-4-chloro-1H-pyrrolo[3,2-c]pyridine. $^1$H NMR (400 MHz, Chloroform-d) δ 8.74 (s, 1H), 7.78-7.67 (m, 4H), 7.52-7.39 (m, 6H), 6.94 (d, J=3.6 Hz, 1H), 6.61 (d, J=3.6 Hz, 1H), 5.94-5.86 (m, 1H), 5.80 (q, J=2.4 Hz, 1H), 4.62-4.48 (m, 2H), 4.13 (d, J=1.2 Hz, 1H), 1.39 (s, 3H), 1.38 (s, 3H), 1.36 (s, 3H), 1.13 (s, 9H), LCMS m/z=574.44 (M+; 100%).

((3aS,4R,6aR)-4-(4-Chloro-7H-pyrrolo[2,3-d]pyrimidin-7-yl)-2,2,6a-trimethyl-3a,6a-dihydro-4H-cyclopenta[d][1,3]dioxol-6-yl)methanol

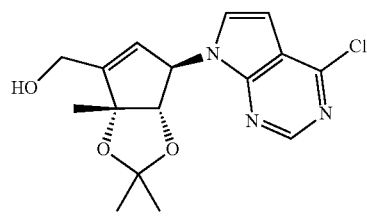 [SMILES: CC1(C)O[C@H]2[C@H](n3ccc4c(Cl)ncnc43)C=C(CO)[C@@]2(C)O1]

The title compound was synthesized by following an analogous reaction protocol as was described in the preparation of ((3aR,6R,6aS)-6-(2-chloro-7H-pyrrolo[2,3-d]pyrimidin-7-yl)-2,2-dimethyl-6,6a-dihydro-3aH-cyclopenta[d][1,3]dioxol-4-yl)methanol. $^1$H NMR (400 MHz, Chloroform-d) δ 8.73 (s, 1H), 7.16 (d, J=3.6 Hz, 1H), 6.62 (d, J=3.6 Hz, 1H), 5.87-5.78 (m, 2H), 4.62-4.44 (m, 2H), 4.25-4.20 (m, 1H), 1.56 (s, 3H), 1.49 (s, 3H), 1.42 (s, 3H); LCMS m/z=336.15 (M+; 100%).

(3aS,4R,6aR)-4-(4-Chloro-7H-pyrrolo[2,3-d]pyrimidin-7-yl)-2,2,6a-trimethyl-3a,6a-dihydro-4H-cyclopenta[d][1,3]dioxole-6-carbaldehyde

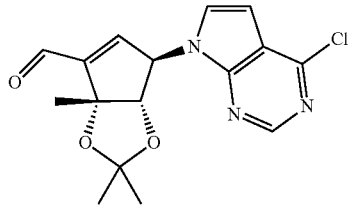 [SMILES: CC1(C)O[C@H]2[C@H](n3ccc4c(Cl)ncnc43)C=C(C=O)[C@@]2(C)O1]

The title compound was synthesized by following an analogous reaction protocol as was described in the preparation of (3aS,4R,6aR)-2,2-dimethyl-4-(4-methyl-7H-pyrrolo[2,3-d]pyrimidin-7-yl)-3a,6a-dihydro-4H-cyclopenta[d][1,3]dioxole-6-carbaldehyde. $^1$H NMR (400 MHz, Chloroform-d) δ 10.01 (s, 1H), 8.73 (s, 1H), 7.09 (d, J=3.6 Hz, 1H), 6.78 (dd, J=2.8, 1.2 Hz, 1H), 6.69 (d, J=3.6 Hz, 1H), 5.99 (dd, J=2.8, 0.8 Hz, 1H), 4.34 (t, J=0.8 Hz, 1H), 1.78 (s, 3H), 1.47 (s, 3H), 1.44 (s, 3H), LCMS m/z=334.22 (M+1; 100%).

4-Chloro-7-((3aS,4R,6aR)-2,2,6a-trimethyl-6-vinyl-3a,6a-dihydro-4H-cyclopenta[d][1,3]dioxol-4-yl)-7H-pyrrolo[2,3-d]pyrimidine

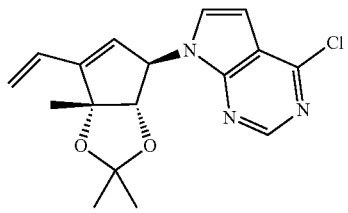 [SMILES: C=CC1=C[C@@H](n2ccc3c(Cl)ncnc32)[C@@H]2OC(C)(C)O[C@]12C]

The title compound was synthesized by following an analogous reaction protocol as was described in the preparation of 4-chloro-7-((3aS,4R,6aR)-2,2-dimethyl-6-vinyl-3a,6a-dihydro-4H-cyclopenta[d][1,3] dioxol-4-yl)-7H-pyrrolo[2,3-d]pyrimidine. $^1$H NMR (400 MHz, Chloroform-d) δ 8.74 (s, 1H), 7.16 (d, J=3.6 Hz, 1H), 6.62 (d, J=3.6 Hz, 1H), 6.49 (dd, J=17.6, 11.2 Hz, 1H), 5.94-5.87 (m, 1H), 5.85-5.76 (m, 2H), 5.47 (dd, J=11.2, 1.2 Hz, 1H), 4.15 (d, J=1.1 Hz, 1H), 1.60 (s, 3H), 1.44 (s, 6H), LCMS m/z=332.22 (M+1; 100%).

7-((3aS,4R,6aR)-6-(((tert-Butyldiphenylsilyl)oxy)methyl)-2,2,6a-trimethyl-3a,6a-dihydro-4H-cyclopenta[d][1,3]dioxol-4-yl)-4-methyl-7H-pyrrolo[2,3-d]pyrimidine

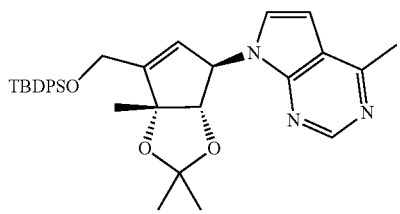

The title compound was synthesized by following an analogous reaction protocol as was described in the preparation of 7-((3aS,4R,6aR)-6-(((tert-butyldiphenylsilyl)oxy)methyl)-2,2-dimethyl-3a,6a-dihydro-4H-cyclopenta[d][1,3]dioxol-4-yl)-4-methyl-7H-pyrrolo[2,3-d]pyrimidine. $^1$H NMR1 (400 MHz, Chloroform-d) δ 8.86 (s, 1H), 7.73 (ddt, J=15.2, 6.7, 1.5 Hz, 4H), 7.52-7.39 (m, 6H), 6.90 (d, J=3.6 Hz, 1H), 6.55 (dd, J=3.7, 2.3 Hz, 1H), 5.90 (dt, J=2.9, 1.5 Hz, 1H), 5.82 (q, J=2.4 Hz, 1H), 4.54 (dq, J=6.2, 1.8 Hz, 2H), 4.14 (dd, J=6.7, 2.1 Hz, 1H), 1.64 (s, 6H), 1.39 (s, 3H), 1.36 (d, J=2.1 Hz, 3H), 1.12 (s, 9H); LCMS m/z=554.32 (M+, 100%).

((3aS,4R,6aR)-2,2,6a-Trimethyl-4-(4-methyl-7H-pyrrolo[2,3-d]pyrimidin-7-yl)-3a,6a-dihydro-4H-cyclopenta[d][1,3]dioxol-6-yl)methanol

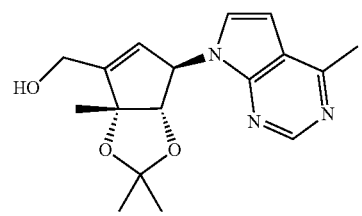 [SMILES: Cc1ncnc2c1ccn2[C@@H]1C=C(CO)[C@@]2(C)OC(C)(C)O[C@@H]12]

The title compound was synthesized by following an analogous reaction protocol as was described in the preparation of ((3aR,6R,6aS)-6-(2-chloro-7H-pyrrolo[2,3-d]pyrimidin-7-yl)-2,2-dimethyl-6,6a-dihydro-3aH-cyclopenta[d][1,3]dioxol-4-yl)methanol.

$^1$H NMR (400 MHz, Chloroform-d) δ 8.86 (s, 1H), 7.08 (d, J=3.7 Hz, 1H), 6.57 (dd, J=3.6, 1.1 Hz, 1H), 5.86-5.78 (m, 2H), 4.59-4.47 (m, 2H), 4.23 (dt, J=6.9, 0.8 Hz, 1H), 2.77 (s, 3H), 1.56 (s, 3H), 1.50 (s, 3H), 1.42 (s, 3H); LCMS m/z=316.21 (M+, 100%).

(3aS,4R,6aR)-2,2,6a-Trimethyl-4-(4-methyl-7H-pyrrolo[2,3-d]pyrimidin-7-yl)-3a,6a-dihydro-4H-cyclopenta[d][1,3]dioxole-6-carbaldehyde

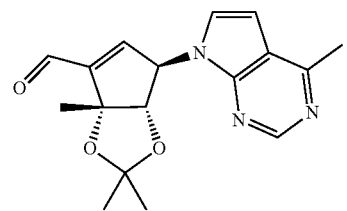 [SMILES: Cc1ncnc2c1ccn2[C@@H]1C=C(C=O)[C@@]2(C)OC(C)(C)O[C@@H]12]

The title compound was synthesized by following an analogous reaction protocol as was described in the preparation of (3aS,4R,6aR)-2,2-dimethyl-4-(4-methyl-7H-pyrrolo[2,3-d]pyrimidin-7-yl)-3a,6a-dihydro-4H-cyclopenta[d][1,3]dioxole-6-carbaldehyde. $^1$H NMR (400 MHz, Chloroform-d) δ 10.01 (s, 1H), 8.87 (s, 1H), 7.03 (d, J=3.7 Hz, 1H), 6.79 (td, J=2.8, 1.1 Hz, 1H), 6.67 (d, J=3.7 Hz, 1H), 6.02 (dd, J=2.9, 0.7 Hz, 1H), 4.33 (d, J=0.9 Hz, 1H), 2.82 (s, 3H), 1.78 (s, 3H), 1.47 (s, 3H), 1.44 (s, 3H); LCMS m/z=314.28 (M+, 100%).

(4-Methyl-7-((3aS,4R,6aR)-2,2,6a-trimethyl-6-vinyl-3a,6a-dihydro-4H-cyclopenta[d][1,3]dioxol-4-yl)-7H-pyrrolo[2,3-d]pyrimidine

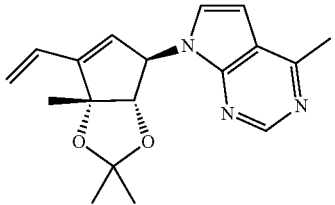 [SMILES: C=CC1=C[C@@H](n2ccc3c(C)ncnc32)[C@@H]2OC(C)(C)O[C@]12C]

The title compound was synthesized by following an analogous reaction protocol as was described in the preparation of 4-chloro-7-((3aS,4R,6aR)-2,2-dimethyl-6-vinyl-3a,6a-dihydro-4H-cyclopenta[d][1,3] dioxol-4-yl)-7H-pyrrolo[2,3-d]pyrimidine. $^1$H NMR (400 MHz, Chloroform-d) δ 8.87 (s, 1H), 7.09 (d, J=3.7 Hz, 1H), 6.60-6.44 (m, 2H), 5.94-5.75 (m, 3H), 5.45 (dd, J=11.3, 1.5 Hz, 1H), 4.21-4.07 (m, 1H), 2.78 (s, 3H), 2.64 (s, 3H), 1.44 (s, 6H); LCMS m/z=312.28 (M+, 100%).

1-((3aR,6R,6aS)-6-(4-Chloro-7H-pyrrolo[2,3-d]pyrimidin-7-yl)-2,2,3a-trimethyl-6,6a-dihydro-3aH-cyclopenta[d][1,3]dioxol-4-yl)ethanol

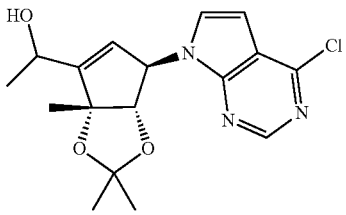 [SMILES: CC(=O)C1=C[C@@H](n2ccc3c(Cl)ncnc32)[C@@H]2OC(C)(C)O[C@]12C]

The title compound was synthesized by following an analogous reaction protocol as was described in the preparation of 1-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethan-1-ol. $^1$H NMR (400 MHz, Chloroform-d) δ 8.73 (d, J=2.0 Hz, 1H), 7.12 (dd, J=31.8, 3.6 Hz, 1H), 6.62 (t, J=3.3 Hz, 1H), 5.87-5.76 (m, 2H), 4.78-4.68 (m, 2H), 4.26-4.20 (m, 1H), 1.61 (d, J=7.1 Hz, 3H), 1.54 (s, 6H), 1.43 (d, J=3.5 Hz, 3H); LCMS m/z=350.22 (M+, 100%).

1-((3aR,6R,6aS)-6-(4-Chloro-7H-pyrrolo[2,3-d]pyrimidin-7-yl)-2,2,3a-trimethyl-6,6a-dihydro-3aH-cyclopenta[d][1,3]dioxol-4-yl)ethanone

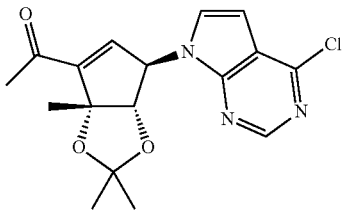

The title compound was synthesized by following an analogous reaction protocol as was described in the preparation of 1-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethan-1-one. $^1$H NMR (400 MHz, Chloroform-d) δ 8.74 (s, 1H), 7.10 (d, J=3.7 Hz, 1H), 6.74-6.56 (m, 2H), 5.95 (d, J=2.9 Hz, 1H), 4.27 (t, J=0.9 Hz, 1H), 2.49 (s, 3H), 1.76 (s, 3H), 1.48 (s, 6H); LCMS m/z=348.16 (M+, 100%).

2-((3aR,6R,6aS)-6-(4-Chloro-7H-pyrrolo[2,3-d]pyrimidin-7-yl)-2,2,3a-trimethyl-6,6a-dihydro-3aH-cyclopenta[d][1,3]dioxol-4-yl)propan-2-ol

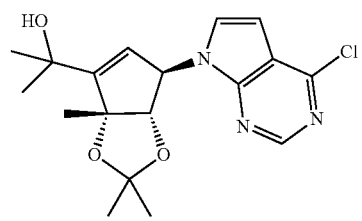 [SMILES: CC1(C)O[C@H]2[C@H](n3ccc4c(Cl)ncnc43)C=C(C(C)(C)O)[C@@]2(C)O1]

The title compound was synthesized by following an analogous reaction protocol as was described in the preparation of 2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)propan-2-ol. LCMS m/z=364.22 (M+, 100%).

4-Chloro-7-((3aS,4R,6aR)-2,2,6a-trimethyl-6-(prop-1-en-2-yl)-4,6a-dihydro-3aH-cyclopenta[d][1,3]dioxol-4-yl)-7H-pyrrolo[2,3-d]pyrimidine

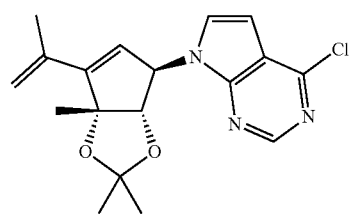 [SMILES: C=C(C)C1=C[C@@H](n2ccc3c(Cl)ncnc32)[C@@H]2OC(C)(C)O[C@]12C]

The title compound was synthesized by following an analogous reaction protocol as was described in the preparation of 4-chloro-7-((3aS,4R,6aR)-2,2-dimethyl-6-(prop-1-en-2-yl)-3a,6a-dihydro-4H-cyclopenta[d][1,3]dioxol-4-yl)-7H-pyrrolo[2,3-d]pyrimidine. $^1$H NMR (400 MHz, Chloroform-d) δ 8.74 (s, 1H), 7.15 (d, J=3.6 Hz, 1H), 6.62 (d, J=3.7 Hz, 1H), 5.84 (d, J=3.0 Hz, 1H), 5.76 (ddd, J=12.2, 2.4, 1.0 Hz, 2H), 5.31 (t, J=1.6 Hz, 1H), 4.15-4.13 (m, 1H), 2.05 (t, J=1.0 Hz, 3H), 1.61 (s, 3H), 1.43 (s, 6H); LCMS m/z=346.02 (M+, 100%).

4-Methyl-7-((3aS,4R,6aR)-2,2,6a-trimethyl-6-(prop-1-en-2-yl)-4,6a-dihydro-3aH-cyclopenta[d][1,3]dioxol-4-yl)-7H-pyrrolo[2,3-d]pyrimidine

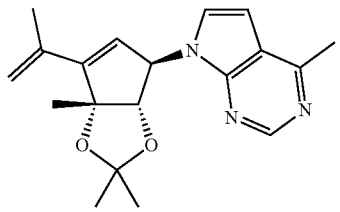 [SMILES: C=C(C)C1=C[C@@H](n2ccc3c(C)ncnc32)[C@@H]2OC(C)(C)O[C@]12C]

The title compound was synthesized by following an analogous reaction protocol as was described in the preparation of 7-((3aS,4R,6aR)-2,2-dimethyl-6-(prop-1-en-2-yl)-4,6a-dihydro-3aH-cyclopenta[d][1,3]dioxol-4-yl)-4-methyl-7H-pyrrolo[2,3-d]pyrimidine. ¹H NMR (400 MHz, Chloroform-d) δ 8.87 (s, 1H), 7.06 (d, J=3.6 Hz, 1H), 6.56 (d, J=3.6 Hz, 1H), 5.89-5.67 (m, 3H), 5.29 (t, J=1.6 Hz, 1H), 4.14 (d, J=1.3 Hz, 1H), 2.76 (s, 3H), 2.05 (t, J=1.0 Hz, 3H), 1.61 (s, 3H), 1.43 (s, 6H); LCMS m/z=326.28 (M+, 100%).

7-((3aS,4R,6aR)-2,2-dimethyl-6-vinyl-3a,6a-dihydro-4H-cyclopenta[d][1,3]dioxol-4-yl)-4-(1-methyl-1H-pyrazol-4-yl)-7H-pyrrolo[2,3-d]pyrimidine

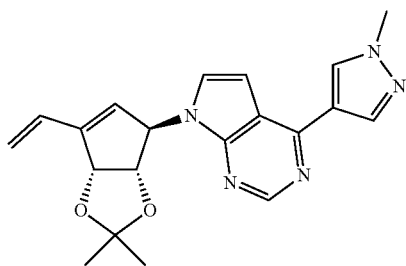 [SMILES: C=CC1=C[C@@H](n2ccc3c(-c4cnn(C)c4)ncnc32)[C@@H]2OC(C)(C)O[C@H]12]

The title compound was synthesized by following an analogous reaction protocol as was described in the preparation of 7-((3aS,4R,6aR)-2,2-dimethyl-6-(prop-1-en-2-yl)-4,6a-dihydro-3aH-cyclo penta[d][1,3] dioxol-4-yl)-4-methyl-7H-pyrrolo[2,3-d]pyrimidine. LCMS m/z=364.22 (M+, 100%).

(3aS,4R,6aS)-5-(((tert-Butyldiphenylsilyl)oxy) methyl)-4-ethyl-2,2-dimethyl-4,6a-dihydro-3aH-cyclopenta[d][1,3]dioxol-4-ol

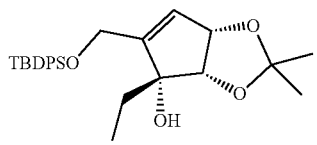

The title compound was synthesized by following an analogous reaction protocol as was described in the preparation of (3aS,4R,6aS)-5-(((tert-Butyldiphenylsilyl)oxy) methyl)-2,2,4-trimethyl-3a,6a-dihydro-4H-cyclopenta[d][1,3]dioxol-4-ol. ¹H NMR (400 MHz, Chloroform-d) δ 7.76-7.74 (m, 2H), 7.73-7.68 (m, 4H), 7.44-7.39 (m, 8H), 5.95 (d, J=1.9 Hz, 1H), 5.01 (ddt, J=5.5, 2.9, 1.5 Hz, 1H), 4.43-4.36 (m, 2H), 1.49 (s, 3H), 1.43 (s, 3H), 1.10 (s, 9H), 0.74 (t, J=7.5 Hz, 3H).

(3aS,4S,6aR)-6-(((tert-Butyldiphenylsilyl)oxy) methyl)-6a-ethyl-2,2-dimethyl-4,6a-dihydro-3aH-cyclopenta[d][1,3]dioxol-4-ol

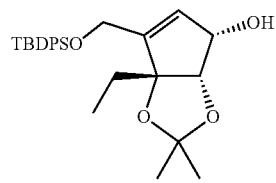

The title compound was synthesized by following an analogous reaction protocol as was described in the preparation of (3aS,4S,6aR)-6-(((tert-Butyldiphenylsilyl)oxy) methyl)-2,2,6a-trimethyl-3a,6a-dihydro-4H-cyclopenta[d][1,3]dioxol-4-ol. ¹H NMR (400 MHz, Chloroform-d) δ 7.72-7.67 (m, 4H), 7.41 (dddt, J=15.6, 7.9, 6.7, 2.1 Hz, 6H), 5.92 (p, J=1.7 Hz, 1H), 4.52 (s, 1H), 4.43-4.35 (m, 2H), 4.22 (ddd, J=15.6, 3.0, 2.0 Hz, 1H), 2.71 (s, 1H), 1.79-1.64 (m, 2H), 1.39 (s, 3H), 1.32 (s, 3H), 1.10 (s, 9H), 0.74 (t, J=7.6 Hz, 3H).

7-((3aS,4R,6aR)-6-(((tert-Butyldiphenylsilyl)oxy) methyl)-6a-ethyl-2,2-dimethyl-4,6a-dihydro-3aH-cyclopenta[d][1,3]dioxol-4-yl)-4-chloro-7H-pyrrolo [2,3-d]pyrimidine

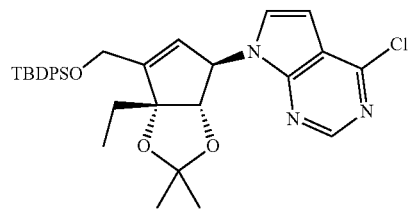

The title compound was synthesized by following an analogous reaction protocol as was described in the preparation of 1-((3aS,4R,6aR)-6-(((tert-butyldiphenylsilyl)oxy) methyl)-2,2-dimethyl-4,6a-dihydro-3aH-cyclopenta[d][1,3] dioxol-4-yl)-4-chloro-1H-pyrrolo[3,2-c] pyridine. ¹H NMR (400 MHz, Chloroform-d) δ 8.76 (s, 1H), 7.79-7.67 (m, 4H), 7.55-7.37 (m, 6H), 6.99 (d, J=3.6 Hz, 1H), 6.60 (d, J=3.6 Hz, 1H), 6.03-5.96 (m, 1H), 5.78 (q, J=2.5 Hz, 1H), 4.61-4.43

(m, 2H), 4.25 (d, J=0.9 Hz, 1H), 1.75 (q, J=7.3 Hz, 1H), 1.55 (dq, J=14.8, 7.4 Hz, 1H), 1.41 (s, 6H), 1.13 (s, 9H), 0.68 (t, J=7.4 Hz, 3H); LCMS m/z=588.21 (M+, 100%).

((3aR,6R,6aS)-6-(4-Chloro-7H-pyrrolo[2,3-d]pyrimidin-7-yl)-3a-ethyl-2,2-dimethyl-6,6a-dihydro-3aH-cyclopenta[d][1,3]dioxol-4-yl)methanol

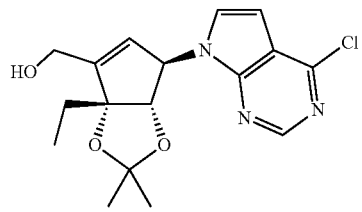 [SMILES: CC[C@]12OC(C)(C)O[C@H]1[C@H](n1ccc3c(Cl)ncnc31)C=C2CO]

The title compound was synthesized by following an analogous reaction protocol as was described in the preparation of ((3aR,6R,6aS)-6-(2-chloro-7H-pyrrolo[2,3-d]pyrimidin-7-yl)-2,2-dimethyl-6,6a-dihydro-3aH-cyclopenta[d][1,3]dioxol-4-yl)methanol. $^1$H NMR (400 MHz, Chloroform-d) δ 8.74 (s, 1H), 7.17 (d, J=3.7 Hz, 1H), 6.60 (d, J=3.6 Hz, 1H), 5.93 (dq, J=2.7, 1.5 Hz, 1H), 5.79 (q, J=2.2 Hz, 1H), 4.60-4.43 (m, 2H), 4.32 (t, J=0.8 Hz, 1H), 1.94 (dq, J=14.8, 7.4 Hz, 1H), 1.74 (dq, J=14.7, 7.5 Hz, 1H), 1.51 (s, 3H), 1.41 (s, 3H), 0.83 (t, J=7.5 Hz, 3H); LCMS m/z=350.22 (M+, 100%).

(3aR,6R,6aS)-6-(4-Chloro-7H-pyrrolo[2,3-d]pyrimidin-7-yl)-3a-ethyl-2,2-dimethyl-6,6a-dihydro-3aH-cyclopenta[d][1,3]dioxole-4-carbaldehyde

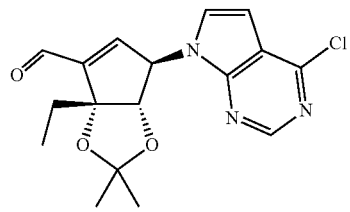 [SMILES: CC[C@]12OC(C)(C)O[C@H]1[C@H](n1ccc3c(Cl)ncnc31)C=C2C=O]

The title compound was synthesized by following an analogous reaction protocol as was described in the preparation of (3aS,4R,6aR)-2,2-dimethyl-4-(4-methyl-7H-pyrrolo[2,3-d]pyrimidin-7-yl)-3a,6a-dihydro-4H-cyclopenta[d][1,3]dioxole-6-carbaldehyde. $^1$H NMR (400 MHz, Chloroform-d) δ 10.02 (s, 1H), 8.75 (s, 1H), 7.09 (d, J=3.7 Hz, 1H), 6.88 (dd, J=2.8, 1.1 Hz, 1H), 6.68 (d, J=3.6 Hz, 1H), 5.98 (dd, J=2.8, 1.0 Hz, 1H), 4.43 (d, J=1.0 Hz, 1H), 2.24 (dq, J=14.9, 7.5 Hz, 1H), 1.97 (dq, J=14.8, 7.4 Hz, 1H), 1.47 (s, 6H), 0.89 (t, J=7.5 Hz, 3H); LCMS m/z=348.22 (M+, 100%).

4-Chloro-7-((3aS,4R,6aR)-6a-ethyl-2,2-dimethyl-6-vinyl-4,6a-dihydro-3aH-cyclopenta[d][1,3]dioxol-4-yl)-7H-pyrrolo[2,3-d]pyrimidine

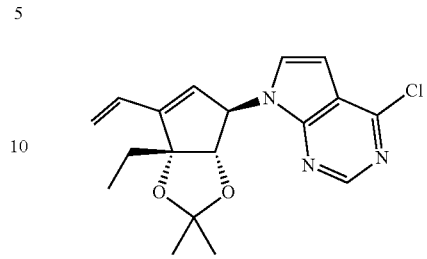

The title compound was synthesized by following an analogous reaction protocol as was described in the preparation of 4-chloro-7-((3aS,4R,6aR)-2,2-dimethyl-6-vinyl-3a,6a-dihydro-4H-cyclopenta[d][1,3] dioxol-4-yl)-7H-pyrrolo[2,3-d]pyrimidine. $^1$H NMR (400 MHz, Chloroform-d) δ 8.75 (s, 1H), 7.16 (d, J=3.7 Hz, 1H), 6.60 (d, J=3.7 Hz, 1H), 6.56-6.36 (m, 1H), 5.99-5.69 (m, 3H), 5.44 (dd, J=11.3, 1.5 Hz, 1H), 4.25 (d, J=0.9 Hz, 1H), 2.15-1.99 (m, 1H), 1.76 (dq, J=14.8, 7.5 Hz, 1H), 1.46 (s, 6H), 0.81 (t, J=7.5 Hz, 3H). LCLCMS m/z=346.22 (M+, 100%).

((3aR,3bR,4aS,5R,5aS)-5-(4-Chloro-7H-pyrrolo[2,3-d]pyrimidin-7-yl)-2,2-dimethyl hexa hydrocyclopropa[3,4]cyclopenta[1,2-d][1,3]dioxol-3b-yl)methanol

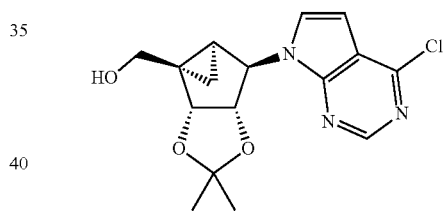

The title compound was prepared by an analogous reaction protocol as described in WO2006/091905 A1.

((3aR,3bR,4aS,5R,5aS)-5-(4-Chloro-7H-pyrrolo[2,3-d]pyrimidin-7-yl)-2,2-dimethyl hexahydrocyclopropa[3,4]cyclopenta[1,2-d][1,3]dioxol-3b-yl)methyl 4-methyl benzenesulfonate

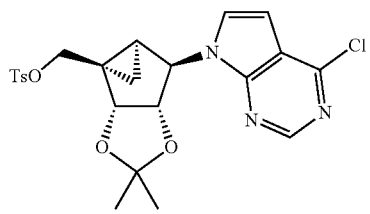 [SMILES: Cc1ccc(S(=O)(=O)OC[C@]23C[C@@H]2[C@@H](n2ccc4c(Cl)ncnc42)[C@@H]2OC(C)(C)O[C@@H]23)cc1]

To a stirred solution of ((3aR,3bR,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)methanol (2 g, 5.96 mmol) in CH$_2$Cl$_2$ (40 ml) at 0° C., was added TEA (2.494 ml, 17.87 mmol), DMAP (0.146 g, 1.191 mmol) and followed by p-TsCl (1.363 g, 7.15 mmol) slowly and stirred for 10 min. The reaction mixture was stirred at 25° C. for 16 h. The reaction mixture was diluted with methylene chloride (100 ml) and washed with water (100 ml). Layers were separated, organic layer was washed with brine (100 ml) and dried over anhydrous Na$_2$SO$_4$. The organic layer was filtered and concentrated in vacuo to give 12 g of crude compound. This residue was purified by combiflash (R$_f$200, Teledyne/Isco) instrument onto a Redisep® R$_f$ column with gradient elution (0 to 7%) of ethyl acetate in petroleum ether to afford the title (0.267 g, 9.15%) as an off-white solid. LCMS m/z=490.17 (M+, 100%).

(3aR,3bS,4aS,5R,5aS)-5-(4-Chloro-7H-pyrrolo[2,3-d]pyrimidin-7-yl)-2,2-dimethylhexahydrocyclopropa [3,4]cyclopenta[1,2-d][1,3]dioxole-3b-carbaldehyde

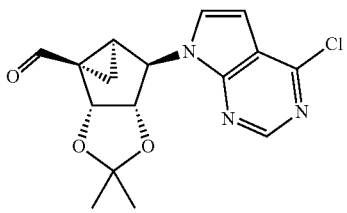 [SMILES: CC1(C)O[C@H]2[C@H](n3ccc4c(Cl)ncnc43)[C@H]3C[C@]3(C=O)[C@H]2O1]

The title compound was synthesized by following an analogous reaction protocol as was described in the preparation of (3aS,4R,6aR)-2,2-dimethyl-4-(4-methyl-7H-pyrrolo[2,3-d]pyrimidin-7-yl)-3a,6a-dihydro-4H-cyclopenta[d][1,3]dioxole-6-carbaldehyde. $^1$H NMR (400 MHz, Chloroform-d) δ 9.34 (s, 1H), 8.63 (s, 1H), 7.18 (d, J=3.6 Hz, 1H), 6.66 (d, J=3.6 Hz, 1H), 5.91 (dd, J=7.1, 1.2 Hz, 1H), 5.11 (s, 1H), 4.82 (dd, J=7.1, 1.6 Hz, 1H), 2.34 (ddd, J=9.4, 6.1, 1.6 Hz, 1H), 1.89-1.77 (m, 2H), 1.58 (s, 3H), 1.30 (s, 3H); LCMS m/z=333.9 (M+, 100%).

4-Chloro-7-((3aR,3bS,4aS,5R,5aS)-2,2-dimethyl-3b-vinylhexahydro cyclopropa [3,4] cyclo penta[1,2-d][1,3]dioxol-5-yl)-7H-pyrrolo[2,3-d]pyrimidine

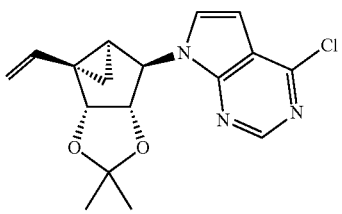 [SMILES: C=C[C@]12C[C@@H]1[C@@H](n1ccc3c(Cl)ncnc31)[C@@H]1OC(C)(C)O[C@@H]12]

To a stirred suspension of methyltriphenylphosphonium bromide (24.62 g, 68.9 mmol) in THF (200 ml), was added 1M KHMDS in THF (68.9 ml, 68.9 mmol) at 25° C. and stirred for 10 min. The resulting yellow suspension was cooled to 0° C. and a solution of (3aR,3bS,4aS,5R,5aS)-5-(4-Chloro-7H-pyrrolo[2,3-d]pyrimidin-7-yl)-2,2-dimethylhexahydrocyclopropa [3,4]cyclopenta[1,2-d][1,3]dioxole-3b-carbaldehyde (9.2 g, 27.6 mmol) in THF (80 ml) was added slowly. The reaction mixture was stirred at the same temperature for 1 h. The reaction mixture was quenched with a saturated aq.NH$_4$Cl (200 ml) and extracted with ethyl acetate (200 ml). Layers were separated, organic layer was washed with brine (250 ml) and dried over anhydrous Na$_2$SO$_4$. The organic layer was filtered and concentrated in vacuo to give 11 g of crude compound. This residue was purified by combiflash (R$_f$200, Teledyne/Isco) instrument onto a Redisep® R$_f$ column with gradient elution (0 to 20%) of ethyl acetate in petroleum ether to afford the title compound (7 g, 77%) as a white solid. $^1$H NMR (400 MHz, Chloroform-d) δ 8.68 (s, 1H), 7.23 (d, J=3.7 Hz, 1H), 6.67 (d, J=3.6 Hz, 1H), 5.86 (dd, J=17.3, 10.6 Hz, 1H), 5.39-5.32 (m, 2H), 5.29 (s, 1H), 5.18 (dd, J=10.6, 0.9 Hz, 1H), 4.59 (dd, J=7.1, 1.6 Hz, 1H), 1.77 (ddd, J=9.3, 4.9, 1.6 Hz, 1H), 1.63 (s, 3H), 1.49 (t, J=5.3 Hz, 1H), 1.27 (s, 3H), 1.18 (ddd, J=9.3, 5.6, 1.6 Hz, 1H); LCMS m/z=332.28 (M+, 50%).

7-((3aR,3bS,4aS,5R,5aS)-2,2-Dimethyl-3b-vinyl-hexahydrocyclopropa [3,4]cyclopenta [1,2-d][1,3]dioxol-5-yl)-7H-pyrrolo[2,3-d]pyrimidin-4-amine

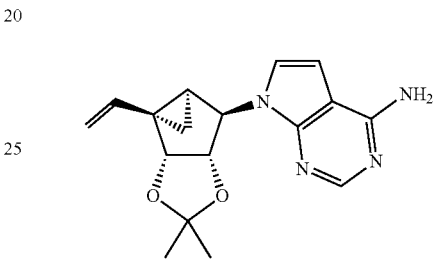

A mixture of 4-chloro-7-((3aR,3bS,4aS,5R,5aS)-2,2-dimethyl-3b-vinylhexahydro cyclopropa [3,4] cyclo penta[1,2-d][1,3]dioxol-5-yl)-7H-pyrrolo[2,3-d]pyrimidine (3 g, 9.04 mmol) and aq. ammonia (19.57 ml, 904 mmol) in dioxane (6 ml) stirred at 130° C. in a steel bomb for 16 h. The reaction mixture was diluted with ethyl acetate (20 ml) and washed with water (20 ml). Layers were separated, organic layer was washed with brine (20 ml) and dried over anhydrous Na$_2$SO$_4$. The organic layer was filtered and concentrated in vacuo to give 4.1 g of crude compound. This residue was purified by combiflash (R$_f$200, Teledyne/Isco) instrument onto a Redisep® R$_f$ column with gradient elution (0 to 3%) of methanol in dichloromethane to afford the title compound (2.45 g, 87%) as a white solid. 1H NMR (400 MHz, DMSO-d$_6$) δ 8.07 (s, 1H), 7.02 (s, 2H), 6.96 (d, J=3.5 Hz, 1H), 6.62 (d, J=3.5 Hz, 1H), 5.86 (dd, J=17.4, 10.7 Hz, 1H), 5.33 (dd, J=7.2, 1.3 Hz, 1H), 5.23 (dd, J=17.4, 1.3 Hz, 1H), 5.10-5.01 (m, 2H), 4.50 (dd, J=7.1, 1.6 Hz, 1H), 1.70 (ddd, J=9.3, 4.8, 1.6 Hz, 1H), 1.46 (s, 3H), 1.29-1.22 (m, 1H), 1.19 (s, 3H), 1.10 (ddd, J=9.1, 5.1, 1.5 Hz, 1H); LCMS m/z=313 (M+1, 100%).

7-((3aR,3bS,4aS,5R,5aS)-2,2-Dimethyl-3b-vinyl-hexahydrocyclopropa [3,4]cyclopenta [1,2-d][1,3]dioxol-5-yl)-4-methyl-7H-pyrrolo[2,3-d]pyrimidine

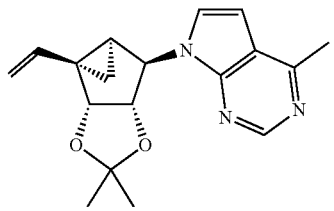 [SMILES: C=C[C@]12C[C@@H]1[C@@H](n1ccc3c(C)ncnc31)[C@@H]1OC(C)(C)O[C@@H]12]

To a degassed mixture dioxane (8 ml) and water (1 ml) in a microwave vial was added 4-chloro-7-((3aR,3bS,4aS,5R,5aS)-2,2-dimethyl-3b-vinylhexahydrocyclopropa[3,4]cyclopenta [1,2-d][1,3]dioxol-5-yl)-7H-pyrrolo[2,3-d]pyrimidine (1.00 g, 3.01 mmol, potassium phosphate, tribasic (1.575 g, 9.04 mmol), dichloro[1,1'-bis(di-t-butylphosphino)ferrocene] palladium(II) (0.196 g, 0.301 mmol) and 2,4,6-trimethyl-1,3,5,2,4,6-trioxatriborinane (2.107 ml, 15.07 mmol) at 25° C. Stirred the reaction mixture at 100° C. for 1 h. The reaction mixture was diluted with ethyl acetate (20 ml) and washed with water (20 ml). Layers were separated, organic layer was washed with brine (20 ml) and dried over anhydrous Na$_2$SO$_4$. The organic layer was filtered and concentrated in vacuo to give 1.1 g of crude compound. This residue was purified by combiflash (R$_f$200, Teledyne/Isco) instrument onto a Redisep® R$_f$ column with gradient elution (0 to 20%) of ethyl acetate in petroleum ether to afford the title compound (0.66 g, 70.3%) as an off white solid. $^1$H NMR (400 MHz, Chloroform-d) δ 8.81 (s, 1H), 7.16 (d, J=3.6 Hz, 1H), 6.63 (d, J=3.6 Hz, 1H), 5.87 (dd, J=17.3, 10.6 Hz, 1H), 5.37-5.31 (m, 3H), 5.17 (dd, J=10.6, 0.9 Hz, 1H), 4.58 (dd, J=7.1, 1.6 Hz, 1H), 2.78 (s, 3H), 1.78 (ddt, J=9.3, 4.9, 1.8 Hz, 1H), 1.59 (d, J=1.8 Hz, 3H), 1.50 (td, J=5.2, 2.7 Hz, 1H), 1.27 (d, J=2.2 Hz, 3H), 1.19-1.14 (m, 1H); LCMS m/z=312.21 (M+1, 100%).

Des chloro compound i.e. 7-((3aR,3bS,4aS,5R,5aS)-2,2-dimethyl-3b-vinylhexahydro cyclo propa[3,4]cyclopenta[1,2-d] [1,3]dioxol-5-yl)-7H-pyrrolo[2,3-d]pyrimidine was also formed, which was separated at final step by reverse phase preparative HPLC.

(S)-1-((3aR,3bR,4aS,5R,5aS)-5-(4-Chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethan-1-ol

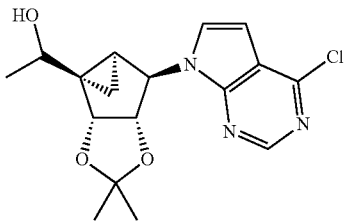

To a solution of (3aR,3bS,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxole-3b(3aH)-carbaldehyde (2.0 g, 5.99 mmol) in tetrahydrofuran (20 ml), was added 1M methyl magnesium bromide in THF (3.00 ml, 8.99 mmol) at 0° C. The reaction mixture was then stirred at 0° C. for 2 h. The reaction mixture was quenched with a sat. aq. ammonium chloride (50 ml) and extracted with ethyl acetate (50 ml×2). The combined organic layer was washed with brine (50 ml), dried over sodium sulfate, filtered and concentrated in vacuo to give 2.2 g of crude compound. This residue was purified by combiflash (R$_f$200, Teledyne/Isco) instrument onto a Redisep® R$_f$ column with gradient elution (0 to 30%) of ethyl acetate in petroleum ether to afford the title compound (1.85 g, 88%) as an off-white solid. LCMS m/z=350.03 (M+1; 100%).

1-((3aR,3bS,4aS,5R,5aS)-5-(4-chloro-7H-pyrrolo[2,3-d]pyrimidin-7-yl)-2,2-dimethyl tetrahydrocyclopropa[3,4]cyclopenta[1,2-d][1,3]dioxol-3b(3aH)-yl)ethan-1-one

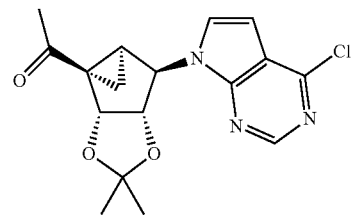

The title compound was synthesized by following an analogous reaction protocol as was described in the preparation of (3aS,4R,6aR)-2,2-dimethyl-4-(4-methyl-7H-pyrrolo[2,3-d]pyrimidin-7-yl)-3a,6a-dihydro-4H-cyclopenta[d][1,3]dioxole-6-carbaldehyde. LCMS m/z=348.03 (M+; 100%).

4-Chloro-7-((3aR,3bS,4aS,5R,5aS)-2,2-dimethyl-3b-vinylhexahydro cyclopropa[3,4] cyclopenta[1,2-d][1,3]dioxol-5-yl)-7H-pyrrolo[2,3-d]pyrimidine

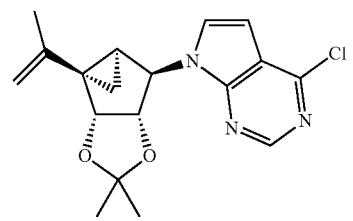

To a stirred suspension of methyltriphenylphosphonium bromide (3.85 g, 10.78 mmol) in THF (40 ml) was added 1M KHMDS in THF (10.78 ml, 10.78 mmol) at 0° C. and stirred for 10 min. To this yellow suspension was added a solution of 1-((3aR,3bS,4aS,5R,5aS)-5-(4-chloro-7H-pyrrolo[2,3-d]pyrimidin-7-yl)-2,2-dimethyl tetra hydrocyclopropa [3,4]cyclopenta[1,2-d][1,3]dioxol-3b(3aH)-yl)ethan-1-one (1.5 g, 4.31 mmol) in THF (20 ml) was added slowly at 0° C. The reaction mixture was stirred at 25° C. for 1 h. The reaction mixture was quenched with a saturated aqueous ammonium chloride (50 ml) and extracted with ethyl acetate (50 ml). Layers were separated, organic layer was washed with brine (50 ml) and dried over anhydrous sodium sulphate. The organic layer was filtered and concentrated in vacuo to give 2.2 g of crude compound. This residue was purified by combiflash (R$_f$200, Teledyne/Isco) instrument onto a Redisep® R$_f$ column with gradient elution (0 to 20%) of ethyl acetate in petroleum ether to afford the title compound (0.7 g, 46.9%) as a white solid. LCMS m/z=346.03 (M+1; 100%).

(R)-((3aR,3bR,4aS,5R,5aS)-5-(4-Chloro-7H-pyrrolo[2,3-d]pyrimidin-7-yl)-2,2-dimethyl tetrahydrocyclopropa[3,4]cyclopenta[1,2-d][1,3]dioxol-3b(3aH)-yl) (cyclopropyl)methanol

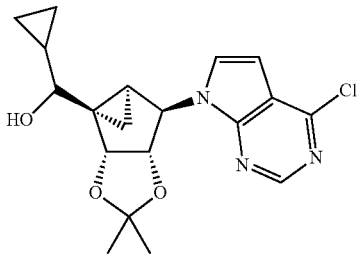

The title compound was synthesized by following an analogous reaction protocol as was described in the preparation of (S)-1-((3aR,3bR,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethan-1-ol. LCMS m/z=375.91 (M+; 100%).

((3aR,3bS,4aS,5R,5aS)-5-(4-Chloro-7H-pyrrolo[2,3-d]pyrimidin-7-yl)-2,2-dimethyl tetra hydrocyclopropa[3,4]cyclopenta[1,2-d][1,3]dioxol-3b(3aH)-yl) (cyclopropyl) methanone

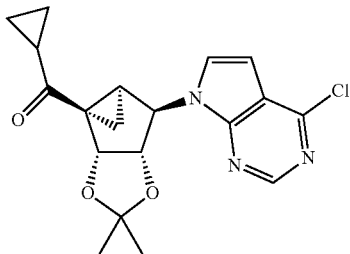

The title compound was synthesized by following an analogous reaction protocol as was described in the preparation of 1-((3aR,3bS,4aS,5R,5aS)-5-(4-chloro-7H-pyrrolo[2,3-d]pyrimidin-7-yl)-2,2-dimethyl tetrahydrocyclopropa[3,4]cyclopenta[1,2-d][1,3]dioxol-3b(3aH)-yl)ethan-1-one. ¹H NMR (400 MHz, DMSO-d6) δ 8.58 (s, 1H), 7.71 (d, J=3.7 Hz, 1H), 6.72 (d, J=3.6 Hz, 1H), 5.84 (dd, J=7.3, 1.2 Hz, 1H), 5.21 (s, 1H), 4.79 (dd, J=7.3, 1.5 Hz, 1H), 2.09 (s, 1H), 2.07-2.01 (m, 1H), 1.79 (ddd, J=9.5, 5.3, 1.4 Hz, 1H), 1.51 (t, J=5.5 Hz, 1H), 1.48 (s, 3H), 1.21 (s, 3H), 0.96-0.74 (m, 4H); LCMS m/z=373.97 (M+; 100%).

4-Chloro-7-((3aR,3bR,4aS,5R,5aS)-3b-(1-cyclopropylvinyl)-2,2-dimethylhexahydro cyclopropa[3,4]cyclopenta[1,2-d][1,3]dioxol-5-yl)-7H-pyrrolo[2,3-d]pyrimidine

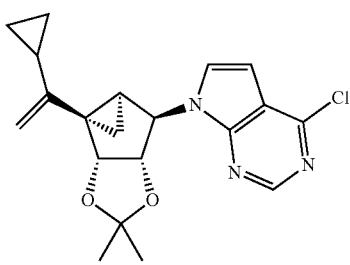

The title compound was synthesized by following an analogous reaction protocol as was described in the preparation of 4-chloro-7-((3aR,3bS,4aS,5R,5aS)-2,2-dimethyl-3b-vinylhexahydro cyclopropa[3,4]cyclopenta[1,2-d][1,3]dioxol-5-yl)-7H-pyrrolo[2,3-d]pyrimidine. ¹H NMR (400 MHz, Chloroform-d) δ 8.67 (s, 1H), 7.29 (d, J=3.6 Hz, 1H), 6.68 (d, J=3.6 Hz, 1H), 5.37-5.35 (m, 2H), 4.98 (d, J=0.8 Hz, 1H), 4.80 (s, 1H), 4.59 (dd, J=7.5, 1.6 Hz, 1H), 2.04 (ddd, J=9.3, 4.7, 1.6 Hz, 1H), 1.67 (s, 2H), 1.42 (t, J=5.1 Hz, 1H), 1.27 (s, 6H), 0.75-0.69 (m, 2H), 0.56-0.52 (m, 2H); LCMS m/z=372.2 (M+; 100%).

4-Chloro-7-((3aR,3bR,4aS,5R,5aS)-3b-((E)-2-iodoprop-1-en-1-yl)-2,2-dimethylhexa hydrocyclopropa[3,4]cyclopenta[1,2-d][1,3]dioxol-5-yl)-7H-pyrrolo[2,3-d]pyrimidine

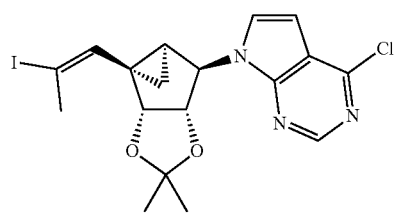

To a suspension of (1-iodoethyl)triphenylphosphonium bromide (4.08 g, 7.49 mmol, synthesized by following same reaction protocol as was described in WO2004/9574, A1) in THF (20 ml)), was added NaHMDS (7.49 ml, 7.49 mmol) at −25° C. The resulting red coloured solution was stirred at −25° C. for 10 min. A solution of (3aR,3bS,4aS,5R,5aS)-5-(4-Chloro-7H-pyrrolo[2,3-d]pyrimidin-7-yl)-2,2-dimethyl-tetrahydro cyclopropa[3,4] cyclopenta [1,2-d][1,3]dioxole-3b(3aH)-carbaldehyde (1.00 g, 3.00 mmol) in THF (20 ml) was added at −30° C. and stirred for 30 mins. The reaction mixture was quenched with sat aq.NH₄Cl (20 ml) and extracted with ethyl acetate (20 ml). Layers were separated, organic layer was washed with brine (20 ml) and dried over anhydrous Na₂SO₄. The organic layer was filtered and concentrated in vacuo to give 1.04 g of crude compound. This residue was purified by combiflash (R/200, Teledyne/Isco) instrument onto a Redisep® R/column with gradient elution (0 to 10%) of ethyl acetate in petroleum ether to afford the title compound (0.79 g, 55.9%) as an off-white solid. LCMS m/z=471.80 (M+; 100%).

7-((3aR,3bR,4aS,5R,5aS)-3b-(((tert-Butyldiphenylsilyl)oxy)methyl)-2,2-dimethylhexahydro cyclopropa[3,4]cyclopenta[1,2-d][1,3]dioxol-5-yl)-4-chloro-6-methyl-7H-pyrrolo[2,3-d]pyrimidine

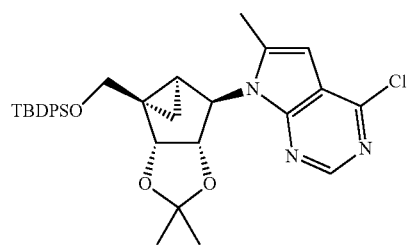

The title compound was synthesized by following an analogous reaction protocol as was described in the preparation of 1-((3aS,4R,6aR)-6-(((tert-butyldiphenylsilyl)oxy)methyl)-2,2-dimethyl-4,6a-dihydro-3aH-cyclopenta[d][1,3]dioxol-4-yl)-4-chloro-1H-pyrrolo[3,2-c] pyridine. LCMS m/z=587.82 (M+; 100%).

((3aR,3bR,4aS,5R,5aS)-5-(4-Chloro-6-methyl-7H-pyrrolo[2,3-d]pyrimidin-7-yl)-2,2-dimethyltetrahydrocyclopropa[3,4]cyclopenta[1,2-d][1,3]dioxol-3b (3aH)-yl)methanol

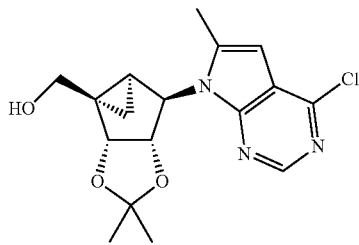

The title compound was synthesized by following an analogous reaction protocol as was described in the preparation of ((3aR,6R,6aS)-6-(2-chloro-7H-pyrrolo[2,3-d]pyrimidin-7-yl)-2,2-dimethyl-6,6a-dihydro-3aH-cyclopenta[d][1,3]dioxol-4-yl)methanol. $^1$H NMR (400 MHz, DMSO-d$_6$) δ 8.57 (s, 1H), 6.48 (d, J=1.1 Hz, 1H), 5.34-5.25 (m, 1H), 4.98 (s, 1H), 4.90 (dt, J=7.4, 1.3 Hz, 1H), 4.66 (t, J=5.7 Hz, 1H), 3.65 (q, J=5.8, 5.3 Hz, 2H), 2.57 (s, 3H), 1.54-1.48 (m, 1H), 1.46 (s, 3H), 1.19 (s, 3H), 0.92 (ddd, J=9.0, 5.0, 1.3 Hz, 1H), 0.85 (q, J=4.7, 4.3 Hz, 1H); LCMS m/z=350.03 (M+; 100%).

(3aR,3bS,4aS,5R,5aS)-5-(4-Chloro-6-methyl-7H-pyrrolo[2,3-d]pyrimidin-7-yl)-2,2-dimethyltetrahydrocyclopropa[3,4]cyclopenta[1,2-d][1,3]dioxole-3b (3aH)-carbaldehyde

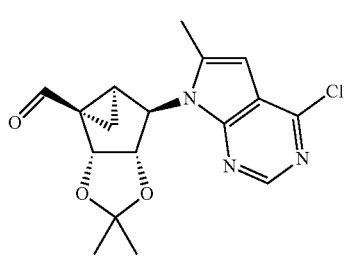

The title compound was synthesized by following an analogous reaction protocol as was described in the preparation of (3aS,4R,6aR)-2,2-dimethyl-4-(4-methyl-7H-pyrrolo[2,3-d]pyrimidin-7-yl)-3a,6a-dihydro-4H-cyclopenta[d][1,3]dioxole-6-carbaldehyde. LCMS m/z=348.03 (M+; 100%).

4-Chloro-7-((3aR,3bS,4aS,5R,5aS)-2,2-dimethyl-3b-vinylhexahydro cyclopropa[3,4] cyclo penta[1,2-d][1,3]dioxol-5-yl)-6-methyl-7H-pyrrolo[2,3-d]pyrimidine

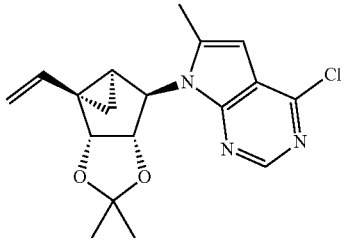

The title compound was synthesized by following an analogous reaction protocol as was described in the preparation of 4-chloro-7-((3aR,3bS,4aS,5R,5aS)-2,2-dimethyl-3b-vinylhexahydro cyclopropa [3,4] cyclo penta[1,2-d][1,3]dioxol-5-yl)-7H-pyrrolo[2,3-d]pyrimidine. $^1$H NMR (400 MHz, Chloroform-d) δ 8.57 (s, 1H), 6.38 (q, J=1.1 Hz, 1H), 5.88 (dd, J=17.3, 10.6 Hz, 1H), 5.64 (dd, J=7.2, 1.4 Hz, 1H), 5.34-5.23 (m, 1H), 5.10 (dd, J=10.6, 1.1 Hz, 1H), 5.02-4.96 (m, 1H), 4.87 (s, 1H), 2.55 (s, 3H), 1.59 (s, 3H), 1.56-1.51 (m, 1H), 1.30 (s, 3H), 1.29-1.26 (m, 1H), 1.19-1.12 (m, 1H); LCMS m/z=346.03 (M+; 100%).

7-((3aR,3bS,4aS,5R,5aS)-2,2-Dimethyl-3b-vinyl-hexahydrocyclopropa [3,4]cyclo penta [1,2-d][1,3]dioxol-5-yl)-6-methyl-7H-pyrrolo[2,3-d]pyrimidin-4-amine

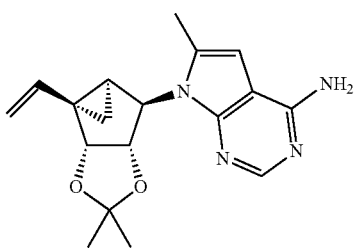

The title compound was synthesized by following an analogous reaction protocol as was described in the preparation of 7-((3aR,3bS,4aS,5R,5aS)-2,2-dimethyl-3b-vinylhexa hydrocyclopropa [3,4]cyclopenta [1,2-d][1,3]dioxol-5-yl)-7H-pyrrolo[2,3-d]pyrimidin-4-amine. $^1$H NMR (400 MHz, DMSO-d$_6$) δ 7.99 (s, 1H), 6.83 (s, 2H), 6.29 (d, J=1.2 Hz, 1H), 5.87-5.74 (m, 2H), 5.44 (d, J=7.3 Hz, 1H), 5.19 (dd, J=17.4, 1.4 Hz, 1H), 5.02 (dd, J=10.7, 1.3 Hz, 1H), 4.80 (d, J=7.3 Hz, 1H), 2.36 (s, 3H), 1.61 (dd, J=9.0, 5.3 Hz, 1H), 1.46 (s, 3H), 1.21 (s, 3H), 1.15-1.08 (m, 2H); LCMS m/z=327.1 (M+1; 100%).

3-Bromo-7-(2-((3aS,4R,6aR)-4-(4-chloro-7H-pyr-rolo[2,3-d]pyrimidin-7-yl)-2,2-dimethyl-3a,6a-dihydro-4H-cyclopenta[d][1,3]dioxol-6-yl)ethyl)-N-(4-methoxybenzyl)quinolin-2-amine

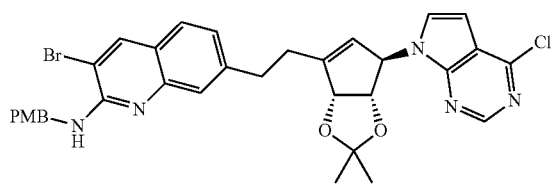

4-Chloro-7-((3aS,4R,6aR)-2,2-dimethyl-6-vinyl-3a,6a-dihydro-4H-cyclo penta[d][1,3]dioxol-4-yl)-7H-pyrrolo[2,3-d]pyrimidine (0.25 g, 0.787 mmol) in 9-BBN (0.5 molar, 6.29 ml, 3.15 mmol) was heated at 70° C. for 2 h under $N_2$ atmosphere. The reaction mixture was cooled to 25° C., then potassium phosphate tribasic (0.685 g, 3.93 mmol) in water (0.5 ml) was added and stirred for 20 mins. A solution of 3-bromo-7-iodo-N-(4-methoxybenzyl)quinolin-2-amine (0.369 g, 0.787 mmol) in THF (1 ml) was added, followed by $PdCl_2$(dppf) (0.058 g, 0.079 mmol). The resulting mixture was stirred at 70° C. for 2 h. The reaction mixture was diluted with ethyl acetate (10 ml) and washed with water (10 ml). Layers were separated, organic layer was washed with brine (10 ml) and dried over anhydrous $Na_2SO_4$. The organic layer was filtered and concentrated in vacuo to give 0.35 g of crude compound. This residue was purified by combiflash ($R_f$200, Teledyne/Isco) instrument onto a Redisep® $R_f$ column with gradient elution (0 to 15%) of ethyl acetate in petroleum ether to afford the title compound (0.25 g, 48.1%) as an off-white solid. 1H NMR (400 MHz, DMSO-d6) δ 8.65 (s, 1H), 8.37 (s, 1H), 7.60 (d, J=8.2 Hz, 1H), 7.45 (s, 1H), 7.33 (d, J=8.5 Hz, 2H), 7.28-7.14 (m, 2H), 6.98 (d, J=3.7 Hz, 1H), 6.87-6.75 (m, 2H), 6.36 (d, J=3.6 Hz, 1H), 5.66 (s, 1H), 5.52 (s, 1H), 5.35 (d, J=5.7 Hz, 1H), 4.63 (d, J=6.0 Hz, 2H), 4.49 (d, J=5.7 Hz, 1H), 3.66 (s, 3H), 3.07-2.97 (m, 2H), 2.65-2.59 (m, 2H), 1.39 (s, 3H), 1.28 (s, 3H). LCMS m/z=658.89, 661.64 (M-2, M+1, 100%).

Intermediates in table-5 were synthesized by an analogous reaction protocol as was used for the preparation of 3-bromo-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-N-(4-methoxy benzyl)quinolin-2-amine using the appropriate starting materials.

TABLE 5

| Structure & IUPAC name | Intermediates used | $^1$H NMR & LCMS data |
|---|---|---|
| 7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-N-methylquinolin-2-amine | 7-Bromo-N-methyl quinolin-2-amine and 4-Chloro-7-((3aS,4R, 6aR)-2,2-dimethyl-6-vinyl-3a,6a-dihydro-4H-cyclopenta[d][1,3] dioxol-4-yl)-7H-pyrrolo[2,3-d]pyrimidine | LCMS m/z = 476.05 (M+, 100%) |
| 3-Bromo-7-(2-((3aS,4R,6aR)-4-(4-chloro-5-fluoro-7H-pyrrolo[2,3-d]pyrimidin-7-yl)-2,2-dimethyl-3a,6a-dihydro-4H-cyclopenta[d] [1,3 ]dioxol-6-yl)ethyl)-N-(4-methoxybenzyl) quinolin-2-amine | 4-Chloro-7-((3aS,4R, 6aR)-2,2-dimethyl-6-vinyl-4,6a-dihydro-3aH-cyclopenta [d] [1,3] dioxol-4-yl)-5-fluoro-7H-pyrrolo[2,3-d]pyrimidine and 3-Bromo-7-iodo-N-(4-methoxybenzyl)quinolin-2-amine | LCMS m/z = 679.85 (M + 1, 100%) |

TABLE 5-continued

| Structure & IUPAC name | Intermediates used | ¹H NMR & LCMS data |
|---|---|---|
| 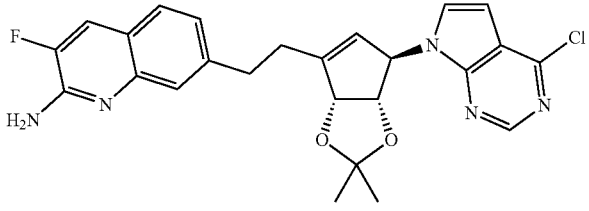 [SMILES: CC1(C)O[C@@H]2[C@H](O1)C(CCc1ccc3cc(F)c(N)nc3c1)=C[C@H]2n1ccc2c(Cl)ncnc21]<br>Chemical Formula: C$_{25}$H$_{23}$ClFN$_5$O$_2$<br>7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-3-fluoroquinolin-2-amine | 7-Bromo-3-fluoro quinolin-2-amine and 4-Chloro-7-((3aS,4R, 6aR)-2,2-dimethyl-6-vinyl-3a, 6a-dihydro-4H-cyclopenta[d][1,3] dioxol-4-yl)-7H-pyrrolo[2,3-d] pyrimidine | ¹H NMR (400 MHz, DMSO-d$_6$) δ 8.65 (s, 1H), 7.81 (d, J = 11.9 Hz, 1H), 7.60 (d, J = 8.2 Hz, 1H), 7.41 (d, J = 1.6 Hz, 1H), 7.19 (dd, J = 8.2, 1.6 Hz, 1H), 6.95 (d, J = 3.7 Hz, 1H), 6.84 – 6.67 (m, 2H), 6.41 (d, J = 3.7 Hz, 1H), 5.66 (s, 1H), 5.52 (s, 1H), 5.34 (d, J = 5.7 Hz, 1H), 4.51 (dd, J = 15.1, 5.6 Hz, 1H), 3.18 – 2.98 (m, 2H), 2.80 – 2.56 (m, 2H), 1.39 (s, 3H), 1.28 (s,, 3H). LCMS m/z = 480.2 (M+, 100%) |
| 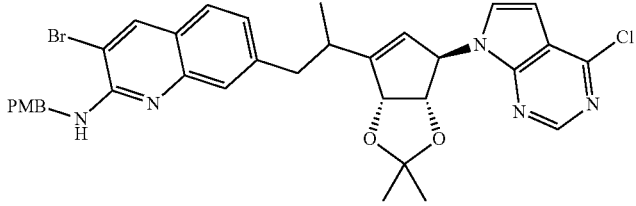<br>3-Bromo-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)propyl)-N-(4-methoxybenzyl)quinolin-2-amine | 4-Chloro-7-((3aS,4R, 6aR)-2,2-dimethyl-6-(prop-1-en-2-yl)-3a, 6a-dihydro-4H-cyclopenta[d][1,3] dioxol-4-yl)-7H-pyrrolo[2,3-d] pyrimidine and 3-Bromo-7-iodo-N-(4-methoxybenzyl)quinolin-2-amine | LCMS m/z = 676.47 (M + 1, 100%) |
| 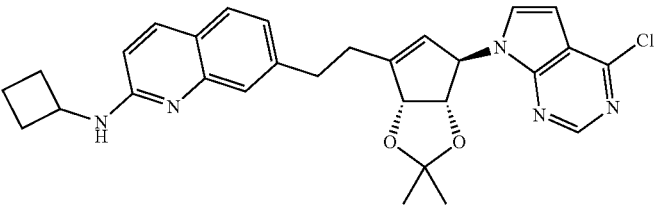 [SMILES: CC1(C)O[C@@H]2[C@H](O1)C(CCc1ccc3ccc(NC4CCC4)nc3c1)=C[C@H]2n1ccc2c(Cl)ncnc21]<br>7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-N-cyclobutylquinolin-2-amine | 4-Chloro-7-((3aS,4R,6aR)-2,2-dimethyl-6-vinyl-3a,6a-dihydro-4H-cyclopenta[d] [1,3] dioxol-4-yl)-7H-pyrrolo[2,3-d]pyrimidine and 7-Bromo-N-cyclobutylquinolin-2-amine | ¹H NMR (400 MHz, Chloroform-d) δ 8.65 (s, 1H), 7.89 (d, J = 8.9 Hz, 1H), 7.60 – 7.51 (m, 2H), 7.16 (dd, J = 8.1, 1.7 Hz, 1H), 6.65 (d, J = 8.9 Hz, 1H), 6.46 (d, J = 3.7 Hz, 1H), 6.25 (d, J = 3.7 Hz, 1H), 5.77 (s, 1H), 5.44 (t, J = 1.7 Hz, 1H), 5.32 – 5.28 (m, 2H), 4.48 – 4.41 (m, 2H), 3.22 – 3.02 (m, 2H), 2.83 – 2.77 (m, 2H), 2.58 – 2.46 (m, 2H), 2.07 – 1.96 (m, 2H), 1.85 (ddd, J = 10.6, 9.0, 6.4 Hz, 2H), 1.51 (s, 3H), 1.38 (s, 3H); LCMS m/z = 515.19 (M − 1, 100%) |

TABLE 5-continued

| Structure & IUPAC name | Intermediates used | ¹H NMR & LCMS data |
|---|---|---|
| 3-Chloro-7-(2-((3aS,4R,6aR)-2,2-dimethyl-4-(4-methyl-7H-pyrrolo[2,3-d]pyrimidin-7-yl)-3a,6a-dihydro-4H-cyclopenta[d][1,3]dioxol-6-yl)ethyl)quinolin-2-amine | 7-((3aS,4R,6aR)-2,2-dimethyl-6-vinyl-3a,6a-dihydro-4H-cyclopenta[d][1,3]dioxol-4-yl)-4-methyl-7H-pyrrolo[2,3-d]pyrimidine & 7-bromo-3-chloro quinolin-2-amine | LCMS m/z = 476.36 (M+, 60%) |
| 3-Chloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)propyl)quinolin-2-amine | 4-Chloro-7-((3aS,4R,6aR)-2,2-dimethyl-6-(prop-1-en-2-yl)-3a,6a-dihydro-4H-cyclopenta[d][1,3]dioxol-4-yl)-7H-pyrrolo[2,3-d]pyrimidine & 7-bromo-3-chloro quinolin-2-amine | LCMS m/z = 510.2 (M+, 100%) |
| | and 4-chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine | ¹H NMR (400 MHz, Chloroform-d) δ 8.76 – 8.62 (m, 2H), 7.76 (s, 1H), 7.25 (dd, J = 10.4, 1.5 Hz, 1H), 6.84 (d, J = 3.7 Hz, 1H), 6.54 (d, J = 3.6 Hz, 1H), 5.81 (s, 1H), 5.55 (s, 1H), 5.37 – 5.29 (m, 1H), 4.58 (d, J = 5.7 Hz, 1H), 3.25 – 3.12 (m, 2H), 2.89 – 2.72 (m, 2H), 1.51 (s, 3H), 1.45 (s, 9H), 1.43 (s, 9H), 1.38 (s, 3H); LCMS m/z = 760.41 (M + 1, 40%). |
| | and 7-((3aS,4R,6aR)-2,2-dimethyl-6-vinyl-3a,6a-dihydro-4H-cyclopenta[d][1,3]dioxol-4-yl)-4-methyl-7H-pyrrolo[2,3-d]pyrimidine | ¹H NMR (400 MHz, DMSO-d₆) δ 8.88 (s, 1H), 8.64 (s, 1H), 7.85 (s, 1H), 7.63 (dd, J = 11.0, 1.5 Hz, 1H), 6.80 (d, J = 3.6 Hz, 1H), 6.48 (d, J = 3.7 Hz, 1H), 5.65 (s, 1H), 5.56 (s, 1H), 5.37 (d, J = 5.6 Hz, 1H), 4.44 (d, J = 5.7 Hz, 1H), 3.22 – 3.13 (m, 2H), 2.78 – 2.66 (m, 2H), 2.61 (s, 3H), 1.38 (s, 9H), 1.35 (s, 3H), 1.33 (s, 9H), 1.27 |

TABLE 5-continued

| Structure & IUPAC name | Intermediates used | ¹H NMR & LCMS data |
|---|---|---|
| 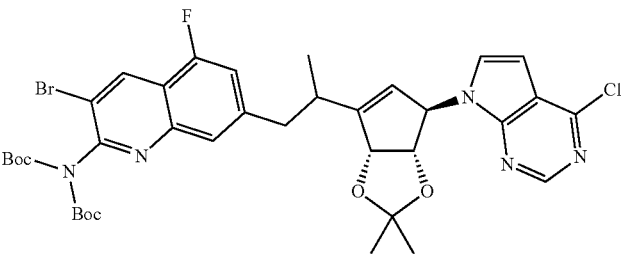<br>4-Chloro-7-((3aS,4R,6aR)-2,2-dimethyl-6-(2-(3-methylimidazo[1,2-a]pyridin-7-yl)ethyl)-3a,6a-dihydro-4H-cyclopenta[d][1,3]dioxol-4-yl)-7H-pyrrolo[2,3-d]pyrimidine | 4-Chloro-7-((3aS,4R,6aR)-2,2-dimethyl-6-(prop-1-en-2-yl)-3a,6a-dihydro-4H-cyclopenta[d][1,3]dioxol-4-yl)-7H-pyrrolo[2,3-d]pyrimidine and 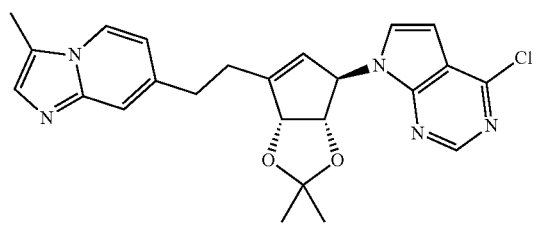 [SMILES: Cc1cnc2cc(CCC3=C[C@@H](n4ccc5c(Cl)ncnc54)[C@@H]4OC(C)(C)O[C@H]34)ccn12]4-Chloro-1-((3aS,4R,6aR)-2,2-dimethyl-6-vinyl-4,6a-dihydro-3aH-cyclopenta[d][1,3]dioxol-4-yl)-1H-pyrrolo[3,2-c]pyridine & 7-Bromo-3-methylimidazo[1,2-a]pyridine | (s, 3H); LCMS m/z = 738.61 (M+, 90%), 740.61 (M + 2, 100%).<br><br>LCMS m/z = 796.20 (M + 23, 60%).<br><br>LCMS m/z = 450.04 (M+, 100%) |

3-Chloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-5-fluoroquinolin-2-amine

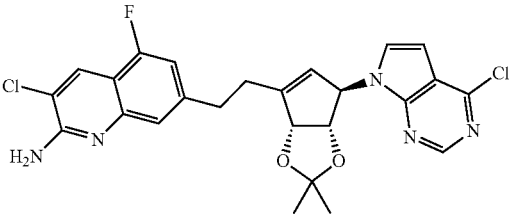 [SMILES: CC1(C)O[C@@H]2[C@H](O1)C(CCc1cc(F)c3cc(Cl)c(N)nc3c1)=C[C@H]2n1ccc2c(Cl)ncnc21]

4-Chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine (0.242 g, 0.762 mmol) in 9-BBN (0.5 molar, 4.36 ml 2.178 mmol) was heated at 50° C. for 1 h under N₂ atmosphere. The reaction mixture was cooled to 25° C., then potassium phosphate tribasic (0.578 g, 2.72 mmol) in water (0.5 ml) was added and stirred for 20 mins. A solution of 7-bromo-3-chloro-5-fluoroquinolin-2-amine (0.150 g, 0.544 mmol) in THF (0.5 ml) was added, followed by dichloro[1,1'-bis(di-t-butylphosphino)ferrocene]palladium(II) (0.035 g, 0.054 mmol). The resulting mixture was stirred at 50° C. for 6 h. The reaction mixture was diluted with water (10 ml) and extracted with ethyl acetate (10 ml). Layers were separated, organic layer was washed with brine (10 ml) and dried over anhydrous Na₂SO₄. The organic layer was filtered and concentrated in vacuo to give 0.345 g of crude compound. This residue was purified by combiflash (R$_f$200, Teledyne/Isco) instrument onto a Redisep® R$_f$ column with gradient elution (0 to 35%) of ethyl acetate in petroleum ether to afford the title compound (0.16 g, 57.5%) as an off-white solid. ¹H NMR (400 MHz, DMSO-d6) δ 8.64 (s, 1H), 8.18 (s, 1H), 7.25 (s, 1H), 7.09-6.96 (m, 4H), 6.44 (d, J=3.6 Hz, 1H), 5.67 (s, 1H), 5.56-5.51 (m, 1H), 5.35 (d, J=5.7 Hz, 1H), 4.52 (d, J=5.7 Hz, 1H), 3.05-2.98 (m, 2H), 2.74-2.56 (m, 2H), 1.38 (s, 3H), 1.28 (s, 3H); LCMS m/z=514.2 (M+, 100%).

Intermediates in table-6 were synthesized by an analogous reaction protocol as was used for the preparation of 3-chloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-5-fluoroquinolin-2-amine using the appropriate starting materials.

TABLE-6

| Structure & IUPAC name | Intermediates used | ¹H NMR & LCMS data |
|---|---|---|
| 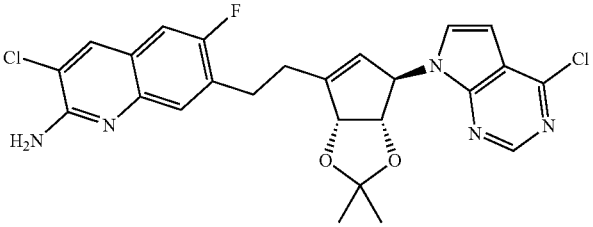<br>3-Chloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-6-fluoroquinolin-2-amine | 4-Chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine and 7-Bromo-3-chloro-6-fluoroquinolin-2-amine | ¹H NMR (400 MHz, DMSO-d6) δ 8.65 (s, 1H), 8.18 (s, 1H), 7.56-7.44 (m, 2H), 7.14 (d, J = 3.7 Hz, 1H), 6.73 (s, 2H), 6.50 (d, J = 3.7 Hz, 1H), 5.69 (s, 1H), 5.60-5.52 (m, 1H), 5.42-5.31 (m, 1H), 4.53 (dd, J = 5.7, 2.8 Hz, 1H), 3.08-3.01 (m, 2H), 2.66-2.62 (m, 2H), 1.39 (s, 3H), 1.28 (s, 3H); LCMS m/z = 515 (M + 1, 100%). |
| 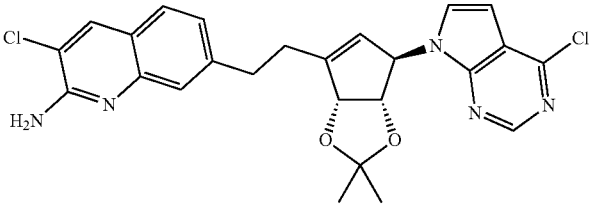<br>3-3-Chloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)quinolin-2-amine. | 4-Chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine and 7-Bromo-3-chloroquinolin-2-amine | ¹H NMR (400 MHz, DMSO-d6) δ 8.65 (s, 1H), 8.19 (s, 1H), 7.61 (d, J = 8.2 Hz, 1H), 7.40 (s, 1H), 7.19 (dd, J = 8.1, 1.7 Hz, 1H), 6.96 (d, J = 3.6 Hz, 1H), 6.72 (s, 2H), 6.41 (d, J = 3.6 Hz, 1H), 5.66 (s, 1H), 5.52 (s, 1H), 5.34 (d, J = 5.7 Hz, 1H), 4.49 (d, J = 5.6 Hz, 1H), 3.10-2.96 (m, 2H), 2.79-2.60 (m, 2H), 1.38 (s, 3H), 1.28 (s, 3H); LCMS m/z = 496.05 (M+, 100%) |
| 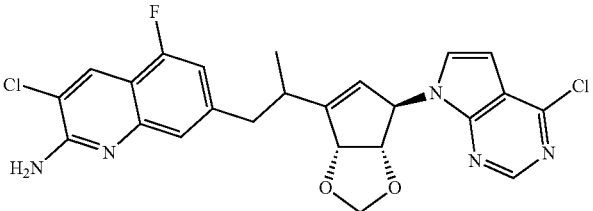<br>3-Chloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)propyl)-5-fluoroquinolin-2-amine | 4-Chloro-7-((3aS,4R,6aR)-2,2-dimethyl-6-(prop-1-en-2-yl)-3a,6a-dihydro-4H-cyclopenta[d][1,3]dioxol-4-yl)-7H-pyrrolo[2,3-d]pyrimidine and 7-Bromo-3-chloro-5-fluoroquinolin-2-amine | ¹H NMR (400 MHz, DMSO-d6) δ 8.64 (d, J = 6.1 Hz, 1H), 8.22-8.16 (m, 1H), 7.29-7.14 (m, 2H), 7.00-6.95 (m, 3H), 6.56 (d, J = 3.6 Hz, 1H), 5.67 (d, J = 14.7 Hz, 1H), 5.57 (s, 1H), 5.40-5.34 (m, 1H), 4.54 (dd, J = 15.1, 5.7 Hz, 1H), 3.04 (q, J = 9.6, 7.8 Hz, 1H), 2.87 (s, 2H), 1.30 (d, J = 9.7 Hz, 3H), 1.19 (d, 6H); LCMS m/z = 528.32 (M+, 100%) |

TABLE-6-continued

| Structure & IUPAC name | Intermediates used | ¹H NMR & LCMS data |
|---|---|---|
| 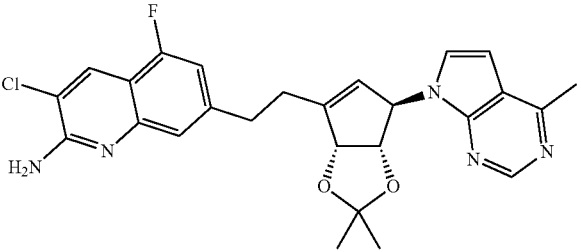<br>3-Chloro-7-(2-((3aS,4R,6aR)-2,2-dimethyl-4-(4-methyl-7H-pyrrolo[2,3-d]pyrimidin-7-yl)-3a,6a-dihydro-4H-cyclopenta[d][1,3]dioxol-6-yl)ethyl)-5-fluoroquinolin-2-amine | 7-((3aS,4R,6aR)-2,2-Dimethyl-6-vinyl-3a,6a-dihydro-4H-cyclopenta[d][1,3]dioxol-4-yl)-4-methyl-7H-pyrrolo[2,3-d]pyrimidine and 7-Bromo-3-chloro-5-fluoroquinolin-2-amine | ¹H NMR (400 MHz, Chloroform-d) δ 8.83 (s, 1H), 8.22 (d, J = 0.8 Hz, 1H), 7.34 (s, 1H), 6.92 (dd, J = 10.6, 1.5 Hz, 1H), 6.88 (d, J = 3.6 Hz, 1H), 6.38 (d, J = 3.6 Hz, 1H), 5.80 (s, 1H), 5.52-5.47 (m, 2H), 4.55 (d, J = 5.7 Hz, 1H), 3.12-3.06 (m, 2H), 2.77-2.74 (m, 2H), 2.74 (s, 3H), 1.51 (s, 3H), 1.38 (s, 3H); LCMS m/z = 494.3 (M+, 80%) |
| 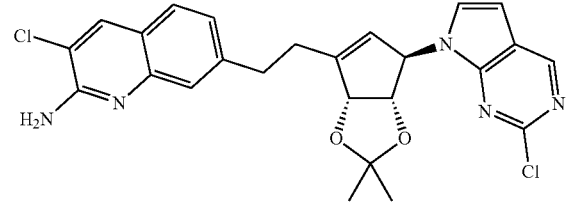<br>3-Chloro-7-(2-((3aS,4R,6aR)-4-(2-chloro-7H-pyrrolo[2,3-d]pyrimidin-7-yl)-2,2-dimethyl-3a,6a-dihydro-4H-cyclopenta[d][1,3]dioxol-6-yl)ethyl)quinolin-2-amine | 2-Chloro-7-((3aS,4R,6aR)-2,2-dimethyl-6-vinyl-4,6a-dihydro-3aH-cyclopenta[d][1,3]dioxol-4-yl)-7H-pyrrolo[2,3-d]pyrimidine and 7-Bromo-3-chloroquinolin-2-amine | ¹H NMR (400 MHz, Chloroform-d) δ 8.76 (s, 1H), 7.98 (s, 1H), 7.55 (d, J = 8.2 Hz, 2H), 7.22 (dd, J = 8.1, 1.7 Hz, 1H), 6.52 (d, J = 3.6 Hz, 1H), 6.28 (d, J = 3.7 Hz, 1H), 5.75 (s, 1H), 5.42 (d, J = 2.4 Hz, 1H), 5.34 (d, J = 10.9 Hz, 3H), 4.52 (d, J = 5.6 Hz, 1H), 3.18-3.07 (m, 2H), 2.81-2.76 (m, 2H), 1.49 (s, 3H), 1.38 (s, 3H); LCMS m/z = 496.24 (M+, 60%) |
| 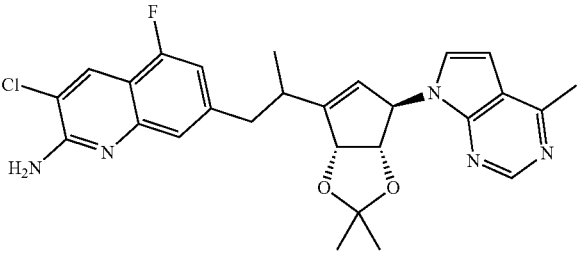<br>3-Chloro-7-(2-((3aS,4R,6aR)-2,2-dimethyl-4-(4-methyl-7H-pyrrolo[2,3-d]pyrimidin-7-yl)-3a,6a-dihydro-4H-cyclopenta[d][1,3]dioxol-6-yl)propyl)-5-fluoroquinolin-2-amine | 7-((3aS,4R,6aR)-2,2-Dimethyl-6-(prop-1-en-2-yl)-4,6a-dihydro-3aH-cyclopenta[d][1,3]dioxol-4-yl)-4-methyl-7H-pyrrolo[2,3-d]pyrimidine and 7-Bromo-3-chloro-5-fluoroquinolin-2-amine | LCMS m/z = 508.31 (M+, 100%) |

TABLE-6-continued

| Structure & IUPAC name | Intermediates used | $^1$H NMR & LCMS data |
|---|---|---|
| 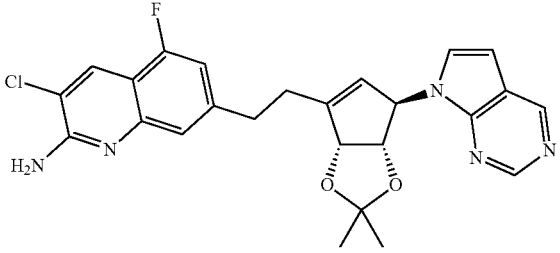 [SMILES: CC1(C)O[C@@H]2[C@H](O1)C(CCc1cc(F)c3cc(Cl)c(N)nc3c1)=C[C@H]2n1ccc2cnccc21]<br>3-Chloro-7-(2-((3aS,4R,6aR)-2,2-dimethyl-4-(7H-pyrrolo[2,3-d]pyrimidin-7-yl)-3a,6a-dihydro-4H-cyclopenta[d][1,3]dioxol-6-yl)ethyl)-5-fluoroquinolin-2-amine | 7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine and 7-Bromo-3-chloro-5-fluoroquinolin-2-amine | $^1$H NMR (400 MHz, Chloroform-d) δ 8.93 (d, J = 10.4 Hz, 2H), 8.24 (s, 1H), 7.37 (s, 1H), 6.94 (dd, J = 10.8, 1.4 Hz, 1H), 6.71 (d, J = 3.6 Hz, 1H), 6.37 (d, J = 3.6 Hz, 1H), 5.83 (s, 1H), 5.72 (s, 2H), 5.50 (s, 1H), 5.31 (d, J = 5.7 Hz, 1H), 4.56 (d, J = 5.7 Hz, 1H), 3.16-3.04 (m, 2H), 2.78-2.76 (m, 2H), 1.52 (s, 3H), 1.38 (s, 3H); LCMS m/z = 480.2 (M+, 70%) |
| 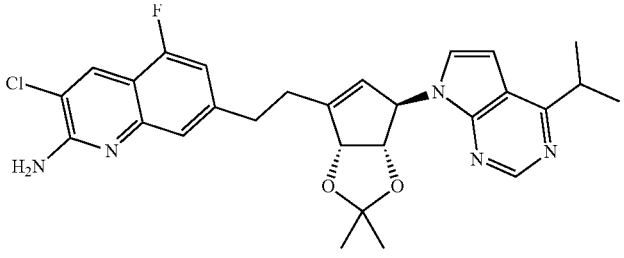<br>Chloro-5-fluoro-7-(2-((3aS,4R,6aR)-4-(4-isopropyl-7H-pyrrolo[2,3-d]pyrimidin-7-yl)-2,2-dimethyl-3a,6a-dihydro-4H-cyclopenta[d][1,3]dioxol-6-yl)ethyl)quinolin-2-amine | 7-((3aS,4R,6aR)-2,2-dimethyl-6-vinyl-3a,6a-dihydro-4H-cyclopenta[d][1,3]dioxol-4-yl)-4-isopropyl-7H-pyrrolo[2,3-d]pyrimidine & 7-Bromo-3-chloro-5-fluoroquinolin-2-amine | LCMS m/z = 522.32 (M+, 100%) |
| 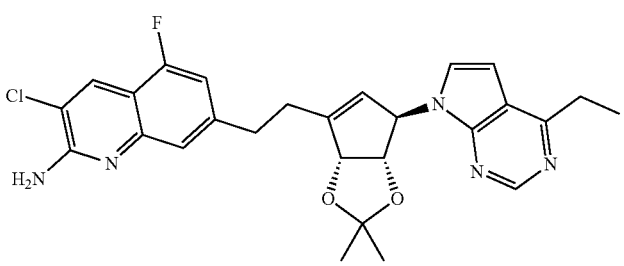<br>Chloro-7-(2-((3aS,4R,6aR)-4-(4-ethyl-7H-pyrrolo[2,3-d]pyrimidin-7-yl)-2,2-dimethyl-3a,6a-dihydro-4H-cyclopenta[d][1,3]dioxol-6-yl)ethyl)-5-fluoroquinolin-2-amine | 7-((3aS,4R,6aR)-2,2-dimethyl-6-vinyl-3a,6a-dihydro-4H-cyclopenta[d][1,3]dioxol-4-yl)-4-ethyl-7H-pyrrolo[2,3-d]pyrimidine & 7-Bromo-3-chloro-5-fluoroquinolin-2-amine | $^1$H NMR (400 MHz, DMSO-d6) δ 8.68 (s, 1H), 8.18 (s, 1H), 7.25 (s, 1H), 7.05 (dd, J = 11.0, 1.4 Hz, 1H), 6.96 (s, 2H), 6.85 (d, J = 3.6 Hz, 1H), 6.49 (d, J = 3.6 Hz, 1H), 5.66 (s, 1H), 5.52 (s, 1H), 5.34 (d, J = 5.7 Hz, 1H), 4.46 (d, J = 5.6 Hz, 1H), 3.05-2.93 (m, 4H), 2.66-2.59 (m, 2H), 1.38 (s, 3H), 1.31-1.24 (m, 6H); LCMS m/z = 508.31 (M+, 100%) |

TABLE-6-continued

| Structure & IUPAC name- | Intermediates used | ¹H NMR & LCMS data |
|---|---|---|
| 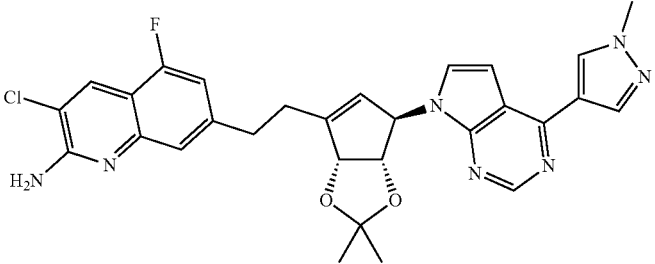<br>3-Chloro-7-(2-((3aS,4R,6aR)-2,2-dimethyl-4-(4-(1-methyl-1H-pyrazol-4-yl)-7H-pyrrolo[2,3-d]pyrimidin-7-yl)-3a,6a-dihydro-4H-cyclopenta[d][1,3]dioxol-6-yl)ethyl)-5-fluoroquinolin-2-amine | 7-((3aS,4R,6aR)-2,2-dimethyl-6-vinyl-3a,6a-dihydro-4H-cyclopenta[d][1,3]dioxol-4-yl)-4-(1-methyl-1H-pyrazol-4-yl)-7H-pyrrollo[2,3-d]pyrimidine & 7-Bromo-3-chloro-5-fluoroquinolin-2-amine | ¹H NMR (400 MHz, DMSO-d6) δ 8.70 (s, 1H), 8.60 (s, 1H), 8.23 (s, 1H), 8.19 (s, 1H), 7.27 (s, 1H), 7.10-6.95 (m, 4H), 6.79 (d, J = 3.7 Hz, 1H), 5.70 (s, 1H), 5.55 (s, 1H), 5.36 (d, J = 5.6 Hz, 1H), 4.50 (d, J = 5.7 Hz, 1H), 3.97 (s, 3H), 3.10-2.94 (m, 2H), 2.71-2.60 (m, 2H), 1.39 (s, 3H), 1.29 (s, 3H); LCMS m/z = 560.33 (M+, 100%) |
| 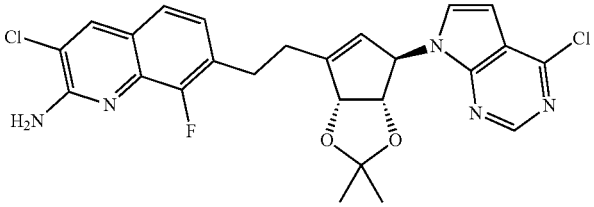<br>3-Chloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-8-fluoroquinolin-2-amine | 4-chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine & 7-Bromo-3-chloro-8-fluoroquinolin-2-amine | ¹H NMR (400 MHz, DMSO-d₆) δ 8.65 (s, 1H), 8.26 (d, J = 1.6 Hz, 1H), 7.62 (s, 1H), 7.45 (d, J = 8.3 Hz, 1H), 7.27-7.15 (m, 1H), 7.03 (s, 2H), 6.51 (d, J = 3.7 Hz, 1H), 5.69 (s, 1H), 5.55 (s, 1H), 5.36 (d, J = 5.7 Hz, 1H), 4.54 (d, J = 5.7 Hz, 1H), 3.12-3.0 (m, 2H), 2.66-2.58 (m, 2H), 1.29 (s, 3H), 1.24 (s, 3H); LCMS m/z = 515.57 (M + 1, 40%) |
| 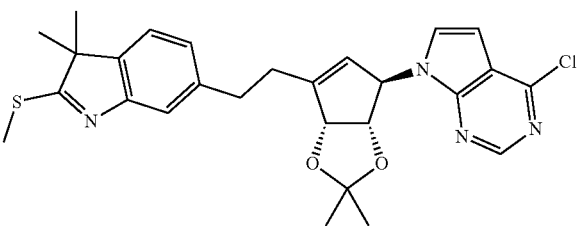<br>4-Chloro-7-((3aS,4R,6aR)-6-(2-(3,3-dimethyl-2-(methylthio)-3H-indol-6-yl)ethyl)-2,2-dimethyl-3a,6a-dihydro-4H-cyclopenta[d][1,3]dioxol-4-yl)-7H-pyrrolo[2,3-d]pyrimidine | 4-chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine & 6-Bromo-3,3-dimethyl-2-(methylthio)-3H-indole | ¹H NMR (400 MHz, DMSO-d₆) δ 8.67 (s, 1H), 7.42-7.28 (m, 2H), 7.17-6.99 (m, 2H), 6.51 (d, J = 3.6 Hz, 1H), 5.68 (s, 1H), 5.53 (s, 1H), 5.36 (d, J = 5.7 Hz, 1H), 4.52 (d, J = 5.6 Hz, 1H), 3.07-2.85 (m, 2H), 2.71-2.56 (m, 5H), 1.38 (s, 3H), 1.29 (d, J = 3.4 Hz, 9H); LCMS m/z = 510.31 (M + 1, 60%) |

TABLE-6-continued

| Structure & IUPAC name | Intermediates used | ¹H NMR & LCMS data |
|---|---|---|
| 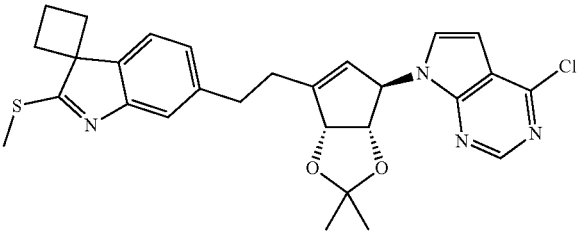<br>6'-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-2'-(methylthio)spiro[cyclobutane-1,3'-indole] | 4-Chloro-1-((3aS,4R,6aR)-2,2-dimethyl-6-vinyl-4,6a-dihydro-3aH-cyclopenta[d][1,3]dioxol-4-yl)-1H-pyrrolo[3,2-c]pyridine & 6'-Bromo-2'-(methylthio)spiro[cyclobutane-1,3'-indole] | ¹H NMR (400 MHz, DMSO-d$_6$) δ 8.66 (s, 1H), 7.61 (d, J = 7.5 Hz, 1H), 7.31 (d, J = 1.4 Hz, 1H), 7.09 (dd, J = 7.6, 1.5 Hz, 1H), 7.01 (d, J = 3.7 Hz, 1H), 6.46 (d, J = 3.6 Hz, 1H), 5.67 (s, 1H), 5.53 (s, 1H), 5.35 (d, J = 5.6 Hz, 1H), 4.52 (d, J = 5.6 Hz, 1H), 3.02-2.86 (m, 2H), 2.69-2.56 (m, 5H), 2.48-2.39 (m, 4H), 2.39-2.18 (m, 2H), 1.39 (s, 3H), 1.29 (s, 3H); LCMS m/z = 521.19 (M+, 30%) |
| 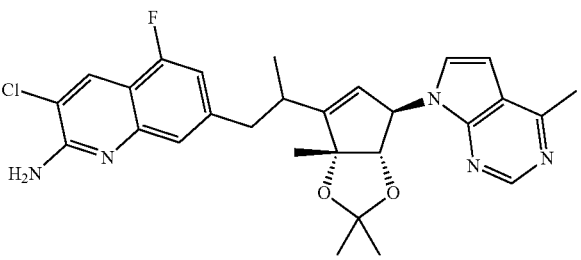<br>3-Chloro-5-fluoro-7-(2-((3aS,4R,6aR)-2,2,6a-trimethyl-4-(4-methyl-7H-pyrrolo[2,3-d]pyrimidin-7-yl)-3a,6a-dihydro-4H-cyclopenta[d][1,3]dioxol-6-yl)propyl)quinolin-2-amine | 4-methyl-7-((3aS,4R,6aR)-2,2,6a-trimethyl-6-(prop-1-en-2-yl)-3a,6a-dihydro-4H-cyclopenta[d][1,3]dioxol-4-yl)-7H-pyrrolo[2,3-d]pyrimidine and 7-bromo-3-chloro-5-fluoroquinolin-2-amine | LCMS m/z = 522.32 (M+, 100%) |
| 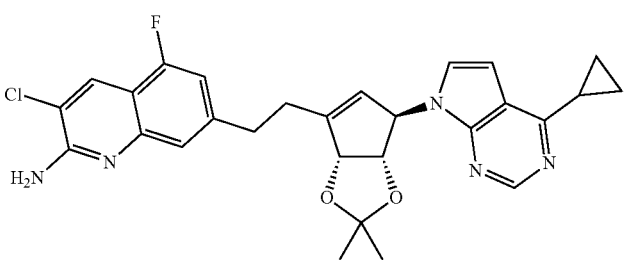<br>3-Chloro-7-(2-((3aS,4R,6aR)-4-(4-cyclopropyl-7H-pyrrolo[2,3-d]pyrimidin-7-yl)-2,2-dimethyl-3a,6a-dihydro-4H-cyclopenta[d][1,3]dioxol-6-yl)ethyl)-5-fluoroquinolin-2-amine | 4-Cyclopropyl-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine and 7-Bromo-3-chloro-5-fluoroquinolin-2-amine | LCMS m/z = 520.14 (M+, 100%) |

TABLE-6-continued

| Structure & IUPAC name | Intermediates used | ¹H NMR & LCMS data |
|---|---|---|
| 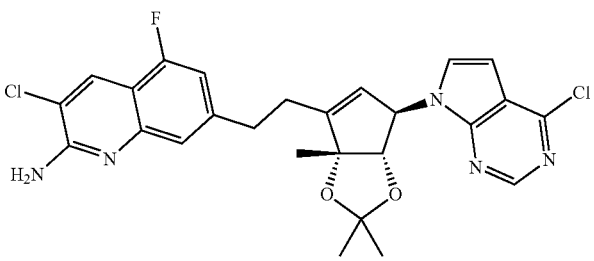<br>3-Chloro-7-(2-((3aS,4R,6aR)-4-(4-chloro-7H-pyrrolo[2,3-d]pyrimidin-7-yl)-2,2,6a-trimethyl-3a,6a-dihydro-4H-cyclopenta[d][1,3]dioxol-6-yl)ethyl)-5-fluoroquinolin-2-amine | 4-Chloro-7-((3aS,4R,6aR)-2,2,6a-trimethyl-6-vinyl-3a,6a-dihydro-4H-cyclopenta[d][1,3]dioxol-4-yl)-7H-pyrrolo[2,3-d]pyrimidine & 7-Bromo-3-chloro-5-fluoroquinolin-2-amine | ¹H NMR (400 MHz, Chloroform-d) δ 8.72 (s, 1H), 8.22 (d, J = 0.8 Hz, 1H), 7.37 (s, 1H), 6.99 (d, J = 3.6 Hz, 1H), 6.96-6.89 (m, 1H), 6.55 (d, J = 3.7 Hz, 1H), 5.76 (s, 1H), 5.58-5.46 (m, 3H), 4.18-4.13 (m, 1H), 3.20-3.05 (m, 2H), 2.77-2.62 (m, 2H), 1.50 (s, 3H), 1.44 (s, 3H), 1.42 (s, 3H); LCMS m/z = 528.19 (M+, 100%) |
| 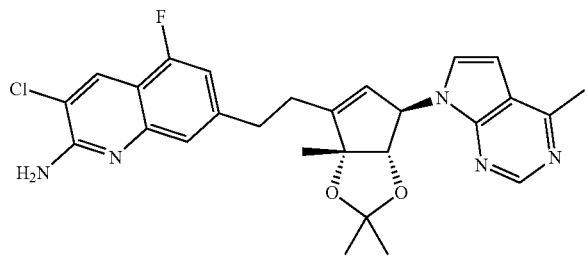<br>3-Chloro-5-fluoro-7-(2-((3aS,4R,6aR)-2,2,6a-trimethyl-4-(4-methyl-7H-pyrrolo[2,3-d]pyrimidin-7-yl)-3a,6a-dihydro-4H-cyclopenta[d][1,3]dioxol-6-yl)ethyl)quinolin-2-amine | 4-Methyl-7-((3aS,4R,6aR)-2,2,6a-trimethyl-6-vinyl-3a,6a-dihydro-4H-cyclopenta[d][1,3]dioxol-4-yl)-7H-pyrrolo[2,3-d]pyrimidine & 7-Bromo-3-chloro-5-fluoroquinolin-2-amine | ¹H NMR (400 MHz, DMSO-d₆) δ 8.68 (s, 1H), 8.18 (s, 1H), 7.27 (s, 1H), 7.12-7.03 (m, 2H), 6.96 (s, 2H), 6.66-6.51 (m, 1H), 5.64 (s, 1H), 5.58 (s, 1H), 4.04 (s, 1H), 3.14-3.02 (m, 2H), 2.74-2.59 (m, 5H), 1.39 (s, 3H), 1.30 (d, J = 3.5 Hz, 6H); LCMS m/z = 508.31 (M+, 100%) |
| 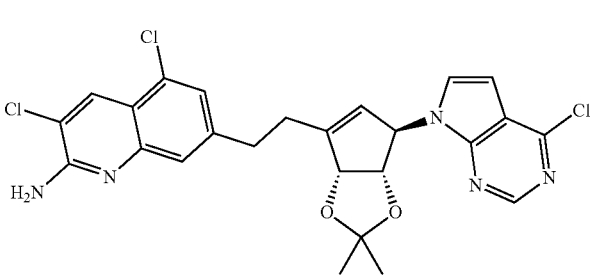<br>3,5-Dichloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)quinolin-6-amine | 4-chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine & 3,5-Dichloro-7-iodoquinolin-2-amine | LCMS m/z = 532.19 (M + 1, 90%) |

TABLE-6-continued

| Structure & IUPAC name | Intermediates used | ¹H NMR & LCMS data |
|---|---|---|
| 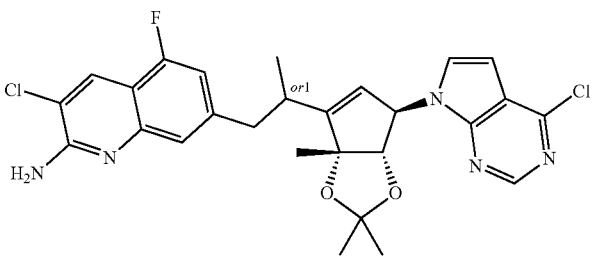<br>3-Chloro-7-(2-((3aS,4R,6aR)-4-(4-chloro-7H-pyrrolo[2,3-d]pyrimidin-7-yl)-2,2,6a-trimethyl-3a,6a-dihydro-4H-cyclopenta[d][1,3]dioxol-6-yl)propyl)-5-fluoroquinolin-2-amine | 4-chloro-7-((3aS,4R,6aR)-2,2,6a-trimethyl-6-(prop-1-en-2-yl)-3a,6a-dihydro-4H-cyclopenta[d][1,3]dioxol-4-yl)-7H-pyrrolo[2,3-d]pyrimidine & 7-bromo-3-chloro-5-fluoroquinolin-2-amine | ¹H NMR (400 MHz, DMSO-$d_6$) δ 8.66 (s, 1H), 8.14 (s, 1H), 7.25 (s, 1H), 7.07 (dd, J = 11.1, 1.3 Hz, 1H), 7.01 (s, 2H), 6.69 (d, J = 3.7 Hz, 1H), 6.35 (d, J = 3.7 Hz, 1H), 5.77 (d, J = 2.7 Hz, 1H), 5.60 (d, J = 2.7 Hz, 1H), 4.01 (s, 1H), 3.10-2.93 (m, 2H), 2.92-2.80 (m, 1H), 1.37 (s, 3H), 1.27 (s, 3H), 1.25 (d, J = 6.0 Hz, 3H), 1.11 (s, 3H). LCMS m/z = 542.20 (M+, 100%) |
| 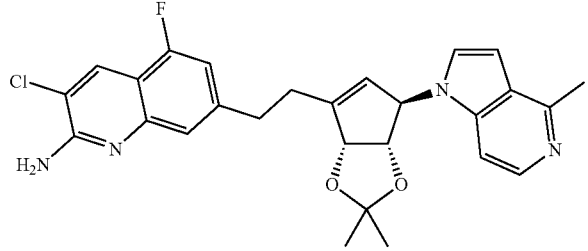<br>3-chloro-7-(2-((3aS,4R,6aR)-2,2-dimethyl-4-(4-methyl-1H-pyrrolo[3,2-c]pyridin-1-yl)-3a,6a-dihydro-4H-cyclopenta[d][1,3]dioxol-6-yl)ethyl)-5-fluoroquinolin-2-amine | 1-((3aS,4R,6aR)-2,2-Dimethyl-6-vinyl-3a,6a-dihydro-4H-cyclopenta[d][1,3]dioxol-4-yl)-4-methyl-1H-pyrrolo[3,2-c]pyridine, 1-((3aS,4R,6aR)-2,2-dimethyl-6-vinyl-3a,6a-dihydro-4H-cyclopenta[d][1,3]dioxol-4-yl)-1H-pyrrolo[3,2-c]pyridine and 7-bromo-3-chloro-5-fluoroquinolin-2-amine | LCMS m/z = 493.36 (M+, 100%) |
| 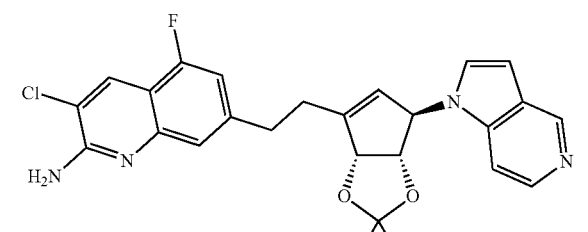 | 1-((3aS,4R,6aR)-2,2-Dimethyl-6-vinyl-3a,6a-dihydro-4H-cyclopenta[d][1,3]dioxol-4-yl)-4-methyl-1H-pyrrolo[3,2-c]pyridine, 1-((3aS,4R,6aR)-2,2-dimethyl-6-vinyl-3a,6a-dihydro-4H-cyclopenta[d][1,3]dioxol-4-yl)-1H-pyrrolo[3,2-c]pyridine and 7-bromo-3-chloro-5-fluoroquinolin-2-amine | LCMS m/z = 479.30 (M+, 100%) |

TABLE-6-continued

| Structure & IUPAC name | Intermediates used | ¹H NMR & LCMS data |
|---|---|---|
| 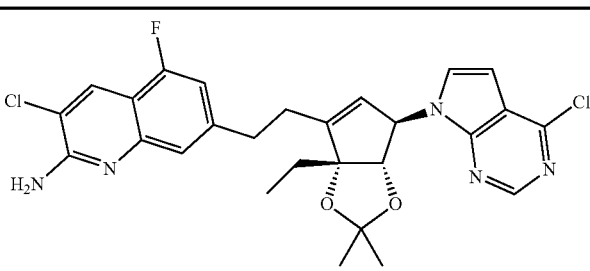<br>3-Chloro-7-(2-((3aS,4R,6aR)-4-(4-chloro-7H-pyrrolo[2,3-d]pyrimidin-7-yl)-6a-ethyl-2,2-dimethyl-3a,6a-dihydro-4H-cyclopenta[d][1,3]dioxol-6-yl)ethyl)-5-fluoroquinolin-2-amine | 4-Chloro-7-((3aS,4R,6aR)-6a-ethyl-2,2-dimethyl-6-vinyl-4,6a-dihydro-3aH-cyclopenta[d][1,3]dioxol-4-yl)-7H-pyrrolo[2,3-d]pyrimidine & 7-Bromo-3-chloro-5-fluoroquinolin-2-amine | ¹H NMR (400 MHz, DMSO-d₆) δ 8.70 (s, 1H), 8.18 (s, 1H), 7.34 (d, J = 3.7 Hz, 1H), 7.28 (s, 1H), 7.07 (dd, J = 11.1, 1.4 Hz, 1H), 6.96 (s, 2H), 6.60 (d, J = 3.7 Hz, 1H), 5.79 (s, 1H), 5.58 (d, J = 2.3 Hz, 1H), 4.23 (s, 1H), 3.18-2.98 (m, 2H), 2.67-2.53 (m, 2H), 1.68-1.52 (m, 2H), 1.31 (s, 3H), 1.28 (s, 3H), 0.70-0.61 (m, 3H); LCMS m/z = 542.3 (M+, 100%) |
| 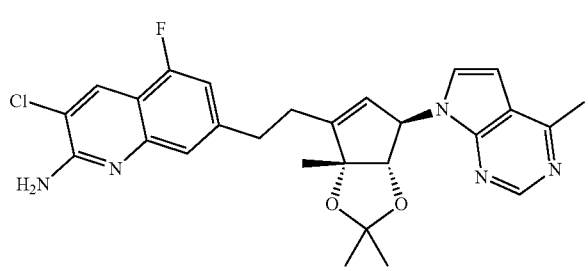<br>Chemical Formula: C₂₈H₂₉ClFN₅O₂<br>3-Chloro-5-fluoro-7-(2-((3aS,4R,6aR)-2,2,6a-trimethyl-4-(4-methyl-7H-pyrrolo[2,3-d]pyrimidin-7-yl)-3a,6a-dihydro-4H-cyclopenta[d][1,3]dioxol-6-yl)propyl)quinolin-2-amine | 4-methyl-7-((3aS,4R,6aR)-2,2,6a-trimethyl-6-(prop-1-en-2-yl)-3a,6a-dihydro-4H-cyclopenta[d][1,3]dioxol-4-yl)-7H-pyrrolo[2,3-d]pyrimidine & 7-bromo-3-chloro-5-fluoroquinolin-2-amine | LCMS m/z = 522.32 (M+, 100%). |

7-(2-((3aR,3bR,4aS,5R,5aS)-5-(4-Amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-3-chloro-5-fluoroquinolin-2-amine

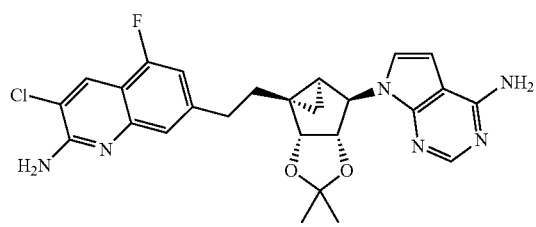 [SMILES: CC1(C)O[C@H]2[C@H](n3ccc4c(N)ncnc43)[C@H]3C[C@]3(CCc3cc(F)c4cc(Cl)c(N)nc4c3)[C@H]2O1]

7-((3aR,3bS,4aS,5R,5aS)-2,2-Dimethyl-3b-vinylhexahydrocyclopropa[3,4]cyclopenta[1,2-d][1,3]dioxol-5-yl)-7H-pyrrolo[2,3-d]pyrimidin-4-amine (1 g, 3.20 mmol) in 9-BBN (0.5 molar, 25.6 ml, 12.81 mmol) was heated at 60° C. for 1 h under N2 atmosphere. The reaction mixture was cooled to 25° C., then potassium phosphate tribasic (3.40 g, 16.01 mmol) in water (2 ml) was added and stirred for 30 mins. A solution of 7-bromo-3-chloro-5-fluoroquinolin-2-amine (0.882 g, 3.20 mmol) in THF (12 ml) was added, followed by PdCl₂(dppf) (0.234 g, 0.320 mmol). The resulting mixture was stirred at 50° C. for 6 h. The reaction mixture was diluted with water (10 ml) and extracted with ethyl acetate (10 ml). Layers were separated, organic layer was washed with brine (10 ml) and dried over anhydrous Na₂SO₄. The organic layer was filtered and concentrated in vacuo to give 1.5 g of crude compound. This residue was purified by combiflash (R_f 200, Teledyne/Isco) instrument onto a Redisep® R_f column with gradient elution (0 to 5%) of methanol in dichloromethane to afford the title compound (1.3 g, 80%) as a pale yellow semisolid. ¹H NMR (400 MHz, DMSO-d₆) δ 8.16 (s, 1H), 8.08 (s, 1H), 7.22 (s, 1H), 7.12 (d, J=3.5 Hz, 1H), 7.05 (d, J=1.4 Hz, 1H), 7.02 (s, 2H), 6.94 (s, 2H), 6.61 (d, J=3.5 Hz, 1H), 5.20 (d, J=7.2 Hz, 1H), 5.01 (s, 1H), 4.52 (dd, J=7.3, 1.5 Hz, 1H), 2.85-2.80 (m, 2H), 2.32-2.26 (m, 1H), 1.72-1.56 (m, 1H), 1.48 (s, 3H), 1.46-1.41 (m, 1H), 1.19 (s, 3H), 0.94-0.92 (s, 1H), 0.77-0.68 (i, 1H); LCMS m/z=509.06 (M+, 20%).

Intermediates in table-7 were synthesized by an analogous reaction protocol as was used for the preparation of 7-(2-((3aR,3bR,4a,5R,5a4)-5-(4-amino-7H-pyrrolo[2,3-d]pyrimidin-7-yl)-2,2-dimethyltetrahydrocyclopropa[3,4]cyclopenta[1,2-d] [1,3]dioxol-3b(3aH)-yl)ethyl)-3-chloro-5-fluoroquinolin-2-amine using the appropriate starting materials and at suitable temperature.

TABLE-7

| Structure & IUPAC name | Intermediates used | ¹H NMR & LCMS data |
|---|---|---|
| 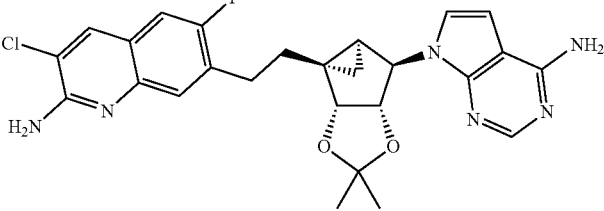<br>7-(2-((3aR,3bR,4aS,5R,5aS)-5-(4-amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-3-chloro-6-fluoroquinolin-2-amine | 7-((3aR,3bS,4aS,5R,5aS)-2,2-Dimethyl-3b-vinylhexahydrocyclopropa[3,4]cyclopenta[1,2-d][1,3]dioxol-5-yl)-7H-pyrrolo[2,3-d]pyrimidin-4-amine and 7-Bromo-3-chloro-6-fluoroquinolin-2-amine | ¹H NMR (400 MHz, DMSO-$d_6$) δ 8.16 (s, 1H), 8.07 (s, 1H), 7.50-7.40 (m, 2H), 7.14 (d, J = 3.5 Hz, 1H), 7.09-7.01 (m, 3H), 6.67 (s, 1H), 6.62 (dd, J = 6.0, 3.6 Hz, 1H), 5.20 (d, J = 7.2 Hz, 1H), 5.01 (s, 1H), 4.54 (d, J = 7.2 Hz, 1H), 2.97-2.76 (m, 2H), 2.30-2.20 (m, 1H), 1.68-1.60 (m, 1H), 1.48 (s, 3H), 1.24 (s, 3H), 1.20-1.14 (m, 1H), 0.97-0.94 (m, 1H), 0.76-0.70 (m, 1H); (M+, 30%) |
| 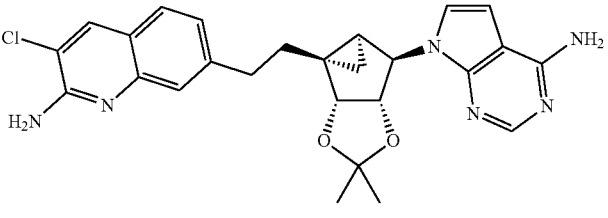<br>7-(2-((3aR,3bR,4aS,5R,5aS)-5-(4-amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-3-chloroquinolin-2-amine | 7-((3aR,3bS,4aS,5R,5aS)-2,2-Dimethyl-3b-vinylhexahydrocyclopropa[3,4]cyclopenta[1,2-d][1,3]dioxol-5-yl)-7H-pyrrolo[2,3-d]pyrimidin-4-amine and 7-Bromo-3-chloroquinolin-2-amine | ¹H NMR (400 MHz, DMSO-$d_6$) δ 8.15 (s, 1H), 8.08 (s, 1H), 7.58 (d, J = 8.2 Hz, 1H), 7.37 (d, J = 1.6 Hz, 1H), 7.20-7.10 (m, 2H), 7.01 (s, 2H), 6.73-6.57 (m, 3H), 5.21 (dd, J = 7.1, 1.3 Hz, 1H), 5.01 (s, 1H), 4.52 (dd, J = 7.3, 1.5 Hz, 1H), 2.86-2.81 (m, 2H), 2.32-2.21 (m, 1H), 1.69-1.65 (m, 1H), 1.48 (s, 3H), 1.47-1.42 (m, 1H), 1.20 (s, 3H), 0.97-0.91 (m, 1H), 0.80-0.72 (m, 1H); LCMS m/z = 491.06 (M+, 100%) |
| 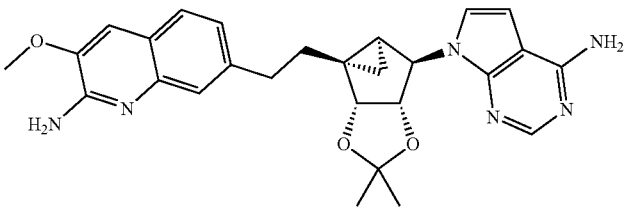<br>7-(2-((3aR,3bR,4aS,5R,5aS)-5-(4-amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-3-methoxyquinolin-2-amine | 7-((3aR,3bS,4aS,5R,5aS)-2,2-Dimethyl-3b-vinylhexahydrocyclopropa[3,4]cyclopenta[1,2-d][1,3]dioxol-5-yl)-7H-pyrrolo[2,3-d]pyrimidin-4-amine and 7-Bromo-3-methoxyquinolin-2-amine | ¹H NMR (400 MHz, DMSO-$d_6$) δ 8.08 (s, 1H), 7.50 (d, J = 8.1 Hz, 1H), 7.40-7.24 (m, 2H), 7.18-7.05 (m, 2H), 7.01 (s, 2H), 6.61 (d, J = 3.5 Hz, 1H), 6.29 (s, 2H), 5.21 (dd, J = 7.2, 1.3 Hz, 1H), 5.02 (s, 1H), 4.52 (dd, J = 7.3, 1.5 Hz, 1H), 3.89 (s, 3H), 2.88-2.74 (m, 2H), 2.30-2.18 (m, 1H), 1.72-1.60 (m, 1H), 1.48 (s, 3H), 1.46-1.41 (m, 1H), 1.20 (s, 3H), 0.98-0.91 (m, 1H), 0.79-0.73 (m, 1H); LCMS m/z = 487.2 (M + 1, 50%) |

TABLE-7-continued

| Structure & IUPAC name- | Intermediates used | ¹H NMR & LCMS data |
|---|---|---|
| 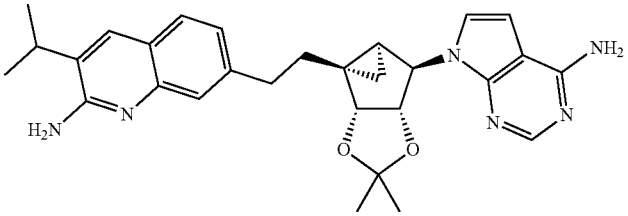<br>7-(2-((3aR,3bR,4aS,5R,5aS)-5-(4-amino-7H-pyrrolo[2,3-d]pyrimidin-7-yl)-2,2-dimethyltetra hydrocyclopropa[3,4]cyclopenta[1,2-d][1,3]dioxol-3b(3aH)-yl)ethyl)-3-isopropylquinolin-2-amine | 7-((3aR,3bS,4aS,5R,5aS)-2,2-Dimethyl-3b-vinylhexahydrocyclopropa[3,4]cyclopenta[1,2-d][1,3]dioxol-5-yl)-7H-pyrrolo[2,3-d]pyrimidin-4-amine and 7-Bromo-3-isopropylquinolin-3-amine | ¹H NMR (400 MHz, DMSO-d₆) δ 8.08 (s, 1H), 7.83 (s, 1H), 7.60 (d, J = 8.1 Hz, 1H), 7.34 (d, J = 1.5 Hz, 1H), 7.14 (dd, J = 7.6, 2.5 Hz, 2H), 7.02 (s, 2H), 6.69-6.59 (m, 3H), 5.27-5.16 (m, 1H), 5.01 (s, 1H), 4.53 (dd, J = 7.3, 1.5 Hz, 1H), 3.10-3.0 (m, 1H), 2.91-2.76 (m, 2H), 2.32-2.19 (m, 1H), 1.72-1.60 (m, 1H), 1.48 (s, 3H), 1.45-1.41 (m, 1H), 1.25-1.23 (m, 6H), 1.20 (s, 3H), 0.96-0.91 (m, 1H), 0.77-0.73 (m, 1H); LCMS m/z = 499.3 (M + 1, 75%) |
| 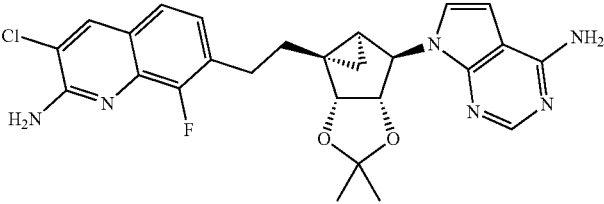<br>7-(2-((3aR,3bR,4aS,5R,5aS)-5-(4-amino-7H-pyrrolo[2,3-d]pyrimidin-7-yl)-2,2-dimethyltetra hydrocyclopropa[3,4]cyclopenta[1,2-d][1,3]dioxol-3b(3aH)-yl)ethyl)-3-chloro-8-fluoroquinolin-2-amine | 7-((3aR,3bS,4aS,5R,5aS)-2,2-Dimethyl-3b-vinylhexahydrocyclopropa[3,4]cyclopenta[1,2-d][1,3]dioxol-5-yl)-7H-pyrrolo[2,3-d]pyrimidin-4-amine and 7-Bromo-3-chloro-8-fluoroquinolin-2-amine | LCMS m/z = 509.12 (M+, 60%) |
| 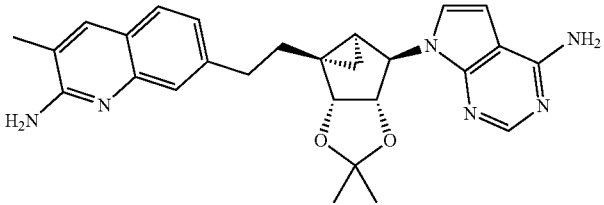<br>7-(2-((3aR,3bR,4aS,5R,5aS)-5-(4-amino-7H-pyrrolo[2,3-d]pyrimidin-7-yl)-2,2-dimethyltetra hydrocyclopropa[3,4]cyclopenta[1,2-d][1,3]dioxol-3b(3aH)-yl)ethyl)-3-methylquinolin-2-amine | 7-((3aR,3bS,4aS,5R,5aS)-2,2-Dimethyl-3b-vinylhexahydrocyclopropa[3,4]cyclopenta[1,2-d][1,3]dioxol-5-yl)-7H-pyrrolo[2,3-d]pyrimidin-4-amine and 7-Bromo-3-methylquinolin-2-amine | ¹H NMR (400 MHz, DMSO-d6) δ 8.08 (s, 1H), 7.73 (s, 1H), 7.51 (d, J = 8.1 Hz, 1H), 7.34 (d, J = 1.6 Hz, 1H), 7.13-7.07 (m, 2H), 7.01 (s, 2H), 6.61 (d, J = 3.5 Hz, 1H), 6.40 (s, 2H), 5.21 (d, J = 7.2 Hz, 1H), 5.01 (s, 1H), 4.53 (dd, J = 7.2, 1.4 Hz, 1H), 2.90-2.76 (m, 2H), 2.31-2.20 (m, 1H), 2.21 (s, 3H), 1.72-1.61 (m, 1H), 1.48 (s, 3H), 1.47-1.41 (m, 1H), 1.23 (s, 3H), 0.97-0.91 (m, 1H), 0.80-0.73 (m, 1H); LCMS m/z = 471.3 (M + 1, 90%) |

TABLE-7-continued

| Structure & IUPAC name- | Intermediates used | ¹H NMR & LCMS data |
|---|---|---|
| 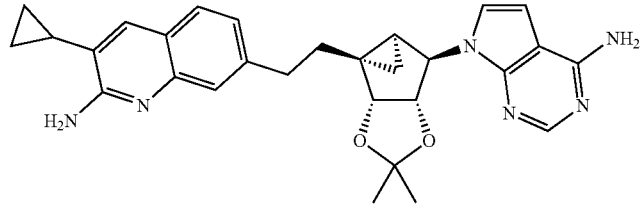<br>7-(2-((3aR,3bR,4aS,5R,5aS)-5-(4-amino-7H-pyrrolo[2,3-d]pyrimidin-7-yl)-2,2-dimethyl tetrahydrocyclopropa[3,4]cyclopenta[1,2-d][1,3]dioxol-3b(3aH)-yl)ethyl)-3-cyclopropylquinolin-2-amine | 7-((3aR,3bS,4aS,5R,5aS)-2,2-Dimethyl-3b-vinylhexahydrocyclopropa[3,4]cyclopenta[1,2-d][1,3]dioxol-5-yl)-7H-pyrrolo[2,3-d]pyrimidin-4-amine and 7-Bromo-3-cyclopropylquinolin-2-amine | ¹H NMR (400 MHz, DMSO-d6) δ 8.07 (s, 1H), 7.59 (s, 1H), 7.52 (d, J = 8.1 Hz, 1H), 7.32 (d, J = 1.6 Hz, 1H), 7.17-7.05 (m, 2H), 7.02 (s, 1H), 6.61 (d, J = 3.5 Hz, 1H), 6.46 (s, 2H), 5.21 (d, J = 7.2 Hz, 1H), 5.01 (s, 1H), 4.52 (dd, J = 7.3, 1.5 Hz, 1H), 2.90-2.73 (m, 2H), 2.30-2.18 (m, 1H), 1.86-1.74 (m, 1H), 1.73-1.60 (m, 1H), 1.51-1.41 (m, 4H), 1.26-1.22 (m, 4H), 1.00-0.90 (m, 3H), 0.79-0.71 (m, 1H), 0.68-0.60 (m, 2H); LCMS m/z = 497.11 (M + 1, 15%) |
| 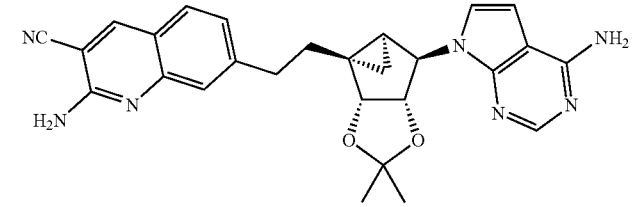<br>2-Amino-7-(2-((3aR,3bR,4aS,5R,5aS)-5-(4-amino-7H-pyrrolo[2,3-d]pyrimidin-7-yl)-2,2-dimethyl tetrahydrocyclopropa[3,4]cyclopenta[1,2-d][1,3]dioxol-3b(3aH)-yl)ethyl)quinoline-3-carbonitrile | 7-((3aR,3bS,4aS,5R,5aS)-2,2-Dimethyl-3b-vinylhexahydrocyclopropa[3,4]cyclopenta[1,2-d][1,3]dioxol-5-yl)-7H-pyrrolo[2,3-d]pyrimidin-4-amine and 2-Amino-7-bromoquinoline-3-carbonitrile | ¹H NMR (400 MHz, DMSO-d6) δ 8.61 (s, 1H), 8.07 (s, 1H), 7.66 (d, J = 8.3 Hz, 1H), 7.38 (s, 1H), 7.29-7.19 (m, 1H), 7.12 (d, J = 3.5 Hz, 1H), 7.01 (s, 2H), 6.89 (s, 2H), 6.61 (dd, J = 8.7, 3.5 Hz, 1H), 5.21 (d, J = 7.1 Hz, 1H), 5.01 (s, 1H), 4.52 (dd, J = 7.0, 1.6 Hz, 1H), 2.89-2.83 (m, 2H), 2.31-2.22 (m, 1H), 1.72-1.60 (m, 1H), 1.48 (s, 3H), 1.45-1.40 (m, 1H), 1.20 (s, 3H), 0.97-0.90 (m, 1H), 0.80-0.60 (m, 1H); LCMS m/z = 482.36 (M + 1, 15%) |
| 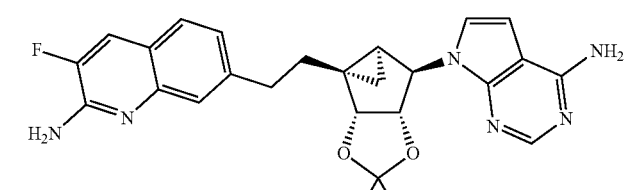<br>7-(2-((3aR,3bR,4aS,5R,5aS)-5-(4-amino-7H-pyrrolo[2,3-d]pyrimidin-7-yl)-2,2-dimethyltetra hydrocyclopropa[3,4]cyclopenta[1,2-d][1,3]dioxol-3b(3aH)-yl)ethyl)-3-fluoroquinolin-2-amine | 7-((3aR,3bS,4aS,5R,5aS)-2,2-Dimethyl-3b-vinylhexahydrocyclopropa[3,4]cyclopenta[1,2-d][1,3]dioxol-5-yl)-7H-pyrrolo[2,3-d]pyrimidin-4-amine and 7-Bromo-3-fluoroquinolin-2-amine | ¹H NMR (400 MHz, DMSO-d6) δ 8.07 (s, 1H), 7.77 (d, J = 11.8 Hz, 1H), 7.57 (d, J = 8.2 Hz, 1H), 7.37 (d, J = 1.6 Hz, 1H), 7.20-7.09 (m, 2H), 7.01 (s, 2H), 6.71 (s, 2H), 6.60 (d, J = 3.5 Hz, 1H), 5.21 (dd, J = 7.2, 1.3 Hz, 1H), 5.02 (s, 1H), 4.52 (dd, J = 7.4, 1.5 Hz, 1H), 2.87-2.77 (m, 2H), 2.31-2.20 (m, 1H), 1.70-1.60 (m, 1H), 1.48 (s, 3H), 1.46-1.43 (m, 1H), 1.20 (s, 3H), 0.96-0.92 (m, 1H), 0.82-0.69 (m, 1H); LCMS m/z = 475.3 (M + 1, 100%) |

TABLE-7-continued

| Structure & IUPAC name- | Intermediates used | ¹H NMR & LCMS data |
|---|---|---|
| 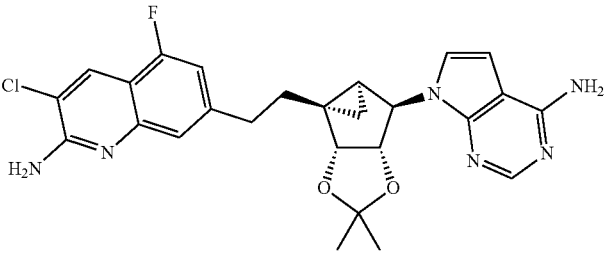<br>7-(2-((3aR,3bR,4aS,5R,5aS)-5-(4-amino-6-methyl-7H-pyrrolo[2,3-d]pyrimidin-7-yl)-2,2-dimethyltetra hydrocyclopropa[3,4]cyclopenta[1,2-d][1,3]dioxol-3b(3aH)-yl)ethyl)-3-chloro-5-fluoroquinolin-2-amine | 7-((3aR,3bS,4aS,5R,5aS)-2,2-Dimethyl-3b-vinylhexahydrocyclopropa[3,4]cyclopenta[1,2-d][1,3]dioxol-5-yl)-6-methyl-7H-pyrrolo[2,3-d]pyrimidin-4-amine and 7-Bromo-3-chloro-5-fluoroquinolin-2-amine | LCMS m/z = 522.94 (M+, 15%) |
| 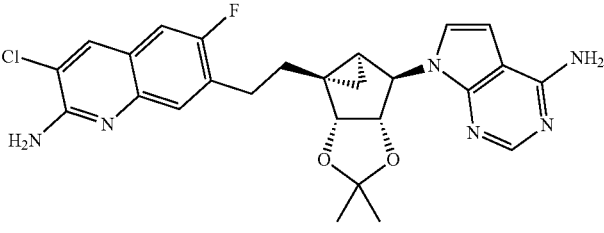<br>7-(2-((3aR,3bR,4aS,5R,5aS)-5-(4-amino-6-methyl-7H-pyrrolo[2,3-d]pyrimidin-7-yl)-2,2-dimethyl tetrahydrocyclopropa[3,4]cyclopenta[1,2-d][1,3]dioxol-3b(3aH)-yl)ethyl)-3-chloro-6-fluoroquinolin-2-amine | 7-((3aR,3bS,4aS,5R,5aS)-2,2-Dimethyl-3b-vinylhexahydrocyclopropa[3,4]cyclopenta[1,2-d][1,3]dioxol-5-yl)-6-methyl-7H-pyrrolo[2,3-d]pyrimidin-4-amine & 7-Bromo-3-chloro-6-fluoroquinolin-2-amine | LCMS m/z = 522.94 (M+, 10%) |
| 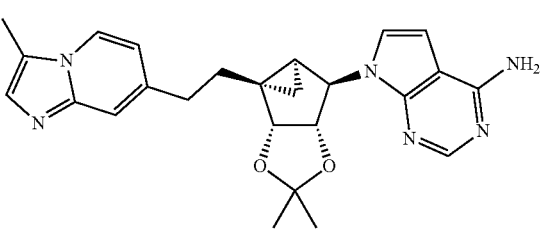<br>7-((3aR,3bR,4aS,5R,5aS)-2,2-dimethyl-3b-(2-(3-methylimidazo[1,2-a]pyridin-7-yl)ethyl)hexahydro cyclopropa[3,4]cyclopenta[1,2-d][1,3]dioxol-5-yl)-7H-pyrrolo[2,3-d]pyrimidin-4-amine | 7-((3aR,3bS,4aS,5R,5aS)-2,2-Dimethyl-3b-vinyl hexahydrocyclopropa[3,4]cyclopenta[1,2-d][1,3]dioxol-5-yl)-7H-pyrrolo[2,3-d]pyrimidin-4-amine and 7-Bromo-3-methylimidazo[1,2-a]pyridine | LCMS m/z = 445.3 (M + 1, 70%) |

TABLE-7-continued

| Structure & IUPAC name | Intermediates used | ¹H NMR & LCMS data |
|---|---|---|
| 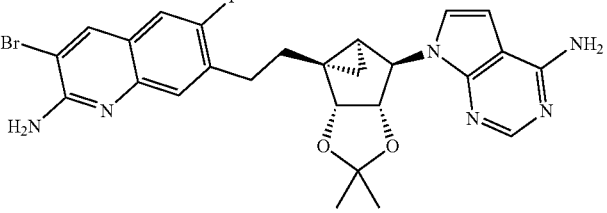<br>7-(2-((3aR,3bR,4aS,5R,5aS)-5-(4-amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-3-bromo-6-fluoroquinolin-2-amine | 7-((3aR,3bS,4aS,5R,5aS)-2,2-Dimethyl-3b-vinyl-hexahydrocyclopropa[3,4]cyclopenta[1,2-d][1,3]dioxol-5-yl)-7H-pyrrolo[2,3-d]pyrimidin-4-amine and 3-Bromo-6-fluoro-7-iodoquinolin-2-amine | LCMS m/z = 553.20 (M+, 100%) |
| 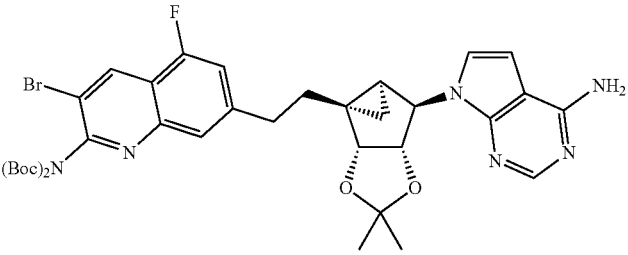 | 7-((3aR,3bS,4aS,5R,5aS)-2,2-Dimethyl-3b-vinyl hexahydrocyclopropa[3,4]cyclopenta[1,2-d][1,3]dioxol-5-yl)-7H-pyrrolo[2,3-d]pyrimidin-4-amine | LCMS m/z = 755.59 (M + 2, 100%). |

7-(2-((3aR,3bR,4aS,5R,5aS)-5-(4-Amino-7H-pyrrolo[2,3-d]pyrimidin-7-yl)-2,2-dimethyl tetrahydrocyclopropa[3,4]cyclopenta[1,2-d][1,3]dioxol-3b(3aH)-yl)ethyl)-N isopropyl quinolin-2-amine

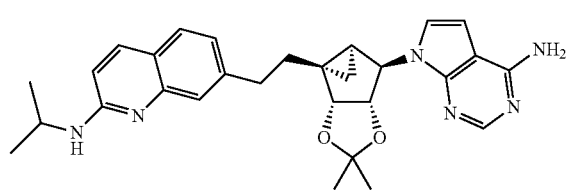 [SMILES: CC(C)Nc1ccc2ccc(CC[C@]34C[C@@H]3[C@@H](n3ccc5c(N)ncnc53)[C@@H]3OC(C)(C)O[C@@H]34)cc2n1]

7-((3aR,3bS,4aS,5R,5aS)-2,2-Dimethyl-3b-vinylhexahydrocyclopropa[3,4]cyclopenta[1,2-d][1,3]dioxol-5-yl)-7H-pyrrolo[2,3-d]pyrimidin-4-amine (150 mg, 0.480 mmol) in 9-BBN (0.5 molar, 3.84 ml, 1.921 mmol) was heated at 50° C. for 1 h under N₂ atmosphere. The reaction mixture was cooled to 25° C., then potassium phosphate tribasic (510 mg, 2.401 mmol) in water (0.5 ml) was added and stirred for 30 mins. A solution of 7-bromo-N-isopropylquinolin-2-amine (0.127 g, 0.480 mmol) in THF (3 ml) was added, followed by dichloro[1,1'-bis(di-t-butylphosphino)ferrocene]palladium(II) (6.26 mg, 9.60 μmol). The resulting mixture was stirred at 50° C. for 6 h. The reaction mixture was diluted with water (10 ml) and extracted with ethyl acetate (10 ml). Layers were separated, organic layer was washed with brine (10 ml) and dried over anhydrous Na₂SO₄. The organic layer was filtered and concentrated in vacuo to give 1.5 g of crude compound. This residue was purified by combiflash (R$_f$200, Teledyne/Isco) instrument onto a Redisep® R$_f$ column with gradient elution (0 to 10%) of 50% 7N NH₃/MeOH in dichloromethane to afford the title compound (0.12 g, 50.1%) as a pale yellow semisolid. LCMS m/z=499.2 (M+1, 40%).

Intermediates in table-8 were synthesized by an analogous reaction protocol as was used for the preparation of 7-(2-((3aR,3bR,4aS,5R,5aS)-5-(4-amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-N-isopropylquinolin-2-amine using the appropriate starting materials and at suitable temperature.

TABLE-8

| Structure & IUPAC name | Intermediates used | ¹H NMR & LCMS data |
|---|---|---|
| 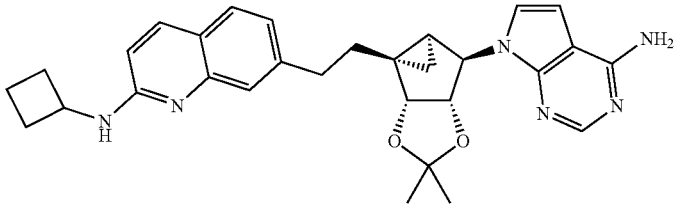<br>7-(2-((3aR,3bR,4aS,5R,5aS)-5-(4-amino-7H-pyrrolo[2,3-d]pyrimidin-7-yl)-2,2-dimethyltetra hydrocyclopropa[3,4]cyclopenta[1,2-d][1,3]dioxol-3b(3aH)-yl)ethyl)-N-cyclobutylquinolin-2-amine | 7-((3aR,3bS,4aS,5R,5aS)-2,2-Dimethyl-3b-vinylhexahydrocyclopropa[3,4]cyclopenta[1,2-d][1,3]dioxol-5-yl)-7H-pyrrolo[2,3-d]pyrimidin-4-amine and 7-Bromo-N-cyclobutylquinolin-2-amine | LCMS m/z = 511.3 (M + 1, 40%) |
| 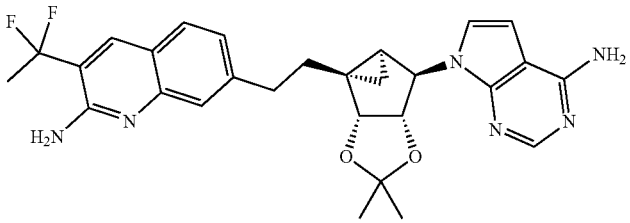<br>7-(2-((3aR,3bR,4aS,5R,5aS)-5-(4-amino-7H-pyrrolo[2,3-d]pyrimidin-7-yl)-2,2-dimethyltetra hydrocyclopropa[3,4]cyclopenta[1,2-d][1,3]dioxol-3b(3aH)-yl)ethyl)-3-(1,1-difluoroethyl)quinolin-2-amine | 7-((3aR,3bS,4aS,5R,5aS)-2,2-Dimethyl-3b-vinylhexahydrocyclopropa[3,4]cyclopenta[1,2-d][1,3]dioxol-5-yl)-7H-pyrrolo[2,3-d]pyrimidin-4-amine and 7-Bromo-3-(1,1-difluoroethyl)quinolin-2-amine | ¹H NMR (400 MHz, DMSO-d₆) δ 8.15 (s, 1H), 8.08 (d, J = 1.4 Hz, 1H), 7.69 (d, J = 8.2 Hz, 1H), 7.38 (s, 1H), 7.22-7.11 (m, 2H), 7.01 (s, 2H), 6.61 (dd, J = 3.6, 1.4 Hz, 1H), 6.23 (s, 2H), 5.22 (d, J = 7.1 Hz, 1H), 5.02 (s, 1H), 4.53 (d, J = 7.1 Hz, 1H), 2.92-2.78 (m, 2H), 2.32-2.22 (m, 1H), 2.08 (t, J = 19.1 Hz, 3H), 1.74-1.60 (m, 1H), 1.48 (s, 3H), 1.46-1.41 (m, 1H), 1.24 (s, 3H), 0.97-0.92 (m, 1H), 0.79-0.71 (m, 1H); LCMS m/z = 520.94 (M+, 50%) |
| 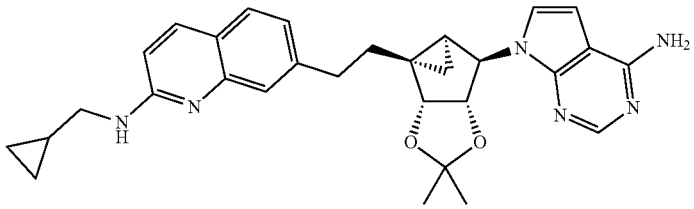<br>7-(2-((3aR,3bR,4aS,5R,5aS)-5-(4-amino-7H-pyrrolo[2,3-d]pyrimidin-7-yl)-2,2-dimethyltetra hydrocyclopropa[3,4]cyclopenta[1,2-d][1,3]dioxol-3b(3aH)-yl)ethyl)-N-(cyclopropylmethyl)quinolin-2-amine | 7-((3aR,3bS,4aS,5R,5aS)-2,2-Dimethyl-3b-vinylhexahydrocyclopropa[3,4]cyclopenta[1,2-d][1,3]dioxol-5-yl)-7H-pyrrolo[2,3-d]pyrimidin-4-amine and 7-Bromo-N-(cyclopropylmethyl)quinolin-2-amine | ¹H NMR (400 MHz, DMSO-d6) δ 8.08 (s, 1H), 7.78 (d, J = 8.9 Hz, 1H), 7.51 (d, J = 8.1 Hz, 1H), 7.39 (d, J = 1.6 Hz, 1H), 7.19-7.05 (m, 3H), 7.02 (s, 2H), 6.73 (d, J = 8.9 Hz, 1H), 6.61 (d, J = 3.6 Hz, 1H), 5.21 (dd, J = 7.2, 1.3 Hz, 1H), 5.02 (s, 1H), 4.52 (dd, J = 7.3, 1.5 Hz, 1H), 3.26 (t, J = 6.1 Hz, 2H), 2.90-2.74 (m, 2H), 2.34-2.22 (m, 1H), 1.75-1.59 (m, 2H), 1.49 (s, 3H), 1.48-1.44 (m, 1H), 1.20 (s, 3H), 0.94 (t, J = 4.6 Hz, 1H), 0.77-0.70 (m, 1H), 0.51-0.43 (m, 2H), 0.29-0.22 (m, 2H); LCMS m/z = 511.12 (M + 1, 100%) |

TABLE-8-continued

| Structure & IUPAC name | Intermediates used | ¹H NMR & LCMS data |
|---|---|---|
| 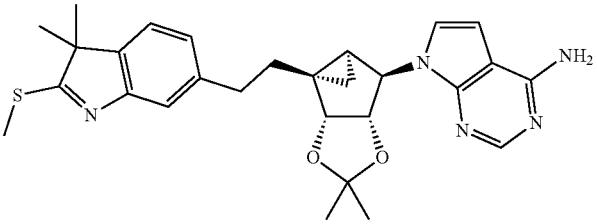<br>7-((3aR,3bR,4aS,5R,5aS)-3b-(2-(3,3-dimethyl-2-(methylthio)-3H-indol-6-yl)ethyl)-2,2-dimethyl hexahydrocyclopropa[3,4]cyclopenta[1,2-d][1,3]dioxol-5-yl)-7H-pyrrolo[2,3-d]pyrimidin-4-amine | 7-((3aR,3bS,4aS,5R,5aS)-2,2-Dimethyl-3b-vinylhexahydrocyclopropa[3,4]cyclopenta[1,2-d][1,3]dioxol-5-yl)-7H-pyrrolo[2,3-d]pyrimidin-4-amine and 6-Bromo-3,3-dimethyl-2-(methylthio)-3H-indole | ¹H NMR (400 MHz, DMSO-d6) δ 8.08 (s, 1H), 7.34-7.26 (m, 2H), 7.12 (d, J = 3.5 Hz, 1H), 7.08-6.94 (m, 3H), 6.61 (d, J = 3.5 Hz, 1H), 5.22-5.15 (m, 1H), 5.02 (s, 1H), 4.52 (dd, J = 7.2, 1.5 Hz, 1H), 2.81-2.69 (m, 2H), 2.59 (s, 3H), 2.29-2.16 (m, 1H), 1.68-1.56 (m, 1H), 1.48 (s, 3H), 1.45-1.41 (m, 1H), 1.27 (s, 6H), 1.20 (s, 3H), 0.94 (t, J = 4.7 Hz, 1H), 0.80-0.71 (m, 1H); LCMS m/z = 504.31 (M + 1, 100%) |
| 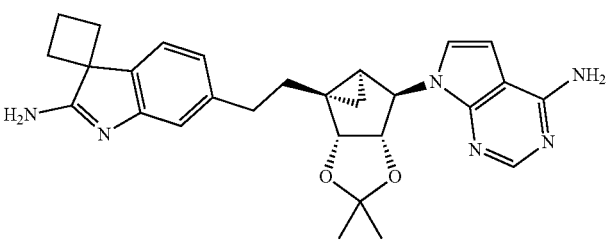<br>6'-(2-((3aR,3bR,4aS,5R,5aS)-5-(4-amino-7H-pyrrolo[2,3-d]pyrimidin-7-yl)-2,2-dimethyltetra hydrocyclopropa[3,4]cyclopenta[1,2-d][1,3]dioxol-3b(3aH)-yl)ethyl)spiro[cyclobutane-1,3'-indol]-2'-amine | 7-((3aR,3bS,4aS,5R,5aS)-2,2-Dimethyl-3b-vinylhexahydrocyclopropa[3,4]cyclopenta[1,2-d][1,3]dioxol-5-yl)-7H-pyrrolo[2,3-d]pyrimidin-4-amine and 6'-Bromospiro[cyclobutane-1,3'-indol]-2'-amine. | LCMS m/z = 485.3 (M + 1, 70%) |

3-Bromo-7-(2-((3aR,3bR,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-N-(4-methoxybenzyl)quinolin-2-amine

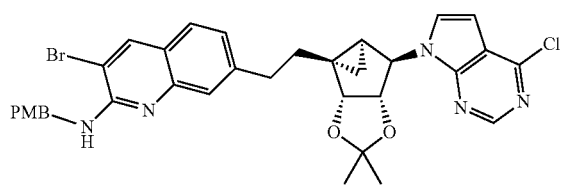

4-Chloro-7-((3aR,3bS,4aS,5R,5aS)-2,2-dimethyl-3b-vinylhexahydrocyclopropa[3,4]cyclo penta[1,2-d][1,3]dioxol-5-yl)-7H-pyrrolo[2,3-d]pyrimidine (2.9 g, 8.74 mmol) in 9-BBN (0.5 molar, 87 ml, 43.7 mmol) was stirred at 70° C. for 1 h. The reaction mixture was cooled to 25° C., then potassium phosphate tribasic (5.57 g, 26.2 mmol) in water (45 ml) was added and stirred for 30 mins. A solution of 3-bromo-7-iodo-N-(4-methoxybenzyl)quinolin-2-amine (4.72 g, 10.05 mmol) in THF (60 ml) was added, followed by PdCl₂(dppf)-CH₂Cl₂ (0.357 g, 0.437 mmol). The resulting mixture was stirred at 70° C. for 3 h. The reaction mixture was diluted with water (50 ml) and extracted with ethyl acetate (50 ml). Layers were separated, organic layer was washed with brine (50 ml) and dried over anhydrous Na₂SO₄. The organic layer was filtered and concentrated in vacuo to give 3.5 g of crude compound. This residue was purified by combiflash (R$_f$200, Teledyne/Isco) instrument onto a Redisep® R$_f$ column with gradient elution (0 to 30%) of ethyl acetate in petroleum ether to afford the title compound (3.1 g, 52.5%) as an off-white solid. ¹H NMR (400 MHz, DMSO-d₆) δ 8.68 (s, 1H), 8.33 (s, 1H), 7.73 (d, J=3.7 Hz, 1H), 7.56 (d, J=8.2 Hz, 1H), 7.43 (d, J=1.6 Hz, 1H), 7.37-7.31 (m, 2H), 7.25-7.12 (m, 1H), 7.15 (dd, J=8.2, 1.6 Hz, 1H), 6.90-6.83 (m, 2H), 6.70 (d, J=3.7 Hz, 1H), 5.27 (dd, J=7.2, 1.3 Hz, 1H), 5.12 (s, 1H), 4.71-4.56 (m, 3H), 3.70 (s, 3H), 2.90-2.75 (m, 2H), 2.38-2.26 (m, 1H), 1.63-1.58 (m, 1H), 1.55-1.51 (m, 1H), 1.49 (s, 3H), 1.20 (s, 3H), 0.95 (t, J=4.7 Hz, 1H), 0.79-0.72 (in, 1H); LCMS m/z=674.1 (M-1, 100%).

Intermediates in table-9 were synthesized by an analogous reaction protocol as was used for the preparation of 3-bromo-7-(2-((3aR,3bR,4a,5R,5a)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-N-(4-methoxybenzyl)quinolin-2-amine using the appropriate starting materials.

TABLE-9

| Structure & IUPAC name | Intermediates used | ¹H NMR & LCMS data |
|---|---|---|
| 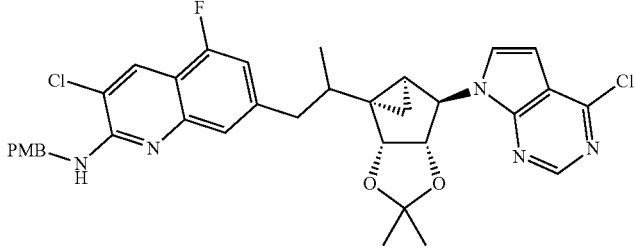<br>3-Chloro-7-(2-((3aR,3bS,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)propyl)-5-fluoro-N-(4-methoxybenzyl)quinolin-2-amine | 4-chloro-7-((3aR,3bR,4aS,5R,5aS)-2,2-dimethyl-3b-(prop-1-en-2-yl)hexahydrocyclopropa[3,4]cyclopenta[1,2-d][1,3]dioxol-5-yl)-7H-pyrrolo[2,3-d]pyrimidine and 7-Bromo-3-chloro-5-fluoro-N-(4-methoxybenzyl)quinolin-2-amine | LCMS m/z = 662.10 (M+, 100%) |
| 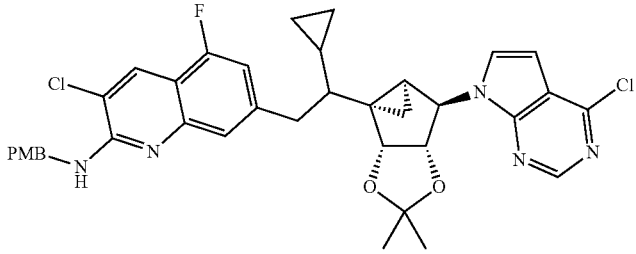<br>3-Chloro-7-(2-((3aR,3bS,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)-2-cyclopropylethyl)-5-fluoro-N-(4-methoxybenzyl)quinolin-2-amine | 4-Chloro-7-((3aR,3bR,4aS,5R,5aS)-3b-(1-cyclopropylvinyl)-2,2-dimethylhexahydro-hydrocyclopropa[3,4]cyclopenta[1,2-d][1,3]dioxol-5-yl)-7H-pyrrolo[2,3-d]pyrimidine and 7-Bromo-3-chloro-5-fluoro-N-(4-methoxybenzyl)quinolin-2-amine | ¹H NMR (400 MHz, DMSO-$d_6$) δ 8.62 (s, 1H), 8.16 (d, J = 3.6 Hz, 1H), 7.78-7.71 (m, 1H), 7.61 (dd, J = 10.1, 5.1 Hz, 1H), 7.40-7.30 (m, 3H), 7.09-7.03 (m, 1H), 6.86 (dd, J = 8.6, 3.2 Hz, 2H), 6.78-6.74 (m, 1H), 5.53 (t, J = 7.2 Hz, 2H), 5.34 (d, J = 7.0 Hz, 1H), 5.16 (s, 1H), 4.63 (d, J = 6.5 Hz, 1H), 3.70 (s, 3H), 2.98-2.88 (m, 2H), 1.73-1.68 (m, 1H), 1.53 (d, J = 7.4 Hz, 4H), 1.26-1.22 (m, 4H), 0.91-0.86 (m, 1H), 0.63-0.55 (m, 1H), 0.43-0.33 (m, 2H), 0.22-0.12 (m, 2H). |
| 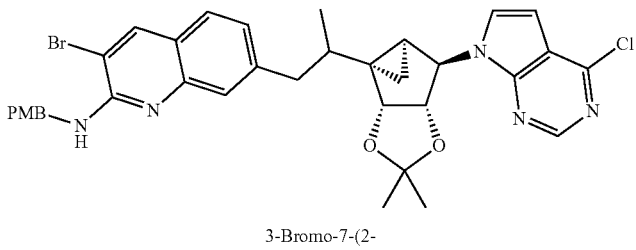<br>3-Bromo-7-(2-((3aR,3bS,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)propyl)-N-(4-methoxybenzyl)quinolin-2-amine | 4-chloro-7-((3aR,3bR,4aS,5R,5aS)-2,2-dimethyl-3b-(prop-1-en-2-yl)hexahydrocyclopropa[3,4]cyclopenta[1,2-d][1,3]dioxol-5-yl)-7H-pyrrolo[2,3-d]pyrimidine & 3-Bromo-7-iodo-N-(4-methoxybenzyl)quinolin-2-amine | LCMS m/z = 687.98 (M − 1, 80%); 689.98 (M + 1, 100%) |

7-(2-((3aR,3bR,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-8-fluoroquinolin-2-amine

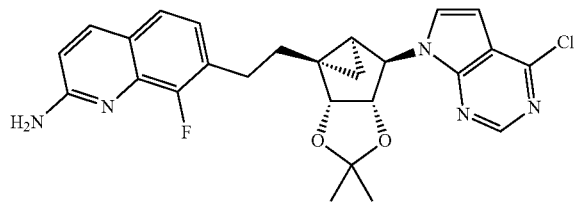

4-chloro-7-((3aR,3bS,4aS,5R,5aS)-2,2-dimethyl-3b-vinylhexahydrocyclopropa[3,4] cyclo penta[1,2-d][1,3]dioxol-5-yl)-7H-pyrrolo[2,3-d]pyrimidine (0.38 g, 1.145 mmol) in 9-BBN (0.5 molar, 9.16 ml, 4.58 mmol) was stirred at 70° C. for 8 h. The reaction mixture was cooled to 25° C., then potassium phosphate tribasic (0.729 g, 3.44 mmol) in water (6 ml) was added and stirred for 30 mins. A solution of 7-bromo-8-fluoroquinolin-2-amine (0.304 g, 1.26 mmol) in THF (30 ml) was added, followed by [1,1'-bis(di-tert-butylphosphino) ferrocene]dichloropalladium(II) (0.022 g, 0.034 mmol). The resulting mixture was stirred at 70° C. for 7 h. The reaction mixture was diluted with water (20 ml) and extracted with ethyl acetate (20 ml). Layers were separated, organic layer was washed with brine (20 ml) and dried over anhydrous $Na_2SO_4$. The organic layer was filtered and concentrated in vacuo to give 0.5 g of crude compound. This residue was purified by combiflash ($R_f$200, Teledyne/Isco) instrument onto a Redisep® $R_f$ column with gradient elution (0 to 50%) of ethyl acetate in petroleum ether to afford the title compound (0.12 g, 21.21%) as an off-white solid. $^1$H NMR (400 MHz, DMSO-d6) δ 8.67 (s, 1H), 7.87 (d, J=8.8 Hz, 1H), 7.75 (d, J=3.6 Hz, 1H), 7.36 (d, J=8.1 Hz, 1H), 7.14-7.05 (m, 1H), 6.79-6.70 (m, 2H), 6.64 (s, 2H), 5.27 (d, J=7.2 Hz, 1H), 5.13 (s, 1H), 4.69 (d, J=7.2 Hz, 1H), 2.96-2.77 (m, 2H), 2.31-2.22 (m, 1H), 1.70-1.60 (m, 1H), 1.59-1.54 (m, 1H), 1.50 (s, 3H), 1.21 (s, 3H), 0.99 (t, J=4.7 Hz, 1H), 0.83-0.77 (m, 1H); LCMS m/z=494 (M+, 100%)

Intermediates in table-10 were synthesized by an analogous reaction protocol as was used for the preparation of 7-(2-((3aR,3bR,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-8-fluoroquinolin-2-amine using the appropriate starting materials and at suitable temperature.

TABLE 10

| Structure & IUPAC name | Intermediates used | $^1$H NMR & LCMS data |
|---|---|---|
| 7-(2-((3aR,3bR,4aS,5R,5aS)-5-(4-chloro-7H-pyrrolo[2,3-d]pyrimidin-7-yl)-2,2-dimethyltetrahydrocyclopropa[3,4] cyclopenta[1,2-d][1,3]dioxol-3b(3aH)-yl)ethyl)-N-(4-methoxybenzyl)quinolin-2-amine | 4-Chloro-7-((3aR,3bS,4aS,5R,5aS)-2,2-dimethyl-3b-vinylhexahydrocyclopropa[3,4]cyclopenta[1,2-d][1,3]dioxol-5-yl)-7H-pyrrolo[2,3-d]pyrimidine & 7-Bromo-N-(4-methoxybenzyl)quinolin-2-amine | $^1$H NMR (400 MHz, Chloroform-d) δ 8.68 (s, 1H), 7.82 (d, J = 8.9 Hz, 1H), 7.60 (d, J = 1.5 Hz, 1H), 7.54 (d, J = 8.1 Hz, 1H), 7.41 – 7.33 (m, 2H), 7.21 – 7.14 (m, 2H), 6.97 – 6.84 (m, 2H), 6.65 – 6.57 (m, 2H), 5.23 (dd, J = 7.3, 1.4 Hz, 1H), 5.15 (s, 1H), 4.70 – 4.62 (m, 3H), 3.83 (s, 3H), 3.11 – 2.86 (m, 2H), 2.48 – 2.37 (m, 1H), 1.83 – 1.76 (m, 1H), 1.55 (s, 3H), 1.50 (dd, J = 4.8, 1.5 Hz, 1H), 1.28 (s, 3H), 1.16 (t, J = 5.0 Hz, 1H), 0.86 – 0.78 (m, 1H); LCMS m/z = 596.20 (M+, 100%) |
| 7-(2-((3aR,3bR,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-N-methylquinolin-2-amine | 4-Chloro-7-((3aR,3bS,4aS,5R,5aS)-2,2-dimethyl-3b-vinylhexahydrocyclopropa[3,4]cyclopenta[1,2-d][1,3]dioxol-5-yl)-7H-pyrrolo[2,3-d]pyrimidine and 7-Bromo-N-methylquinolin-2-amine | $^1$H NMR (400 MHz, DMSO-d$_6$) δ 8.69 (s, 1H), 7.77 (d, J = 8.9 Hz, 1H), 7.74 (d, J = 3.7 Hz, 1H), 7.51 (d, J = 8.1 Hz, 1H), 7.41 (d, J = 1.6 Hz, 1H), 7.07 (dd, J = 8.1, 1.7 Hz, 1H), 6.93 (d, J = 5.9 Hz, 1H), 6.71 (d, J = 3.6 Hz, 1H), 6.67 (d, J = 8.9 Hz, 1H), 5.27 (dd, J = 7.2, 1.3 Hz, 1H), 5.13 (s, 1H), 4.67 (dd, J = 7.3, 1.5 Hz, 1H), 2.88 (d, J = 4.7 Hz, 3H), 2.85 – 2.74 (m, 2H), 2.36 – 2.30 (m, 1H), 1.71 – 1.65 (m, 1H), 1.57 – 1.52 (m, 1H), 1.50 (s, 3H), 1.21 (s, 3H), 0.96 (t, J = 4.7 Hz, 1H), 0.82 – 0.76 (m, 1H); LCMS m/z = 490.24 (M+, 60%) |

TABLE 10-continued

| Structure & IUPAC name | Intermediates used | ¹H NMR & LCMS data |
|---|---|---|
| 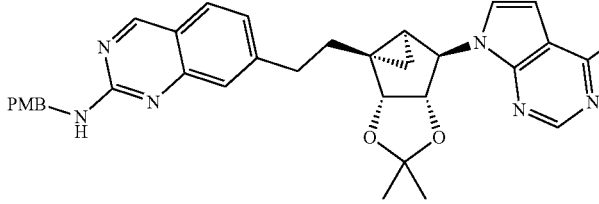<br>7-(2-((3aR,3bR,4aS,5R,5aS)-5-(4-chloro-7H-pyrrolo[2,3-d]pyrimidin-7-yl)-2,2-dimethyltetrahydrocyclopropa[3,4] cyclopenta[1,2-d][1,3]dioxol-3b(3aH)-yl)ethyl)-N-(4-methoxybenzyl)quinazolin-2-amine | 4-Chloro-7-((3aR,3bS,4a S,5R,5aS)-2,2-dimethyl-3b-vinylhexahydrocyclopropa[3,4]cyclopenta[1,2-d][1,3]dioxol-5-yl)-7H-pyrrolo[2,3-d]pyrimidine & 7-Bromo-N-(4-methoxybenzyl)quinazolin-2-amine | ¹H NMR (400 MHz, DMSO-d₆) δ 9.04 (s, 1H), 8.68 (s, 1H), 7.79 (s, 1H), 7.74 (d, J = 3.7 Hz, 1H), 7.69 (d, J = 8.2 Hz, 1H), 7.35 (s, 1H), 7.30 (d, J = 8.2 Hz, 2H), 7.17 (dd, J = 8.3, 1.6 Hz, 1H), 6.89 – 6.83 (m, 2H), 6.71 (d, J = 3.7 Hz, 1H), 5.27 (d, J = 7.1 Hz, 1H), 5.13 (s, 1H), 4.71 – 4.64 (m, 1H), 4.52 (d, J = 6.3 Hz, 2H), 3.71 (s, 3H), 2.90 – 2.80 (m, 2H), 2.37 – 2.27 (m, 1H), 1.67 – 1.62 (m, 1H), 1.56 – 1.52 (m, 1H), 1.49 (s, 3H), 1.20 (s, 3H), 0.95 (t, J = 4.6 Hz, 1H), 0.79 – 0.74 (m, 1H); LCMS m/z = 597.3 (M+, 100%) |
| 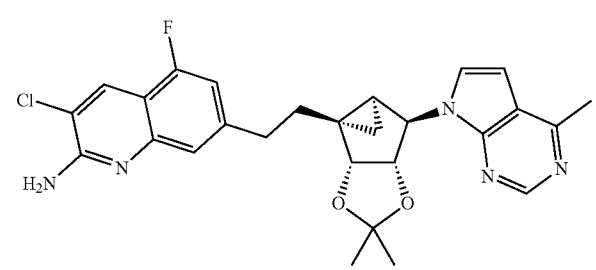<br>3-Chloro-7-(2-((3aR,3bR,4aS,5R,5aS)-2,2-dimethyl-5-(4-methyl-7H-pyrrolo[2,3-d]pyrimidin-7-yl)tetrahydrocyclopropa[3,4]cyclopenta[1,2-d][1,3]dioxol-3b(3aH)-yl)ethyl)-5-fluoroquinolin-2-amine | 7-((3aR,3bS,4a S,5R,5aS)-2,2-Dimethyl-3b-vinylhexahydrocyclopropa[3,4]cyclopenta[1,2-d][1,3]dioxol-5-yl)-4-methyl-7H-pyrrolo[2,3-d]pyrimidine and 7-Bromo-3-chloro-5-fluoroquinolin-2-amine | LCMS m/z = 508.19 (M+, 80%) |

7-(1-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethoxy)-N-methylquinolin-2-amine

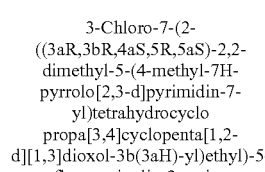

To a stirred solution of 1-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethan-1-ol (0.2 g, 0.596 mmol), 2-(methylamino)quinolin-7-ol (0.145 g, 0.834 mmol) and triphenylphosphine (0.469 g, 1.787 mmol) at 0° C. was added DEAD (0.283 ml, 1.787 mmol) slowly and stirred for 30 min. The resulting mixture was stirred at 25° C. for 1 h. The solvent was evaporated under reduced pressure and the residue was purified by combiflash (R$_f$200, Teledyne/Isco) instrument onto a Redisep® R$_f$ column with gradient elution (0 to 20%) of ethyl acetate in petroleum ether to afford the title compound (0.1 g, 34.1%) as an off-white solid. LCMS m/z=492.2 (M+, 100%).

7-(((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)methoxy)-N-methylquinolin-2-amine

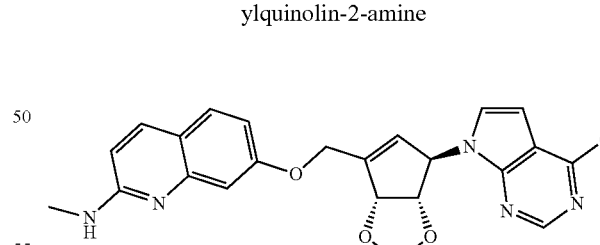

To a stirred solution of ((3aR,6R,6aS)-6-(4-chloro-7H-pyrrolo[2,3-d]pyrimidin-7-yl)-2,2-dimethyl-6,6a-dihydro-3aH-cyclopenta[d][1,3]dioxol-4-yl)methanol (0.25 g, 0.777 mmol), 2-(methylamino)quinolin-7-ol (0.338 g, 1.942 mmol) and triphenylphosphine (0.611 g, 2.331 mmol) in THF (20 ml) was added DEAD (0.369 ml, 2.331 mmol) dropwise at 0° C. The resulting mixture was stirred at 25° C. for 20 h. The solvent was evaporated under reduced pressure and the residue was purified by combiflash (R$_f$200, Teledyne/Isco) instrument onto a Redisep® R$_f$ column with gradient elution (0 to 70%) of ethyl acetate in petroleum ether (0.2 g, 53.9%) as an off-white solid. $^1$H NMR (400 MHz, DMSO-d6) δ 8.66 (s, 1H), 7.74 (d, J=8.8 Hz, 1H), 7.53 (d, J=1.7 Hz, 1H), 7.51 (d, J=3.5 Hz, 1H), 7.07 (d, J=2.5 Hz, 1H), 6.95 (d, J=5.0 Hz, 1H), 6.85 (dd, J=8.7, 2.5 Hz, 1H), 6.69-6.51 (m, 2H), 5.87 (s, 1H), 5.78 (s, 1H), 5.55-5.42 (m, 1H), 5.04-4.85 (m, 2H), 4.74-4.63 (m, 1H), 2.89 (d, J=4.7 Hz, 3H), 1.49 (s, 3H), 1.24 (s, 3H); LCMS m/z=479.3 (M+1, 100%).

3-Bromo-7-(((3aR,3bR,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)methoxy)-N-(4-methoxybenzyl)quinolin-2-amine

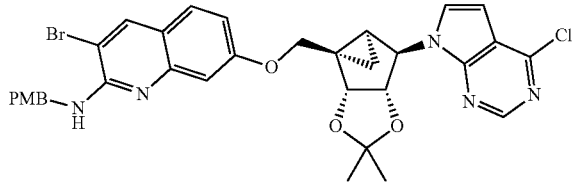

To a stirred solution of ((3aR,3bR,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)methanol (0.09 g, 0.268 mmol), 3-bromo-2-((4-methoxybenzyl)amino)quinolin-7-ol (0.106 g, 0.295 mmol) and triphenylphosphine (0.176 g, 0.670 mmol) in THF (8 ml), was added DEAD (0.106 ml, 0.670 mmol) dropwise at 0° C. and stirred for 30 min. The resulting mixture stirred for at 25° C. for 14 h. The solvent was evaporated under reduced pressure and the residue was purified by combiflash (R$_f$200, Teledyne/Isco) instrument onto a Redisep® R$_f$ column with gradient elution (0 to 60%) of ethyl acetate in petroleum ether (0.12 g, 66.1%) as an off-white solid. LCMS m/z=677.97 (M+1, 100%).

3-Bromo-7-((E)-1-((3aR,3bS,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)prop-1-en-2-yl)-N-(4-methoxybenzyl)quinolin-2-amine

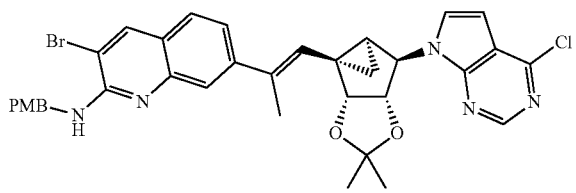

A mixture of 4-chloro-7-((3aR,3bR,4aS,5R,5aS)-3b-((E)-2-iodoprop-1-en-1-yl)-2,2-dimethylhexahydro cyclopropa[3,4]cyclopenta[1,2-d][1,3]dioxol-5-yl)-7H-pyrrolo[2,3-d]pyrimidine (0.12 g, 0.254 mmol), triphenylphosphine (6.67 mg, 0.025 mmol), 3-bromo-N-(4-methoxybenzyl)-7-(4,4,5,5-tetramethyl-1,3,2-dioxaborolan-2-yl)quinolin-2-amine (0.179 g, 0.382 mmol), sodium carbonate (0.054 g, 0.509 mmol) and Pd(OAc)$_2$ (2.86 mg, 0.013 mmol) in DMF (4 ml) and water (1 ml) was stirred at 25° C. for 16 h. The reaction mixture was diluted with water (20 ml) and extracted with ethyl acetate (20 ml). Layers were separated, organic layer was washed with brine (20 ml) and dried over anhydrous Na$_2$SO$_4$. The organic layer was filtered and concentrated in vacuo to give 0.3 g of crude compound. This residue was purified by combiflash (R$_f$200, Teledyne/Isco) instrument onto a Redisep® R$_f$ column with gradient elution (0 to 15%) of ethyl acetate in petroleum ether to afford the title compound (0.13 g, 74.4%) as an off-white solid. LCMS m/z=687.98 (M+1, 100%).

N7-(((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)methyl)-N2-(4-methoxybenzyl)quinoline-2,7-diamine

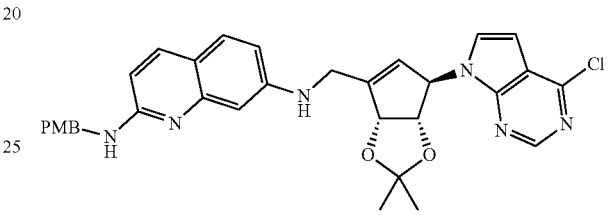

To a stirred solution of (3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxole-6-carbaldehyde (0.18 g, 0.563 mmol) and N2-(4-methoxybenzyl)quinoline-2,7-diamine (0.157 g, 0.563 mmol) in methanol (5 ml) was added acetic acid (0.1 mL) at 25° C. and stirred for 2 h. Sodium cyanoborohydride (0.106 g, 1.689 mmol) was added stirred for 16 h. The reaction was quenched by addition of sat. NH$_4$Cl (15 mL). The reaction mixture was concentrated under reduced pressure and the residue was diluted with ethyl acetate (40 mL). The organic phase was washed with water (30 ml), saturated aqueous sodium bicarbonate (30 ml) and brine (30 ml) successively. Dried the organic layer over anhydrous Na$_2$SO$_4$, filtered and concentrated under reduced pressure to give 0.2 g of crude compound. This residue was purified by combiflash (R$_f$200, Teledyne/Isco) instrument onto a Redisep® R$_f$ column with gradient elution (0 to 15%) of methanol in dichloromethane to afford the title compound (0.15 g, 45.7%) as a pale yellow solid. $^1$H NMR (400 MHz, DMSO-d6) δ 8.66 (s, 1H), 7.59 (d, J=8.8 Hz, 1H), 7.48 (d, J=3.7 Hz, 1H), 7.30 (m, 3H), 7.10 (t, J=5.8 Hz, 1H), 6.92-6.86 (m, 2H), 6.65 (dd, J=8.6, 2.3 Hz, 1H), 6.57 (d, J=2.2 Hz, 1H), 6.51 (d, J=3.7 Hz, 1H), 6.45 (d, J=8.7 Hz, 1H), 5.72 (s, 1H), 5.69 (s, 1H), 5.38 (d, J=5.7 Hz, 1H), 4.65-4.52 (m, 1H), 4.55 (d, J=5.8 Hz, 2H), 4.13-3.93 (m, 3H), 3.72 (s, 3H), 1.48 (s, 3H), 1.30 (s, 3H); LCMS m/z=583.4 (M+, 100%).

N7-(((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)methyl)-N2-(4-methoxybenzyl)-N7-methylquinoline-2,7-diamine

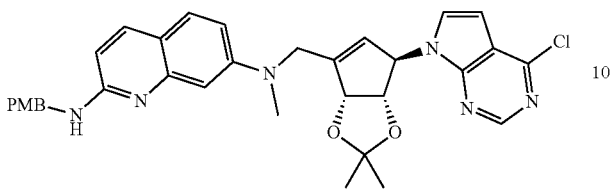

To a stirred solution of N2-(4-methoxybenzyl)-N7-methylquinoline-2,7-diamine in DMF (2 ml) was added K₂CO₃ (0.058 g, 0.420 mmol) at 0° C. slowly followed by ((3aS,4R,6aR)-4-(4-chloro-7H-pyrrolo[2,3-d]pyrimidin-7-yl)-2,2-dimethyl-3a,6a-dihydro-4H-cyclopenta[d][1,3] dioxol-6-yl)methyl 4-methylbenzenesulfonate (0.1 g, 0.210 mmol) and stirred the reaction mixture for 10 mins. The resulting mixture was stirred at 25° C. for 16 h. The reaction mixture was diluted with water (20 ml) and extracted with ethyl acetate (20 ml). Layers were separated, organic layer was washed with brine (20 ml) and dried over anhydrous Na₂SO₄. The organic layer was filtered and concentrated in vacuo to give 0.3 g of crude compound. This residue was purified by combiflash (R_f200, Teledyne/Isco) instrument onto a Redisep® R_f column with gradient elution (0 to 7%) of ethyl acetate in petroleum ether to afford the title compound (0.025 g, 19.93%) as a colourless oil. LCMS m/z=597.29 (M+, 80%).

7-(((((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)methyl)thio)-N-(4-methoxybenzyl)quinolin-2-amine

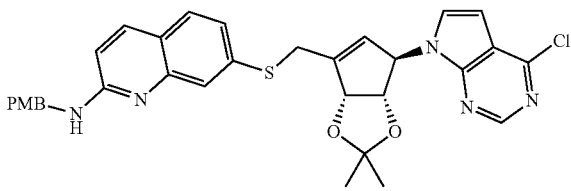

To a stirred solution of 2-((4-methoxybenzyl)amino)quinoline-7-thiol (125 mg, 0.422 mmol) in DMSO (3 ml) at 0° C. was added Cs₂CO₃ (302 mg, 0.928 mmol) and ((3aS,4R,6aR)-4-(4-chloro-7H-pyrrolo[2,3-d]pyrimidin-7-yl)-2,2-dimethyl-3a,6a-dihydro-4H-cyclopenta[d][1,3] dioxol-6-yl) methyl 4-methylbenzenesulfonate (201 mg, 0.422 mmol). The resulting mixture was stirred at 25° C. for 3 h. The reaction mixture was diluted with water (20 ml) and extracted with ethyl acetate (20 ml). Layers were separated, organic layer was washed with brine (20 ml) and dried over anhydrous Na₂SO₄. The organic layer was filtered and concentrated in vacuo to give 0.3 g of crude compound. This residue was purified by combiflash (R_f200, Teledyne/Isco) instrument onto a Redisep® R_f column with gradient elution (0 to 20%) of ethyl acetate in petroleum ether to afford the title compound (0.112 g, 44.3%) as an off-white solid. ¹H NMR (400 MHz, DMSO-d6) δ 8.60 (s, 1H), 7.85 (d, J=8.9 Hz, 1H), 7.60-7.48 (m, 3H), 7.33-7.26 (m, 2H), 7.19 (dd, J=8.3, 1.9 Hz, 1H), 6.85-6.79 (m, 3H), 6.48 (d, J=3.7 Hz, 1H), 6.06 (d, J=3.6 Hz, 1H), 5.72 (s, 1H), 5.65 (s, 1H), 5.43 (d, J=5.7 Hz, 1H), 4.54 (d, J=5.7 Hz, 2H), 4.48 (d, J=5.7 Hz, 1H), 4.22 (d, J=15.3 Hz, 1H), 3.77-3.70 (m, 1H), 3.68 (s, 3H), 1.43 (s, 3H), 1.28 (s, 3H); LCMS m/z=600.21 (M+, 100%).

3-Chloro-7-(1-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethoxy)-5-fluoro-N-(4-methoxybenzyl)quinolin-2-amine

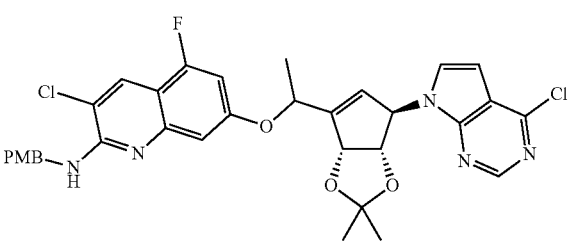

To a stirred solution of 1-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethan-1-ol (0.7 g, 2.085 mmol), 3-chloro-5-fluoro-2-((4-methoxybenzyl)amino)quinolin-7-ol (0.416 g, 1.251 mmol) and triphenylphosphine (1.640 g, 6.25 mmol) in THF (10 ml), was added DEAD (0.990 ml, 6.25 mmol) dropwise at 0° C. and stirred for 30 mins. The resulting mixture stirred at 25° C. for 16 h. The solvent was evaporated under reduced pressure and this residue was purified by combiflash (R_f200, Teledyne/Isco) instrument onto a Redisep® R_f column with gradient elution (0 to 15%) of ethyl acetate in petroleum ether to afford the title compound (0.5 g, 36.9% yield) as an off-white solid. LCMS m/z=650.3 (M+, 100%).

3-chloro-7-(((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)methoxy)-5-fluoro-N-(4-methoxybenzyl)quinolin-2-amine

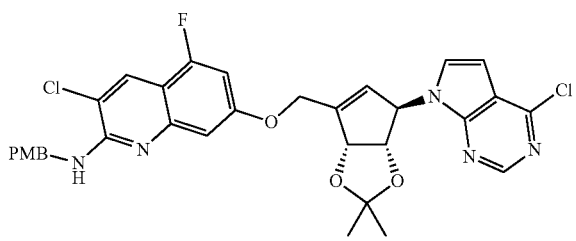

Cesium carbonate (558 mg, 1.713 mmol) was add to a solution of ((3aS,4R,6aR)-4-(4-chloro-7H-pyrrolo[2,3-d]pyrimidin-7-yl)-2,2-dimethyl-3a,6a-dihydro-4H-cyclopenta[d] [1,3]dioxol-6-yl)methyl 4-methylbenzenesulfonate (272 mg, 0.571 mmol) and 3-chloro-5-fluoro-2-((4-methoxybenzyl)amino) quinolin-7-ol (190 mg, 0.571 mmol) in DMF (4 ml) at 0° C. and stirred at 25° C. for 1 h. Ice cold water (20 ml) was added to the reaction mixture and stirred for 10 minutes, precipitated solid was filtered, washed with water and dried under vacuum to afford the title compound (300 mg, 83%) as a brown solid. ¹H NMR (400 MHz, DMSO-d6) δ 8.64 (s, 1H), 8.11 (s, 1H), 7.65 (t, J=6.1 Hz, 1H), 7.50 (d, J=3.7 Hz, 1H), 7.36-7.30 (m, 2H), 6.94 (d, J=2.3 Hz, 1H), 6.89-6.79 (m, 3H), 6.60 (d, J=3.7 Hz, 1H), 5.87 (s, 1H), 5.78 (s, 1H), 5.48 (d, J=5.7 Hz, 1H), 5.05-4.89 (m, 2H), 4.70 (d, J=5.7 Hz, 1H), 4.64 (d, J=6.1 Hz, 2H), 3.71 (s, 3H), 1.45 (s, 3H), 1.30 (s, 3H); LCMS m/z=636.34 (M+, 100%).

Intermediates in table-11 were synthesized by an analogous reaction protocol as was used for the preparation of 3-chloro-7-(((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)methoxy)-5-fluoro-N-(4-methoxybenzyl)quinolin-2-amine using the appropriate starting materials and at suitable temperature.

TABLE-11

| Structure & IUPAC name | Intermediates used | ¹H NMR & LCMS data |
|---|---|---|
| 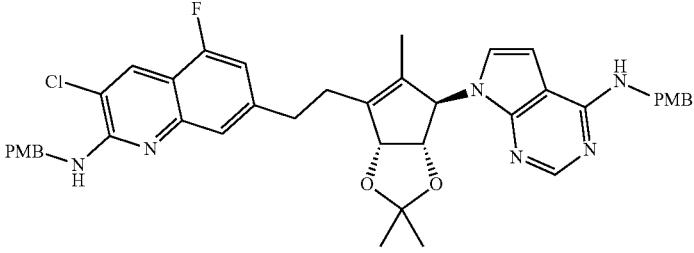<br>3-Chloro-5-fluoro-N-(4-methoxybenzyl)-7-(((3aS,4R,6aR)-4-(4-((4-methoxybenzyl)amino)-7H-pyrrolo[2,3-d]pyrimidin-7-yl)-2,2,5-trimethyl-3a,6a-dihydro-4H-cyclopenta[d][1,3]dioxol-6-yl)methoxy)quinolin-2-amine | ((3aS,4R,6aR)-4-(4-((4-methoxybenzyl)amino)-7H-pyrrolo[2,3-d]pyrimidin-7-yl)-2,2,5-trimethyl-3a,6a-dihydro-4H-cyclopenta[d][1,3]dioxol-6-yl)methyl 4-methylbenzenesulfonate & 3-chloro-5-fluoro-2-((4-methoxybenzyl)amino)quinolin-7-ol | LCMS m/z = 751.61 (M+, 100%). |
| 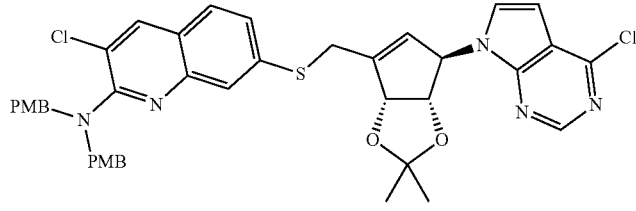<br>3-Chloro-7-((((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)methyl)thio)-N,N-bis(4-methoxybenzyl)quinolin-2-amine | ((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)methyl 4-methylbenzenesulfonate & 2-(bis(4-methoxybenzyl)amino)-3-chloroquinoline-7-thiol | ¹H NMR (400 MHz, DMSO-d6) δ 8.53 (s, 1H), 8.41 (s, 1H), 7.74 (d, J = 8.6 Hz, 1H), 7.67 (d, J = 1.8 Hz, 1H), 7.43 (dd, J = 8.5, 1.9 Hz, 1H), 7.26-7.20 (m, 4H), 6.81-6.75 (m, 4H), 6.38 (d, J = 3.7 Hz, 1H), 5.98 (d, J = 3.6 Hz, 1H), 5.72 (s, 1H), 5.63 (s, 1H), 5.44 (d, J = 5.7 Hz, 1H), 4.57-4.42 (m, 5H), 4.28 (d, J = 15.4 Hz, 1H), 3.82-3.76 (m, 1H), 3.64 (s, 6H), 1.42 (s, 3H), 1.28 (s, 3H); LCMS m/z = 754.49 (M+, 100%) |
| 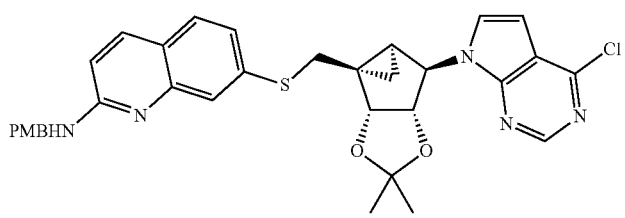<br>7-((((3aR,3bS,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)methyl)thio)-N-(4-methoxybenzyl)quinolin-2-amine | ((3aR,3bR,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)methyl 4-methylbenzenesulfonate & 2-((4-methoxybenzyl)amino)quinoline-7-thiol | ¹H NMR (400 MHz, Chloroform-d) δ 8.68 (s, 1H), 7.76 (d, J = 8.9 Hz, 1H), 7.64 (d, J = 1.8 Hz, 1H), 7.48 (d, J = 8.3 Hz, 1H), 7.39 (d, J = 3.6 Hz, 1H), 7.37-7.32 (m, 2H), 7.20 (dd, J = 8.4, 1.9 Hz, 1H), 6.93-6.87 (m, 2H), 6.59 (d, J = 8.8 Hz, 1H), 6.55 (d, J = 3.6 Hz, 1H), 5.39 (dd, J = 7.2, 1.5 Hz, 1H), 5.21 (s, 1H), 4.65 (d, J = 5.3 Hz, 1H), 4.64-4.60 (m, 1H), 3.82 (s, 3H), 3.62 (d, J = 13.3 Hz, 1H), 3.43 (d, J = 13.3 Hz, 1H), 1.76-1.73 (m, 1H), 1.60 (s, 1H), 1.33-1.30 (m, 1H), 1.26 (s, 3H), 1.12-1.06 (m, 1H); LCMS m/z = 614.21 (M+, 100%) |

181

3-Chloro-7-(((3aS,4R,6aR)-4-(4-chloro-7H-pyrrolo[2,3-d]pyrimidin-7-yl)-2,2,6a-trimethyl-3a,6a-dihydro-4H-cyclopenta[d][1,3]dioxol-6-yl)methoxy)-5-fluoro-N-(4-methoxybenzyl)quinolin-2-amine

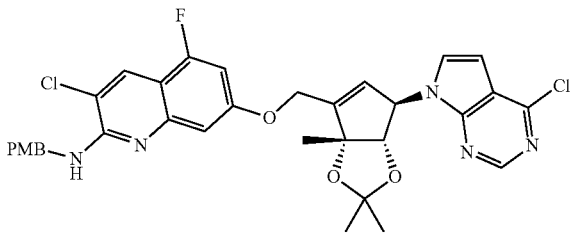

To a stirred solution of ((3aS,4R,6aR)-4-(4-chloro-7H-pyrrolo[2,3-d]pyrimidin-7-yl)-2,2,6a-trimethyl-3a,6a-dihydro-4H-cyclopenta[d][1,3]dioxol-6-yl) methanol (250 mg, 0.745 mmol) and 3-chloro-5-fluoro-2-((4-methoxybenzyl)amino)quinolin-7-ol (297 mg, 0.893 mmol) in toluene (2 ml) was added triphenyl phosphine (234 mg, 0.893 mmol) and stirred for 5 minutes then added DEAD (0.118 ml, 0.745 mmol) dropwise at 25° C. and reaction mixture was stirred at 90° C. for 2 hours. The volatiles were removed in vacuo and obtained residue was purified by combiflash (R$_f$200, Teledyne/Isco) instrument onto a Redisep® R$_f$ column with gradient elution (0 to 50%) of ethyl acetate in petroleum ether to afford the title compound (420 mg, 87%) as a off-white solid. $^1$H NMR (400 MHz, DMSO-d$_6$) δ 8.70 (s, 1H), 8.12 (s, 1H), 7.69 (t, J=6.1 Hz, 1H), 7.48 (d, J=3.7 Hz, 1H), 7.42-7.36 (m, 1H), 7.36-7.30 (m, 2H), 6.97 (d, J=2.2 Hz, 1H), 6.88-6.86 (m, 2H), 6.62 (d, J=3.6 Hz, 1H), 5.86 (d, J=2.8 Hz, 1H), 5.68 (d, J=2.5 Hz, 1H), 5.08 (d, J=15.5 Hz, 1H), 4.89 (d, J=15.5 Hz, 1H), 4.65 (d, J=6.0 Hz, 2H), 4.25 (s, 1H), 3.70 (s, 3H), 1.55 (s, 3H), 1.41 (s, 3H), 1.34 (s, 3H); LCMS m/z=650.34 (M+, 100%).

182

7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)ethyl)-N-methylquinolin-2-amine

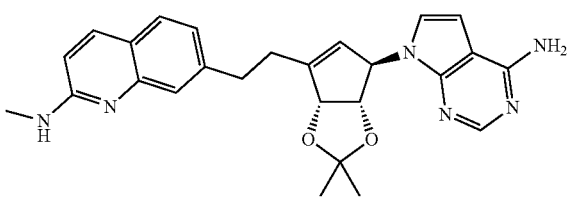 [SMILES: CNc1ccc2ccc(CCC3=C[C@@H](n4ccc5c(N)ncnc54)[C@@H]4OC(C)(C)O[C@H]34)cc2n1]

A mixture of 7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-N-methylquinolin-2-amine (0.100 g, 0.210 mmol) in dioxane (3 ml) was added aq. ammonia (0.227 ml, 10.50 mmol) at 25° C. and stirred the reaction mixture at 130° C. for 16 h. The reaction mixture was diluted with brine (20 ml) and extracted with ethyl acetate (20 ml). Layers were separated, the organic layer was dried over anhydrous Na$_2$SO$_4$, filtered and concentrated in vacuo to give 0.15 g of crude compound. The obtained residue was purified by combiflash (R$_f$200, Teledyne/Isco) instrument onto a Redisep® R$_f$ column with gradient elution (0 to 5%) of methanol in dicholomethane to afford the title compound (0.07 g, 73%) as an off-white solid. LCMS m/z=457.2 (M+1; 40%).

Intermediates in table-12 were synthesized by an analogous reaction protocol as was used for the preparation of 7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)ethyl)-N-methylquinolin-2-amine using the appropriate starting materials (Instead of aq.NH$_3$, 7N NH$_3$ in MeOH could also be used).

TABLE 12

| Structure & IUPAC name | Intermediate used | $^1$H NMR & LCMS data |
|---|---|---|
| 7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)ethyl)-N-cyclobutylquinolin-2-amine | 7-(2-((3aS,4R,6aR)-4-(4-Chloro-7H-pyrrolo[2,3-d]pyrimidin-7-yl)-2,2-dimethyl-3a,6a-dihydro-4H-cyclopenta[d][1,3]dioxol-6-yl)ethyl)-N-cyclobutylquinolin-2-amine | $^1$H NMR (400 MHz, Chloroform-d) δ 8.35 (s, 1H), 7.86 (d, J = 8.9 Hz, 1H), 7.58 – 7.53 (m, 2H), 7.15 (dd, J = 8.2, 1.7 Hz, 1H), 6.62 (d, J = 8.9 Hz, 1H), 6.31 (d, J = 3.6 Hz, 1H), 6.09 (d, J = 3.6 Hz, 1H), 5.75 (s, 1H), 5.51 – 5.45 (m, 2H), 5.26 (d, J = 6.0 Hz, 1H), 5.15 (s, 2H), 4.47 (d, J = 5.7 Hz, 1H), 4.45 – 4.37 (m, 1H), 3.19 – 3.01 (m, 2H), 2.87 – 2.68 (m, 2H), 2.57 – 2.46 (m, 2H), 2.02 – 1.93 (m, 2H), 1.89 – 1.79 (m, 2H), 1.50 (s, 3H), 1.37 (s, 3H); LCMS m/z = 497.3 (M + 1; 70%). |

TABLE 12-continued

| Structure & IUPAC name | Intermediate used | ¹H NMR & LCMS data |
|---|---|---|
| 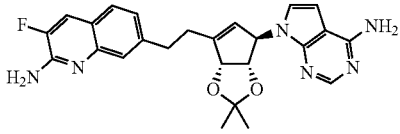 [SMILES: CC1(C)O[C@@H]2[C@H](O1)C(CCc1ccc3cc(F)c(N)nc3c1)=C[C@H]2n1ccc2c(N)ncnc21]<br>7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)ethyl)-3-fluoroquinolin-2-amine | 7-(2-((3aS,4R,6aR)-4-(4-Chloro-7H-pyrrolo[2,3-d]pyrimidin-7-yl)-2,2-dimethyl-3a,6a-dihydro-4H-cyclopenta[d][1,3]dioxol-6-yl)ethyl)-3-fluoroquinolin-2-amine | ¹H NMR (400 MHz, DMSO-d6) δ 8.05 (s, 1H), 7.79 (d, J = 11.8 Hz, 1H), 7.60 (d, J = 8.2 Hz, 1H), 7.41 (s, 1H), 7.19 (d, J = 8.2 Hz, 1H), 6.96 (s, 2H), 6.72 (s, 2H), 6.35 – 6.31 (m, 2H), 5.54 (s, 1H), 5.50 (s, 1H), 5.29 (d, J = 5.9 Hz, 1H), 4.35 (d, J = 5.7 Hz, 1H), 3.10 – 2.93 (m, 2H), 2.70 – 2.60 (m, 2H), 1.37 (s, 3H), 1.24 (s, 3H); LCMS m/z = 461.3 (M + 1; 60%). |
| 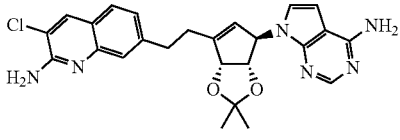 [SMILES: CC1(C)O[C@@H]2[C@H](O1)C(CCc1ccc3cc(Cl)c(N)nc3c1)=C[C@H]2n1ccc2c(N)ncnc21]<br>7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)ethyl)-3-chloroquinolin-2-amine | 3-Chloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)quinolin-2-amine | ¹H NMR (400 MHz, DMSO-d6) δ 8.17 (s, 1H), 8.05 (s, 1H), 7.61 (d, J = 8.3 Hz, 1H), 7.41 (d, J = 1.6 Hz, 1H), 7.19 (dd, J = 8.2, 1.7 Hz, 1H), 6.98 (s, 2H), 6.69 (s, 2H), 6.41 (d, J = 3.6 Hz, 1H), 6.35 (d, J = 3.5 Hz, 1H), 5.55 (s, 1H), 5.51 (s, 1H), 5.29 (d, J = 5.7 Hz, 1H), 4.36 (d, J = 5.7 Hz, 1H), 3.09 2.94 (m, 2H), 2.72 – 2.56 (m, 2H), 1.37 (s, 3H), 1.28 (s, 3H); LCMS m/z = 477.05 (M+; 20%). |
| 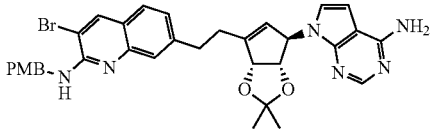<br>7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)ethyl)-3-bromo-N-(4-methoxybenzyl)quinolin-2-amine | 3-Bromo-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-N-(4-methoxybenzyl)quinolin-2-amine | ¹H NMR (400 MHz, DMSO-d6) δ 8.35 (s, 1H), 8.07 (s, 1H), 7.60 (d, J = 8.2 Hz, 1H), 7.45 (s, 1H), 7.38 – 7.31 (m, 2H), 7.22 – 7.16 (m, 2H), 7.01 (s, 2H), 6.88 – 6.82 (m, 2H), 6.52 (d, J = 3.5 Hz, 1H), 6.40 (d, J = 3.6 Hz, 1H), 5.56 (s, 1H), 5.52 (s, 1H), 5.30 (d, J = 5.7 Hz, 1H), 4.66 – 4.61 (m, 2H), 4.38 (d, J = 5.6 Hz, 1H), 3.69 (s, 3H), 3.06 – 2.93 (m, 2H), 2.70 – 2.59 (m, 2H), 1.38 (s, 3H), 1.27 (s, 3H); LCMS m/z = 641.97 (M+; 60%). |

TABLE 12-continued

| Structure & IUPAC name | Intermediate used | ¹H NMR & LCMS data |
|---|---|---|
| 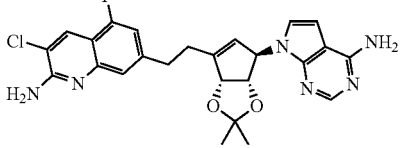<br>7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)ethyl)-3-chloro-5-fluoroquinolin-2-amine | 3-Chloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-5-fluoroquinolin-2-amine | ¹H NMR (400 MHz, DMSO-d6) δ 8.17 (d, J = 0.7 Hz, 1H), 8.05 (s, 1H), 7.26 (s, 1H), 7.05 (dd, J = 11.1, 1.4 Hz, 1H), 7.01 – 6.91 (m, 4H), 6.41 (d, J = 3.5 Hz, 1H), 6.35 (d, J = 3.5 Hz, 1H), 5.54 (s, 1H), 5.51 (s, 1H), 5.30 (d, J = 5.7 Hz, 1H), 4.37 (d, J = 5.7 Hz, 1H), 3.07 – 2.95 (m, 2H), 2.71 – 2.56 (m, 2H), 1.37 (s, 3H), 1.27 (s, 3H); LCMS m/z = 495.05 (M+; 40%). |
| 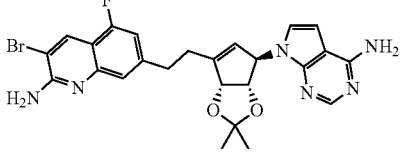<br>7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)ethyl)-3-bromo-5-fluoroquinolin-2-amine | 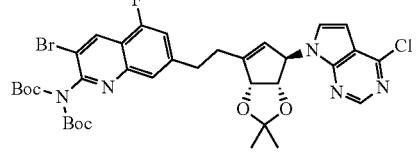 | ¹H NMR (400 MHz, DMSO-d6) δ 8.34 (s, 1H), 8.05 (s, 1H), 7.25 (s, 1H), 7.04 (dd, J = 11.0, 1.4 Hz, 1H), 6.97 (s, 2H), 6.86 (s, 2H), 6.43 (d, J = 3.5 Hz, 1H), 6.37 (d, J = 3.5 Hz, 1H), 5.55 (s, 1H), 5.51 (s, 1H), 5.30 (d, J = 5.7 Hz, 1H), 4.38 (d, J = 5.7 Hz, 1H), 3.08 – 2.95 (m, 2H), 2.71 – 2.58 (m, 2H), 1.37 (s, 3H), 1.28 (s, 3H); LCMS m/z = 541.20 (M + 2; 100%) |
| 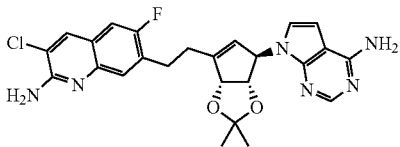 [SMILES: CC1(C)O[C@@H]2[C@H](O1)C(CCc1cc3nc(N)c(Cl)cc3cc1F)=C[C@H]2n1ccc2c(N)ncnc21]<br>7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)ethyl)-3-chloro-6-fluoroquinolin-2-amine | 3-Chloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-6-fluoroquinolin-2-amine | ¹H NMR (400 MHz, DMSO-d6) δ 8.17 (s, 1H), 8.06 (s, 1H), 7.53 – 7.44 (m, 2H), 6.99 (s, 2H), 6.71 (s, 2H), 6.52 (d, J = 3.5 Hz, 1H), 6.40 (d, J = 3.5 Hz, 1H), 5.57 (s, 1H), 5.55 (s, 1H), 5.32 (d, J = 5.7 Hz, 1H), 4.40 (d, J = 5.7 Hz, 1H), 3.12 – 2.99 (m, 2H), 2.70 – 2.56 (m, 2H), 1.36 (s, 3H), 1.28 (s, 3H); LCMS m/z = 494.99 (M+; 20%). |
| 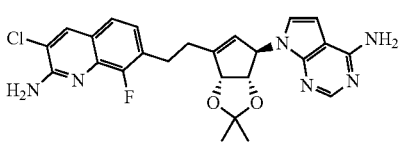 [SMILES: CC1(C)O[C@@H]2[C@H](O1)C(CCc1ccc3cc(Cl)c(N)nc3c1F)=C[C@H]2n1ccc2c(N)ncnc21]<br>7-(2-((3aS,4R,6aR)-4-(4-Amino-7H-pyrrolo[2,3-d]pyrimidin-7-yl)-2,2-dimethyl-3a,6a-dihydro- | 3-Chloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-2-amine | LCMS m/z ethyl)-8-fluoroquinolin-495.30 (M +; 70%). |

TABLE 12-continued

| Stucture & IUPAC name | Intermediate used | ¹H NMR & LCMS data |
|---|---|---|
| 4H-cyclopenta[d][1,3]dioxol-6-yl)ethyl)-3-chloro-8-fluoroquinolin-2-amine | | |
| 7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)ethyl)-3,5-dichloroquinolin-2-amine | 3,5-Dichloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)quinolin-2-amine | LCMS m/z = 511.2 (M+; 100%). |
| 7-((3aS,4R,6aR)-2,2-Dimethyl-6-(2-(3-methylimidazo[1,2-a]pyridin-7-yl)ethyl)-3a, 6a-dihydro-4H-cyclopenta[d][1,3]dioxol-4-yl)-7H-pyrrolo[2,3-d]pyrimidin-4-amine | 4-Chloro-7-((3aS,4R,6aR)-2,2-dimethyl-6-(2-(3-methylimidazo[1,2-a]pyridin-7-yl)ethyl)-3a, 6a-dihydro-4H-cyclopenta[d][1,3]dioxol-4-yl)-7H-pyrrolo[2,3-d]pyrimidine | ¹H NMR (400 MHz, DMSO-d6) δ 8.19 (d, J = 7.0 Hz, 1H), 8.04 (s, 1H), 7.43 (s, 1H), 7.31 (d, J = 1.1 Hz, 1H), 6.98 (s, 2H), 6.91 (dd, J = 7.1, 1.7 Hz, 1H), 6.44 (d, J = 3.5 Hz, 1H), 6.35 (d, J = 3.5 Hz, 1H), 5.55 (s, 1H), 5.50 (s, 1H), 5.32 (d, J = 5.6 Hz, 1H), 4.38 (d, J = 5.7 Hz, 1H), 3.02 – 2.91 (m, 2H), 2.71 – 2.57 (m, 2H), 2.45 (d, J = 1.0 Hz, 3H), 1.38 (s, 3H), 1.28 (s, 3H); LCMS m/z = 430.98 (M+; 30%). |
| 7-((3aS,4R,6aR)-6-(2-(2-Amino-3,3-dimethyl-3H-indol-6-yl)ethyl)-2,2-dimethyl-3a,6a-dihydro-4H-cyclopenta[d][1,3]dioxol-4-yl)-7H-pyrrolo[2,3-d]pyrimidin-4-amine | 4-chloro-7-((3aS,4R,6aR)-6-(2-(3,3-dimethyl-2-(methylthio)-3H-indol-6-yl)ethyl)-2,2-dimethyl-3a, 6a-dihydro-4H-cyclopenta[d][1,3]dioxol-4-yl)-7H-pyrrolo[2,3-d]pyrimidine | ¹H NMR (400 MHz, DMSO-d6) δ 9.42 (s, 2H), 8.06 (s, 1H), 7.32 (d, J = 7.6 Hz, 1H), 7.10 – 6.95 (m, 4H), 6.45 (s, 2H), 5.56 (s, 1H), 5.51 (s, 1H), 5.28 (d, J = 5.6 Hz, 1H), 4.37 (d, J = 5.7 Hz, 1H), 3.02 – 2.84 (m, 2H), 2.65 – 2.54 (m, 2H), 1.46 (s, 6H), 1.36 (s, 3H), 1.28 (s, 3H); LCMS m/z = 459.36 (M + 1; 20%). |

TABLE 12-continued

| Structure & IUPAC name | Intermediate used | ¹H NMR & LCMS data |
|---|---|---|
| 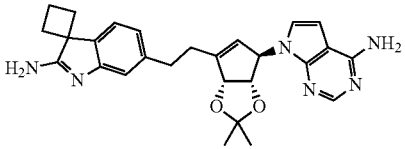 [SMILES: CC1(C)O[C@@H]2[C@H](O1)C(CCc1ccc3c(c1)N=C(N)C31CCC1)=C[C@H]2n1ccc2c(N)ncnc21]<br>6'-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)ethyl)spiro[cyclobutane-1,3'-indol]-2'-amine | 6'-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-2'-(methylthio)spiro[cyclobutane-1,3'-indole] | ¹H NMR (400 MHz, DMSO-d6) δ 8.06 (s, 1H), 7.64 (d, J = 7.6 Hz, 1H), 7.09 – 6.97 (m, 4H), 6.47 – 6.40 (m, 2H), 5.55 (s, 1H), 5.50 (s, 1H), 5.28 (d, J = 5.7 Hz, 1H), 4.37 (d, J = 5.6 Hz, 1H), 2.99 – 2.87 (m, 2H), 2.83 – 2.71 (m, 2H), 2.64 – 2.53 (m, 2H), 2.36 – 2.29 (m, 2H), 2.27 – 2.16 (m, 2H), 1.37 (s, 3H), 1.28 (s, 3H); LCMS m/z = 472.3 (M + 2; 100%). |
| 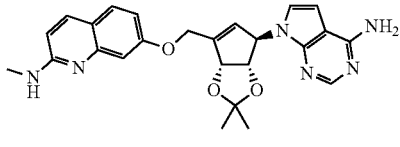 [SMILES: CNc1ccc2ccc(OCC3=C[C@@H](n4ccc5c(N)ncnc54)[C@@H]4OC(C)(C)O[C@H]34)cc2n1]<br>7-(((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)methoxy)-N-methylquinolin-2-amine | 7-(((3aS,4R,6aR)-4-(4-Chloro-7H-pyrrolo[2,3-d]pyrimidin-7-yl)-2,2-dimethyl-3a,6a-dihydro-4H-cyclopenta[d][1,3]dioxol-6-yl)methoxy)-N-methylquinolin-2-amine | ¹H NMR (400 MHz, DMSO-d6) δ 8.08 (s, 1H), 7.80 (d, J = 8.9 Hz, 1H), 7.57 (d, J = 8.7 Hz, 1H), 7.15 (s, 1H), 7.06 (s, 2H), 6.90 (dd, J = 8.6, 2.4 Hz, 1H), 6.86 (d, J = 3.6 Hz, 1H), 6.64 (d, J = 8.9 Hz, 1H), 6.52 (d, J = 3.6 Hz, 1H), 5.84 (s, 1H), 5.65 (s, 1H), 5.42 (d, J = 5.6 Hz, 1H), 4.93 (s, 2H), 4.53 (d, J = 5.7 Hz, 1H), 2.93 (d, J = 4.8 Hz, 3H), 1.46 (s, 3H), 1.30 (s, 3H); LCMS m/z = 459.40 (M + 1; 30%). |
| 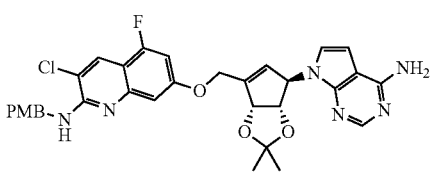<br>7-(((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)methoxy)-3-chloro-5-fluoro-N-(4-methoxybenzyl)quinolin-2-amine | 3-Chloro-7-(((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)methoxy)-5-fluoro-N-(4-methoxybenzyl)quinolin-2-amine | ¹H NMR (400 MHz, DMSO-d6) δ 8.11 (s, 1H), 8.07 (s, 1H), 7.67 (t, J = 6.2 Hz, 1H), 7.36 – 7.31 (m, 2H), 7.01 (s, 2H), 6.94 (d, J = 2.2 Hz, 1H), 6.90 – 6.81 (m, 4H), 6.51 (d, J = 3.6 Hz, 1H), 5.83 (s, 1H), 5.65 (s, 1H), 5.42 (d, J = 5.7 Hz, 1H), 4.94 (q, J = 15.3 Hz, 2H), 4.65 (d, J = 6.1 Hz, 2H), 4.55 (d, J = 5.7 Hz, 1H), 3.70 (s, 3H), 1.43 (s, 3H), 1.29 (s, 3H); LCMS m/z = 617.34 (M+; 100%). |

TABLE 12-continued

| Structure & IUPAC name | Intermediate used | ¹H NMR & LCMS data |
|---|---|---|
| N7-((((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)methyl)-N2-(4-methoxybenzyl)quinoline-2,7-diamine | N7-(((3aS,4R,6aR)-4-(4-Chloro-7H-pyrrolo[2,3-d]pyrimidin-7-yl)-2,2-dimethyl-3a,6a-dihydro-4H-cyclopenta[d][1,3]dioxol-6-yl)methyl)-N2-(4-methoxybenzyl)quinoline-2,7-diamine | LCMS m/z = 564.40 (M + 1; 100%). |
| N7-((((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)methyl)-N2-(4-methoxybenzyl)-N7-methylquinoline-2,7-diamine | N7-(((3aS,4R,6aR)-4-(4-Chloro-7H-pyrrolo[2,3-d]pyrimidin-7-yl)-2,2-dimethyl-3a,6a-dihydro-4H-cyclopenta[d][1,3]dioxol-6-yl)methyl)-N2-(4-methoxybenzyl)-N7-methylquinoline-2,7-diamine | LCMS m/z = 576.95 (M − 1; 100%). |
| 7-((((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)methyl)thio)-N-(4-methoxybenzyl)quinolin-2-amine | 7-((((3aS,4R,6aR)-4-(4-Chloro-7H-pyrrolo[2,3-d]pyrimidin-7-yl)-2,2-dimethyl-3a,6a-dihydro-4H-cyclopenta[d][1,3]dioxol-6-yl)methyl)thio)-N-(4-methoxybenzyl)quinolin-2-amine | ¹H NMR (400 MHz, DMSO-d6) δ 8.03 (s, 1H), 7.84 (d, J = 8.9 Hz, 1H), 7.57 (d, J = 8.3 Hz, 1H), 7.49 (s, 2H), 7.36 – 7.26 (m, 2H), 7.18 (d, J = 8.4 Hz, 1H), 6.96 (s, 2H), 6.84 (d, J = 8.2 Hz, 2H), 6.82 – 6.76 (m, 1H), 6.16 (s, 1H), 6.01 (s, 1H), 5.76 (s, 2H), 5.71 (s, 1H), 5.54 (s, 1H), 5.38 (s, 1H), 4.55 (s, 1H), 4.34 (d, J = 5.5 Hz, 1H), 4.19 (d, J = 15.2 Hz, 1H), 3.70 (s, 3H), 1.42 (s, 3H), 1.27 (s, 3H); LCMS m/z = 580.83 (M+; 100%). |
| 7-((((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)methyl)thio)-3-chloro-N,N-bis(4-methoxybenzyl)quinolin-2-amine | 3-Chloro-7-((((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)methyl)thio)-N,N-bis(4-methoxybenzyl)quinolin-2-amine | LCMS m/z = 735.61 (M+; 80%). |

TABLE 12-continued

| Structure & IUPAC name | Intermediate used | ¹H NMR & LCMS data |
|---|---|---|
| 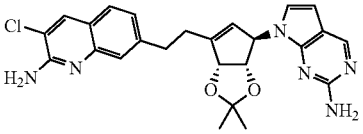 [SMILES: CC1(C)O[C@@H]2[C@H](O1)C(CCc1ccc3cc(Cl)c(N)nc3c1)=C[C@H]2n1ccc2cnc(N)nc21]<br>7-(2-((3aS,4R,6aR)-4-(2-Amino-7H-pyrrolo[2,3-d]pyrimidin-7-yl)-2,2-dimethyl-3a,6a-dihydro-4H-cyclopenta[d][1,3]dioxol-6-yl)ethyl)-3-chloroquinolin-2-amine | 3-Chloro-7-(2-((3aS,4R,6aR)-4-(2-chloro-7H-pyrrolo[2,3-d]pyrimidin-7-yl)-2,2-dimethyl-3a,6a-dihydro-4H-cyclopenta[d][1,3]dioxol-6-yl)ethyl)quinolin-2-amine | ¹H NMR (400 MHz, DMSO-d6) δ 8.43 (s, 1H), 8.17 (s, 1H), 7.61 (d, J = 8.3 Hz, 1H), 7.40 (d, J = 1.5 Hz, 1H), 7.28 (s, 2H), 7.19 (dd, J = 8.3, 1.7 Hz, 1H), 6.69 (s, 2H), 6.23 (d, J = 3.7 Hz, 1H), 6.03 (d, J = 3.6 Hz, 1H), 5.46 (s, 1H), 5.43 (s, 1H), 5.33 (d, J = 5.7 Hz, 1H), 4.36 (d, J = 5.6 Hz, 1H), 3.10 – 2.93 (m, 2H), 2.67 – 2.56 (m, 2H), 1.36 (s, 3H), 1.28 (s, 3H); LCMS m/z = 476.98 (M+; 100%). |
| 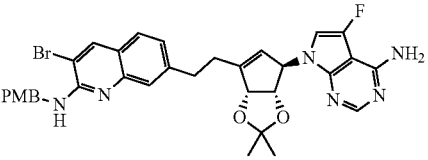<br>7-(2-((3aS,4R,6aR)-4-(4-Amino-5-fluoro-7H-pyrrolo[2,3-d]pyrimidin-7-yl)-2,2-dimethyl-3a, 6a-dihydro-4H-cyclopenta[d][1,3]dioxol-6-yl)ethyl)-3-bromo-N-(4-methoxybenzyl)quinolin-2-amine | 3-Bromo-7-(2-((3aS,4R,6aR)-4-(4-chloro-5-fluoro-7H-pyrrolo[2,3-d]pyrimidin-7-yl)-2,2-dimethyl-3a,6a-dihydro-4H-cyclopenta[d][1,3]dioxol-6-yl)ethyl)-N-(4-methoxybenzyl)quinolin-2-amine | ¹H NMR (400 MHz, DMSO-d6) δ 8.35 (s, 1H), 8.06 (s, 1H), 7.60 (d, J = 8.3 Hz, 1H), 7.45 (s, 1H), 7.36 – 7.31 (m, 2H), 7.21 – 7.16 (m, 2H), 6.95 (s, 2H), 6.86 – 6.82 (m, 2H), 6.35 (d, J = 2.1 Hz, 1H), 5.58 (s, 1H), 5.48 (s, 1H), 5.28 (d, J = 5.6 Hz, 1H), 4.37 (d, J = 5.6 Hz, 1H), 4.27 (d, J = 4.1 Hz, 2H), 3.68 (s, 3H), 3.05 – 2.97 (m, 2H), 2.67 – 2.57 (m, 2H), 1.36 (s, 3H), 1.27 (s, 3H); LCMS m/z = 660.97 (M + 1; 25%). |
| 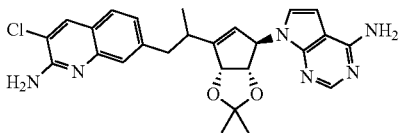<br>7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)propyl)-3-chloroquinolin-2-amine | 3-Chloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)propyl)quinolin-2-amine | Diastereomeric mixture was separated by chiral preparative HPLC. Run Time (min): 10.00, Injection Volume: 5.00 μL Wavelength: 225 nm HEX_0.1%DEA_I PA_DCM_60_40 A_C_1.2ML_10M IN Flow Rate: 1.2 ml/min. Column : CHIRALPAK IA CRL-027 OLD Column Temp: 25.0° C. Mobile Phase A: HEX_0.1%DEA |

TABLE 12-continued

| Stucture & IUPAC name | Intermediate used | ¹H NMR & LCMS data |
|---|---|---|
| 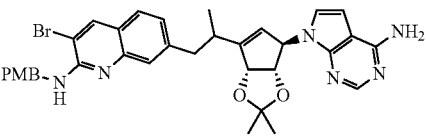<br>7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)propyl)-3-bromo-N-(4-methoxybenzyl)quinolin-2-amine | 3-Bromo-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)propyl)-N-(4-methoxybenzyl)quinolin-2-amine | Mobile Phase C: IPA:DCMMobile Phase B: NA Mobile Phase D: NA Diastereomer-1 ¹H NMR (400 MHz, DMSO-d6) δ 8.17 (s, 1H), 8.04 (s, 1H), 7.61 (d, J = 8.2 Hz, 1H), 7.38 (s, 1H), 7.16 (dd, J = 8.1, 1.6 Hz, 1H), 6.98 (s, 2H), 6.67 (s, 2H), 6.32 (d, J = 3.5 Hz, 1H), 6.29 (d, J = 3.6 Hz, 1H), 5.55 (s, 1H), 5.52 (s, 1H), 5.41 (d, J = 5.8 Hz, 1H), 4.35 (d, J = 5.8 Hz, 1H), 3.12 – 3.03 (m, 1H), 2.96 – 2.90 (m, 1H), 2.88 – 2.81 (m, 1H), 1.31 (s, 3H), 1.27 (s, 3H), 1.17 (d, J = 6.8 Hz, 3H); LCMS m/z = 491.36 (M+; 80%). Diastereomer-2 ¹H NMR (400 MHz, DMSO-d6) δ 8.17 (s, 1H), 8.06 (s, 1H), 7.61 (d, J = 8.2 Hz, 1H), 7.36 (s, 1H), 7.15 (dd, J = 8.3, 1.6 Hz, 1H), 6.97 (s, 2H), 6.67 (s, 2H), 6.56 (d, J = 3.6 Hz, 1H), 6.44 (d, J = 3.6 Hz, 1H), 5.60 – 5.56 (m, 1H), 5.52 (d, J = 2.5 Hz, 1H), 5.34 (d, J = 5.7 Hz, 1H), 4.40 (d, J = 5.7 Hz, 1H), 3.13 – 3.04 (m, 1H), 2.93 (q, J = 7.2 Hz, 1H), 2.83 (d, J = 10.0 Hz, 1H), 1.40 (s, 3H), 1.28 (s, 3H), 1.14 (d, J = 6.8 Hz, 3H); LCMS m/z = 491.36 (M+; 80%). Diastereomeric mixture was separatedby chiral preparative HPLC. Run Time (min): 10.00 Injection Volume: 5.00 μL, Wavelength: 251 nm, HEX_0.1%DEA_IPA-DCM_50_50_A_C_ |

TABLE 12-continued

| Stucture & IUPAC name | Intermediate used | ¹H NMR & LCMS data |
|---|---|---|
| | | 1.0 ML_10 MIN 251 nm Flow Rate: 1.0 ml/min. Column: CHIRALPAK IG CRL-071 Column Temp: 25.0 ° C. Mobile Phase A: HEX_0.1%DEA Mobile Phase C: IPA-DCM_1-1, Mobile Phase B: NA Mobile Phase D: NA Diastereomer-1: ¹H NMR (400 MHz, DMSO-d6) δ 8.36 (s, 1H), 8.07 (s, 1H), 7.60 (d, J = 8.2 Hz, 1H), 7.41 (d, J = 1.4 Hz, 1H), 7.37 – 7.33 (m, 2H), 7.19 – 7.13 (m, 2H), 6.99 (s, 2H), 6.87 – 6.83 (m, 2H), 6.63 (d, J = 3.6 Hz, 1H), 6.46 (d, J = 3.5 Hz, 1H), 5.59 (s, 1H), 5.53 (s, 1H), 5.32 (d, J = 5.7 Hz, 1H), 4.65 (d, J = 6.0 Hz, 2H), 4.40 (d, J = 5.8 Hz, 1H), 3.69 (s, 3H), 3.11 – 3.04 (m, 1H), 2.86 – 2.76 (m, 2H), 1.41 (s, 3H), 1.28 (s, 3H), 1.14 (d, J = 6.5 Hz, 3H); LCMS m/z = 657.47 (M + 2; 45%). Diastereomer-2: ¹H NMR (400 MHz, DMSO-d6) δ 8.35 (s, 1H), 8.05 (s, 1H), 7.60 (d, J = 8.1 Hz, 1H), 7.42 (s, 1H), 7.33 (d, J = 8.5 Hz, 2H), 7.18 – 7.13 (m, 2H), 7.00 (s, 2H), 6.84 (d, J = 8.6 Hz, 2H), 6.43 (d, J = 3.6 Hz, 1H), 6.38 (d, J = 3.5 Hz, 1H), 5.55 (s, 1H), 5.52 (s, 1H), 5.42 (d, J = 5.7 Hz, 1H), 4.63 (d, J = 6.0 Hz, 2H), 4.38 (d, J = 5.7 Hz, 1H), 3.69 (s, 3H), 3.10 – 3.05 (m, 1H), 2.96 – 2.90 (m, 2H), 1.32 (s, 3H), 1.27 (s, 3H), 1.16 (d, J = 6.8 Hz, 3H); LCMS m/z = 655.47 (M+; 35%). |

TABLE 12-continued

| Stucture & IUPAC name | Intermediate used | ¹H NMR & LCMS data |
|---|---|---|
| 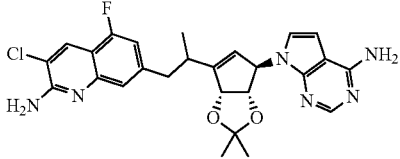<br>7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)propyl)-3-chloro-5-fluoroquinolin-2-amine | 3-Chloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)propyl)-5-fluoroquinolin-2-amine | LCMS m/z = 509.3 (M+; 60%). |
| 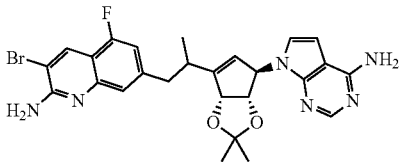 [SMILES: CC(Cc1cc(F)c2cc(Br)c(N)nc2c1)C1=C[C@@H](n2ccc3c(N)ncnc32)[C@@H]2OC(C)(C)O[C@H]12]<br>7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)propyl)-3-bromo-5-fluoroquinolin-2-amine | 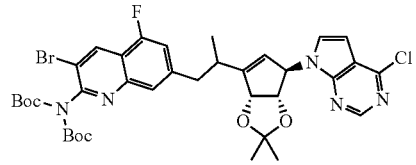 | Diastereomeric mixture was separated by chiral preparative HPLC. Run Time (min): 15.00, Injection Volume: 10.00 μL, Wavelength: 254 nm, Flow Rate: 1.50 ml/min, Column Temp: 30.0° C., Instrument Method: ACN_DEA_100_B_1.5 ML_15 MIN_254 NM, Column: CHIRALPAK OX-H CRL-061, Mobile Phase A: NA, Mobile Phase B: ACN_0.1%DEA Diastereomer-1: LCMS m/z = 553.20, 555.20 (M+;M + 2; 100%) Diastereomer-2: ¹H NMR (400 MHz, DMSO-d6) δ 8.35 (s, 1H), 8.06 (s, 1H), 7.20 (s, 1H), 7.00 – 6.96 (m, 3H), 6.86 (s, 2H), 6.57 (d, J = 3.5 Hz, 1H), 6.45 (d, J = 3.5 Hz, 1H), 5.57 (s, 1H), 5.53 (s, 1H), 5.34 (d, J = 5.8 Hz, 1H), 4.41 (d, J = 5.7 Hz, 1H), 3.09 – 3.01 (m, 2H), 2.85 – 2.83 (m, 1H), 1.40 (s, 3H), 1.28 (s, 3H), 1.15 (d, J = 6.0 Hz, 3H); LCMS m/z = 555.20 (M + 2; 100%) |
| 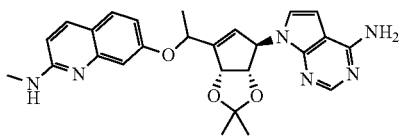 [SMILES: CNc1ccc2ccc(OC(C)C3=C[C@@H](n4ccc5c(N)ncnc54)[C@@H]4OC(C)(C)O[C@H]34)cc2n1]<br>7-(1-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)ethoxy)-N-methylquinolin-2-amine | 7-(1-((3aS,4R,6aR)-4-(4-Chloro-7H-pyrrolo[2,3-d]pyrimidin-7-yl)-2,2-dimethyl-3a,6a-dihydro-4H-cyclopenta[d][1,3]dioxol-6-yl)ethoxy)-N-methylquinolin-2-amine | LCMS m/z = 473.11 (M + 1; 20%). |

TABLE 12-continued

| Structure & IUPAC name | Intermediate used | ¹H NMR & LCMS data |
|---|---|---|
| 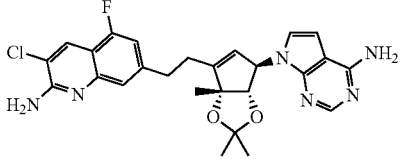 [SMILES: CC1(C)O[C@H]2[C@H](n3ccc4c(N)ncnc43)C=C(CCc3cc(F)c4cc(Cl)c(N)nc4c3)[C@@]2(C)O1]<br>7-(2-((3aS,4R,6aR)-4-(4-Amino-7H-pyrrolo[2,3-d]pyrimidin-7-yl)-2,2,6a-trimethyl-3a,6a-dihydro-4H-cyclopenta[d][1,3]dioxol-6-yl)ethyl)-3-chloro-5-fluoroquinolin-2-amine | 3-Chloro-7-(2-((3aS,4R,6aR)-4-(4-chloro-7H-pyrrolo[2,3-d]pyrimidin-7-yl)-2,2,6a-trimethyl-3a,6a-dihydro-4H-cyclopenta[d][1,3]dioxol-6-yl)ethyl)-5-fluoroquinolin-2-amine | ¹H NMR (400 MHz, DMSO-d6) δ 8.17 (d, J = 0.7 Hz, 1H), 8.09 (s, 1H), 7.27 (s, 1H), 7.09 – 7.01 (m, 3H), 6.95 (s, 2H), 6.65 (d, J = 3.5 Hz, 1H), 6.47 (d, J = 3.5 Hz, 1H), 5.63 – 5.58 (m, 1H), 5.49 – 5.44 (m, 1H), 4.00 (d, J = 0.9 Hz, 1H), 3.06 (t, J = 7.6 Hz, 2H), 2.70 – 2.59 (m, 1H), 2.59 – 2.53 (m, 1H), 1.39 (s, 3H), 1.30 (s, 3H), 1.28 (s, 3H); LCMS m/z = 509.2 (M+; 90%). |
| 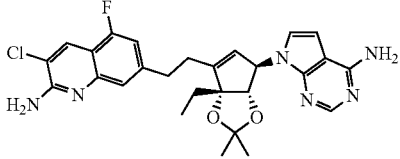 [SMILES: CC[C@]12OC(C)(C)O[C@H]1[C@H](n1ccc3c(N)ncnc31)C=C2CCc1cc(F)c2cc(Cl)c(N)nc2c1]<br>7-(2-((3aS,4R,6aR)-4-(4-Amino-7H-pyrrolo[2,3-d]pyrimidin-7-yl)-6a-ethyl-2,2-dimethyl-3a,6a-dihydro-4H-cyclopenta[d][1,3]dioxol-6-yl)ethyl)-3-chloro-5-fluoroquinolin-2-amine | 3-Chloro-7-(2-((3aS,4R,6aR)-4-(4-chloro-7H-pyrrolo[2,3-d]pyrimidin-7-yl)-6a-ethyl-2,2-dimethyl-3a,6a-dihydro-4H-cyclopenta[d][1,3]dioxol-6-yl)ethyl)-5-fluoroquinolin-2-amine | ¹H NMR (400 MHz, DMSO-d6) δ 8.18 (s, 1H), 8.09 (s, 1H), 7.28 (s, 1H), 7.06 (dd, J = 11.1, 1.4 Hz, 1H), 6.99 (s, 2H), 6.95 (s, 2H), 6.68 (d, J = 3.5 Hz, 1H), 6.45 (d, J = 3.5 Hz, 1H), 5.73 (d, J = 2.3 Hz, 1H), 5.47 – 5.43 (m, 1H), 4.09 (s, 1H), 3.07 (t, J = 7.6 Hz, 2H), 2.70 – 2.54 (m, 2H), 1.84 (dq, J = 14.9, 7.4 Hz, 1H), 1.59 (dq, J = 14.7, 7.4 Hz, 1H), 1.31 (s, 3H), 1.27 (s, 3H), 0.68 (t, J = 7.4 Hz, 3H); LCMS m/z = 523.44 (M+; 95%). |
| 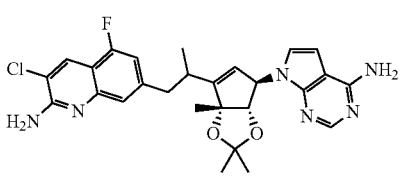 [SMILES: CC(Cc1cc(F)c2cc(Cl)c(N)nc2c1)C1=C[C@@H](n2ccc3c(N)ncnc32)[C@@H]2OC(C)(C)O[C@]12C]<br>7-(2-((3aS,4R,6aR)-4-(4-Amino-7H-pyrrolo[2,3-d]pyrimidin-7-yl)-2,2,6a-trimethyl-3a,6a-dihydro-4H-cyclopenta[d][1,3]dioxol-6-yl)propyl)-3-chloro-5-fluoroquinolin-2-amine | 3-Chloro-7-(2-((3aS,4R,6aR)-4-(4-chloro-7H-pyrrolo [2,3-d]pyrimidin-7-yl)-2,2,6a-trimethyl-3a,6a-dihydro-4H-cyclopenta[d][1,3]dioxol-6-yl)propyl)-5-fluoroquinolin-2-amine | Diastereomer-1: ¹H NMR (400 MHz, DMSO-d6) δ 8.20 (s, 1H), 8.06 (s, 1H), 7.26 (s, 1H), 7.06 (dd, J = 11.1, 1.4 Hz, 1H), 6.96 (s, 4H), 6.21 (d, J = 3.5 Hz, 1H), 5.97 (d, J = 3.6 Hz, 1H), 5.69 (d, J = 2.6 Hz, 1H), 5.45 (d, J = 2.7 Hz, 1H), 3.86 (s, 1H), 3.10 – 2.97 (m, 2H), 2.93 – 2.84 (m, 1H), 1.36 (s, 3H), 1.27 (s, 3H), 1.24 (d, J = 3.0 Hz, 3H), 1.19 (s, 3H); LCMS m/z = 523.32 (M+; 50%). Note- Only desired isomer was isolated |

TABLE 12-continued

| Structure & IUPAC name | Intermediate used | ¹H NMR & LCMS data |
|---|---|---|
| 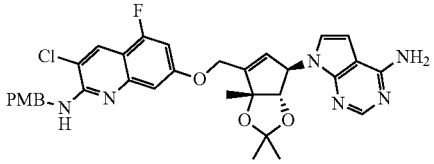<br><br>7-(((3aS,4R,6aR)-4-(4-Amino-7H-pyrrolo[2,3-d]pyrimidin-7-yl)-2,2,6a-trimethyl-3a,6a-dihydro-4H-cyclopenta[d][1,3]dioxol-6-yl)methoxy)-3-chloro-5-fluoro-N-(4-methoxybenzyl)quinolin-2-amine | 3-Chloro-7-(((3aS,4R,6aR)-4-(4-chloro-7H-pyrrolo[2,3-d]pyrimidin-7-yl)-2,2,6a-trimethyl-3a,6a-dihydro-4H-cyclopenta[d][1,3]dioxol-6-yl)methoxy)-5-fluoro-N-(4-methoxybenzyl)quinolin-2-amine | LCMS m/z = 631.30 (M+; 60%). |
| 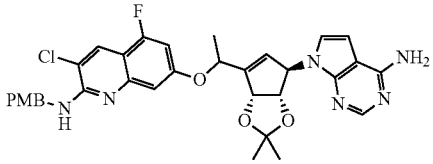<br><br>7-(1-((3aS,4R,6aR)-4-(4-Amino-7H-pyrrolo[2,3-d]pyrimidin-7-yl)-2,2-dimethyl-3a, 6a-dihydro-4H-cyclopenta[d][1,3]dioxol-6-yl)ethoxy)-3-chloro-5-fluoro-N-(4-methoxybenzyl)quinolin-2-amine | 3-Chloro-7-(1-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethoxy)-5-fluoro-N-(4-methoxybenzyl)quinolin-2-amine | Diastereomer-1 LCMS m/z = 631.34 (M+; 100%). Diastereomer-2 LCMS m/z = 631.34 (M+; 100%). |
| 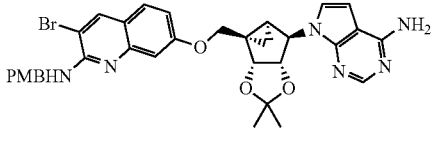<br><br>7-(2-((3aR,3bR,4aS,5R,5aS)-5-(4-amino-7H-pyrrolo[2,3-d]pyrimidin-7-yl)-2,2-dimethylhexahydrocyclopropa[3,4]cyclopenta[1,2-d][1,3]dioxol-3b-yl)ethyl)-3-bromo-N-(4-methoxybenzyl)quinolin-2-amine | 3-bromo-7-(2-((3aR,3bR,4aS,5R,5aS)-5-(4-chloro-7H-pyrrolo[2,3-d]pyrimidin-7-yl)-2,2-dimethylhexahydrocyclopropa[3,4]cyclopenta[1,2-d][1,3]dioxol-3b-yl)ethyl)-N-(4-methoxybenzyl)quinolin-2-amine | ¹H NMR (400 MHz, DMSO-d6) δ 8.33 (s, 1H), 8.08 (s, 1H), 7.57 (d, J = 8.2 Hz, 1H), 7.43 (d, J = 1.6 Hz, 1H), 7.37 – 7.31 (m, 2H), 7.19 (t, J = 6.1 Hz, 1H), 7.16 (dd, J = 8.2, 1.6 Hz, 1H), 7.14 (d, J = 3.5 Hz, 1H), 7.03 (s, 2H), 6.90 – 6.84 (m, 2H), 6.61 (d, J = 3.5 Hz, 1H), 5.21 (d, J = 7.3 Hz, 1H), 5.01 (s, 1H), 4.62 (d, J = 6.1 Hz, 2H), 4.51 (dd, J = 7.4, 1.5 Hz, 1H), 3.71 (s, 3H), 2.88 – 2.79 (m, 2H), 2.36 – 2.24 (m, 1H), 1.67 – 1.58 (m, 1H), 1.48 (s, 3H), 1.46 – 1.41 (m, 1H), 1.19 (s, 3H), 0.92 (t, J = 4.7 Hz, 1H), 0.74 – 0.68 (m, 1H); LCMS m/z = 656.2 (M + 1; 40%). |

TABLE 12-continued

| Stucture & IUPAC name | Intermediate used | ¹H NMR & LCMS data |
|---|---|---|
| 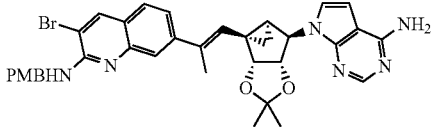<br>7-((E)-1-((3aR,3bS,4aS,5R,5aS)-5-(4-amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)prop-1-en-2-yl)-3-bromo-N-(4-methoxybenzyl)quinolin-2-amine | 3-bromo-7-((E)-1-((3aR,3bS,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)prop-1-en-2-yl)-N-(4-methoxybenzyl)quinolin-2-amine | ¹H NMR (400 MHz, DMSO-d6) δ 8.38 (s, 1H), 8.08 (s, 1H), 7.64 (s, 1H), 7.58 (d, J = 8.3 Hz, 1H), 7.45 – 7.40 (m, 1H), 7.33 (d, J = 8.4 Hz, 2H), 7.16 (d, J = 3.6 Hz, 1H), 7.12 (t, J = 6.0 Hz, 1H), 7.01 (s, 2H), 6.87 (d, J = 8.6 Hz, 2H), 6.63 (d, J = 3.5 Hz, 1H), 6.17 (s, 1H), 5.26 (d, J = 6.9 Hz, 1H), 4.94 (s, 1H), 4.70 (dd, J = 14.7, 6.0 Hz, 1H), 4.59 (dd, J = 14.7, 6.0 Hz, 1H), 4.48 (d, J = 6.9 Hz, 1H), 3.71 (s, 3H), 2.12 (s, 3H), 1.51 (s, 3H), 1.46 – 1.39 (m, 1H), 1.19 (s, 3H), 0.90 (t, J = 5.1 Hz, 1H), 0.26 – 0.18 (m, 1H); LCMS m/z = 668.97 (M + 1; 30%). |
| 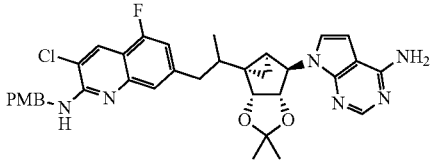<br>7-(2-((3aR,3bS,4aS,5R,5aS)-5-(4-amino-7H-pyrrolo[2,3-d]pyrimidin-7-yl)-2,2-dimethyltetrahydrocyclopropa[3,4]cyclopenta [1,2-d][1,3]dioxol-3b(3aH)-yl)propyl)-3-chloro-5-fluoro-N-(4-methoxybenzyl)quinolin-2-amine | 3-chloro-7-(2-((3aR,3bS,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)propyl)-5-fluoro-N-(4-methoxybenzyl)quinolin-2-amine | Diastereomeric mixture was separated by chiral preparative HPLC. Wavelength: 225 nm, Instrument Method: HEX-0.1%DEA_IPA-DCM_50_50 A_C_1.2ML_8M IN Flow Rate: 1.2 ml/min, Column CHIRALPAK IG CRL-071 Column Temp: 25° C., Mobile Phase A: HEX_0.1%DEA Mobile Phase C: IPA-DCM, Mobile Phase B: NA Mobile Phase D: NA First Diastereomer: LCMS m/z = 643.09(M+; 30%). Second Diastereomer: LCMS m/z = 643.09(M+; 30%). |

TABLE 12-continued

| Stucture & IUPAC name | Intermediate used | ¹H NMR & LCMS data |
|---|---|---|
| 7-(2-((3aR,3bS,4aS,5R,5aS)-5-(4-amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)-2-cyclopropylethyl)-3-chloro-5-fluoro-N-(4-methoxybenzyl)quinolin-2-amine | 3-chloro-7-(2-((3aR,3bS,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)-2-cyclopropylethyl)-5-fluoro-N-(4-methoxybenzyl)quinolin-2-amine | LCMS m/z = 669.10(M+; 20%). |
| 7-(2-((3aR,3bS,4aS,5R,5aS)-5-(4-amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)propyl)-3-bromo-N-(4-methoxybenzyl)quinolin-2-amine | 3-Bromo-7-(2-((3aR,3bS,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)propyl)-N-(4-methoxybenzyl)quinolin-2-amine | LCMS m/z = 670.97(M + 1; 20%). |
| 7-(2-((3aR,3bR,4aS,5R,5aS)-5-(4-amino-7H-pyrrolo[2,3-d]pyrimidin-7-yl)-2,2-dimethyltetrahydrocyclopropa[3,4]cyclopenta [1,2-d][1,3]dioxol-3b(3aH)-yl)ethyl)-N-(4-methoxybenzyl)quinazolin-2-amine | 7-(2-((3aR,3bR,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-N-(4-methoxybenzyl)quinazolin-2-amine | ¹H NMR (400 MHz, DMSO-d6) δ 9.04 (s, 1H), 8.07 (s, 1H), 7.79 (t, J = 6.3 Hz, 1H), 7.69 (d, J = 8.2 Hz, 1H), 7.35 (s, 1H), 7.30 (d, J = 8.2 Hz, 2H), 7.17 (dd, J = 8.2, 1.6 Hz, 1H), 7.13 (d, J = 3.5 Hz, 1H), 7.01 (s, 2H), 6.90 – 6.84 (m, 2H), 6.61 (d, J = 3.5 Hz, 1H), 5.21 (d, J = 7.1 Hz, 1H), 5.01 (s, 1H), 4.57 – 4.48 (m, 3H), 3.71 (s, 3H), 2.91 – 2.80 (m, 2H), 2.35 – 2.24 (m, 1H), 1.69 – 1.58 (m, 1H), 1.48 (s, 3H), 1.47 – 1.42 (m, 1H), 1.20 (s, 3H), 0.93 (t, J = 4.7 Hz, 1H), 0.75 – 0.69 (m, 1H); LCMS m/z = 578.3 (M + 1; 90%). |
|  | 7-(2-((3aR,3bR,4aS,5R,5aS)-5-(4-Chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-8-fluoroquinolin-2-amine | ¹H NMR (400 MHz, DMSO-d6) δ 8.07 (s, 1H), 7.88 (d, J = 8.9 Hz, 1H), 7.36 (d, J = 8.2 Hz, 1H), 7.13 (d, J = 3.7 |

TABLE 12-continued

| Stucture & IUPAC name | Intermediate used | $^1$H NMR & LCMS data |
|---|---|---|
| 7-(2-((3aR,3bR,4aS,5R,5aS)-5-(4-amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-8-fluoroquinolin-2-amine | | Hz, 1H), 7.09 (t, J = 7.4 Hz, 1H), 7.00 (s, 2H), 6.75 (d, J = 8.9 Hz, 1H), 6.65 (s, 2H), 6.61 (d, J = 3.5 Hz, 1H), 5.21 (d, J = 7.2 Hz, 1H), 5.01 (s, 1H), 4.55 (d, J = 7.2 Hz, 1H), 2.93 – 2.79 (m, 2H), 2.29 – 2.20 (m, 1H), 1.68 – 1.58 (m, 1H), 1.49 (s, 3H), 1.47 – 1.43 (m, 1H), 1.21 (s, 3H), 0.96 (t, J = 4.8 Hz, 1H), 0.75 (dd, J = 9.0, 5.0 Hz, 1H); LCMS m/z = 475.2 (M + 1; 30%). |
| 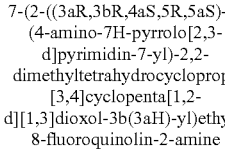<br>7-(2-((3aR,3bR,4aS,5R,5aS)-5-(4-amino-7H-pyrrolo[2,3-d]pyrimidin-7-yl)-2,2-dimethylhexahydrocyclopropa[3,4]cyclopenta[1,2-d][1,3]dioxol-3b-yl)ethyl)-N-methylquinolin-2-amine | 7-(2-((3aR,3bR,4aS,5R,5aS)-5-(4-chloro-7H-pyrrolo[2,3-d]pyrimidin-7-yl)-2,2-dimethylhexahydrocyclopropa[3,4]cyclopenta[1,2-d][1,3]dioxol-3b-yl)ethyl)-N-methylquinolin-2-amine | $^1$H NMR (400 MHz, DMSO-d6) δ 8.08 (s, 1H), 7.84 (d, J = 8.9 Hz, 1H), 7.55 (d, J = 8.1 Hz, 1H), 7.46 (s, 1H), 7.16 – 7.10 (m, 2H), 7.06 (s, 2H), 6.72 (d, J = 8.9 Hz, 1H), 6.62 (d, J = 3.5 Hz, 1H), 5.22 (d, J = 7.2 Hz, 1H), 5.02 (s, 1H), 4.52 (dd, J = 7.3, 1.5 Hz, 1H), 2.91 (d, J = 4.7 Hz, 3H), 2.88 – 2.77 (m, 2H), 2.32 – 2.24 (m, 1H), 1.70 – 1.61 (m, 1H), 1.49 (s, 3H), 1.48 – 1.44 (m, 1H), 1.20 (s, 3H), 0.94 (t, J = 4.7 Hz, 1H), 0.74 (dd, J = 9.2, 5.0 Hz, 1H); LCMS m/z = 471.23 (M + 1; 15%). |
| 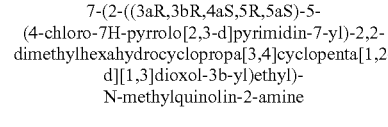<br>7-(((3aR,3bR,4aS,5R,5aS)-5-(4-amino-7H-pyrrolo[2,3-d]pyrimidin-7-yl)-2,2-dimethyltetrahydrocyclopropa[3,4]cyclopenta [1,2-d][1,3]dioxol-3b(3aH)-yl)methoxy)-3-bromo-N-(4-methoxybenzyl)quinolin-2-amine | 3-bromo-7-(((3aR,3bR,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)methoxy)-N-(4-methoxybenzyl)quinolin-2-amine | $^1$H NMR (400 MHz, DMSO-d6) δ 8.30 (s, 1H), 8.09 (s, 1H), 7.64 – 7.59 (m, 1H), 7.38 (d, J = 3.6 Hz, 1H), 7.37 – 7.31 (m, 2H), 7.16 (t, J = 5.9 Hz, 1H), 7.04 (s, 2H), 7.00 (d, J = 2.5 Hz, 1H), 6.97 – 6.92 (m, 1H), 6.91 – 6.84 (m, 2H), 6.65 (d, J = 3.6 Hz, 1H), 5.30 (d, J = 7.1 Hz, 1H), 5.14 (s, 1H), 4.63 (d, J = 6.0 Hz, 2H), 4.50 (d, J = 7.1 Hz, 1H), |

TABLE 12-continued

| Structure & IUPAC name | Intermediate used | ¹H NMR & LCMS data |
|---|---|---|
| 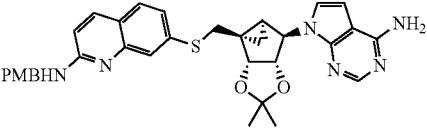<br>7-((((3aR,3bS,4aS,5R,5aS)-5-(4-amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)methyl)thio)-N-(4-methoxybenzyl)quinolin-2-2-amine | 7-((((3aR,3bS,4aS,5R,5aS)-5-(4-chloro-7H-pyrrolo[2,3-d]pyrimidin-7-yl)-2,2-dimethyltetrahydrocyclopropa[3,4]cyclopenta[1,2-d][1,3]dioxol-3b(3aH)-yl)methyl)thio)-N-(4-methoxybenzyl)quinolin-2-amine | 4.35 (d, J = 10.5 Hz, 1H), 4.21 (d, J = 10.5 Hz, 1H), 3.71 (s, 3H), 1.78 – 1.71 (m, 1H), 1.48 (s, 3H), 1.18 (s, 3H), 1.11 – 1.06 (m, 1H), 0.88 – 0.83 (m, 1H); LCMS m/z = 659.3 (M + 2; 100%).<br><br>¹H NMR (400 MHz, DMSO-d6) δ 8.09 (s, 1H), 7.80 (d, J = 8.9 Hz, 1H), 7.53 (d, J = 8.4 Hz, 1H), 7.46 (t, J = 5.7 Hz, 1H), 7.41 (d, J = 1.8 Hz, 1H), 7.35 – 7.30 (m, 2H), 7.23 (d, J = 3.5 Hz, 1H), 7.12 (dd, J = 8.3, 1.9 Hz, 1H), 7.01 (s, 2H), 6.91 – 6.86 (m, 2H), 6.75 (d, J = 8.9 Hz, 1H), 6.58 (d, J = 3.5 Hz, 1H), 5.23 (dd, J = 7.3, 1.4 Hz, 1H), 5.03 (s, 1H), 4.55 (d, J = 5.7 Hz, 2H), 4.51 (dd, J = 7.4, 1.5 Hz, 1H), 3.72 (s, 3H), 3.67 (d, J = 12.6 Hz, 1H), 3.32 (d, J = 12.7 Hz, 1H), 1.71 – 1.63 (m, 1H), 1.47 (s, 3H), 1.17 (s, 3H), 1.06 (t, J = 4.8 Hz, 1H), 1.01 – 0.95 (m, 1H); LCMS m/z = 595.21 (M+; 70%) |
| 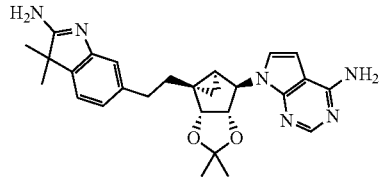<br>7-((3aR,3bR,4aS,5R,5aS)-3b-(2-(2-amino-3,3-dimethyl-3H-indol-6-yl)ethyl)-2,2-dimethylhexahydrocyclopropa[3,4]cyclopenta[1,2-d][1,3]dioxol-5-yl)-7H-pyrrolo[2,3-d]pyrimidin-4-amine | 7-((3aR,3bR,4aS,5R,5aS)-3b-(2-(3,3-dimethyl-2-(methylthio)-3H-indol-6-yl)ethyl)-2,2-dimethylhexahydrocyclopropa[3,4]cyclopenta[1,2-d][1,3]dioxol-5-yl)-7H-pyrrolo[2,3-d]pyrimidin-4-amine | ¹H NMR (400 MHz, DMSO-d6) δ 8.07 (s, 1H), 7.18 (d, J = 7.5 Hz, 1H), 7.11 (d, J = 3.6 Hz, 1H), 7.01 (s, 2H), 6.94 (s, 1H), 6.88 (d, J = 7.6 Hz, 1H), 6.61 (d, J = 3.5 Hz, 1H), 5.18 (d, J = 7.2 Hz, 1H), 5.00 (s, 1H), 4.52 (d, J = 7.1 Hz, 1H), 2.77 – 2.65 (m, 2H), 2.22 – 2.12 (m, 1H), 1.66 – 1.55 (m, 1H), 1.47 (s, 3H), 1.44 (dd, J = 9.2, 4.3 Hz, 1H), 1.36 (s, 3H), 1.24 (s, 3H), 1.19 (s, 3H), 0.93 (t, J = 4.7 |

| Structure & IUPAC name | Intermediate used | ¹H NMR & LCMS data |
|---|---|---|
| 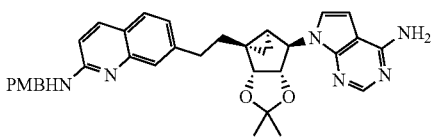<br>7-(2-((3aR,3bR,4aS,5R,5aS)-5-(4-amino-7H-pyrrolo[2,3-d]pyrimidin-7-yl)-2,2-dimethylhexahydrocyclopropa[3,4]cyclopenta [1,2-d][1,3]dioxol-3b-yl)ethyl)-N-(4-methoxybenzyl)quinolin-2-amine | 7-(2-((3aR,3bR,4aS,5R,5aS)-5-(4-chloro-7H-pyrrolo[2,3-d]pyrimidin-7-yl)-2,2-dimethylhexahydrocyclopropa[3,4]cyclopenta[1,2-d][1,3]dioxol-3b-yl)ethyl)-N-(4-methoxybenzyl)quinolin-2-amine | Hz, 1H), 0.75 (dd, J = 9.1, 5.0 Hz, 1H); LCMS m/z = 473.4 (M + 1; 80%)<br>¹H NMR (400 MHz, Chloroform-d) δ 8.34 (s, 1H), 7.87 (d, J = 8.9 Hz, 1H), 7.63 (s, 1H), 7.55 (d, J = 8.0 Hz, 1H), 7.35 (d, J = 8.5 Hz, 2H), 7.22 (d, J = 8.1 Hz, 1H), 6.97 (d, J = 3.6 Hz, 1H), 6.91 (d, J = 8.7 Hz, 2H), 6.65 (d, J = 9.0 Hz, 1H), 6.39 (d, J = 3.6 Hz, 1H), 5.25 (s, 2H), 5.19 (d, J = 7.1 Hz, 1H), 5.14 (s, 1H), 4.67 – 4.62 (m, 3H), 3.82 (s, 3H), 3.06 – 2.93 (m, 2H), 2.41 – 2.36 (m, 1H), 2.06 – 2.01 (m, 1H), 1.60 (s, 3H), 1.51 (dd, J = 8.7, 4.2 Hz, 1H), 1.28 (s, 3H), 1.15 (t, J = 4.8 Hz, 1H), 0.78 (dd, J = 5.5, 3.2 Hz, 1H); LCMS m/z = 577.5 (M + 1; 60%) |

7-(1-((3aR,3bR,4aS,5R,5aS)-5-(4-Amino-7H-pyrrolo[2,3-d]pyrimidin-7-yl)-2,2-dimethyltetrahydrocyclopropa[3,4]cyclopenta[1,2-d][1,3]dioxol-3b (3aH)-yl)propan-2-yl)-N-(4-methoxybenzyl) quinolin-2-amine

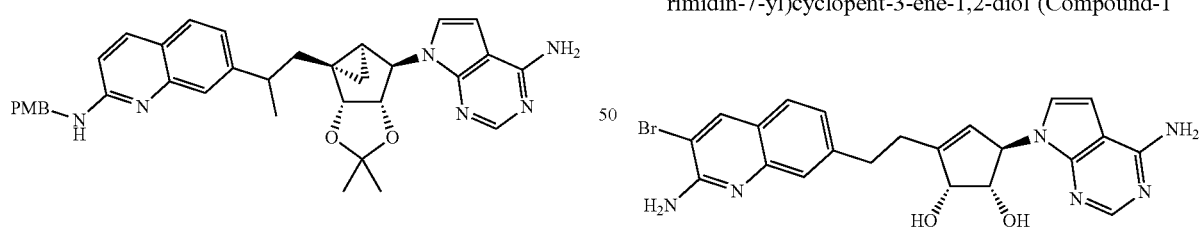

A mixture of 7-((E)-1-((3aR,3bS,4aS,5R,5aS)-5-(4-amino-7H-pyrrolo[2,3-d]pyrimidin-7-yl)-2,2-dimethyltetrahydrocyclopropa[3,4]cyclopenta[1,2-d][1,3]dioxol-3b (3aH)-yl)prop-1-en-2-yl)-3-bromo-N-(4-methoxybenzyl) quinolin-2-amine (0.05 g, 0.075 mmol), ammonium formate (0.331 g, 5.24 mmol) and Pd/C (0.024 g, 0.225 mmol) in EtOH (15 ml) was heated at 75° C. for 8 h. The reaction mixture was cooled 25° C., filtered through celite and concentrated in vacuo to get 0.06 g of crude compound. The obtained residue was purified by combiflash (R_f 200, Teledyne/Isco) instrument onto a Redisep® R_f column with gradient elution (0 to 5%) of methanol in dichloromethane to afford the title compound (0.042 g, 95%) as an off-white solid. LCMS m/z=591.29 (M+1, 100%).

EXAMPLES

Example-1: (1S,2R,5R)-3-(2-(2-Amino-3-bromoquinolin-7-yl)ethyl)-5-(4-amino-7H pyrrolo[2,3-d]pyrimidin-7-yl)cyclopent-3-ene-1,2-diol (Compound-1

The mixture of 7-(2-((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)ethyl)-3-bromo-N-(4-methoxy benzyl)quinolin-2-amine (0.220 g, 0.343 mmol) in TFA (3.96 ml, 51.4 mmol) was stirred at 50° C. for 1.5 h. The resulting mixture was concentrated in vacuo and obtained residue was dissolved in MeOH (5 ml). K₂CO₃ (0.142 g, 1.029 mmol) was added and stirred the reaction mixture at 50° C. for 1.5 h. Reaction mixture was filtered and filtrate was concentrated under reduced pressure to get 0.27 g of crude compound. This residue was purified by combiflash (R_f 200, Teledyne/Isco) instrument onto a Redisep® R_f column with gradient elution (0 to 7%) of methanol in dichloromethane to afford the title compound (0.03 g, 18%) as an off-white solid. $^1$H NMR (400 MHz, DMSO-d6) δ 8.35 (s, 1H), 8.06 (s, 1H), 7.61 (d, J=8.2 Hz, 1H), 7.36 (d, J=1.6 Hz, 1H), 7.16 (dd, J=8.2, 1.7 Hz, 1H), 7.08 (s, 2H), 6.67 (d, J=3.5 Hz, 1H), 6.61 (s, 2H), 6.45 (d, J=3.5 Hz, 1H), 5.50 (d, J=4.4 Hz, 1H), 5.44 (t, J=1.7 Hz, 1H), 4.98 (d, J=6.4 Hz, 2H), 4.45 (t, J=5.9 Hz, 1H), 3.97 (d, J=5.0 Hz, 1H), 3.04-2.87 (m, 2H), 2.61-2.53 (m, 2H); LCMS m/z=483.01 (M+2, 90%).

Examples in table-13 were synthesized by following an analogous reaction protocol as was used for the preparation of (1S,2R,5R)-3-(2-(2-amino-3-bromoquinolin-7-yl)ethyl)-5-(4-amino-7H-pyrrolo[2,3-d]pyrimidin-7-yl)cyclopent-3-ene-1,2-diol using the appropriate starting materials (Instead of TFA, 3N HCl/MeOH could also be used).

TABLE 13

| Structure & IUPAC name | Intermediate used | $^1$H NMR & LCMS data |
|---|---|---|
| Compound-2 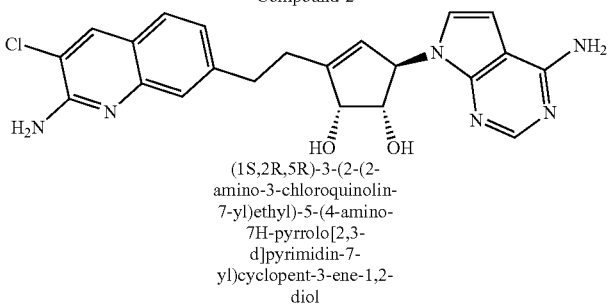 (1S,2R,5R)-3-(2-(2-amino-3-chloroquinolin-7-yl)ethyl)-5-(4-amino-7H-pyrrolo[2,3-d]pyrimidin-7-yl)cyclopent-3-ene-1,2-diol | 7-(2-((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)ethyl)-3-chloro-N-(4-methoxybenzyl)quinolin-2-amine | $^1$H NMR (400 MHz, DMSO-d6) δ 8.17 (s, 1H), 8.09 (s, 1H), 7.61 (d, J = 8.2 Hz, 1H), 7.37 (s, 1H), 7.29 (s, 2H), 7.16 (dd, J = 8.3, 1.7 Hz, 1H), 6.75-6.66 (m, 3H), 6.49 (d, J = 3.6 Hz, 1H), 5.50 (d, J = 4.4 Hz, 1H), 5.43 (d, J = 1.9 Hz, 1H), 5.01 (d, J = 6.7 Hz, 2H), 4.45 (t, J = 5.9 Hz, 1H), 3.96 (d, J = 5.0 Hz, 1H), 2.94 (ddt, J = 21.4, 14.1, 7.2 Hz, 2H), 2.58-2.55 (m, 2H); LCMS m/z = 436.92 (M+, 20%) |
| Compound-3 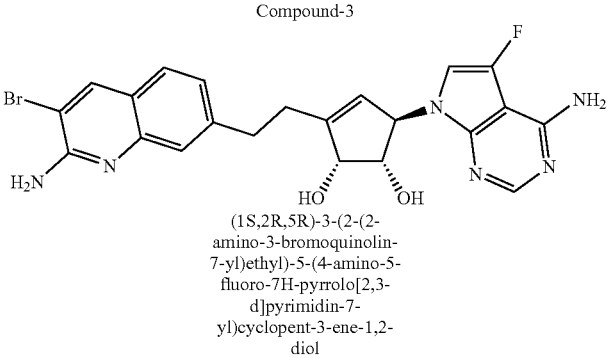 (1S,2R,5R)-3-(2-(2-amino-3-bromoquinolin-7-yl)ethyl)-5-(4-amino-5-fluoro-7H-pyrrolo[2,3-d]pyrimidin-7-yl)cyclopent-3-ene-1,2-diol | 7-(2-((3aS,4R,6aR)-4-(4-amino-5-fluoro-7H-pyrrolo[2,3-d]pyrimidin-7-yl)-2,2-dimethyl-3a,6a-dihydro-4H-cyclopenta[d][1,3]dioxol-6-yl)ethyl)-3-bromo-N-(4-methoxybenzyl)quinolin-2-amine | $^1$H NMR (400 MHz, DMSO-d6) δ 8.39 (s, 1H), 8.08 (s, 1H), 7.63 (d, J = 8.2 Hz, 1H), 7.37 (s, 1H), 7.18 (dd, J = 8.2, 1.6 Hz, 3H), 6.72 (d, J = 27.4 Hz, 2H), 6.55 (d, J = 2.1 Hz, 1H), 5.54 (s, 1H), 5.40 (q, J = 1.7 Hz, 1H), 5.10-4.91 (m, 2H), 4.43 (d, J = 5.7 Hz, 1H), 3.92 (q, J = 5.2 Hz, 1H), 3.04-2.87 (m, 2H) 2.65-2.52 (m, 2H),; LCMS m/z = 501 (M + 1, 30%) |
| Compound-4 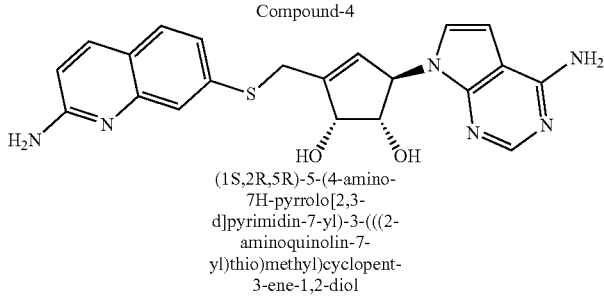 (1S,2R,5R)-5-(4-amino-7H-pyrrolo[2,3-d]pyrimidin-7-yl)-3-(((2-aminoquinolin-7-yl)thio)methyl)cyclopent-3-ene-1,2-diol | 7-((((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)methyl)thio)-N-(4-methoxybenzyl)quinolin-2-amine | $^1$H NMR (400 MHz, DMSO-d6) δ 8.00 (s, 1H), 7.86 (d, J = 8.8 Hz, 1H), 7.56 (d, J = 8.3 Hz, 1H), 7.40 (d, J = 1.8 Hz, 1H), 7.15 (dd, J = 8.3, 1.9 Hz, 1H), 6.89 (s, 2H), 6.72 (d, J = 8.8 Hz, 1H), 6.48 (s, 2H), 6.26 (d, J = 3.5 Hz, 1H), 6.21 (d, J = 3.6 Hz, 1H), 5.57 (s, 1H), 5.49 (s, 1H), 5.11 (d, J = 5.5 Hz, 1H), 5.04 (d, J = 6.4 Hz, 1H), 4.58 (s, 1H), 4.01 (d, J = 14.7 Hz, 1H), 3.88-3.81 (m, 1H), 3.75-3.66 (m, 1H); LCMS m/z = 420.85 (M+, 100%) |
| Compound-5 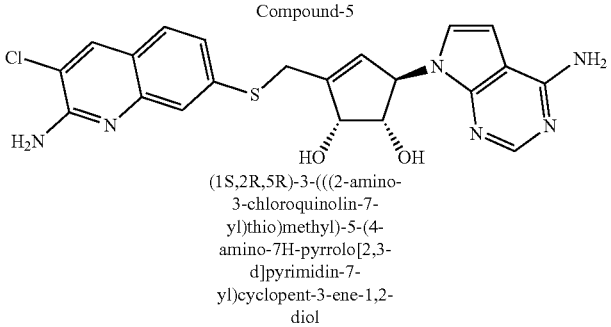 (1S,2R,5R)-3-(((2-amino-3-chloroquinolin-7-yl)thio)methyl)-5-(4-amino-7H-pyrrolo[2,3-d]pyrimidin-7-yl)cyclopent-3-ene-1,2-diol | 7-((((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)methyl)thio)-3-chloro-N,N-bis(4-methoxybenzyl)quinolin-2-amine | $^1$H NMR (400 MHz, DMSO-d6) δ 8.19 (s, 1H), 8.00 (s, 1H), 7.62 (d, J = 8.4 Hz, 1H), 7.43 (s, 1H), 7.23 (dd, J = 8.4, 1.9 Hz, 1H), 6.94 (s, 2H), 6.82 (s, 2H), 6.28 (q, J = 3.5 Hz, 2H), 5.61 (s, 1H), 5.50 (s, 1H), 5.09 (dd, J = 24.6, 6.5 Hz, 2H), 4.57 (t, J = 6.0 Hz, 1H), 4.04 (d, J = 14.9 Hz, 1H), 3.87 (q, J = 5.7 Hz, 1H), 3.74 (d, J = 15.0 Hz, 1H); LCMS m/z = 455.50 (M+, 50%) |

TABLE 13-continued

| Structure & IUPAC name | Intermediate used | ¹H NMR & LCMS data |
|---|---|---|
| Compound-6 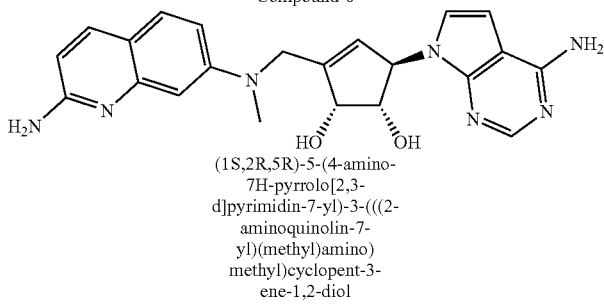<br>(1S,2R,5R)-5-(4-amino-7H-pyrrolo[2,3-d]pyrimidin-7-yl)-3-(((2-aminoquinolin-7-yl)(methyl)amino)methyl)cyclopent-3-ene-1,2-diol | N7-(((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)methyl)-N2-(4-methoxybenzyl)-N7-methylquinoline-2,7-diamine | ¹H NMR (400 MHz, DMSO-d6) δ 8.02 (s, 1H), 7.65 (d, J = 8.7 Hz, 1H), 7.39 (d, J = 8.8 Hz, 1H), 6.95-6.86 (m, 3H), 6.81 (dd, J = 8.9, 2.6 Hz, 1H), 6.61 (d, J = 2.5 Hz, 1H), 6.49 (d, J = 3.5 Hz, 1H), 6.41 (d, J = 8.7 Hz, 1H), 6.09 (s, 2H), 5.51 (s, 1H), 5.41 (d, J = 1.9 Hz, 1H), 5.06 (dd, J = 6.5, 2.5 Hz, 2H), 4.44 (t, J = 6.0 Hz, 1H), 4.17 (d, J = 4.9 Hz, 2H), 4.11-4.04 (m, 1H), 3.05 (s, 3H); LCMS m/z = 417.10 (M+, 100%) |
| Compound-7a and 7b 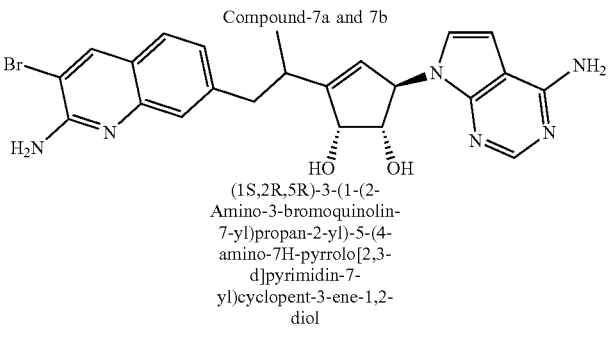<br>(1S,2R,5R)-3-(1-(2-Amino-3-bromoquinolin-7-yl)propan-2-yl)-5-(4-amino-7H-pyrrolo[2,3-d]pyrimidin-7-yl)cyclopent-3-ene-1,2-diol | 7-(2-((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)propyl)-3-bromo-N-(4-methoxybenzyl)quinolin-2-amine | First Diastereomer(Compound-7a): ¹H NMR (400 MHz, DMSO-d6) δ 8.35 (s, 1H), 8.05 (s, 1H), 7.60 (d, J = 8.2 Hz, 1H), 7.33 (s, 1H), 7.13 (d, J = 8.4 Hz, 1H), 6.93 (s, 2H), 6.78 (d, J = 3.6 Hz, 1H), 6.59 (s, 2H), 6.49 (d, J = 3.6 Hz, 1H), 5.53 (d, J = 4.5 Hz, 1H), 5.42 (s, 1H), 5.01-4.88 (m, 2H), 4.46 (t, J = 5.8 Hz, 1H), 3.99 (t, J = 7.8 Hz, 1H), 3.03 (dd, J = 11.9, 4.4 Hz, 1H), 2.73 (q, J = 10.6, 8.9 Hz, 2H), 1.24 (s, 3H); LCMS m/z = 497.30 (M + 2, 100%)<br>Second Diastereomer(Compound-7b): ¹H NMR (400 MHz, DMSO-d6) δ 8.36 (s, 1H), 8.05 (s, 1H), 7.61 (d, J = 8.2 Hz, 1H), 7.33 (s, 1H), 7.21-7.02 (m, 3H), 6.61 (s, 2H), 6.50 (d, J = 3.5 Hz, 1H), 6.43 (d, J = 3.6 Hz, 1H), 5.52 (d, J = 5.0 Hz, 1H), 5.35 (s, 1H), 5.00 (s, 1H), 4.91 (d, J = 6.4 Hz, 1H), 4.56 (s, 1H), 3.90 (d, J = 5.8 Hz, 1H), 3.07-2.99 (m, 1H), 2.83-2.74 (m, 2H) 1.09 (d, J = 5.8 Hz, 3H); LCMS m/z = 495.24 (M+, 40%) |
| (Compound-8a and 8b) 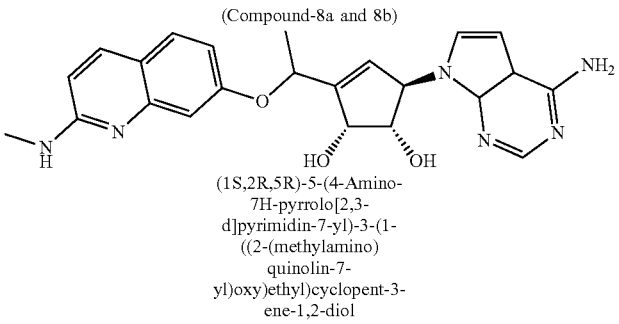<br>(1S,2R,5R)-5-(4-Amino-7H-pyrrolo[2,3-d]pyrimidin-7-yl)-3-(1-((2-(methylamino)quinolin-7-yl)oxy)ethyl)cyclopent-3-ene-1,2-diol | 7-(1-((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)ethoxy)-N-methylquinolin-2-amine | Diastereomeric mixture was separated by chiral preparative HPLC. Wavelength: 225 nm, Instrument Method: IPA_0.1% DEA_MeOH_0.1% DEA_50_50_0.7ML_12 MIN, Flow Rate: 0.70 ml/min Column: CHIRALPAK IB CRL-043 OLD, Column Temp: 30° C., Mobile Phase A: IPA_0.1% DEA, Mobile Phase B: MeOH_0.1%DEA First Diastereomer (Compound-8a): ¹H NMR (400 MHz, DMSO-d6) δ 8.04 (s, 1H), 7.73 (d, J = 8.8 Hz, 1H), 7.49 (d, J = 8.7 Hz, 1H), 7.00 (d, J = 2.5 Hz, 1H), 6.92 (d, J = 4.2 Hz, 2H), 6.84-6.80 (m, 2H), 6.57 (d, J = 8.8 Hz, 1H), 6.44 (d, J = 3.5 Hz, 1H), 5.70 (t, J = 1.7 Hz, 1H), 5.60-5.56 (m, 1H), 5.21 (d, J = 6.7 Hz, 1H), 5.14-5.08 (m, 1H), 5.04-4.99 (m, 1H), 4.62-4.58 (m, 1H), 4.15-4.11 (m, 1H), 3.19-3.16 (m, |

TABLE 13-continued

| Structure & IUPAC name | Intermediate used | ¹H NMR & LCMS data |
|---|---|---|
| | | 1H), 2.90 (d, J = 4.7 Hz, 3H), 1.54 (d, J = 6.3 Hz, 3H); LCMS m/z = 433.04 (M + 1, 30%) Second Diastereomer(Compound-8b): ¹H NMR (400 MHz, DMSO-d6) δ 8.02 (s, 1H), 7.73 (d, J = 8.9 Hz, 1H), 7.49 (d, J = 8.7 Hz, 1H), 7.04 (d, J = 2.5 Hz, 1H), 6.94 (d, J = 3.5 Hz, 3H), 6.81 (dd, J = 8.7, 2.5 Hz, 1H), 6.57 (d, J = 8.8 Hz, 1H), 6.54 (d, J = 3.6 Hz, 1H), 5.72 (t, J = 1.5 Hz, 1H), 5.57 (d, J = 5.0 Hz, 1H), 5.26 (d, J = 6.7 Hz, 1H), 5.15 (s, 1H), 5.10 (s, 1H), 4.48 (s, 1H), 4.36 (d, J = 4.2 Hz, 1H), 3.94 (d, J = 5.8 Hz, 1H), 2.91 (d, J = 4.7 Hz, 3H), 1.57 (d, J = 6.5 Hz, 3H); LCMS (m/z) = 433.04 (M+, 30%). |
| 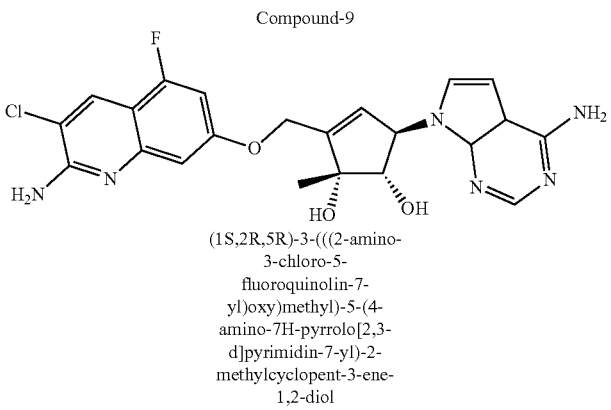 Compound-9<br><br>(1S,2R,5R)-3-(((2-amino-3-chloro-5-fluoroquinolin-7-yl)oxy)methyl)-5-(4-amino-7H-pyrrolo[2,3-d]pyrimidin-7-yl)-2-methylcyclopent-3-ene-1,2-diol | 7-(((3aS,4R,6aR)-4-(4-amino-7H-pyrrolo[2,3-d]pyrimidin-7-yl)-2,2,6a-trimethyl-3a,6a-dihydro-4H-cyclopenta[d][1,3]dioxol-6-yl)methoxy)-3-chloro-5-fluoro-N-(4-methoxybenzyl)quinolin-2-amine | ¹H NMR (400 MHz, DMSO-d6) δ 8.37 (s, 1H), 8.14 (s, 1H), 7.71 (d, J = 3.7 Hz, 1H), 7.07 (s, 2H), 6.97 (d, J = 3.6 Hz, 1H), 6.90 (d, J = 2.2 Hz, 1H), 6.79 (dd, J = 11.5, 2.2 Hz, 1H), 5.61 (s, 2H), 4.89-4.77 (m, 2H), 4.76-4.63 (m, 3H), 1.82 (s, 3H); LCMS m/z = 471.07 (M+, 100%) |
| 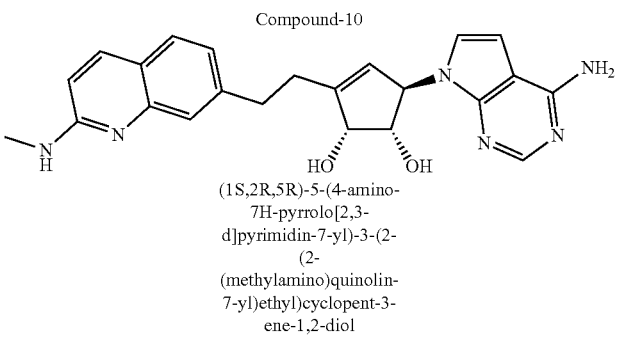 Compound-10<br><br>(1S,2R,5R)-5-(4-amino-7H-pyrrolo[2,3-d]pyrimidin-7-yl)-3-(2-(2-(methylamino)quinolin-7-yl)ethyl)cyclopent-3-ene-1,2-diol | 7-(2-((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)ethyl)-N-methylquinolin-2-amine | ¹H NMR (400 MHz, DMSO-d6) δ 8.03 (s, 1H), 7.79 (d, J = 8.9 Hz, 1H), 7.54 (d, J = 8.0 Hz, 1H), 7.39 (s, 1H), 7.07 (dd, J = 8.1, 1.6 Hz, 1H), 6.93 (s, 2H), 6.72-6.64 (m, 2H), 6.41 (d, J = 3.5 Hz, 1H), 5.51 (s, 1H), 5.43 (d, J = 1.9 Hz, 1H), 4.95 (dd, J = 10.7, 6.5 Hz, 2H), 4.45 (t, J = 6.0 Hz, 1H), 4.01-3.90 (m, 1H), 3.12-3.08 (m, 2H), 2.90 (d, J = 4.7 Hz, 3H), 2.60-2.52 (m, 2H); LCMS m/z = 416.48 (M+, 60%) |
| 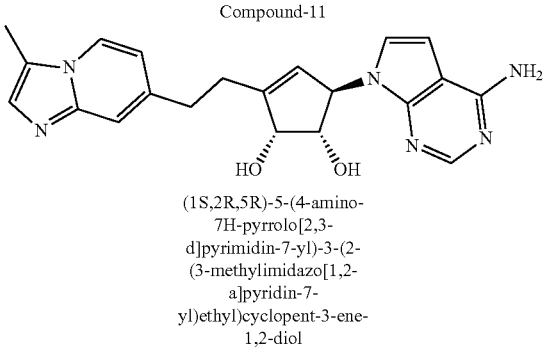 Compound-11<br><br>(1S,2R,5R)-5-(4-amino-7H-pyrrolo[2,3-d]pyrimidin-7-yl)-3-(2-(3-methylimidazo[1,2-a]pyridin-7-yl)ethyl)cyclopent-3-ene-1,2-diol | 7-((3aS,4R,6aR)-2,2-dimethyl-6-(2-(3-methylimidazo[1,2-a]pyridin-7-yl)ethyl)-3a,6a-dihydro-4H-cyclopenta[d][1,3]dioxol-4-yl)-7H-pyrrolo[2,3-d]pyrimidin-4-amine | ¹H NMR (400 MHz, DMSO-d6) δ 8.20 (d, J = 7.0 Hz, 1H), 8.03 (s, 1H), 7.39 (s, 1H), 7.32 (s, 1H), 7.00-6.86 (m, 3H), 6.66 (d, J = 3.5 Hz, 1H), 6.42 (d, J = 3.5 Hz, 1H), 5.53-5.41 (m, 2H), 4.98 (d, J = 6.4 Hz, 2H), 4.46 (t, J = 6.0 Hz, 1H), 3.98 (q, J = 5.5 Hz, 1H), 3.40 (d, J = 7.0 Hz, 2H), 2.99-2.82 (m, 2H), 2.45 (s, 3H); LCMS m/z = 390.91 (M+, 90%) |

TABLE 13-continued

| Structure & IUPAC name | Intermediate used | ¹H NMR & LCMS data |
|---|---|---|
| Compound-12<br>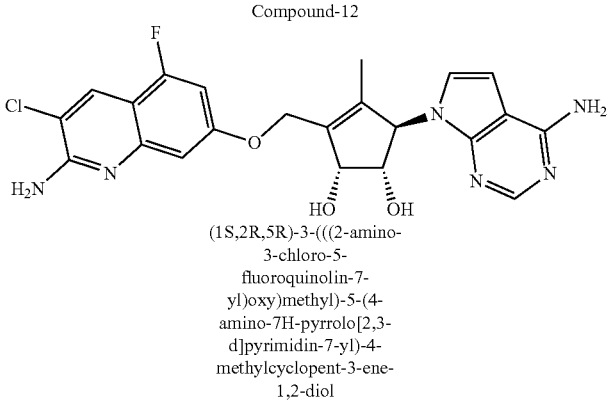<br>(1S,2R,5R)-3-(((2-amino-3-chloro-5-fluoroquinolin-7-yl)oxy)methyl)-5-(4-amino-7H-pyrrolo[2,3-d]pyrimidin-7-yl)-4-methylcyclopent-3-ene-1,2-diol | 3-chloro-5-fluoro-N-(4-methoxybenzyl)-7-(((3aS,4R,6aR)-4-(4-((4-methoxybenzyl)amino)-7H-pyrrolo[2,3-d]pyrimidin-7-yl)-2,2,5-trimethyl-3a,6a-dihydro-4H-cyclopenta[d][1,3]dioxol-6-yl)methoxy)quinolin-2-amine | LCMS m/z = 471.23 (M+, 60%) |
| Compound-13<br>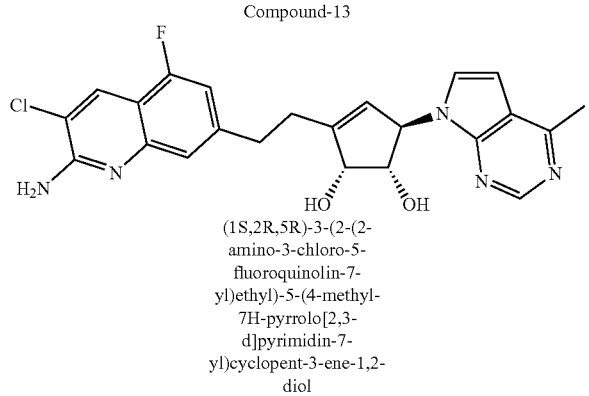<br>(1S,2R,5R)-3-(2-(2-amino-3-chloro-5-fluoroquinolin-7-yl)ethyl)-5-(4-methyl-7H-pyrrolo[2,3-d]pyrimidin-7-yl)cyclopent-3-ene-1,2-diol | 3-chloro-7-(2-((3aS,4R,6aR)-2,2-dimethyl-4-(4-methyl-7H-pyrrolo[2,3-d]pyrimidin-7-yl)-3a,6a-dihydro-4H-cyclopenta[d][1,3]dioxol-6-yl)ethyl)-5-fluoroquinolin-2-amine | ¹H NMR (400 MHz, DMSO-d6) δ 8.62 (s, 1H), 8.18 (s, 1H), 7.22 (s, 1H), 7.13-6.90 (m, 4H), 6.55 (d, J = 3.6 Hz, 1H), 5.61 (d, J = 4.4 Hz, 1H), 5.46 (t, J = 1.7 Hz, 1H), 5.02 (dd, J = 6.5, 4.3 Hz, 2H), 4.47 (t, J = 6.0 Hz, 1H), 4.08-3.98 (m, 1H), 3.04-2.85 (m, 2H), 2.63 (s, 3H), 2.60-2.54 (m, 2H); LCMS m/z = 454.17 (M+, 100%) |
| Compound-14<br>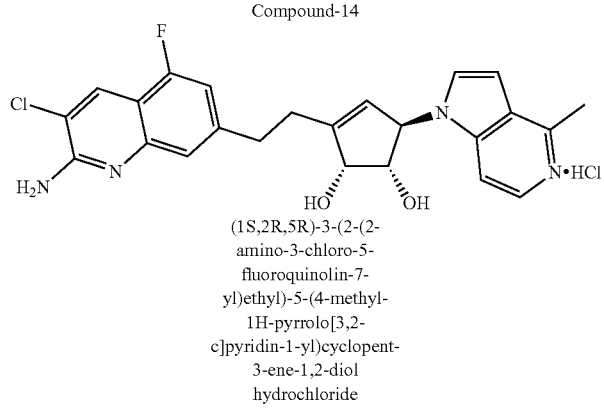<br>(1S,2R,5R)-3-(2-(2-amino-3-chloro-5-fluoroquinolin-7-yl)ethyl)-5-(4-methyl-1H-pyrrolo[3,2-c]pyridin-1-yl)cyclopent-3-ene-1,2-diol hydrochloride | 3-chloro-7-(2-((3aS,4R,6aR)-2,2-dimethyl-4-(4-methyl-1H-pyrrolo[3,2-c]pyridin-1-yl)-3a,7*6a-dihydro-4H-cyclopenta[d][1,3]dioxol-6-yl)ethyl)-5-fluoroquinolin-2-amine | ¹H NMR (400 MHz, DMSO-d6) δ 14.95 (s, 1H), 8.41 (s, 1H), 8.26 (t, J = 5.9 Hz, 1H), 7.94 (d, J = 6.9 Hz, 1H), 7.53 (d, J = 3.5 Hz, 1H), 7.43-7.29 (m, 2H), 7.29-7.03 (m, 3H), 5.64 (s, 1H), 5.58 (d, J = 5.3 Hz, 1H), 4.41 (d, J = 5.6 Hz, 1H), 3.88 (t, J = 5.6 Hz, 1H), 3.10-2.99 (m, 2H)), 2.93 (s, 3H), 2.62-2.50 (m, 2H); LCMS m/z = 453.11 (M + 1, 100%) |
| Compound-15<br>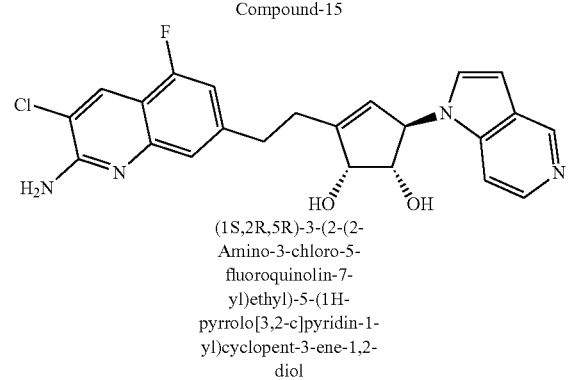<br>(1S,2R,5R)-3-(2-(2-Amino-3-chloro-5-fluoroquinolin-7-yl)ethyl)-5-(1H-pyrrolo[3,2-c]pyridin-1-yl)cyclopent-3-ene-1,2-diol | 3-Chloro-7-(2-((3aS,4R,6aR)-2,2-dimethyl-4-(1H-pyrrolo[3,2-c]pyridin-1-yl)-3a,6a-dihydro-4H-cyclopenta[d][1,3]dioxol-6-yl)ethyl)-5-fluoroquinolin-2-amine | ¹H NMR (400 MHz, DMSO-d6) δ 8.91 (s, 1H), 8.20 (s, 1H), 8.09 (d, J = 6.2 Hz, 1H), 7.49 (d, J = 6.1 Hz, 1H), 7.24 (s, 1H), 7.11 (d, J = 3.3 Hz, 1H), 7.07-7.01 (m, 1H), 6.98 (s, 2H), 6.60 (d, J = 3.3 Hz, 1H), 5.58 (d, J = 1.8 Hz, 1H), 5.39 (s, 1H), 5.18 (dd, J = 17.2, 6.7 Hz, 2H), 4.41 (t, J = 5.4 Hz, 1H), 3.84 (q, J = 5.9 Hz, 1H), 3.11-2.91 (m, 2H), 2.68-2.58 (m, 2H); LCMS (m/z) = 439.23 (M+, 100%). |

TABLE 13-continued

| Structure & IUPAC name | Intermediate used | $^1$H NMR & LCMS data |
|---|---|---|
| Compound-16 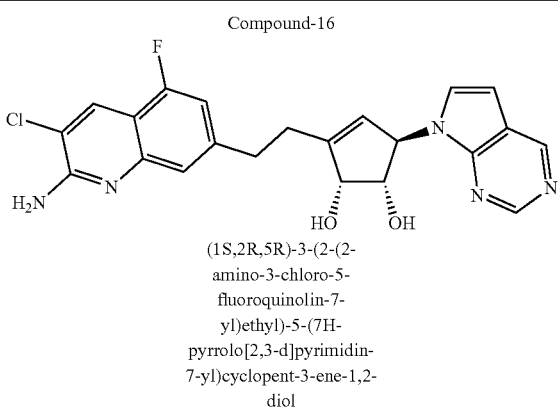 (1S,2R,5R)-3-(2-(2-amino-3-chloro-5-fluoroquinolin-7-yl)ethyl)-5-(7H-pyrrolo[2,3-d]pyrimidin-7-yl)cyclopent-3-ene-1,2-diol | 3-chloro-7-(2-(((3aS,4R,6aR)-2,2-dimethyl-4-(7H-pyrrolo[2,3-d]pyrimidin-7-yl)-3a,6a-dihydro-4H-cyclopenta[d][1,3]dioxol-6-yl)ethyl)-5-fluoroquinolin-2-amine | $^1$H NMR (400 MHz, DMSO-d6) δ 8.98 (s, 1H), 8.76 (s, 1H), 8.18 (s, 1H), 7.22 (s, 1H), 7.11 (d, J = 3.6 Hz, 1H), 7.02 (dd, J = 11.1, 1.4 Hz, 1H), 6.96 (s, 2H), 6.49 (d, J = 3.6 Hz, 1H), 5.65 (s, 1H), 5.47 (d, J = 1.9 Hz, 1H), 5.03 (d, J = 6.4 Hz, 2H), 4.48 (t, J = 6.1 Hz, 1H), 4.06-4.02 (m, 1H), 3.02-2.93 (m, 2H), 2.60-2.55 (m, 2H); LCMS m/z = 440.17 (M+, 60%) |
| Compound-17 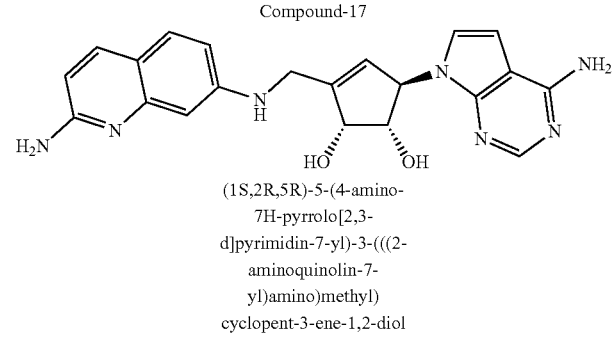 (1S,2R,5R)-5-(4-amino-7H-pyrrolo[2,3-d]pyrimidin-7-yl)-3-(((2-aminoquinolin-7-yl)amino)methyl)cyclopent-3-ene-1,2-diol | N7-(((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)methyl)-N2-(4-methoxybenzyl)quinoline-2,7-diamine | $^1$H NMR (400 MHz, DMSO-d6) δ 8.04 (s, 1H), 7.60 (d, J = 8.6 Hz, 1H), 7.29 (d, J = 8.6 Hz, 1H), 6.96-6.91 (m, 3H), 6.64 (dd, J = 8.7, 2.3 Hz, 1H), 6.51 (d, J = 3.5 Hz, 1H), 6.48 (d, J = 2.2 Hz, 1H), 6.37 (d, J = 8.6 Hz, 1H), 6.20 (t, J = 5.6 Hz, 1H), 6.08 (s, 2H), 5.61 (q, J = 1.8 Hz, 1H), 5.55 (s, 1H), 5.09-5.04 (m, 2H), 4.52 (t, J = 5.9 Hz, 1H), 4.11 (q, J = 5.8 Hz, 1H), 3.90 (s, 2H); LCMS m/z = 404.16 (M+, 100%) |
| Compound-18 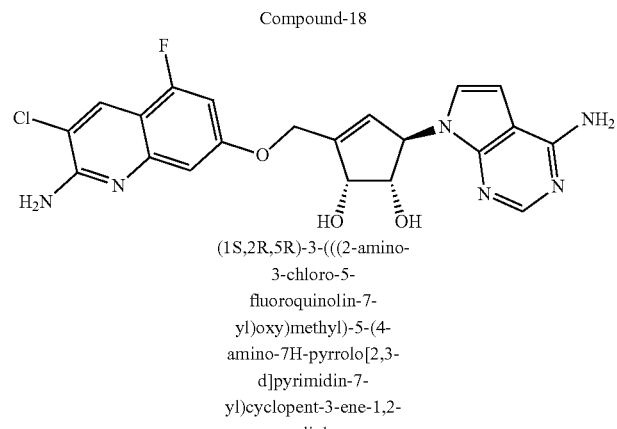 (1S,2R,5R)-3-(((2-amino-3-chloro-5-fluoroquinolin-7-yl)oxy)methyl)-5-(4-amino-7H-pyrrolo[2,3-d]pyrimidin-7-yl)cyclopent-3-ene-1,2-diol | 7-(((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)methoxy)-3-chloro-5-fluoro-N-(4-methoxybenzyl)quinolin-2-amine | $^1$H NMR (400 MHz, DMSO-d6) δ 8.58 (bs, 2H), 8.32 (s, 1H), 8.11 (s, 1H), 7.32 (d, J = 3.6 Hz, 1H), 6.99 (bs, 2H), 6.89-6.83 (m, 2H), 6.81 (d, J = 2.3 Hz, 1H), 5.82 (q, J = 1.8 Hz, 1H), 5.63 (d, J = 5.2 Hz, 1H), 5.27 (bs, 2H), 4.93-4.80 (m, 2H), 4.56 (d, J = 5.7 Hz, 1H), 4.21 (t, J = 5.6 Hz, 1H); LCMS m/z = 457.17 (M+, 70%) |
| Compound-19 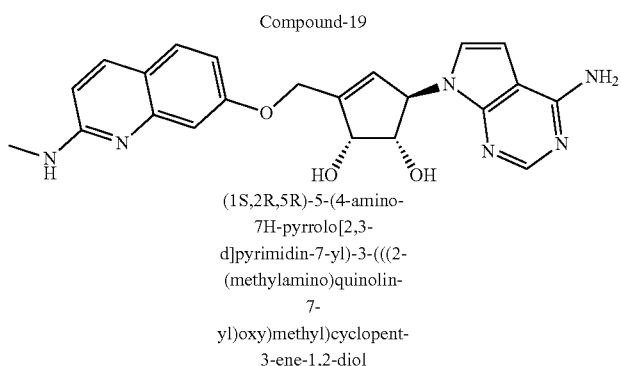 (1S,2R,5R)-5-(4-amino-7H-pyrrolo[2,3-d]pyrimidin-7-yl)-3-(((2-(methylamino)quinolin-7-yl)oxy)methyl)cyclopent-3-ene-1,2-diol | 7-(((3aR,6R,6aS)-6-(4-amino-7H-pyrrolo[2,3-d]pyrimidin-7-yl)-2,2-dimethyl-6,6a-dihydro-3aH-cyclopenta[d][1,3]dioxol-4-yl)methoxy)-N-methylquinolin-2-amine | $^1$H NMR (400 MHz, DMSO-d6) δ 8.12 (s, 1H), 8.00 (d, J = 8.9 Hz, 1H), 7.69 (d, J = 8.8 Hz, 1H), 7.40 (d, J = 13.8 Hz, 3H), 7.12 (d, J = 3.7 Hz, 1H), 7.03 (d, J = 8.9 Hz, 1H), 6.80 (d, J = 9.0 Hz, 1H), 6.64 (d, J = 3.5 Hz, 1H), 5.82 (d, J = 2.0 Hz, 1H), 5.61 (s, 1H), 5.30-5.08 (m, 2H), 4.86 (s, 2H), 4.60 (t, J = 5.6 Hz, 1H), 4.28-4.04 (m, 2H) 3.05 (d, J = 4.6 Hz, 3H); LCMS m/z = 419.16 (M+, 100%) |

TABLE 13-continued

| Structure & IUPAC name | Intermediate used | $^1$H NMR & LCMS data |
|---|---|---|
| Compound-20a and 20b<br>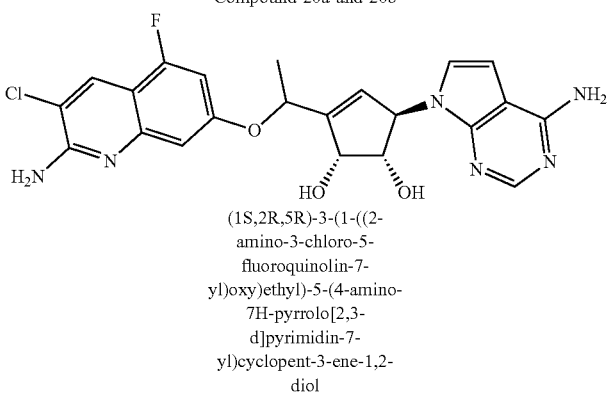<br>(1S,2R,5R)-3-(1-((2-amino-3-chloro-5-fluoroquinolin-7-yl)oxy)ethyl)-5-(4-amino-7H-pyrrolo[2,3-d]pyrimidin-7-yl)cyclopent-3-ene-1,2-diol | 7-(1-(((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)ethoxy)-3-chloro-5-fluoro-N-(4-methoxybenzyl) quinolin-2-amine | Diastereomeric mixture was separated by chiral preparative HPLC.<br>First Diastereomer (Compound-20a): $^1$H NMR (400 MHz, DMSO-d6) δ 8.12 (s, 1H), 7.92 (s, 1H), 7.36 (d, J = 3.6 Hz, 1H), 7.16 (d, J = 3.5 Hz, 1H), 6.83 (s, 2H), 6.65-6.35 (m, 3H), 5.96 (t, J = 9.7 Hz, 1H), 5.82-5.54 (m, 2H), 5.07-4.91 (m, 2H), 4.61-4.36 (m, 2H), 4.18 (dd, J = 9.6, 4.8 Hz, 1H), 1.65 (ddd, J = 26.6, 6.9, 2.5 Hz, 3H); LCMS m/z = 471.23 (M+, 90%)<br>Second Diastereomer (Compound-20b): $^1$H NMR (400 MHz, DMSO-d6) δ 8.08 (s, 1H), 8.01 (s, 1H), 6.93 (s, 5H), 6.87-6.75 (m, 2H), 6.54 (d, J = 3.6 Hz, 1H), 5.62 (d, J = 1.6 Hz, 1H), 5.53-5.49 (m, 1H), 5.26 (d, J = 5.9 Hz, 1H), 5.23-5.13 (m, 2H), 4.55 (t, J = 5.7 Hz, 1H), 4.15-4.00 (m, 1H), 1.57 (d, J = 6.5 Hz, 3H); LCMS m/z = 471.23 (M+, 80%) |
| Compound-21<br>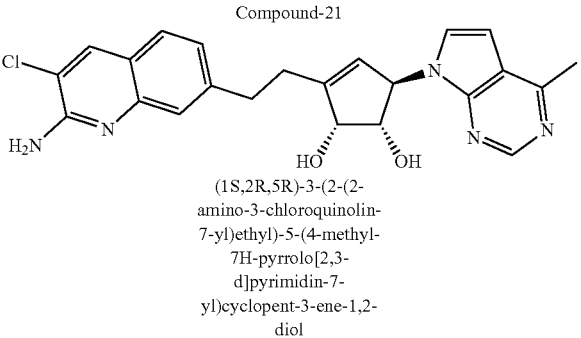<br>(1S,2R,5R)-3-(2-(2-amino-3-chloroquinolin-7-yl)ethyl)-5-(4-methyl-7H-pyrrolo[2,3-d]pyrimidin-7-yl)cyclopent-3-ene-1,2-diol | 3-chloro-7-(2-((3aS,4R,6aR)-2,2-dimethyl-4-(4-methyl-7H-pyrrolo[2,3-d]pyrimidin-7-yl)-3a,6a-dihydro-4H-cyclopenta[d][1,3]dioxol-6-yl)ethyl) quinolin-2-amine | $^1$H NMR (400 MHz, DMSO-d$_6$) δ 8.62 (s, 1H), 8.17 (s, 1H), 7.61 (d, J = 8.3 Hz, 1H), 7.44 (s, 1H), 7.37 (s, 1H), 7.17 (d, J = 8.2 Hz, 1H), 7.02 (d, J = 3.6 Hz, 1H), 6.70 (s, 2H), 5.62 (s, 1H), 5.45 (s, 1H), 5.04 (s, 2H), 4.47 (d, J = 5.5 Hz, 1H), 4.14-3.91 (m, 1H), 3.06-2.87 (m, 2H) 2.58 (d, J = 32.3 Hz, 5H); LCMS m/z = 436.23 (M+, 90%) |
| Compound-22<br>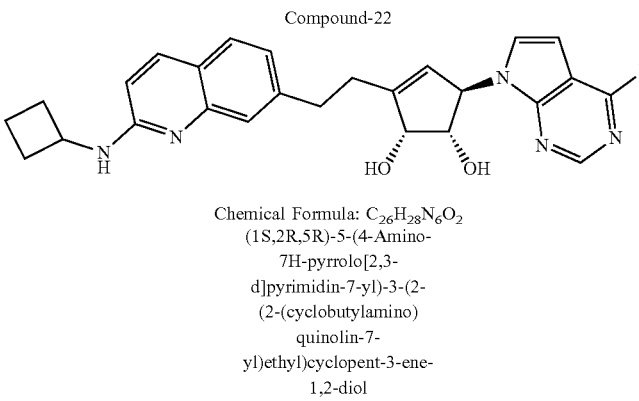<br>Chemical Formula: C$_{26}$H$_{28}$N$_6$O$_2$<br>(1S,2R,5R)-5-(4-Amino-7H-pyrrolo[2,3-d]pyrimidin-7-yl)-3-(2-(2-(cyclobutylamino) quinolin-7-yl)ethyl)cyclopent-3-ene-1,2-diol | 7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)ethyl)-N-cyclobutylquinolin-2-amine | $^1$H NMR (400 MHz, DMSO-d6) δ 8.15 (s, 1H), 8.05 (d, J = 9.1 Hz, 1H), 7.77-7.51 (m, 4H), 7.24 (d, J = 8.1 Hz, 1H), 6.82 (dd, J = 17.2, 6.4 Hz, 2H), 6.57 (d, J = 3.6 Hz, 1H), 5.53 (s, 1H), 5.45 (s, 1H), 5.03 (s, 2H), 4.55-4.43 (m, 2H), 4.01 (t, J = 5.2 Hz, 1H), 3.06-2.87 (m, 2H), 2.59-2.54 (m, 2H), 2.41 (d, J = 8.7 Hz, 2H), 2.01 (q, J = 9.8 Hz, 2H), 1.76 (q, J = 9.4 Hz, 2H); LCMS m/z = 457.3 (M+, 90%) |

Example-2: (1S,2R,5R)-3-(2-(2-Amino-3-fluoroquinolin-7-yl)ethyl)-5-(4-amino-7H-pyrrolo[2,3-d]pyrimidin-7-yl)cyclopent-3-ene-1,2-diol (Compound-23

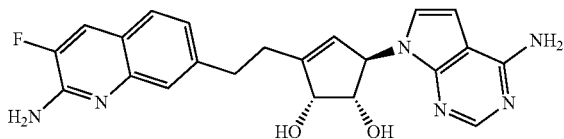 [SMILES: Nc1nc2cc(CCC3=C[C@@H](n4ccc5c(N)ncnc54)[C@H](O)[C@@H]3O)ccc2cc1F]

The mixture of 7-(2-((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)ethyl)-3-fluoroquinolin-2-amine (0.060 g, 0.130 mmol) in TFA (1.004 ml, 13.03 mmol) was stirred at 25° C. for 6 h under $N_2$ atmosphere. The reaction mixture was basified with ice cold solution of aq.sat.$NaHCO_3$ (20 ml) and extracted with ethyl acetate (20 ml). Layers were separated, organic layer was washed with brine (20 ml) and dried over anhydrous $Na_2SO_4$. The organic layer was filtered and concentrated in vacuo to give 0.12 g of crude compound. This residue was purified by combiflash ($R_f$200, Teledyne/Isco) instrument onto a Redisep® $R_f$ column with gradient elution (0 to 10%) of methanol in dichloromethane to afford the title compound (25 mg, 45.6% yield) as an off-white solid. $^1$H NMR (400 MHz, DMSO-d6) δ 8.05 (d, J=7.3 Hz, 1H), 7.79 (d, J=11.8 Hz, 1H), 7.59 (d, J=8.2 Hz, 1H), 7.37 (s, 1H), 7.16 (d, J=8.3 Hz, 1H), 6.99 (s, 2H), 6.74 (s, 2H), 6.58 (d, J=3.5 Hz, 1H), 6.40 (d, J=3.5 Hz, 1H), 5.50 (d, J=9.5 Hz, 1H), 5.42 (d, J=1.9 Hz, 1H), 4.97 (dd, J=6.6, 3.1 Hz, 2H), 4.45 (t, J=6.0 Hz, 1H), 3.95 (q, J=5.5 Hz, 1H), 3.04-2.85 (m, 2H), 2.60-2.53 (m, 2H); LCMS m/z=420.92 (M+, 100%).

Examples in table-14 were synthesized by following an analogous reaction protocol as was used for the preparation of (1S,2R,5R)-3-(2-(2-amino-3-fluoroquinolin-7-yl)ethyl)-5-(4-amino-7H-pyrrolo[2,3-d]pyrimidin-7-yl)cyclopent-3-ene-1,2-diol using the appropriate starting materials (Instead of TFA, aq.TFA or $FeCl_3$.DCM could also be used at appropriate temperature).

TABLE 14

| Structure & IUPAC name | Intermediate used | $^1$H NMR & LCMS data |
|---|---|---|
| Compound-24<br><br>(1S,2R,5R)-3-(2-(2-amino-3-chloro-5-fluoroquinolin-7-yl)ethyl)-5-(4-amino-7H-pyrrolo[2,3-d]pyrimidin-7-yl)cyclopent-3-ene-1,2-diol | 7-(2-((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)ethyl)-3-chloro-5-fluoroquinolin-2-amine | $^1$H NMR (400 MHz, DMSO-d6) δ 8.17 (d, J = 0.8 Hz, 1H), 8.03 (s, 1H), 7.22 (s, 1H), 7.01 (dd, J = 11.0, 1.4 Hz, 1H), 6.95 (s, 2H), 6.92 (s, 2H), 6.63 (d, J = 3.5 Hz, 1H), 6.42 (d, J = 3.5 Hz, 1H), 5.50 (t, J = 3.2 Hz, 1H), 5.45 (t, J = 1.7 Hz, 1H), 4.96 (dd, J = 6.3, 3.0 Hz, 2H), 4.45 (t, J = 5.8 Hz, 1H), 3.97 (q, J = 5.5 Hz, 1H), 3.03-2.87 (m, 2H), 2.56 (t, J = 7.0 Hz, 2H); LCMS m/z = 454.98 (M+, 40%) |
| Compound-25<br><br>(1S,2R,5R)-3-(2-(2-amino-3-chloro-6-fluoroquinolin-7-yl)ethyl)-5-(4-amino-7H-pyrrolo[2,3-d]pyrimidin-7-yl)cyclopent-3-ene-1,2-diol | 7-(2-((3aS,4R,6aR)-4-(4-amino-7H-pyrrolo [2,3-d]pyrimidin-7-yl)-2,2-dimethyl-3a,6a-dihydro-4H-cyclopenta[d][1,3]dioxol-6-yl)ethyl)-3-chloro-6-fluoroquinolin-2-amine | $^1$H NMR (400 MHz, DMSO-$d_6$) δ 8.17 (s, 1H), 8.03 (s, 1H), 7.53-7.30 (m, 2H), 6.97 (s, 2H), 6.75-6.55 (m, 3H), 6.44 (d, J = 3.6 Hz, 1H), 5.57-5.31 (m, 2H), 4.98 (dd, J = 6.4, 1.8 Hz, 2H), 4.45 (t, J = 6.0 Hz, 1H), 3.98 (q, J = 5.6 Hz, 1H), 2.98 (q, J = 6.7 Hz, 2H), 2.59-2.52 (m, 2H); LCMS m/z = 455.10 (M+, 90%) |
| Compound-26<br><br>(1S,2R,5R)-3-(2-(2-amino-3-chloro-8-fluoroquinolin-7-yl)ethyl)-5-(4-amino-7H-pyrrolo[2,3-d]pyrimidin-7-yl)cyclopent-3-ene-1,2-diol | 7-(2-((3aS,4R,6aR)-4-(4-amino-7H-pyrrolo [2,3-d]pyrimidin-7-yl)-2,2-dimethyl-3a,6a-dihydro-4H-cyclopenta[d][1,3]dioxol-6-yl)ethyl)-3-chloro-8-fluoroquinolin-2-amine | $^1$H NMR (400 MHz, DMSO-d6) δ 8.24 (d, J = 1.6 Hz, 1H), 8.04 (s, 1H), 7.44 (d, J = 8.3 Hz, 1H), 7.17 (dd, J = 8.3, 6.5 Hz, 1H), 7.00 (bs, 4H), 6.66 (d, J = 3.6 Hz, 1H), 6.44 (d, J = 3.5 Hz, 1H), 5.51 (d, J = 4.5 Hz, 1H), 5.42 (d, J = 1.8 Hz, 1H), 4.96 (dd, J = 6.6, 4.8 Hz, 2H), 4.44 (t, J = 5.9 Hz, 1H), 3.98 (q, J = 5.6 Hz, 1H), 2.98 (d, J = 8.3 Hz, 2H), 2.49-2.40 (m, 2H); LCMS m/z = 455.05 (M+, 100%) |

TABLE 14-continued

| Structure & IUPAC name | Intermediate used | ¹H NMR & LCMS data |
|---|---|---|
| Compound-27<br>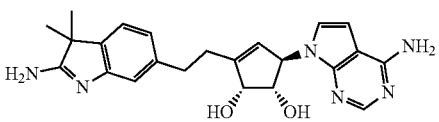 [SMILES: CC1(C)C(N)=Nc2cc(CCC3=C[C@@H](n4ccc5c(N)ncnc54)[C@H](O)[C@@H]3O)ccc21]<br>(1S,2R,5R)-3-(2-(2-amino-3,3-dimethyl-3H-indol-6-yl)ethyl)-5-(4-amino-7H-pyrrolo[2,3-d]pyrimidin-7-yl)cyclopent-3-ene-1,2-diol | 7-((3aS,4R,6aR)-6-(2-(2-amino-3,3-dimethyl-3H-indol-6-yl)ethyl)-2,2-dimethyl-3a,6a-dihydro-4H-cyclopenta[d][1,3]dioxol-4-yl)-7H-pyrrolo[2,3-d]pyrimidin-4-amine | ¹H NMR (400 MHz, DMSO-d6) δ 8.04 (s, 1H), 7.02 (d, J = 7.3 Hz, 1H), 6.97-6.85 (m, 4H), 6.81 (d, J = 1.4 Hz, 1H), 6.67 (dd, J = 7.4, 1.5 Hz, 1H), 6.63 (d, J = 3.5 Hz, 1H), 6.46 (d, J = 3.5 Hz, 1H), 5.55-5.46 (m, 1H), 5.42 (t, J = 1.7 Hz, 1H), 4.95 (s, 2H), 4.44 (d, J = 5.5 Hz, 1H), 3.93 (q, J = 4.8 Hz, 1H), 2.87-2.62 (m, 2H), 2.49-2.41 (m, 2H), 1.30-1.17 (m, 6H); LCMS m/z = 418.41 (M+, 100%) |
| Compound-28<br>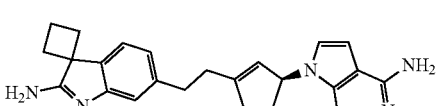<br>(1S,2R,5R)-5-(4-amino-7H-pyrrolo[2,3-d]pyrimidin-7-yl)-3-(2-(2'-aminospiro[cyclobutane-1,3'-indol]-6'-yl)ethyl)cyclopent-3-ene-1,2-diol | 6'-(2-((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)ethyl)spiro[cyclobutane-1,3'-indol]-2'-amine | 1H NMR (400 MHz, DMSO-d6) δ 8.04 (s, 1H), 7.39 (d, J = 7.3 Hz, 1H), 7.07 (s, 2H), 6.92 (s, 2H), 6.77 (d, J = 1.4 Hz, 1H), 6.71 (dd, J = 7.5, 1.5 Hz, 1H), 6.62 (d, J = 3.5 Hz, 1H), 6.45 (d, J = 3.5 Hz, 1H), 5.49 (d, J = 4.3 Hz, 1H), 5.41 (d, J = 1.9 Hz, 1H), 4.93 (d, J = 5.9 Hz, 2H), 4.45 (d, J = 5.5 Hz, 1H), 3.93 (q, J = 5.3 Hz, 1H), 2.87-2.64 (m, 2H), 2.62-2.49 (m, 4H), 2.40-2.30 (m, 1H), 2.24-2.13 (m, 3H); LCMS m/z = 431.23 (M+, 50%) |
| Compound-29<br>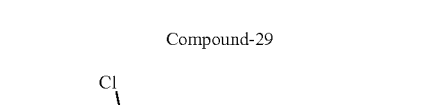<br>(1S,2R,5R)-3-(2-(2-amino-3,5-dichloroquinolin-7-yl)ethyl)-5-(4-amino-7H-pyrrolo[2,3-d]pyrimidin-7-yl)cyclopent-3-ene-1,2-diol | 7-(2-((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)ethyl)-3,5-dichloroquinolin-2-amine | ¹H NMR (400 MHz, DMSO-d6) δ 8.20 (s, 1H), 8.03 (s, 1H), 7.35 (d, J = 8.7 Hz, 2H), 7.14-6.88 (m, 4H), 6.62 (d, J = 3.5 Hz, 1H), 6.43 (d, J = 3.6 Hz, 1H), 5.49 (s, 1H), 5.43 (s, 1H), 4.98 (dd, J = 11.2, 6.4 Hz, 2H), 4.46 (t, J = 5.9 Hz, 1H), 3.96 (q, J = 5.5 Hz, 1H), 3.04-2.85 (m, 2H), 2.62-2.56 (m, 2H); LCMS m/z = 471.30 (M+, 50%) |
| Compound-30<br>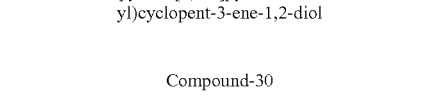<br>(1S,2R,5R)-3-(2-(2-amino-3-chloroquinolin-7-yl)ethyl)-5-(2-amino-7H-pyrrolo[2,3-d]pyrimidin-7-yl)cyclopent-3-ene-1,2-diol | 7-(2-((3aS,4R,6aR)-4-(2-amino-7H-pyrrolo[2,3-d]pyrimidin-7-yl)-2,2-dimethyl-3a,6a-dihydro-4H-cyclopenta[d][1,3]dioxol-6-yl)ethyl)-3-chloroquinolin-2-amine | ¹H NMR (400 MHz, DMSO-$d_6$) δ 8.69 (s, 1H), 8.37 (s, 1H), 7.69 (d, J = 8.2 Hz, 1H), 7.42 (s, 1H), 7.26 (d, J = 8.3 Hz, 1H), 6.95 (d, J = 3.9 Hz, 1H), 6.46 (d, J = 3.8 Hz, 1H), 5.42 (dd, J = 10.5, 3.3 Hz, 2H), 5.30-4.81 (m, 2H), 4.47 (d, J = 5.5 Hz, 1H), 4.22-3.88 (m, 1H), 3.09-2.87 (m, 2H) 2.57 (d, J = 7.7 Hz, 2H); LCMS m/z = 437.21 (M + 1, 70%) |

TABLE 14-continued

| Structure & IUPAC name | Intermediate used | ¹H NMR & LCMS data |
|---|---|---|
| Compound-31<br><br>(1S,2R,5R)-3-(2-(2-amino-3-chloro-5-fluoroquinolin-7-yl)ethyl)-5-(4-isopropyl-7H-pyrrolo[2,3-d]pyrimidin-7-yl)cyclopent-3-ene-1,2-diol | 3-chloro-5-fluoro-7-(2-((3aS,4R,6aR)-4-(4-isopropyl-7H-pyrrolo[2,3-d]pyrimidin-7-yl)-2,2-dimethyl-3a,6a-dihydro-4H-cyclopenta[d][1,3]dioxol-6-yl)ethyl)quinolin-2-amine | ¹H NMR (400 MHz, DMSO-d6) δ 8.68 (s, 1H), 8.18 (s, 1H), 7.22 (s, 1H), 7.05 (d, J = 3.7 Hz, 1H), 7.02 (dd, J = 11.0, 1.4 Hz, 1H), 6.96 (s, 2H), 6.57 (d, J = 3.6 Hz, 1H), 5.63 (d, J = 4.5 Hz, 1H), 5.46 (d, J = 1.8 Hz, 1H), 5.01 (d, J = 6.5 Hz, 2H), 4.47 (t, J = 6.1 Hz, 1H), 4.10-3.98 (m, 1H), 3.40 (dt, J = 13.9, 6.9 Hz, 1H), 3.04-2.89 (m, 2H), 2.57 (d, J = 8.3 Hz, 2H), 1.32 (d, J = 2.1 Hz, 3H), 1.30 (d, J = 2.1 Hz, 3H); LCMS m/z = 483.92 (M+, 30%) |
| Compound-32<br><br>(1S,2R,5R)-3-(2-(2-amino-3-chloro-5-fluoroquinolin-7-yl)ethyl)-5-(4-(1-methyl-1H-pyrazol-4-yl)-7H-pyrrolo[2,3-d]pyrimidin-7-yl)cyclopent-3-ene-1,2-diol | 3-chloro-7-(2-((3aS,4R,6aR)-2,2-dimethyl-4-(4-(1-methyl-1H-pyrazol-4-yl)-7H-pyrrolo[2,3-d]pyrimidin-7-yl)-3a,6a-dihydro-4H-cyclopenta[d][1,3]dioxol-6-yl)ethyl)-5-fluoroquinolin-2-amine | ¹H NMR (400 MHz, DMSO-d6) δ 8.68 (s, 1H), 8.62 (s, 1H), 8.21 (d, J = 19.9 Hz, 2H), 7.26-7.17 (m, 2H), 7.03 (dd, J = 11.0, 1.4 Hz, 2H), 6.98 (s, 1H), 6.87 (d, J = 3.7 Hz, 1H), 5.66 (d, J = 4.6 Hz, 1H), 5.50 (t, J = 1.7 Hz, 1H), 5.04 (d, J = 6.1 Hz, 2H), 4.48 (s, 1H), 4.08 (d, J = 5.4 Hz, 1H), 3.97 (s, 3H), 3.06-2.88 (m, 2H), 2.60-2.55 (m, 2H); LCMS m/z = 520.32 (M+, 100%) |
| Compound-33a and 33b<br><br>(1S,2R,5R)-3-(1-(2-amino-3-chloro-5-fluoroquinolin-7-yl)propan-2-yl)-5-(4-amino-7H-pyrrolo[2,3-d]pyrimidin-7-yl)cyclopent-3-ene-1,2-diol | 7-(2-((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)propyl)-3-chloro-5-fluoroquinolin-2-amine | Diastereomeric mixture was separated by chiral preparative HPLC.<br>First Diastereomer(Compound-33a):<br>¹H NMR (400 MHz, DMSO-d6) δ 8.18 (s, 1H), 8.03 (s, 1H), 7.18 (s, 1H), 7.14-6.83 (m, 5H), 6.50 (d, J = 3.5 Hz, 1H), 6.42 (d, J = 3.5 Hz, 1H), 5.51 (d, J = 5.1 Hz, 1H), 5.36 (d, J = 1.8 Hz, 1H), 5.00 (d, J = 6.8 Hz, 1H), 4.89 (d, J = 6.2 Hz, 1H), 4.56 (t, J = 5.8 Hz, 1H), 3.91 (d, J = 5.5 Hz, 1H), 3.08-2.94 (m, 1H), 2.79 (d, J = 9.3 Hz, 2H), 1.09 (d, J = 6.7 Hz, 3H); LCMS m/z = 469.36 (M+, 30%)<br>Second Diastereomer (Compound-33b):<br>¹H NMR (400 MHz, DMSO-d6) δ 8.18 (s, 1H), 8.05 (s, 1H), 7.19 (s, 1H), 7.08-6.86 (m, 5H), 6.78 (d, J = 3.5 Hz, 1H), 6.50 (d, J = 3.5 Hz, 1H), 5.56-5.47 (m, 1H), 5.43 (t, J = 1.4 Hz, 1H), 4.97 (t, J = 5.5 Hz, 2H), 4.51-4.42 (m, 1H), 3.98 (q, J = 6.1, 5.3 Hz, 1H), 3.09-2.96 (m, 1H), 2.75 (s, 2H), 1.08 (d, J = 6.3 Hz, 3H); LCMS m/z = 469.36 (M+, 30%) |

TABLE 14-continued

| Structure & IUPAC name | Intermediate used | ¹H NMR & LCMS data |
|---|---|---|
| Compound-34a and 34b<br>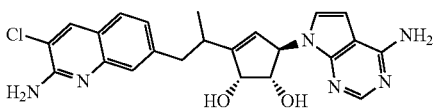 [SMILES: CC(Cc1ccc2cc(Cl)c(N)nc2c1)C1=C[C@@H](n2ccc3c(N)ncnc32)[C@H](O)[C@@H]1O]<br>(1S,2R,5R)-3-(1-(2-amino-3-chloroquinolin-7-yl)propan-2-yl)-5-(4-amino-7H-pyrrolo[2,3-d]pyrimidin-7-yl)cyclopent-3-ene-1,2-diol | 7-(2-((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)propyl)-3-chloroquinolin-2-amine | Diastereomeric mixture was separated by chiral preparative HPLC. First Diastereomer (Compound-34a): ¹H NMR (400 MHz, DMSO-d6) δ 8.17 (s, 1H), 8.03 (s, 1H), 7.60 (d, J = 8.2 Hz, 1H), 7.33 (d, J = 1.5 Hz, 1H), 7.13 (dd, J = 8.2, 1.6 Hz, 1H), 6.94 (s, 2H), 6.67 (s, 2H), 6.47 (d, J = 3.5 Hz, 1H), 6.39 (d, J = 3.5 Hz, 1H), 5.56-5.46 (m, 1H), 5.35 (d, J = 1.8 Hz, 1H), 4.98 (d, J = 6.7 Hz, 1H), 4.88 (d, J = 6.3 Hz, 1H), 4.57 (t, J = 5.9 Hz, 1H), 3.90 (q, J = 5.7 Hz, 1H), 3.10-2.96 (m, 1H), 2.84-2.73 (m, 2H), 1.13-1.09 (m, 3H); LCMS m/z = 451.2 (M+, 100%)<br>Second Diastereomer (Compound-34b): ¹H NMR (400 MHz, DMSO-d6) δ 8.17 (s, 1H), 8.05 (s, 1H), 7.60 (d, J = 8.2 Hz, 1H), 7.34 (d, J = 1.6 Hz, 1H), 7.13 (dd, J = 8.2, 1.6 Hz, 1H), 6.94 (s, 2H), 6.77 (d, J = 3.6 Hz, 1H), 6.67 (s, 2H), 6.49 (d, J = 3.5 Hz, 1H), 5.59-5.49 (m, 1H), 5.47-5.38 (m, 1H), 4.95 (t, J = 7.2 Hz, 2H), 4.47 (t, J = 6.0 Hz, 1H), 3.98 (q, J = 5.5 Hz, 1H), 3.04 (dd, J = 12.0, 4.5 Hz, 1H), 2.82-2.64 (m, 2H), 1.07 (d, J = 6.3 Hz, 3H); LCMS m/z = 452.98 (M + 1, 80%) |
| Compound-35a and 35b<br>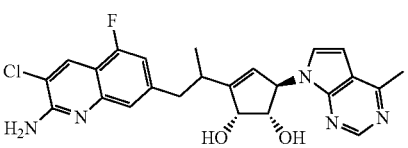 [SMILES: Cc1ncnc2c1ccn2[C@@H]1C=C(C(C)Cc2cc(F)c3cc(Cl)c(N)nc3c2)[C@@H](O)[C@H]1O]<br>(1S,2R,5R)-3-(1-(2-Amino-3-chloro-5-fluoroquinolin-7-yl)propan-2-yl)-5-(4-methyl-7H-pyrrolo[2,3-d]pyrimidin-7-yl)cyclopent-3-ene-1,2-diol | 3-chloro-7-(2-((3aS,4R,6aR)-2,2-dimethyl-4-(4-methyl-7H-pyrrolo[2,3-d]pyrimidin-7-yl)-3a,6a-dihydro-4H-cyclopenta[d][1,3]dioxol-6-yl)propyl)-5-fluoroquinolin-2-amine | Diastereomeric mixture was separated by chiral preparative HPLC. First Diastereomer (Compound-35a): ¹H NMR (400 MHz, DMSO-d6) δ 8.63 (s, 1H), 8.18 (s, 1H), 7.27-7.12 (m, 2H), 6.96 (s, 3H), 6.64 (d, J = 3.6 Hz, 1H), 5.64 (d, J = 4.9 Hz, 1H), 5.46 (d, J = 2.0 Hz, 1H), 5.01 (dd, J = 6.5, 3.4 Hz, 2H), 4.46 (t, J = 5.9 Hz, 1H), 4.03 (q, J = 5.7 Hz, 1H), 3.02 (q, J = 9.1 Hz, 1H), 2.86-2.68 (m, 2H), 2.64 (s, 3H), 1.09 (d, J = 7.0 Hz, 3H); LCMS m/z = 468.36 (M+, 80%)<br>Second Diastereomer (Compound-35b): ¹H NMR (400 MHz, DMSO-d6) δ 8.60 (s, 1H), 8.19 (s, 1H), 7.19 (s, 1H), 7.04-6.89 (m, 4H), 6.52 (d, J = 3.6 Hz, 1H), 5.63 (d, J = 5.0 Hz, 1H), |

TABLE 14-continued

| Structure & IUPAC name | Intermediate used | ¹H NMR & LCMS data |
|---|---|---|
| | | 5.39 (d, J = 1.8 Hz, 1H), 5.08-5.00 (m, 1H), 4.95 (d, J = 6.2 Hz, 1H), 4.58 (t, J = 5.9 Hz, 1H), 3.98 (dt, J = 6.8, 5.4 Hz, 1H), 3.03 (q, J = 10.1 Hz, 1H), 2.81 (s, 2H), 2.62 (s, 3H), 1.11 (d, J = 5.3 Hz, 3H); LCMS m/z = 468.36 (M+, 80%) |
| Compound-36a and 36b 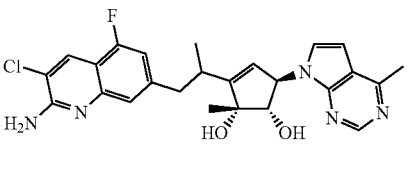 [SMILES: Cc1ncnc2c1ccn2[C@@H]1C=C(C(C)Cc2cc(F)c3cc(Cl)c(N)nc3c2)[C@@](C)(O)[C@H]1O] (1S,2R,5R)-3-(1-(2-amino-3-chloro-5-fluoroquinolin-7-yl)propan-2-yl)-2-methyl-5-(4-methyl-7H-pyrrolo[2,3-d]pyrimidin-7-yl)cyclopent-3-ene-1,2-diol | 3-chloro-5-fluoro-7-(2-((3aS,4R,6aR)-2,2,6a-trimethyl-4-(4-methyl-7H-pyrrolo[2,3-d]pyrimidin-7-yl)-3a,6a-dihydro-4H-cyclopenta[d][1,3]dioxol-6-yl)propyl)quinolin-2-amine | Diastereomeric mixture was separated by chiral preparative HPLC. First Diastereomer (Compound 36a): ¹H NMR (400 MHz, DMSO-d6) δ 8.63 (s, 1H), 8.19 (s, 1H), 7.22-7.12 (m, 2H), 7.03-6.90 (m, 3H), 6.66 (d, J = 3.7 Hz, 1H), 5.64-5.54 (m, 2H), 5.05 (d, J = 7.1 Hz, 1H), 4.49 (s, 1H), 3.66 (t, J = 6.5 Hz, 1H), 2.96 (dd, J = 13.2, 7.1 Hz, 1H), 2.85-2.68 (m, 2H), 2.65 (s, 3H), 1.24 (s, 3H), 1.13 (d, J = 6.5 Hz, 3H); LCMS m/z = 482.2 (M+, 40%) Second Diastereomer (Compound 36b): ¹H NMR (400 MHz, DMSO-d6) δ 8.64 (s, 1H), 8.17 (s, 1H), 7.43 (d, J = 3.6 Hz, 1H), 7.21 (s, 1H), 7.00 (dd, J = 11.1, 1.3 Hz, 1H), 6.95 (s, 2H), 6.69 (d, J = 3.6 Hz, 1H), 5.68-5.61 (m, 1H), 5.46 (d, J = 1.4 Hz, 1H), 5.18 (d, J = 7.3 Hz, 1H), 4.63 (s, 1H), 3.90 (t, J = 6.9 Hz, 1H), 3.23-3.16 (m, 1H), 2.73 (s, 2H), 2.65 (s, 3H), 1.42 (s, 3H), 0.99 (d, J = 6.6 Hz, 3H); LCMS m/z = 482.2 (M+, 40%). |
| Compound-37 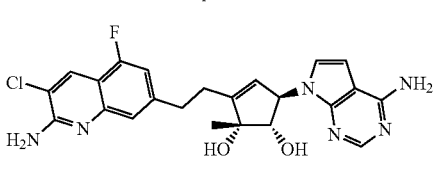 (1S,2R,5R)-3-(2-(2-amino-3-chloro-5-fluoroquinolin-7-yl)ethyl)-5-(4-amino-7H-pyrrolo[2,3-d]pyrimidin-7-yl)-2-methylcyclopent-3-ene-1,2-diol | 7-(2-((3aS,4R,6aR)-4-(4-amino-7H-pyrrolo[2,3-d]pyrimidin-7-yl)-2,2,6a-trimethyl-3a,6a-dihydro-4H-cyclopenta[d][1,3]dioxol-6-yl)ethyl)-3-chloro-5-fluoroquinolin-2-amine | ¹H NMR (400 MHz, DMSO-d6) δ 8.17 (s, 1H), 8.12 (s, 1H), 7.34 (s, 2H), 7.22 (s, 1H), 7.07-6.92 (m, 4H), 6.65-6.57 (m, 1H), 5.56-5.41 (m, 2H), 5.15-4.99 (m, 1H), 4.62 (s, 1H), 3.83 (d, J = 6.0 Hz, 1H), 2.99-2.86 (m, 2H), 2.46-2.31 (m, 2H), 1.27 (s, 3H); LCMS m/z = 469.30 (M+, 40%) |

TABLE 14-continued

| Structure & IUPAC name | Intermediate used | ¹H NMR & LCMS data |
|---|---|---|
| Compound-38<br>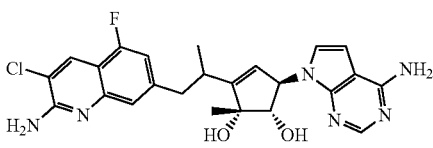 [SMILES: CC(Cc1cc(F)c2cc(Cl)c(N)nc2c1)C1=C[C@@H](n2ccc3c(N)ncnc32)[C@H](O)[C@]1(C)O]<br>(1S,2R,5R)-3-(1-(2-amino-3-chloro-5-fluoroquinolin-7-yl)propan-2-yl)-5-(4-amino-7H-pyrrolo[2,3-d]pyrimidin-7-yl)-2-methylcyclopent-3-ene-1,2-diol | 7-(2-((3aS,4R,6aR)-4-(4-amino-7H-pyrrolo[2,3-d]pyrimidin-7-yl)-2,2,6a-trimethyl-3a,6a-dihydro-4H-cyclopenta[d][1,3]dioxol-6-yl)propyl)-3-chloro-5-fluoroquinolin-2-amine | First Diastereomer: ¹H NMR (400 MHz, DMSO-d6) δ 8.18 (s, 1H), 8.04 (s, 1H), 7.18 (s, 1H), 7.01-6.90 (m, 5H), 6.70 (d, J = 3.6 Hz, 1H), 6.47 (d, J = 3.5 Hz, 1H), 5.55 (d, J = 1.7 Hz, 1H), 5.47 (d, J = 5.9 Hz, 1H), 5.06 (d, J = 7.0 Hz, 1H), 4.44 (s, 1H), 3.63 (dd, J = 7.0, 5.8 Hz, 1H), 2.97 (dd, J = 12.9, 6.7 Hz, 1H), 2.82-2.68 (m, 2H), 1.24 (s, 3H), 1.11 (s, 3H); LCMS m/z = 482.67 (M+, 80%) |
| Compound-39<br>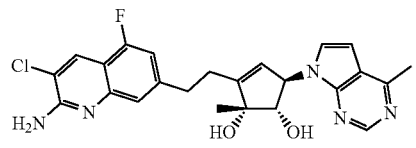 [SMILES: Cc1ncnc2c1ccn2[C@@H]1C=C(CCc2cc(F)c3cc(Cl)c(N)nc3c2)[C@@](C)(O)[C@H]1O]<br>(1S,2R,5R)-3-(2-(2-amino-3-chloro-5-fluoroquinolin-7-yl)ethyl)-2-methyl-5-(4-methyl-7H-pyrrolo[2,3-d]pyrimidin-7-yl)cyclopent-3-ene-1,2-diol | 3-chloro-5-fluoro-7-(2-((3aS,4R,6aR)-2,2,6a-trimethyl-4-(4-methyl-7H-pyrrolo[2,3-d]pyrimidin-7-yl)-3a,6a-dihydro-4H-cyclopenta[d][1,3]dioxol-6-yl)ethyl)quinolin-2-amine | ¹H NMR (400 MHz, DMSO-d6) δ 8.63 (s, 1H), 8.17 (s, 1H), 7.38 (d, J = 3.7 Hz, 1H), 7.22 (s, 1H), 7.02 (dd, J = 11.0, 1.5 Hz, 1H), 6.96 (s, 2H), 6.67 (d, J = 3.5 Hz, 1H), 5.64-5.57 (m, 1H), 5.50-5.45 (m, 1H), 5.07 (d, J = 7.3 Hz, 1H), 4.65 (s, 1H), 3.89 (dd, J = 7.4, 6.1 Hz, 1H), 2.94 (t, J = 7.8 Hz, 2H), 2.64 (s, 3H), 2.57-2.53 (m, 2H), 1.28 (s, 3H); LCMS m/z = 468.36 (M+, 60%) |
| Compound-40<br>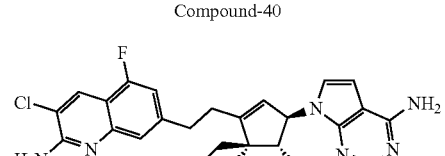<br>(1S,2R,5R)-3-(2-(2-amino-3-chloro-5-fluoroquinolin-7-yl)ethyl)-5-(4-amino-7H-pyrrolo[2,3-d]pyrimidin-7-yl)-2-ethylcyclopent-3-ene-1,2-diol | 7-(2-((3aS,4R,6aR)-4-(4-amino-7H-pyrrolo[2,3-d]pyrimidin-7-yl)-6a-ethyl-2,2-dimethyl-3a,6a-dihydro-4H-cyclopenta[d][1,3]dioxol-6-yl)ethyl)-3-chloro-5-fluoroquinolin-2-amine | ¹H NMR (400 MHz, DMSO-d6) δ 8.16 (s, 1H), 8.05 (s, 1H), 7.22 (s, 1H), 7.07-6.89 (m, 6H), 6.56 (d, J = 3.6 Hz, 1H), 5.57-5.43 (m, 2H), 5.04 (d, J = 7.6 Hz, 1H), 4.56 (s, 1H), 3.95 (t, J = 6.4 Hz, 1H), 2.94 (t, J = 8.0 Hz, 2H), 2.48-2.42 (m, 2H), 1.69 (dq, J = 14.4, 7.2 Hz, 1H), 1.56 (dq, J = 14.4, 7.2 Hz, 1H), 0.85 (t, J = 7.2 Hz, 3H); LCMS m/z = 482.67 (M+, 80%) |
| Compound-41<br>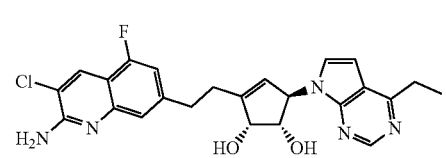 [SMILES: CCc1ncnc2c1ccn2[C@@H]1C=C(CCc2cc(F)c3cc(Cl)c(N)nc3c2)[C@@H](O)[C@H]1O]<br>(1S,2R,5R)-3-(2-(2-amino-3-chloro-5-fluoroquinolin-7-yl)ethyl)-5-(4-ethyl-7H-pyrrolo[2,3-d]pyrimidin-7-yl)cyclopent-3-ene-1,2-diol | 3-chloro-7-(2-((3aS,4R,6aR)-4-(4-ethyl-7H-pyrrolo[2,3-d]pyrimidin-7-yl)-2,2-dimethyl-3a,6a-dihydro-4H-cyclopenta[d][1,3]dioxol-6-yl)ethyl)-5-fluoroquinolin-2-amine | ¹H NMR (400 MHz, DMSO-d6) δ 8.66 (s, 1H), 8.18 (s, 1H), 7.22 (s, 1H), 7.11-6.91 (m, 4H), 6.56 (d, J = 3.6 Hz, 1H), 5.63 (s, 1H), 5.46 (d, J = 1.9 Hz, 1H), 5.02 (dd, J = 6.5, 4.3 Hz, 2H), 4.47 (t, J = 6.0 Hz, 1H), 4.08-4.00 (m, 1H), 2.96 (q, J = 7.7 Hz, 4H), 2.57 (d, J = 7.2 Hz, 2H), 1.31 (d, J = 7.6 Hz, 3H); LCMS m/z = 468.08 (M+, 100%) |

TABLE 14-continued

| Structure & IUPAC name | Intermediate used | ¹H NMR & LCMS data |
|---|---|---|
| Compound-42<br>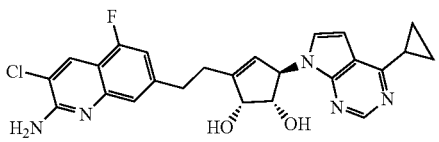 [SMILES: Nc1nc2cc(CCC3=C[C@@H](n4ccc5c(C6CC6)ncnc54)[C@H](O)[C@@H]3O)cc(F)c2cc1Cl]<br>(1S,2R,5R)-3-(2-(2-amino-3-chloro-5-fluoroquinolin-7-yl)ethyl)-5-(4-cyclopropyl-7H-pyrrolo[2,3-d]pyrimidin-7-yl)cyclopent-3-ene-1,2-diol | 3-Chloro-7-(2-((3aS,4R,6aR)-4-(4-cyclopropyl-7H-pyrrolo[2,3-d]pyrimidin-7-yl)-2,2-dimethyl-3a,6a-dihydro-4H-cyclopenta[d][1,3]dioxol-6-yl)ethyl)-5-fluoroquinolin-2-amine | ¹H NMR (400 MHz, DMSO-d6) δ 8.63 (s, 1H), 8.27 (s, 1H), 7.30 (d, J = 36.5 Hz, 3H), 7.18 (d, J = 3.7 Hz, 1H), 7.08 (d, J = 10.9 Hz, 1H), 6.76 (d, J = 3.7 Hz, 1H), 5.62 (d, J = 3.7 Hz, 1H), 5.47 (d, J = 1.9 Hz, 1H), 4.47 (d, J = 5.5 Hz, 1H), 4.06 (t, J = 5.2 Hz, 1H), 3.07-2.88 (m, 2H), 2.62-2.54 (m, 3H) 1.27-1.14 (m, 4H); LCMS m/z = 479.86 (M+, 100%) |
| Compound-43<br>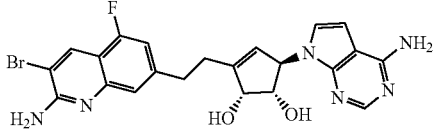<br>(1S,2R,5R)-3-(2-(2-Amino-3-bromo-5-fluoroquinolin-7-yl)ethyl)-5-(4-amino-7H-pyrrolo[2,3-d]pyrimidin-7-yl)cyclopent-3-ene-1,2-diol | 7-(2-((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)ethyl)-3-bromo-5-fluoroquinolin-2-amine | ¹H NMR (400 MHz, DMSO-d6) δ 8.34 (s, 1H), 8.04 (s, 1H), 7.21 (s, 1H), 7.06-6.94 (m, 3H), 6.86 (s, 2H), 6.65 (d, J = 3.5 Hz, 1H), 6.43 (d, J = 3.5 Hz, 1H), 5.49 (d, J = 4.4 Hz, 1H), 5.45 (t, J = 1.7 Hz, 1H), 4.96 (dd, J = 6.5, 2.1 Hz, 2H), 4.45 (t, J = 6.0 Hz, 1H), 3.97 (q, J = 5.5 Hz, 1H), 3.04-2.86 (m, J = 7.4 Hz, 2H), 2.55 (d, J = 6.4 Hz, 2H); LCMS m/z = 499.30, 501.24 (M+, M + 2, 100%) |
| Compound-44<br>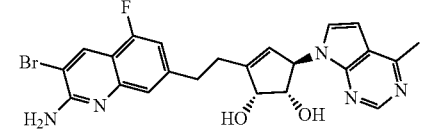 [SMILES: Cc1ncnc2c1ccn2[C@@H]1C=C(CCc2cc(F)c3cc(Br)c(N)nc3c2)[C@@H](O)[C@H]1O]<br>(1S,2R,5R)-3-(2-(2-Amino-3-bromo-5-fluoroquinolin-7-yl)ethyl)-5-(4-methyl-7H-pyrrolo[2,3-d]pyrimidin-7-yl)cyclopent-3-ene-1,2-diol | 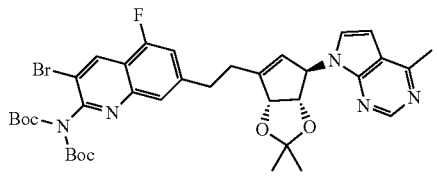 | ¹H NMR (400 MHz, DMSO-d6) δ 8.61 (s, 1H), 8.34 (s, 1H), 7.21 (s, 1H), 7.06 (d, J = 3.6 Hz, 1H), 7.02-6.98 (m, 1H), 6.87 (s, 2H), 6.54 (d, J = 3.6 Hz, 1H), 5.61 (t, J = 3.3 Hz, 1H), 5.46 (q, J = 1.6 Hz, 1H), 5.01 (dd, J = 6.5, 5.2 Hz, 2H), 4.47 (t, J = 6.0 Hz, 1H), 4.08-3.99 (m, 1H), 3.07-2.86 (m, 2H), 2.62 (s, 3H), 2.57 (t, J = 8.3 Hz, 2H); LCMS m/z = 498.24, 500.24 (M+, M + 2, 100%). |
| Compound-45a and 45b<br>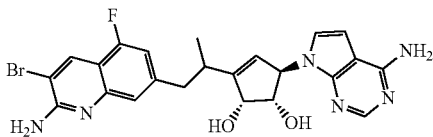 [SMILES: CC(Cc1cc(F)c2cc(Br)c(N)nc2c1)C1=C[C@@H](n2ccc3c(N)ncnc32)[C@H](O)[C@@H]1O]<br>(1S,2R,5R)-3-(1-(2-Amino-3-bromo-5-fluoro quinolin-7-yl)propan-2-yl)-5-(4-amino-7H-pyrrolo[2,3-d]pyrimidin-7-yl)cyclopent-3-ene-1,2-diol | 7-(2-((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)propyl)-3-bromo-5-fluoroquinolin-2-amine | First Diastereomer (Compound 45a): ¹H NMR (400 MHz, DMSO-d6) δ 8.34 (s, 1H), 8.03 (s, 1H), 7.18 (s, 1H), 7.11-6.68 (m, 5H), 6.52 (d, J = 3.7 Hz, 1H), 6.41 (d, J = 3.4 Hz, 1H), 5.51 (d, J = 4.8 Hz, 1H), 5.37 (s, 1H), 5.00 (d, J = 7.1 Hz, 1H), 4.89 (d, J = 6.2 Hz, 1H), 4.56 (s, 1H), 3.91 (d, J = 6.2 Hz, 1H), 3.01 (d, J = 7.4 Hz, 1H), 2.88-2.71 (m, 2H), 1.10 (d, J = 7.1, Hz, 3H). LCMS m/z = 514.19 (M + 1, 100%)<br>Second Diastereomer (Compound 45b): 1H NMR (400 MHz, DMSO-d6) δ 8.34 (s, 1H), 8.04 (s, 1H), 7.18 (s, 1H), 7.02-6.92 (m, 3H), 6.86 (s, 2H), 6.78 (d, J = |

| Structure & IUPAC name | Intermediate used | ¹H NMR & LCMS data |
|---|---|---|
| | | 3.5 Hz, 1H), 6.50 (d, J = 3.5 Hz, 1H), 5.52 (d, J = 4.8 Hz, 1H), 5.43 (s, 1H), 4.97 (dd, J = 6.5, 3.6 Hz, 2H), 4.46 (t, J = 6.1 Hz, 1H), 3.98 (q, J = 5.6 Hz, 1H), 3.01 (d, J = 9.0 Hz, 1H), 2.84-2.65 (m, 2H), 1.07 (d, J = 5.9 Hz, 3H). LCMS m/z = 514.19 (M + 1, 100%) |

Example-3: (1S,2R,5R)-3-(2-(2-Amino-6-fluoroquinolin-7-yl)ethyl)-5-(4-amino-7H-pyrrolo[2,3-d]pyrimidin-7-yl)cyclopent-3-ene-1,2-diol (Compound-46

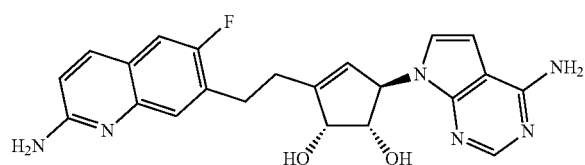 [SMILES: Nc1ccc2cc(F)c(CCC3=C[C@@H](n4ccc5c(N)ncnc54)[C@H](O)[C@@H]3O)cc2n1]

The mixture of (1S,2R,5R)-3-(2-(2-amino-3-chloro-6-fluoroquinolin-7-yl)ethyl)-5-(4-amino-7H-pyrrolo[2,3-d]pyrimidin-7-yl)cyclopent-3-ene-1,2-diol (311 mg, 0.684 mmol) and palladium hydroxide (168 mg, 0.239 mmol) in ethanol (40 ml) was stirred at 25° C. for 8 h under hydrogen atmosphere (60 psi). The resulting mixture was filtered through celite and filtrate was concentrated in vacuo to give 0.32 g of crude compound. Obtained residue was purified by combiflash (R_f 200, Teledyne/Isco) instrument onto a Redisep® R_f column with gradient elution (0 to 10%) of methanolic ammonia in dichloromethane to afford the title compound (7 mg, 2.4% yield) as an off-white solid. ¹H NMR (400 MHz, DMSO-d6) δ 8.03 (s, 1H), 7.85 (d, J=8.8 Hz, 1H), 7.40 (t, J=9.3 Hz, 2H), 6.91 (s, 2H), 6.75 (d, J=8.8 Hz, 1H), 6.65 (d, J=3.6 Hz, 1H), 6.43 (d, J=3.6 Hz, 1H), 6.36 (s, 2H), 5.51 (s, 1H), 5.45 (s, 1H), 4.97 (d, J=6.3 Hz, 2H), 4.46 (s, 1H), 3.97 (d, J=5.7 Hz, 1H), 3.05-2.88 (m, 2H), 2.48-2.26 (m, 2H).
LCMS m/z=420.98 (M+, 50%).

Example-4: (1S,2R,5R)-3-(2-(2-amino-5-fluoroquinolin-7-yl)ethyl)-5-(4-amino-7H-pyrrolo[2,3-d]pyrimidin-7-yl)cyclopent-3-ene-1,2-diol (Compound-47

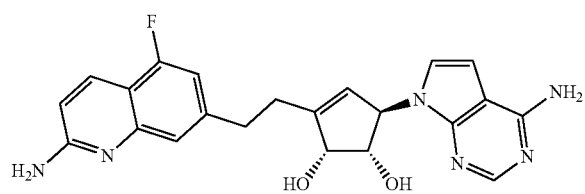 [SMILES: Nc1ccc2c(F)cc(CCC3=C[C@@H](n4ccc5c(N)ncnc54)[C@H](O)[C@@H]3O)cc2n1]

The mixture of (1S,2R,5R)-3-(2-(2-amino-3-chloro-5-fluoroquinolin-7-yl)ethyl)-5-(4-amino-7H-pyrrolo[2,3-d]pyrimidin-7-yl)cyclopent-3-ene-1,2-diol (30 mg, 0.066 mmol), Pd—C(1.755 mg, 1.649 μmol) and ammonium formate (16.63 mg, 0.264 mmol) in MeOH (2 ml) was stirred at 78° C. for 8 h. The resulting mixture was filtered through celite and filtrate was concentrated in vacuo to give 0.32 g of crude compound. Obtained residue was purified by combiflash (R_f 200, Teledyne/Isco) instrument onto a Redisep® R_f column with gradient elution (0 to 10%) of methanolic ammonia in dichloromethane to afford the title compound (9 mg, 32.5%) as an off-white solid. ¹H NMR (400 MHz, DMSO-d6) –8.03 (s, 1H), 7.97 (d, J=9.0 Hz, 1H), 7.15 (s, 1H), 6.94-6.87 (m, 3H), 6.77 (d, J=9.0 Hz, 1H), 6.64-6.59 (m, 3H), 6.41 (d, J=3.5 Hz, 1H), 5.49 (d, J=3.9 Hz, 1H), 5.44 (t, J=1.7 Hz, 1H), 4.97 (d, J=5.5 Hz, 2H), 4.46 (s, 1H), 3.96 (q, J=5.3 Hz, 1H), 3.00-2.86 (m, 2H), 2.54 (d, J=10.1 Hz, 2H); LCMS m/z=420.98 (M+, 90%).

Example-5: (1R,2R,3S,4R,5S)-1-(2-(2-Amino-3-chloro-5-fluoroquinolin-7-yl)ethyl)-4-(4-amino-7H-pyrrolo[2,3-d]pyrimidin-7-yl)bicyclo[3.1.0]hexane-2,3-diol (Compound-48)

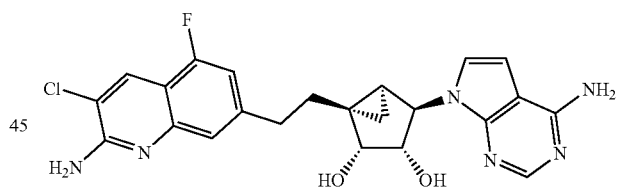

TFA (44.3 ml, 575 mmol) was added to 7-(2-((3aR,3bR,4aS,5R,5aS)-5-(4-amino-7H-pyrrolo[2,3-d]pyrimidin-7-yl)-2,2-dimethyl tetrahydrocyclopropa[3,4]cyclopenta[1,2-d][1,3]dioxol-3b(3aH)-yl)ethyl)-3-chloro-5-fluoro quinolin-2-amine (4.5 g, 8.84 mmol) at 0° C. The resulting mixture was stirred at 25° C. for 16 h under N₂ atmosphere. The solvent was removed in vacuo at 30° C. The obtained residue was dissolved with ethyl acetate (100 ml) and basified with aq.sat. NaHCO₃. Layers were separated, organic layer was washed with brine (50 ml) and dried over anhydrous Na₂SO₄. The organic layer was filtered and concentrated in vacuo to give 5.1 g of crude compound. This residue was purified by combiflash (R_f 200, Teledyne/Isco) instrument onto a Redisep® R_f column with gradient elution (0 to 10%) of methanol in dichloromethane to afford the title compound (2.8 g, 67.5%) as a light Brown solid. ¹H NMR (400 MHz, DMSO-d6) δ 8.16 (s, 1H), 8.07 (s, 1H), 7.21 (s, 1H), 7.04 (d, J=3.6 Hz, 1H), 7.03-6.99 (m, 1H), 6.99-6.90 (m, 4H), 6.58 (d, J=3.5 Hz, 1H), 5.12 (d, J=3.8 Hz, 1H), 4.90 (s, 1H), 4.52 (d, J=4.1 Hz, 2H), 3.72 (s, 1H), 2.96-2.80 (m, 2H), 2.14 (ddd, J=16.1, 11.3, 5.3 Hz, 1H), 1.84 (ddd, J=13.7, 11.2, 5.6 Hz, 1H), 1.24 (d, J=5.3 Hz, 2H), 0.57 (q, J=5.9 Hz, 1H); LCMS m/z=469.23 (M+1, 50%).

Examples in table-15 were synthesized by following an analogous reaction protocol as was used for the preparation of (1R,2R,3S,4R,5S)-4-(4-amino-7H-pyrrolo[2,3-d]pyrimidin-7-yl)-1-(2-(2-aminoquinolin-7-yl)ethyl)bicyclo[3.1.0]hexane-2,3-diol using the appropriate starting materials.

TABLE 15

| Structure & IUPAC name | Intermediate used | ¹H NMR & LCMS data |
|---|---|---|
| Compound-49<br><br>(1R,2R,3S,4R,5S)-4-(4-Amino-7H-pyrrolo[2,3-d]pyrimidin-7-yl)-1-(2-(2-(methylamino)quinolin-7-yl)ethyl)bicyclo[3.1.0]hexane-2,3-diol | 7-(2-((3aR,3bR,4aS,5R,5aS)-5-(4-Amino-7H-pyrrolo[2,3-d]pyrimidin-7-yl)-2,2-dimethylhexahydrocyclopropa[3,4]cyclopenta[1,2-d][1,3]dioxol-3b-yl)ethyl)-N-methylquinolin-2-amine | ¹H NMR (400 MHz, DMSO-d6) δ 8.09 (s, 1H), 7.91 (d, J = 9.0 Hz, 1H), 7.60 (d, J = 8.1 Hz, 1H), 7.52 (s, 1H), 7.16 (d, J = 8.2 Hz, 1H), 7.12-7.03 (m, 2H), 6.77 (d, J = 9.0 Hz, 1H), 6.61 (d, J = 3.5 Hz, 1H), 5.12 (d, J = 4.5 Hz, 1H), 4.91 (s, 1H), 4.53 (d, J = 7.0 Hz, 2H), 3.74 (t, J = 5.0 Hz, 1H), 2.95 (d, J = 4.8 Hz, 3H), 2.87-2.84 (m, 2H), 2.21-2.05 (m, 1H), 1.88 (ddd, J = 13.7, 11.5, 5.5 Hz, 1H), 1.32-1.19 (m, 2H), 0.61-0.58 (m, 1H); LCMS m/z = 431.06 (M + 1; 60%). |
| Compound-50<br><br>(1R,2R,3S,4R,5S)-4-(4-Amino-7H-pyrrolo[2,3-d]pyrimidin-7-yl)-1-(2-(2-(isopropylamino)quinolin-7-yl)ethyl)bicyclo[3.1.0]hexane-2,3-diol. | 7-(2-((3aR,3bR,4aS,5R,5aS)-5-(4-Amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-N-isopropylquinolin-2-amine. | ¹H NMR (400 MHz, DMSO-d6) δ 8.13 (s, 1H), 7.99 (s, 1H), 7.70-7.53 (m, 2H), 7.27 (d, J = 38.6 Hz, 3H), 7.10 (d, J = 3.6 Hz, 1H), 6.83 (d, J = 9.0 Hz, 1H), 6.66 (d, J = 3.5 Hz, 1H), 5.14 (d, J = 4.4 Hz, 1H), 4.91 (d, J = 1.3 Hz, 1H), 4.54 (d, J = 3.2 Hz, 2H), 4.31-4.18 (m, 1H) 3.75 (s, 1H), 3.03-2.80 (m, 2H), 2.14 (ddd, J = 17.0, 11.9, 6.1 Hz, 1H), 1.94-1.79 (m, 1H), 1.27-1.23 (m, 8H), 0.64-0.54 (m, 1H); LCMS m/z = 459.3 (M + 1; 100%). |
| Compound-51<br><br>(1R,2R,3S,4R,5S)-4-(4-Amino-7H-pyrrolo[2,3-d]pyrimidin-7-yl)-1-(2-(2-(cyclobutylamino)quinolin-7-yl)ethyl)bicyclo [3.1.0]hexane-2,3-diol. | 7-(2-((3aR,3bR,4aS,5R,5aS)-5-(4-Amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-N-cyclobutyl quinolin-2-amine. | ¹H NMR (400 MHz, DMSO-d6) δ 8.13 (s, 1H), 7.96 (d, J = 9.2 Hz, 1H), 7.62 (d, J = 8.1 Hz, 1H), 7.52 (s, 1H), 7.29 (s, 1H), 7.19 (d, J = 8.4 Hz, 1H), 7.10 (d, J = 3.6 Hz, 1H), 6.77 (d, J = 9.1 Hz, 1H), 6.65 (d, J = 3.5 Hz, 1H), 5.13 (d, J = 4.5 Hz, 1H), 4.91 (d, J = 1.3 Hz, 1H), 4.57-4.45 (m, 3H), 3.75 (s, 1H), 3.17 (s, 1H), 2.95-2.85 (m, 2H), 2.45-2.33 (m, 2H), 2.13 (ddd, J = 13.4, 11.3, 5.2 Hz, 1H), 2.06-1.81 (m, 2H), 1.74 (ddd, J = 15.3, 10.1, 7.1 Hz, 2H), 1.33-1.21 (m, 2H), 0.64-0.55 (m, 1H); LCMS m/z = 471.3 (M + 1; 100%). |

TABLE 15-continued

| Structure & IUPAC name | Intermediate used | $^1$H NMR & LCMS data |
|---|---|---|
| Compound-52 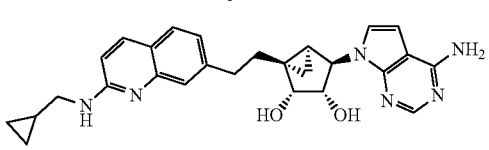 (1R,2R,3S,4R,5S)-4-(4-Amino-7H-pyrrolo[2,3-d]pyrimidin-7-yl)-1-(2-(2-((cyclopropylmethyl)amino)quinolin-7-yl)ethyl)bicyclo[3.1.0]hexane-2,3-diol | 7-(2-((3aR,3bR,4aS,5R,5aS)-5-(4-Amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-N-(cyclopropylmethyl)quinolin-2-amine. | $^1$H NMR (400 MHz, DMSO-d6) δ 8.10 (s, 1H), 7.89 (d, J = 9.0 Hz, 1H), 7.58 (d, J = 8.1 Hz, 1H), 7.46 (s, 1H), 7.18-7.04 (m, 4H), 6.81 (d, J = 9.0 Hz, 1H), 6.61 (d, J = 3.5 Hz, 1H), 5.12 (d, J = 4.4 Hz, 1H), 4.91 (d, J = 1.2 Hz, 1H), 4.53 (d, J = 5.6 Hz, 2H), 3.74 (t, J = 4.8 Hz, 1H), 3.31-3.28 (m, 1H), 2.94-2.83 (m, 2H), 2.12 (ddd, J = 13.7, 11.5, 5.2 Hz, 1H), 1.88 (ddd, J = 13.7, 11.5, 5.4 Hz, 1H), 1.28-1.23 (m, 3H), 1.19-1.08 (m, 1H), 0.59 (q, J = 5.9 Hz, 1H), 0.53-0.45 (m, 2H), 0.33-0.22 (m, 2H); LCMS m/z = 471.05 (M + 1; 90%). |
| Compound-53 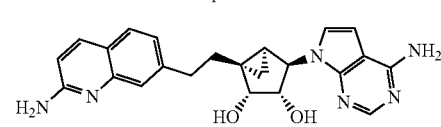 (1R,2R,3S,4R,5S)-4-(4-Amino-7H-pyrrolo[2,3-d]pyrimidin-7-yl)-1-(2-(2-amino-8-fluoroquinolin-7-yl)ethyl)bicyclo[3.1.0]hexane-2,3-diol. | 7-(2-((3aR,3bR,4aS,5R,5aS)-5-(4-Amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-8-fluoroquinolin-2-amine. | $^1$H NMR (400 MHz, DMSO-d6) δ 8.10 (s, 1H), 7.90 (dd, J = 9.0, 1.6 Hz, 1H), 7.38 (d, J = 8.2 Hz, 1H), 7.30-7.00 (m, 4H), 6.77 (d, J = 9.1 Hz, 3H), 6.62 (d, J = 3.6 Hz, 1H), 5.15 (d, J = 4.5 Hz, 1H), 4.91 (s, 1H), 4.53 (d, J = 3.0 Hz, 2H), 3.75 (s, 1H), 2.97 (td, J = 12.6, 5.1 Hz, 1H), 2.84 (td, J = 12.6, 5.3 Hz, 1H), 2.19-2.01 (m, 1H), 1.82 (td, J = 12.7, 5.2 Hz, 1H), 1.28 (d, J = 3.5 Hz, 2H), 0.63-0.54 (m, 1H); LCMS m/z = 435.04 (M + 1; 40%). |
| Compound-54 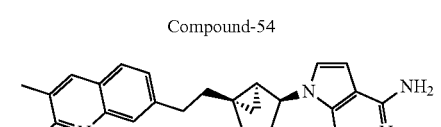 (1R,2R,3S,4R,5S)-1-(2-(2-Amino-3-methylquinolin-7-yl)ethyl)-4-(4-amino-7H-pyrrolo[2,3-d]pyrimidin-7-yl)bicyclo[3.1.0]hexane-2,3-diol. | 7-(2-((3aR,3bR,4aS,5R,5aS)-5-(4-Amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-3-methylquinolin-2-amine. | $^1$H NMR (400 MHz, DMSO-d6) δ 8.07 (s, 1H), 7.71 (s, 1H), 7.51 (d, J = 8.2 Hz, 1H), 7.33 (d, J = 1.6 Hz, 1H), 7.08 (dd, J = 8.2, 1.7 Hz, 1H), 7.03 (d, J = 3.6 Hz, 1H), 6.98 (s, 2H), 6.58 (d, J = 3.5 Hz, 1H), 6.36 (s, 2H), 5.12 (d, J = 4.5 Hz, 1H), 4.90 (d, J = 1.2 Hz, 1H), 4.59-4.46 (m, 2H), 3.72 (t, J = 5.2 Hz, 1H), 2.92-2.83 (m, 2H), 2.20 (d, J = 1.1 Hz, 3H), 2.10 (ddd, J = 12.7, 11.0, 5.2 Hz, 1H), 1.88 (ddd, J = 13.8, 11.5, 5.5 Hz, 1H), 1.23 (d, J = 3.5 Hz, 2H), 0.58 (q, J = 5.5 Hz, 1H); LCMS m/z = 431.08 (M + 1; 100%). |

TABLE 15-continued

| Structure & IUPAC name | Intermediate used | ¹H NMR & LCMS data |
|---|---|---|
| Compound-55<br>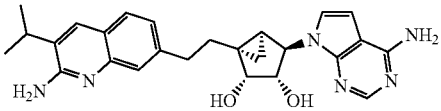 [SMILES: CC(C)c1cc2ccc(CC[C@@]34C[C@@H]3[C@@H](n3ccc5c(N)ncnc53)[C@H](O)[C@@H]4O)cc2nc1N]<br>(1R,2R,3S,4R,5S)-1-(2-(2-Amino-3-isopropyl quinolin-7-yl)ethyl)-4-(4-amino-7H-pyrrolo[2,3-d]pyrimidin-7-yl)bicyclo[3.1.0]hexane-2,3-diol. | 7-(2-((3aR,3bR,4aS,5R,5aS)-5-(4-amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-3-isopropylquinolin-2-amine | ¹H NMR (400 MHz, DMSO-d6) δ 8.09 (d, J = 6.3 Hz, 2H), 7.74 (d, J = 8.2 Hz, 3H), 7.45 (s, 1H), 7.30 (dd, J = 8.1, 1.5 Hz, 1H), 7.07 (dd, J = 9.1, 3.6 Hz, 3H), 6.61 (d, J = 3.5 Hz, 1H), 5.16 (d, J = 4.5 Hz, 1H), 4.90 (d, J = 1.2 Hz, 1H), 4.53 (d, J = 7.5 Hz, 2H), 3.74 (t, J = 5.1 Hz, 1H), 3.10 (p, J = 6.7 Hz, 1H), 3.01-2.83 (m, 2H), 2.14 (ddd, J = 15.8, 12.1, 6.4 Hz, 1H), 1.85 (ddd, J = 13.6, 11.1, 5.9 Hz, 1H), 1.26 (d, J = 6.6 Hz, 8H), 0.56 (q, J = 6.0 Hz, 1H); LCMS m/z = 459.3 (M+; 40%). |
| Compound-56<br>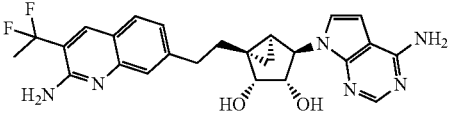 [SMILES: CC(F)(F)c1cc2ccc(CC[C@]34C[C@@H]3[C@@H](n3ccc5c(N)ncnc53)[C@H](O)[C@@H]4O)cc2nc1N]<br>(1R,2R,3S,4R,5S)-1-(2-(2-Amino-3-(1,1-difluoroethyl)quinolin-7-yl)ethyl)-4-(4-amino-7H-pyrrolo[2,3-d]pyrimidin-7-yl)bicyclo[3.1.0]hexane-2,3-diol. | 7-(2-((3aR,3bR,4aS,5R,5aS)-5-(4-Amino-7H-pyrrolo[2,3-d]pyrimidin-7-yl)-2,2-dimethyltetrahydrocyclo propa[3,4]cyclopenta[1,2-d][1,3]dioxol-3b(3aH)-yl)ethyl)-3-(1,1-difluoro ethyl)quinolin-2-amine. | ¹H NMR (400 MHz, DMSO-d6) δ 8.15 (s, 1H), 8.09 (s, 1H), 7.70 (d, J = 8.1 Hz, 1H), 7.38 (s, 1H), 7.21-7.15 (m, 1H), 7.10-7.00 (m, 3H), 6.61 (d, J = 3.6 Hz, 1H), 6.25 (s, 2H), 5.11 (d, J = 4.5 Hz, 1H), 4.91 (s, 1H), 4.53 (d, J = 7.5 Hz, 2H), 3.74 (t, J = 5.2 Hz, 1H), 2.83-2.91 (m, 2H), 2.18-1.98 (m, 4H), 1.88 (td, J = 12.4, 5.5 Hz, 1H), 1.28-1.25 (m, 2H), 0.58 (q, J = 5.9 Hz, 1H); LCMS m/z = 481.2 (M + 1; 90%). |
| Compound-57<br>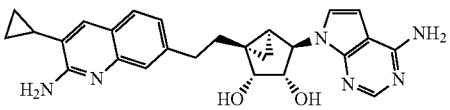 [SMILES: Nc1nc2cc(CC[C@]34C[C@@H]3[C@@H](n3ccc5c(N)ncnc53)[C@H](O)[C@@H]4O)ccc2cc1C1CC1]<br>(1R,2R,3S,4R,5S)-1-(2-(2-Amino-3-cyclopropylquinolin-7-yl)ethyl)-4-(4-amino-7H-pyrrolo[2,3-d]pyrimidin-7-yl)bicyclo[3.1.0]hexane-2,3-diol. | 7-(2-((3aR,3bR,4aS,5R,5aS)-5-(4-Amino-7H-pyrrolo[2,3-d]pyrimidin-7-yl)-2,2-dimethyltetrahydrocyclo propa[3,4]cyclopenta[1,2-d][1,3]dioxol-3b(3aH)-yl)ethyl)-3-cyclopropyl quinolin-2-amine. | ¹H NMR (400 MHz, DMSO-d6) δ 8.09 (s, 1H), 7.91 (s, 1H), 7.80 (s, 2H), 7.67 (d, J = 8.2 Hz, 1H), 7.44 (s, 1H), 7.27 (dd, J = 8.2, 1.5 Hz, 1H), 7.11 (s, 2H), 7.06 (d, J = 3.5 Hz, 1H), 6.61 (d, J = 3.5 Hz, 1H), 5.17 (d, J = 4.5 Hz, 1H), 4.90 (d, J = 1.2 Hz, 1H), 4.53 (d, J = 4.3 Hz, 2H), 3.73 (s, 1H), 2.95-2.87 (m, 2H), 2.12 (ddd, J = 13.8, 11.0, 5.4 Hz, 1H), 1.90-1.74 (m, 2H), 1.23 (d, J = 3.4 Hz, 2H), 1.08-0.96 (m, 2H), 0.78-0.68 (m, 2H), 0.55 (q, J = 5.8 Hz, 1H); LCMS m/z = 457.13 (M+; 50%). |

TABLE 15-continued

| Structure & IUPAC name | Intermediate used | ¹H NMR & LCMS data |
|---|---|---|
| Compound-58<br>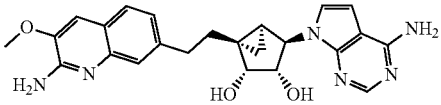<br>(1R,2R,3S,4R,5S)-1-(2-(2-Amino-3-methoxyquinolin-7-yl)ethyl)-4-(4-amino-7H-pyrrolo[2,3-d]pyrimidin-7-yl)bicyclo[3.1.0]hexane-2,3-diol. | 7-(2-((3aR,3bR,4aS,5R,5aS)-5-(4-Amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-3-methoxyquinolin-2-amine. | ¹H NMR (400 MHz, DMSO-d6) δ 8.08 (s, 1H), 7.54 (d, J = 8.1 Hz, 1H), 7.40-7.31 (m, 2H), 7.15-7.05 (m, 3H), 7.04 (d, J = 3.5 Hz, 1H), 6.67 (d, J = 18.5 Hz, 2H), 6.60 (d, J =3.5 Hz, 1H), 5.12 (d, J = 4.5 Hz, 1H), 4.90 (d, J = 1.3 Hz, 1H), 4.52 (d, J = 5.8 Hz, 2H), 3.91 (s, 3H), 3.79-3.66 (m, 1H), 2.90-2.80 (m, 2H), 2.09 (ddd, J = 13.7, 11.2, 5.4 Hz, 1H), 1.88 (ddd, J = 13.8, 11.5, 5.7 Hz, 1H), 1.24 (d, J = 5.2 Hz, 2H), 0.58 (q, J = 5.8 Hz, 1H). ); LCMS m/z = 447.01 (M + 1; 90%). |
| Compound-59<br>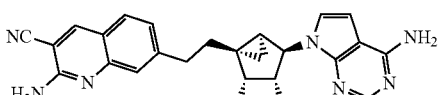<br>2-amino-7-(2-((1R,2R,3S,4R,5S)-4-(4-Amino-7H-pyrrolo[2,3-d]pyrimidin-7-yl)-2,3-dihydroxybicyclo[3.1.0]hexan-1-yl)ethyl)quinoline-3-carbonitrile. | 2-amino-7-(2-((3aR,3bR,4aS,5R,5aS)-5-(4-Amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)quinoline-3-carbonitrile. | ¹H NMR (400 MHz, DMSO-d6) δ 8.62 (s, 1H), 8.06 (d, J = 2.3 Hz, 1H), 7.66 (d, J = 8.3 Hz, 1H), 7.37 (s, 1H), 7.22 (dd, J = 8.3, 1.6 Hz, 1H), 7.03 (d, J = 3.6 Hz, 1H), 6.97 (s, 2H), 6.89 (s, 2H), 6.58 (d, J = 3.5 Hz, 1H), 5.11 (d, J = 4.5 Hz, 1H), 4.90 (s, 1H), 4.57-4.48 (m, 2H), 3.73 (t, J = 5.3 Hz, 1H), 3.0-2.81 (m, 2H), 2.21-2.04 (m, 1H) 1.93-1.81 (m, 1H), 1.26-1.23 (m, 2H), 0.57 (q, J = 5.9 Hz, 1H); LCMS m/z = 442.23 (M + 1; 80%). |
| Compound-60<br><br>(1R,2R,3S,4R,5S)-1-(2-(2-Amino-3-fluoroquinolin-7-yl)ethyl)-4-(4-amino-7H-pyrrolo[2,3-d]pyrimidin-7-yl)bicyclo[3.1.0]hexane-2,3-diol. | 7-(2-((3aR,3bR,4aS,5R,5aS)-5-(4-Amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-3-fluoroquinolin-2-amine. | 1H NMR (400 MHz, DMSO-d6) δ 8.15 (s, 1H), 7.78 (d, J = 11.8 Hz, 1H), 7.58 (d, J = 8.2 Hz, 1H), 7.49 (s, 2H), 7.37 (d, J = 1.6 Hz, 1H), 7.15 (dd, J = 8.2, 1.6 Hz, 1H), 7.11 (d, J = 3.6 Hz, 1H), 6.77 (s, 2H), 6.67 (d, J = 3.6 Hz, 1H), 5.14 (d, J = 4.3 Hz, 1H), 4.90 (d, J = 1.3 Hz, 1H), 4.54 (d, J = 8.9 Hz, 2H), 3.74 (d, J = 5.5 Hz, 1H), 2.92-2.82 (m, 2H), 2.10 (ddd, J = 13.8, 11.2, 5.4 Hz, 1H), 1.87 (ddd, J = 13.8, 11.6, 5.6 Hz, 1H), 1.27-1.23 (m, 2H), 0.63-0.55 (m, 1H). ); LCMS m/z = 435.3 (M+; 80%). |

TABLE 15-continued

| Structure & IUPAC name | Intermediate used | ¹H NMR & LCMS data |
| --- | --- | --- |
| Compound-61<br><br>(1R,2R,3S,4R,5S)-1-(2-(2-Amino-3-chloroquinolin-7-yl)ethyl)-4-(4-amino-7H-pyrrolo[2,3-d]pyrimidin-7-yl)bicyclo[3.1.0]hexane-2,3-diol. | 7-(2-((3aR,3bR,4aS,5R,5aS)-5-(4-Amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-3-chloroquinolin-2-amine. | ¹H NMR (400 MHz, DMSO-d6) δ 8.15 (s, 1H), 8.07 (s, 1H), 7.58 (d, J = 8.2 Hz, 1H), 7.36 (s, 1H), 7.15 (dd, J = 8.2, 1.6 Hz, 1H), 7.08-6.89 (m, 3H), 6.66 (s, 2H), 6.58 (d, J = 3.5 Hz, 1H), 5.11 (d, J = 4.5 Hz, 1H), 4.90 (s, 1H), 4.55-4.50 (m, 2H), 3.73 (t, J = 5.3 Hz, 1H), 2.96-2.80 (m, 2H), 2.11 (ddd, J = 13.7, 11.3, 5.3 Hz, 1H), 1.87 (ddd, J = 13.9, 11.6, 5.6 Hz, 1H), 1.26-1.23 (m, 2H), 0.58 (q, J = 5.9 Hz, 1H); LCMS m/z = 451.3 (M + 1; 80%). |
| Compound-62<br><br>(1R,2R,3S,4R,5S)-1-(2-(2-Amino-3-chloro-6-fluoroquinolin-7-yl)ethyl)-4-(4-amino-7H-pyrrolo[2,3-d]pyrimidin-7-yl) bicyclo[3.1.0]hexane-2,3-diol. | 7-(2-((3aR,3bR,4aS,5R,5aS)-5-(4-Amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-3-chloro-6-fluoroquinolin-2-amine. | ¹H NMR (400 MHz, DMSO-d6) δ 8.15 (d, J = 6.2 Hz, 2H), 7.56-7.35 (m, 4H), 7.13 (d, J = 3.6 Hz, 1H), 6.68 (d, J = 3.1 Hz, 3H), 5.16 (s, 1H), 4.91 (s, 1H), 4.53 (d, J = 7.2 Hz, 2H), 3.75 (s, 1H), 2.98 (t, J = 12.0 Hz, 1H), 2.91-2.78 (m, 1H), 2.13 (q, J = 8.2, 4.7 Hz, 1H), 1.89-1.76 (m, 1H), 1.25 (d, J = 11.4 Hz, 2H), 0.59 (q, J = 6.0 Hz, 1H); LCMS m/z = 451.3 (M + 1; 80%). |
| Compound-63<br><br>(1R,2R,3S,4R,5S)-1-(2-(2-Amino-3-chloro-8-fluoroquinolin-7-yl)ethyl)-4-(4-amino-7H-pyrrolo[2,3-d]pyrimidin-7-yl)bicyclo[3.1.0]hexane-2,3-diol. | 7-(2-((3aR,3bR,4aS,5R,5aS)-5-(4-Amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-3-chloro-8-fluoroquinolin-2-amine. | ¹H NMR (400 MHz, DMSO-d6) δ 8.23 (s, 1H), 8.07 (s, 1H), 7.42 (d, J = 8.3 Hz, 1H), 7.17 (t, J = 7.4 Hz, 1H), 7.04 (d, J = 3.6 Hz, 1H), 7.01-6.92 (m, 4H), 6.58 (d, J = 3.5 Hz, 1H), 5.16 (d, J = 4.6 Hz, 1H), 4.90 (s, 1H), 4.59-4.44 (m, 2H), 3.73 (t, J = 5.4 Hz, 1H), 3.09-2.92 (m, 1H), 2.92-2.77 (m, 1H) 2.13 (t, J = 7.2 Hz, 1H), 1.87-1.74 (m, 1H), 1.27 (t, J = 6.5 Hz, 2H), 0.58 (d, J = 5.6 Hz, 1H); LCMS m/z = 468.68 (M+; 80%). |
| Compound-64<br><br>(1R,2R,3S,4R,5S)-1-(2-(2-amino-3-bromo-6-fluoroquinolin-7-yl)ethyl)-4-(4-amino-7H-pyrrolo[2,3-d]pyrimidin-7-yl)bicyclo[3.1.0]hexane-2,3-diol. | 7-(2-((3aR,3bR,4aS,5R,5aS)-5-(4-Amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-3-bromo-6-fluoroquinolin-2-amine. | ¹H NMR (400 MHz, DMSO-d6) δ 8.35 (s, 1H), 8.24 (s, 1H), 7.96 (d, J = 30.9 Hz, 2H), 7.45 (t, J = 8.4 Hz, 1H), 7.24 (d, J = 3.6 Hz, 1H), 6.80 (d, J = 3.5 Hz, 1H), 6.60 (s, 1H), 5.17 (s, 1H), 4.91 (d, J = 4.0 Hz, 1H), 4.53 (s, 1H), 4.40 (d, J = 6.8 Hz, 1H), 3.78 (d, J = 6.4 Hz, 1H), 3.04-2.80 |

TABLE 15-continued

| Structure & IUPAC name | Intermediate used | $^1$H NMR & LCMS data |
|---|---|---|
| Compound-65<br>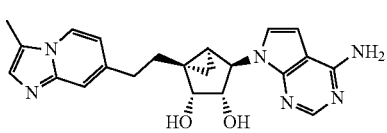<br>(1R,2R,3S,4R,5S)-4-(4-Amino-7H-pyrrolo[2,3-d]pyrimidin-7-yl)-1-(2-(3-methylimidazo[1,2-a]pyridin-7-yl)ethyl) bicyclo[3.1.0]hexane-2,3-diol. | 7-((3aR,3bR,4aS,5R,5aS)-2,2-Dimethyl-3b-(2-(3-methylimidazo[1,2-a]pyridin-7-yl)ethyl)hexahydrocyclopropa[3,4]cyclopenta[1,2-d][1,3]dioxol-5-yl)-7H-pyrrolo[2,3-d]pyrimidin-4-amine. | (m, 2H), 2.15 (s, 1H), 1.82 (s, 1H), 1.30-1.27 (m, 2H), 0.60-0.55 (m, 1H); LCMS m/z = 514.19 (M + 1; 80%).<br><br>$^1$H NMR (400 MHz, DMSO-d6) δ 8.16 (d, J = 6.9 Hz, 1H), 8.07 (s, 1H), 7.36 (s, 1H), 7.28 (s, 1H), 7.08-6.85 (m, 4H), 6.58 (d, J = 3.4 Hz, 1H), 5.12 (d, J = 4.5 Hz, 1H), 4.90 (s, 1H), 4.52 (s, 2H), 3.72 (s, 1H), 3.29 (s, 1H), 2.95-2.75 (m, 2H), 2.61-2.53 (m, 1H), 2.44 (s, 3H), 2.21-2.03 (m, 1H), 1.97-1.74 (m, 1H), 0.61-0.47 (m, 1H); LCMS m/z = 405.16 (M + 1; 100%). |
| Compound-66<br>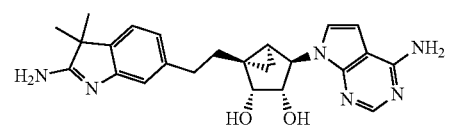<br>(1R,2R,3S,4R,5S)-1-(2-(2-Amino-3,3-dimethyl-3H-indol-6-yl)ethyl)-4-(4-amino-7H-pyrrolo[2,3-d]pyrimidin-7-yl) bicyclo[3.1.0]hexane-2,3-diol. | 7-((3aR,3bR,4aS,5R,5aS)-3b-(2-(2-Amino-3,3-dimethyl-3H-indol-6-yl)ethyl)-2,2-dimethylhexahydrocyclopropa[3,4]cyclopenta[1,2-d][1,3]dioxol-5-yl)-7H-pyrrolo[2,3-d]pyrimidin-4-amine. | $^1$H NMR (400 MHz, DMSO-d6) δ 8.06 (s, 1H), 7.09 (d, J = 7.4 Hz, 1H), 7.01 (d, J = 3.6 Hz, 1H), 6.98 (s, 2H), 6.87 (d, J = 1.4 Hz, 1H), 6.79-6.74 (m, 1H), 6.58 (d, J = 3.5 Hz, 1H), 5.11 (s, 1H), 4.90 (d, J = 1.2 Hz, 1H), 4.49 (s, 2H), 3.71 (s, 1H), 2.82-2.59 (m, 2H), 2.09-1.96 (m, 1H), 1.81 (td, J = 12.7, 5.3 Hz, 1H), 1.30 (s, 6H), 1.26-1.19 (m, 2H), 0.63-0.51 (m, 1H); LCMS m/z = 433.40 (M + 1; 80%). |
| Compound-67<br>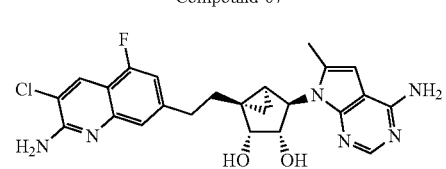<br>(1R,2R,3S,4R,5S)-1-(2-(2-Amino-3-chloro-5-fluoroquinolin-7-yl)ethyl)-4-(4-amino-6-methyl-7H-pyrrolo[2,3-d]pyrimidin-7-yl)bicyclo[3.1.0]hexane-2,3-diol. | 7-(2-((3aR,3bR,4aS,5R,5aS)-5-(4-Amino-6-methyl-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-3-chloro-5-fluoroquinolin-2-amine. | $^1$H NMR (400 MHz, DMSO-d6) δ 8.15 (s, 1H), 8.03 (s, 1H), 7.18 (s, 1H), 7.06-6.87 (m, 5H), 6.36-6.29 (m, 1H), 4.93 (d, J = 5.4 Hz, 1H), 4.74 (t, J = 6.7 Hz, 1H), 4.51 (d, J = 6.6 Hz, 1H), 4.41 (d, J = 3.4 Hz, 1H), 4.28 (s, 1H), 2.95 (td, J = 12.6, 11.3, 4.9 Hz, 1H), 2.82 (td, J = 12.8, 12.1, 5.7 Hz, 1H), 2.38 (s, 3H), 2.14-1.98 (m, 1H), 1.79 (ddd, J = 13.6, 11.3, 5.8 Hz, 1H), 0.99-0.79 (m, 2H), 0.58 (dd, J = 8.4, 4.7 Hz, 1H); LCMS m/z = 485.05 (M + 2; 40%). |

TABLE 15-continued

| Structure & IUPAC name | Intermediate used | ¹H NMR & LCMS data |
|---|---|---|
| Compound-68<br>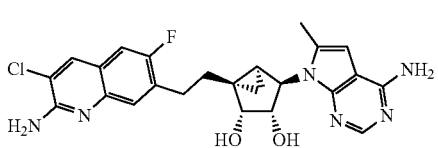<br>(1R,2R,3S,4R,5S)-1-(2-(2-Amino-3-chloro-6-fluoroquinolin-7-yl)ethyl)-4-(4-amino-6-methyl-7H-pyrrolo[2,3-d]pyrimidin-7-yl)bicyclo[3.1.0]hexane-2,3-diol. | 7-(2-((3aR,3bR,4aS,5R,5aS)-5-(4-Amino-6-methyl-7H-pyrrolo[2,3-d]pyrimidin-7-yl)-2,2-dimethyltetra hydrocyclo propa[3,4]cyclopenta[1,2-d][1,3]dioxol-3b(3aH)-yl)ethyl)-3-chloro-6-fluoroquinolin-2-amine. | ¹H NMR (400 MHz, DMSO-d6) δ 8.15 (s, 1H), 8.01 (s, 1H), 7.46-7.39 (m, 2H), 6.94 (s, 2H), 6.67 (s, 2H), 6.32 (d, J = 1.2 Hz, 1H), 4.98-4.91 (m, 1H),4.76 (t, J = 6.7 Hz, 1H), 4.53 (d, J = 6.6 Hz, 1H), 4.42 (d, J = 3.4 Hz, 1H), 4.28 (s, 1H), 3.08-2.94 (m, 1H), 2.84 (td, J = 13.3, 12.7, 5.3 Hz, 1H), 2.43-2.37 (m, 3H), 2.04 (dq, J = 19.8, 7.7, 6.3 Hz, 1H), 1.86-1.72 (m, 1H), 1.32-1.26 (m, 2H), 0.59 (dd, J = 8.3, 4.7 Hz, 1H); LCMS m/z = 482.30 (M; 80%). |
| Compound-69<br>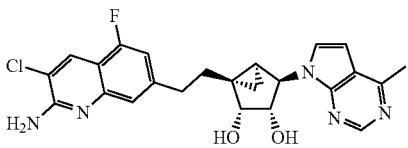<br>(1R,2R,3S,4R,5S)-1-(2-(2-amino-3-chloro-5-fluoroquinolin-7-yl)ethyl)-4-(4-methyl-7H-pyrrolo[2,3-d]pyrimidin-7-yl) bicyclo[3.1.0]hexane-2,3-diol. | 3-Chloro-7-(2-((3aR,3bR,4aS,5R,5aS)-2,2-dimethyl-5-(4-methyl-7H-pyrrolo[2,3-d]pyrimidin-7-yl)tetrahydrocyclo propa[3,4]cyclopenta[1,2-d][1,3]dioxol-3b(3aH)-yl)ethyl)-5-fluoroquinolin-2-amine. | A mixture of two compound was separated by reverse phase HPLC to afford compound X and compound Y as shown below. ¹H NMR (400 MHz, DMSO-d6) δ 8.66 (s, 1H), 8.16 (s, 1H), 7.43 (d, J = 3.7 Hz, 1H), 7.21 (s, 1H), 7.00 (dd, J = 11.1, 1.4 Hz, 1H), 6.93 (s, 2H), 6.70 (d, J = 3.6 Hz, 1H), 5.16 (s, 1H), 4.99 (d, J = 1.4 Hz, 1H), 4.56 (d, J = 6.5 Hz, 2H), 3.80 (d, J = 5.8 Hz, 1H), 2.97-2.80 (m, 2H), 2.65 (s, 3H), 2.22-2.09 (m, 1H), 1.91-1.81 (m, 1H), 1.31-1.25 (m, 2H), 0.60 (q, J = 5.8 Hz, 1H)); LCMS m/z = 468.2 (M + 1; 80%). |
| Compound-70<br>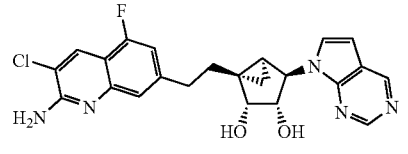<br>(1R,2R,3S,4R,5S)-1-(2-(2-Amino-3-chloro-5-fluoroquinolin-7-yl)ethyl)-4-(7H-pyrrolo[2,3-d]pyrimidin-7-yl)bicyclo [3.1.0]hexane-2,3-diol. | 3-Chloro-7-(2-((3aR,3bR,4aS,5R,5aS)-2,2-dimethyl-5-(7H-pyrrolo[2,3-d]pyrimidin-7-yl)tetrahydrocyclo propa[3,4]cyclopenta[1,2-d][1,3]dioxol-3b(3aH)-yl)ethyl)-5-fluoroquinolin-2-amine. | ¹H NMR (400 MHz, DMSO-d6) δ 9.02 (s, 1H), 8.81 (s, 1H), 8.16 (s, 1H), 7.51 (d, J = 3.7 Hz, 1H), 7.22 (s, 1H), 7.03-6.98 (m, 1H), 6.92 (bs, 2H), 6.67 (d, J = 3.6 Hz, 1H), 5.02 (d, J = 1.5 Hz, 1H), 4.56 (d, J = 6.7 Hz, 1H), 3.81 (d, J = 6.4 Hz, 1H), 2.87 (ddd, J = 19.0, 14.0, 8.5 Hz, 2H), 2.20-2.10 (m, 1H), 1.88 (d, J = 10.5 Hz, 1H), 1.32-1.26 (m, 2H), 0.64-0.58 (m, 1H); LCMS m/z = 454.11 (M + 1; 40%). |

TABLE 15-continued

| Structure & IUPAC name | Intermediate used | ¹H NMR & LCMS data |
| --- | --- | --- |
| Compound-71<br>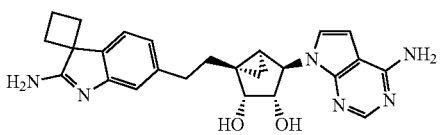<br>(1R,2R,3S,4R,5S)-4-(4-Amino-7H-pyrrolo[2,3-d]pyrimidin-7-yl)-1-(2-(2'-aminospiro[cyclobutane-1,3'-indol]-6'-yl)ethyl)bicyclo[3.1.0]hexane-2,3-diol. | 6'-(2-((3aR,3bR,4aS,5R,5aS)-5-(4-Amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)spiro[cyclobutane-1,3'-indol]-2'-amine. | ¹H NMR (400 MHz, DMSO-d6) δ 8.07 (s, 1H), 7.68 (d, J = 7.7 Hz, 1H), 7.22-7.07 (m, 4H), 7.07-6.96 (m, 3H) 6.59 (d, J = 3.5 Hz, 1H), 5.14 (d, J = 4.6 Hz, 1H), 4.89 (s, 1H), 4.51 (d, J = 7.2 Hz, 1H), 3.74 (t, J = 5.4 Hz, 1H), 2.79 (dd, J = 24.0, 14.1 Hz, 3H), 2.35 (d, J = 12.3 Hz, 2H), 2.20 (d, J = 9.9 Hz, 1H), 2.04 (d, J = 17.8 Hz, 1H), 1.87-1.74 (m, 1H), 1.26-1.18 (m, 5H), 0.60-0.50 (m, 1H); LCMS m/z = 445.03 (M + 1; 90%). |
| Compound-72<br>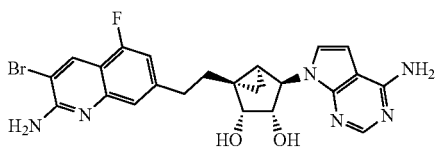<br>(1R,2R,3S,4R,5S)-1-(2-(2-Amino-3-bromo-5-fluoroquinolin-7-yl)ethyl)-4-(4-amino-7H-pyrrolo[2,3-d]pyrimidin-7-yl)bicyclo[3.1.0]hexane-2,3-diol | 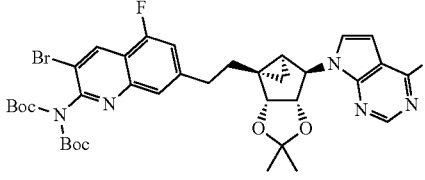 | ¹H NMR (400 MHz, DMSO-d6) d 8.33 (s, 1H), 8.08 (s, 1H), 7.20 (s, 2H), 7.17-6.96 (m, 3H), 6.84 (s, 2H), 6.60 (d, J = 3.5 Hz, 1H), 5.11 (d, J = 4.5 Hz, 1H), 4.90 (d, J = 1.2 Hz, 1H), 4.52 (d, J = 2.7 Hz, 2H), 3.72 (s, 1H), 3.00-2.74 (m, 2H), 2.14 (s, 1H), 1.90-1.76 (m, 1H), 1.42-1.28 (m, 1H), 0.91-0.75 (m, 1H), 0.57 (q, J = 5.9 Hz, 1H); LCMS m/z = 514.19, 516.19 (M+, M + 2, 100%). |

Example-6: (1R,2R,3S,4R,5S)-1-(2-(2-Amino-3-bromoquinolin-7-yl)ethyl)-4-(4-amino-7H-pyrrolo[2,3-d]pyrimidin-7-yl)bicyclo[3.1.0]hexane-2,3-diol (Compound-73)

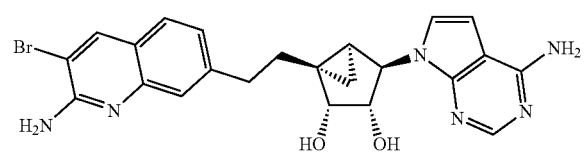 [SMILES: Nc1nc2cc(CC[C@]34C[C@@H]3[C@@H](n3ccc5c(N)ncnc53)[C@H](O)[C@@H]4O)ccc2cc1Br]

7-(2-((3aR,3bR,4aS,5R,5aS)-5-(4-Amino-7H-pyrrolo[2,3-d]pyrimidin-7-yl)-2,2-dimethyl hexahydrocyclopropa[3,4]cyclopenta[1,2-d][1,3]dioxol-3b-yl)ethyl)-3-bromo-N-(4-methoxy benzyl)quinolin-2-amine (2.6 g, 3.97 mmol) in TFA (55.0 ml, 714 mmol) was stirred at 50° C. for 1 h under N₂ atmosphere. The resulting mixture was concentrated in vacuo and obtained residue was dissolved in MeOH (50 ml). K₂CO₃ (0.982 g, 7.10 mmol) was added and stirred the reaction mixture at 60° C. for 1 h. The reaction mixture was filtered, and filtrate was concentrated under reduced pressure to get 2.7 g of crude compound. This residue was purified by combiflash (R$_f$200, Teledyne/Isco) instrument onto a Redisep® R$_f$ column with gradient elution (0 to 9%) of methanol in dichloromethane to afford the title compound (1.35 g, 77%) as a white solid. ¹H NMR (400 MHz, DMSO-d₆): δ 8.34 (s, 1H), 8.12 (s, 1H), 7.58 (d, J=8.3 Hz, 1H), 7.36 (d, J=1.6 Hz, 1H), 7.26 (s, 2H), 7.15 (dd, J=8.2, 1.7 Hz, 1H), 7.09 (d, J=3.5 Hz, 1H), 6.64 (d, J=3.5 Hz, 1H), 6.60 (s, 2H), 5.13 (d, J=4.6 Hz, 1H), 4.97-4.83 (m, 1H), 4.53 (d, J=3.9 Hz, 2H), 3.74 (s, 1H), 2.94-2.81 (m, 2H), 2.11 (dt, J=11.2, 6.5 Hz, 1H), 1.87 (ddd, J=13.9, 11.5, 5.6 Hz, 1H), 1.33-1.12 (m, 2H); 0.60-0.57 (m, 1H). LCMS m/z=494.99, 496.99 (M+, M+2; 100%).

Examples in table-16 were synthesized by following an analogous reaction protocol as was used for the preparation of (1R,2R,3S,4R,5S)-1-(2-(2-amino-3-bromoquinolin-7-yl)ethyl)-4-(4-amino-7H-pyrrolo [2,3-d]pyrimidin-7-yl)bicyclo[3.1.0]hexane-2,3-diol using the appropriate starting materials.

TABLE 16

| Structure & IUPAC name | Intermediate used | ¹H NMR & LCMS data |
|---|---|---|
| Compound-74<br><br>(1R,2R,3S,4R,5S)-4-(4-Amino-7H-pyrrolo[2,3-d]pyrimidin-7-yl)-1-(2-(2-aminoquinolin-7-yl)ethyl)bicyclo[3.1.0]hexane-2,3-diol | 7-(2-((3aR,3bR,4aS,5R,5aS)-5-(4-Amino-7H-pyrrolo[2,3-d]pyrimidin-7-yl)-2,2-dimethyl-hexahydrocyclopropa[3,4]cyclopenta[1,2-d][1,3]dioxol-3b-yl)ethyl)quinolin-2-amine | ¹H NMR (400 MHz, DMSO-d6) δ 8.07 (s, 1H), 7.82 (d, J = 8.8 Hz, 1H), 7.52 (d, J = 8.2 Hz, 1H), 7.30 (d, J = 1.6 Hz, 1H), 7.08-7.02 (m, 2H), 6.97 (s, 2H), 6.68 (d, J = 8.8 Hz, 1H), 6.58 (d, J = 3.5 Hz, 1H), 6.34 (s, 2H), 5.11 (d, J = 4.5 Hz, 1H), 4.91 (d, J = 1.2 Hz, 1H), 4.55-4.49 (m, 2H), 3.73 (t, J = 5.2 Hz, 1H), 2.91-2.78 (m, 2H), 2.10 (ddd, J = 13.6, 11.3, 5.3 Hz, 1H), 1.92-1.85 (m, 1H), 1.28-1.24 (m, 2H), 0.59 (td, J = 6.6, 3.2 Hz, 1H); LCMS m/z = 418.17 (M + 2; 40%). |
| Compound-75<br><br>(1R,2R,3S,4R,5S)-4-(4-amino-7H-pyrrolo[2,3-d]pyrimidin-7-yl)-1-(2-(2-aminoquinazolin-7-yl)ethyl)bicyclo[3.1.0]hexane-2,3-diol. | N-(7-(2-((1R,2R,3S,4R,5S)-4-(4-Amino-7H-pyrrolo[2,3-d]pyrimidin-7-yl)-2,3-dihydroxybicyclo[3.1.0]hexan-1-yl)ethyl)quinazolin-2-yl)-2,2,2-trifluoroacetamide. | ¹H NMR (400 MHz, DMSO-d6) δ 9.04 (s, 1H), 8.16 (s, 1H), 7.71 (d, J = 8.2 Hz, 1H), 7.53 (s, 2H), 7.28 (s, 1H), 7.15 (dd, J = 11.1, 5.8 Hz, 2H), 6.83 (s, 2H), 6.69 (d, J =3.6 Hz, 1H), 5.14 (s, 1H), 4.90 (s, 1H), 4.55 (s, 2H), 3.75 (s, 1H), 2.99-2.79 (m, 2H), 2.11 (d, J = 15.9 Hz, 1H), 1.87 (q, J = 10.9, 8.1 Hz, 1H), 1.29-1.23 (m, 2H), 0.61-0.56 (m, 1H); LCMS m/z = 418.10 (M + 1; 80%). |
| Compound-76a and 76b<br><br>(1S,2R,3S,4R,5S)-1-((S)-1-(2-Amino-3-bromoquinolin-7-yl)propan-2-yl)-4-(4-amino-7H-pyrrolo[2,3-d]pyrimidin-7-yl)bicyclo[3.1.0]hexane-2,3-diol. | 7-(2-((3aR,3bS,4aS,5R,5aS)-5-(4-Amino-7H-pyrrolo[2,3-d]pyrimidin-7-yl)-2,2-dimethyltetrahydrocyclopropa[3,4]cyclopenta[1,2-d][1,3] dioxol-3b(3aH)-yl)propyl)-3-bromo-N-(4-methoxybenzyl) quinolin-2-amine. | Diastereomeric mixture was separated by chiral preparative HPLC. Wavelength: 225 nm, Instrument Method: HEX-0.1% DEA_IPA-DCM_A_C_40_60_1.2ML 10MIN Flow Rate: 1.2 ml/min, Column: CHIRALPAK IA CRL-025 Column Temp: 25° C., Mobile Phase A: HEX_0.1%DEA Mobile Phase C: IPA-DCM_1-1, Mobile Phase B: NA Mobile Phase D: NA<br>First Diastereomer (Compound 76a): ¹H NMR (400 MHz, DMSO-d6) δ 8.33 (s, 1H), 8.06 (s, 1H), 7.58 (d, J = 8.2 Hz, 1H), 7.33 (s, 1H), 7.12 (d, J = 8.4 Hz, 1H), 7.01-6.87 (m, 3H), 6.64-6.47 (m, 3H), 5.13 (d, J = 5.2 Hz, 1H), 4.80 (d, J = 2.9 Hz, 1H), 4.61 (t, J = 6.7 Hz, 1H), 4.47 (d, J = 7.2 Hz, 1H), 3.96-3.85 (m, 1H), 3.22 (dd, J = 13.2, 3.9 Hz, 1H), 2.94-2.88 (m, 1H), 1.97 - 1.83 (m, 1H), 1.31-1.21 (m, 2H), 0.79 (d, J = 6.8 Hz, 3H), 0.67-0.59 (m, 1H); LCSMm/z = 510.94 (M + 2; 40%)<br>Second Diastereomer (Compound 76b): ¹H NMR (400 MHz, DMSO-d6) δ 8.32 (s, 1H), 8.06 (s, 1H), 7.57 (d, J = 8.2 Hz, 1H), 7.32 (s, 1H), 7.11 (dd, J = 8.2, 1.6 Hz, 1H), 7.07 (d, J = 3.6 Hz, 1H), 6.97 (s, 2H), 6.58 (d, J = 3.5 Hz, 1H), 6.55 (s, 2H), 5.15 (d, J = 5.1 Hz, 1H), 4.80 (d, J = 2.6 Hz,1H), 4.64 (t, J = 7.0 Hz, 1H), 4.43 (d, J = 7.3 Hz, 1H), 3.97-3.88 (m, 1H), 3.07-2.97 (m, 1H), 2.97-2.88 (m, 1H), 1.70-1.55(m, 1H), 1.31-1.21 (m, 2H), 0.98 (d, J = 6.8 Hz, 3H), 0.61-0.52 (m, 1H); LCMS m/z = 510.94 (M + 2; 40%) |

TABLE 16-continued

| Structure & IUPAC name | Intermediate used | ¹H NMR & LCMS data |
|---|---|---|
| Compound-77a and 77b 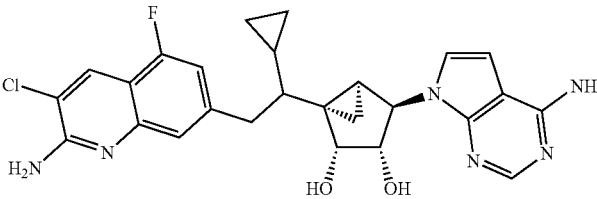 (1S,2R,3S,4R,5S)-1-((S)-2-(2-Amino-3-chloro-5-fluoroquinolin-7-yl)-1-cyclopropylethyl)-4-(4-amino-7H-pyrrolo[2,3-d]pyrimidin-7-yl)bicyclo[3.1.0]hexane-2,3-diol. | 7-(2-((3aR,3bS,4aS,5R,5aS)-5-(4-Amino-7H-pyrrolo[2,3-d]pyrimidin-7-yl)-2,2-dimethyltetrahydrocyclopropa[3,4]cyclopenta[1,2-d][1,3] dioxol-3b(3aH)-yl)-2-cyclopropyl ethyl)-3-chloro-5-fluoro-N-(4-methoxybenzyl)quinolin-2-amine. | Diastereomeric mixture was separated by chiral preparative HPLC. Wavelength: 225 nm, Instrument Method: MeOH_0.1%DEA_100_1.0ML_12MIN Flow Rate: 1.00 ml/min Column: CHIRALPAK IE CRL-042 Column Temp: 30° C., Mobile Phase A: MEOH_0.1%DEA, Mobile Phase B: NA<br>First Diastereomer (Compound 77a): ¹H NMR (400 MHz, DMSO-d6) δ 8.39 (s, 1H), 8.16 (s, 1H), 8.04 (s, 1H), 7.28 (s, 1H), 7.05 (dd, J = 11.3, 1.3 Hz, 1H), 6.93 (dd, J = 11.6, 8.0 Hz, 4H), 6.52 (d, J = 3.5 Hz, 1H), 5.28-5.08 (m, 1H), 4.82 (d, J = 2.8 Hz, 1H), 4.61 (d, J = 6.7 Hz, 1H), 3.86 (s, 1H), 2.90 (dd, J = 13.3, 8.5 Hz, 1H), 2.77 (q, J = 7.2 Hz, 2H), 2.68 (q, J = 1.8 Hz, 1H), 1.37 (dd, J = 8.8, 4.0 Hz,1H), 1.27-1.01 (m, 3H), 0.66 (dd, J = 8.6, 4.9 Hz, 1H), 0.46 (s, 1H), 0.26-0.17 (m, 1H), 0.16-0.01 (m, 1H), LCMS m/z = 509.4 (M + 1; 50%)<br>Second Diastereomer (Compound 77b): ¹H NMR (400 MHz, DMSO-d6) δ 8.15 (s, 1H), 8.05 (s, 1H), 7.31-7.17 (m, 2H), 7.08-6.81 (m, 5H), 6.59 (d, J = 3.5 Hz, 1H), 5.18 (s, 1H), 4.82 (dd, J = 9.3, 4.6 Hz, 2H), 4.54 (s, 1H), 3.92(d, J = 6.7 Hz, 1H), 3.16 (q, J = 6.5 Hz, 1H), 2.99-2.89 (m, 1H), 1.22-1.06 (m, 4H), 0.57 (q, J = 8.5, 7.9 Hz, 1H), 0.50-0.34 (m, 1H), 0.26 (ddd, J = 13.1, 8.4, 4.7 Hz, 2H), 0.06 (dd, J = 9.4, 4.7 Hz, 1H) ; LCMS m/z = 509.4 (M + 1; 50%) |
| Compound-78a and 78b 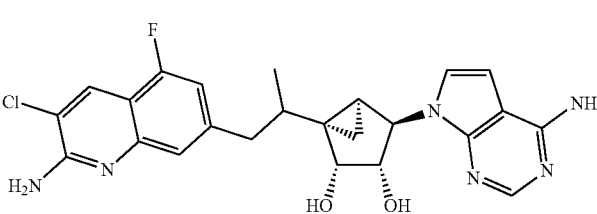 (1S,2R,3S,4R,5S)-1-(1-(2-Amino-3-chloro-5-fluoroquinolin-7-yl)propan-2-yl)-4-(4-amino-7H-pyrrolo[2,3-d]pyrimidin-7-yl)bicyclo[3.1.0]hexane-2,3-diol. | N-(7-(2-((1S,2R,3S,4R,5S)-4-(4-Amino-7H-pyrrolo[2,3-d]pyrimidin-7-yl)-2,3-dihydroxybicyclo [3.1.0] hexan-1-yl)propyl)-3-chloro-5-fluoroquinolin-2-yl)-2,2,2-trifluoroacetamide. | First Diastereomer(Compound-78a): ¹H NMR (400 MHz, DMSO-d6) δ 8.15 (s, 2H), 8.06 (s, 1H), 7.17 (s, 1H), 7.07 (d, J = 3.6 Hz, 1H), 7.04-6.90 (m, 4H), 6.58 (d, J = 3.5 Hz, 1H), 5.16 (d, J = 5.1 Hz, 1H), 4.79 (d, J = 2.6 Hz, 1H), 4.63 (t, J = 7.1 Hz, 1H), 4.45 (d, J = 7.3 Hz, 1H), 3.93 (d, J = 6.9 Hz, 1H), 2.99 (dd, J = 13.3, 4.9 Hz, 1H), 2.61 (d, J = 11.2 Hz, 1H), 1.63 (s, 1H), 1.17 (d, J = 5.8 Hz, 2H), 0.99 (d, J = 6.7 Hz, 3H), 0.57 (d, J = 4.3 Hz, 1H); LCMS m/z = 485.03 (M + 2; 40%)<br>Second Diastereomer (Compound-78b): ¹H NMR (400 MHz, DMSO-d6) δ 8.16 (s, 1H), 8.08 (s, 1H), 7.19 (s, 1H), 7.10 (s, 2H), 6.98 (dd, J = 10.0, 2.2 Hz, 2H), 6.92 (s, 2H), 6.56 (d, J = 3.6 Hz, 1H), 5.13 (d, J = 5.3 Hz, 1H), 4.80 (d, J = 2.9 Hz, 1H), 4.61 (t, J = 6.7 Hz, 1H), 4.48 (d, J = 7.1 Hz, 1H), 3.90 (s, 1H), 3.21 (dd, J = 13.3, 4.1 Hz, 1H), 2.68 (p, J = 1.9 Hz, 1H), 2.36-2.32 (m, 1H), 1.17 (t, J = 4.3 Hz, 2H), 0.79 (d, J = 6.8 Hz, 3H), 0.63 (dd, J = 8.6, 4.7 Hz, 1H); LCMS m/z = 483.02 (M+; 90%) |

TABLE 16-continued

| Structure & IUPAC name | Intermediate used | ¹H NMR & LCMS data |
|---|---|---|
| Compound-79a and 79b<br><br>(1R,2R,3S,4R,5S)-4-(4-Amino-7H-pyrrolo[2,3-d]pyrimidin-7-yl)-1-(2-(2-aminoquinolin-7-yl)propyl)bicyclo[3.1.0]hexane-2,3-diol. | 7-(1-(((3aR,3bR,4a5,5R,5aS)-5-(4-Amino-7H-pyrrolo[2,3-d]pyrimidin-7-yl)-2,2-dimethyltetrahydrocyclo-prop[3,4]cyclopenta[1,2-d][1,3] dioxol-3b-(3aH)-yl)propan-2-yl)-N-(4-methoxybenzyl)quinolin-2-amine. | Diastereomeric mixture was separated by chiral preparative HPLC. Wavelength: 225 nm, Instrument Method: MeOH_0.1%DEA_A_1.0ML_10MIN Flow Rate: 1.00 ml/min, Column: CHIRALPAK IB CRL-043 Column Temp: 30° C., Mobile Phase A: MeOH_0.1%DEA,Mobile Phase B: NA<br>First Diastereomer(Compound 79a): ¹H NMR (400 MHz, DMSO-d6) δ 8.13-8.03 (m, 2H), 7.66 (d, J = 8.2 Hz, 1H), 7.53-7.43 (m, 3H) 7.31 (d, J = 8.3 Hz, 1H), 7.03 (s, 2H), 6.93 (d, J =3.5 Hz, 1H), 6.84 (d, J = 9.1 Hz, 1H), 6.56 (d, J = 3.5 Hz, 1H), 5.15 (d, J = 4.7 Hz, 1H), 4.76 (d, J = 1.4 Hz, 1H), 4.49-4.32 (m, 2H), 3.70 (t, J = 5.5 Hz, 1H), 3.30-3.18 (m, 1H),2.25 (dd, J = 14.1, 4.8 Hz, 1H), 1.82 (dd, J = 14.2, 9.1 Hz, 1H), 1.31-1.22 (m, 4H), 1.02-0.91 (m, 1H), 0.64 (dd, J = 8.5, 4.7 Hz, 1H); LCMS m/z = 430.92 (M + 1; 90%).<br>Second Diastereomer(Compound 79a): ¹H NMR (400 MHz, DMSO-d6) δ 8.02 (d, J = 13.7 Hz, 2H), 7.64 (d, J = 8.2 Hz, 1H), 7.37 (d, J = 1.6 Hz, 1H), 7.21 (dd, J = 8.2, 1.6 Hz, 3H), 6.98 (s, 2H), 6.81 (d, J = 9.0 Hz, 1H), 6.69 (d, J = 3.6 Hz, 1H), 6.42 (d, J = 3.5 Hz, 1H), 5.16 (d, J = 4.8 Hz, 1H), 4.83 (d, J = 1.7 Hz, 1H), 4.47 (d, J = 2.4 Hz, 2H), 3.68 (s, 1H), 2.37-2.27 (m, 1H), 1.68-1.57 (m, 1H), 1.39-1.26 (m, 5H), 1.04 (dd, J = 8.6, 3.8 Hz, 1H), 0.69-0.60 (m, 1H); LCMS m/z = 430.98 (M + 1; 90%) |
| Compound-80<br><br>(1R,2R,3S,4R,5S)-1-(((2-Amino-3-bromoquinolin-7-yl)oxy)methyl)-4-(4-amino-7H-pyrrolo[2,3-d]pyrimidin-7-yl)bicyclo[3.1.0]hexane-2,3-diol. | N-(7-(((1R,2R,3S,4R,5S)-4-(4-Amino-7H-pyrrolo[2,3-d]pyrimidin-7-yl)-2,3-dihydroxybicyclo[3.1.0]hexan-1-yl)methoxy)-3-bromoquinolin-2-yl)-2,2,2-trifluoroacetamide. | ¹H NMR (400 MHz, DMSO-d6) δ 9.39 (bs, 2H), 8.45-8.36 (m, 3H), 7.83-7.62 (m, 2H), 7.03-7.14 (m, 3H), 6.99 (d, J = 3.6 Hz, 1H), 5.28 (s, 1H), 5.05 (s, 1H), 4.86 (s, 1H), 4.71-4.57 (m, 2H),3.93 (d, J = 10.4 Hz, 1H), 3.72 (d, J = 6.4 Hz, 1H), 1.62 (d, J = 8.6 Hz, 1H), 1.53 (t, J = 4.4 Hz, 1H), 0.90-0.82 (m, 1H); LCMS m/z = 499.2 (M + 2; 40%). |
| Compound-81<br><br>(1S,2R,3S,4R,5S)-4-(4-Amino-7H-pyrrolo[2,3-d]pyrimidin-7-yl)-1-(((2-aminoquinolin-7-yl)thio)methyl) bicyclo [3.1.0] hexane-2,3-diol. | 7-((((3aR,3bS,4aS,5R,5aS)-5-(4-Amino-7H-pyrrolo[2,3-d]pyrimidin-7-yl)-2,2-dimethyltetra hydrocyclo-propa [3,4]cyclopent[1,2-d][1,3]dioxol-3b(3aH)-yl)methyl)thio)-N-(4-methoxybenzyl)quinolin-2-amine. | ¹H NMR (400 MHz, DMSO-d6) δ 8.05 (s, 1H), 7.82 (d, J = 8.8 Hz, 1H), 7.53 (d, J = 8.4 Hz, 1H), 7.38(d, J = 1.8 Hz, 1H), 7.16 (d, J = 3.5 Hz, 1H), 7.13 (dd, J = 8.4, 1.9 Hz, 1H), 6.96 (s, 2H), 6.67 (d, J = 8.8 Hz, 1H), 6.52 (d, J = 3.5 Hz, 1H), 6.44 (s, 2H), 5.21-5.11 (m, 1H), 4.90 (s, 1H), 4.68 (d, J = 7.1 Hz, 1H), 4.57 (s, 1H), 3.71-3.60 (m, 2H), 3.38 (d, J = 13.5 Hz, 1H), 1.43-1.38 (m, 2H), 0.84-0.77 (m, 1H); LCMS m/z = 435.10 (M + 2; 90%). |

Example-7: (1R,2R,3S,4R,5S)-1-(2-(2-Amino-3-(4-fluorophenyl)quinolin-7-yl)ethyl)-4-(4-amino-7H-pyrrolo[2,3-d]pyrimidin-7-yl)bicyclo[3.1.0]hexane-2,3-diol (Compound-82)

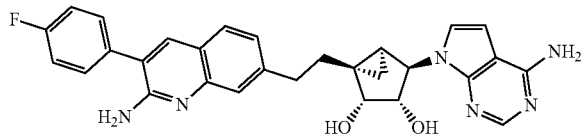

In a sealed tube, the mixture of (1R,2R,3S,4R,5S)-1-(2-(2-amino-3-bromoquinolin-7-yl)ethyl)-4-(4-amino-7H-pyrrolo[2,3-d]pyrimidin-7-yl)bicyclo[3.1.0]hexane-2,3-diol (100 mg, 0.202 mmol), $K_2CO_3$ (84 mg, 0.606 mmol), (4-fluorophenyl)boronic acid (42.4 mg, 0.303 mmol) in dioxane (10 ml) was deggassed for 10 min with nitrogen at 25° C. $PdCl_2(dppf)$-$CH_2Cl_2$ adduct (16.49 mg, 0.020 mmol) was added and stirred the reaction mixture at 100° C. for 16 h. The resulting mixture was filtered through celite and filtrate was concentrated in vacuo to get 0.15 g of crude compound. This residue was purified by combiflash ($R_f$200, Teledyne/Isco) instrument onto a Redisep® $R_f$ column with gradient elution (0 to 8%) of methanol in dichloromethane to afford the title compound (0.025 g, 93.81%) as an off-white solid. $^1$H NMR (400 MHz, DMSO-$d_6$) δ 8.07 (s, 1H), 7.78 (s, 1H), 7.68-7.50 (m, 3H), 7.43-7.24 (m, 3H), 7.13 (dd, J=8.2, 1.7 Hz, 1H), 7.05 (d, J=3.6 Hz, 1H), 6.97 (s, 2H), 6.59 (d, J=3.5 Hz, 1H), 5.96 (s, 2H), 5.11 (d, J=4.5 Hz, 1H), 4.97-4.81 (m, 1H), 4.58-4.39 (m, 2H), 3.74 (t, J=5.5 Hz, 1H), 3.04-2.72 (m, 2H), 2.18-2.09 (m, 1H), 1.90 (td, J=12.5, 5.6 Hz, 1H), 1.34-1.16 (m, 2H), 0.64-0.54 (m, 1H); LCMS m/z=511.09 (M+1; 90%).

Examples in table-17 were synthesized by following an analogous reaction protocol as was used for the preparation of (1R,2R,3S,4R,5S)-1-(2-(2-amino-3-bromoquinolin-7-yl)ethyl)-4-(4-amino-7H-pyrrolo [2,3-d]pyrimidin-7-yl)bicyclo[3.1.0]hexane-2,3-diol using the appropriate starting materials.

TABLE 17

| Srtucture & IUPAC name | Intermediate used | $^1$H NMR & LCMS data |
|---|---|---|
| Compound-83<br><br>(1R,2R,3S,4R,5S)-1-(2-(2-Amino-3-(pyridin-3-yl)quinolin-7-yl)ethyl)-4-(4-amino-7H-pyrrolo[2,3-d]pyrimidin-7-yl)bicyclo[3.1.0]hexane-2,3-diol. | (1R,2R,3S,4R,5S)-1-(2-(2-Amino-3-bromoquinolin-7-yl)ethyl)-4-(4-amino-7H-pyrrolo[2,3-d]pyrimidin-7-yl)bicyclo[3.1.0]hexane-2,3-diol. | $^1$H NMR (400 MHz, DMSO-$d_6$) δ 8.07 (s, 1H), 7.78 (s, 1H), 7.68-7.50 (m, 3H), 7.43-7.24 (m, 3H), 7.13 (dd, J = 8.2, 1.7 Hz, 1H), 7.05 (d, J = 3.6 Hz, 1H), 6.97 (s, 2H), 6.59 (d, J = 3.5 Hz, 1H), 5.96 (s, 2H), 5.11 (d, J = 4.5 Hz, 1H), 4.97-4.81 (m, 1H), 4.58-4.39 (m, 2H), 3.74 (t, J = 5.5 Hz, 1H), 3.04-2.72 (m, 2H), 2.18-2.09 (m, 1H), 1.90 (td, J = 12.5, 5.6 Hz, 1H), 1.34-1.16 (m, 2H), 0.64-0.54 (m, 1H); LCMS m/z = 494.2 (M + 1; 30%) |
| Compound-84<br><br>(1R,2R,3S,4R,5S)-1-(2-(2-Amino-3-(3-methyl isoxazol-4-yl)quinolin-7-yl)ethyl)-4-(4-amino-7H-pyrrolo[2,3-d]pyrimidin-7-yl)bicyclo[3.1.0]hexane-2,3-diol. | (1R,2R,3S,4R,5S)-1-(2-(2-Amino-3-bromoquinolin-7-yl)ethyl)-4-(4-amino-7H-pyrrolo[2,3-d]pyrimidin-7-yl)bicyclo[3.1.0]hexane-2,3-diol | $^1$H NMR (400 MHz, DMSO-d6) δ 9.01 (s, 1H), 8.07 (s, 1H), 7.85 (s, 1H), 7.59 (d, J = 8.2 Hz, 1H), 7.37 (d, J = 1.5 Hz, 1H), 7.13 (dd, J = 8.2, 1.6 Hz, 1H), 7.04 (d, J = 3.6 Hz, 1H), 6.97 (s, 2H), 6.58 (d, J = 3.5 Hz, 1H), 6.15 (s, 2H), 5.12 (d, J = 4.1 Hz, 1H), 4.59-4.47 (m, 2H), 3.74 (d, J = 5.2 Hz, 1H), 3.00-2.77 (m, 3H), 2.22 (s, 3H), 1.89 (ddd, J = 13.9, 11.4, 5.7 Hz, 1H), 1.30-1.25 (m, 2H), 0.90-0.80 (m, 1H), 0.59 (q, J = 5.8 Hz, 1H); 498.07 (M + 1; 100%) |

BIOLOGICAL EXAMPLES

Biochemical Assay Protocol 1

Inhibitory effect of compounds on PRMT5 was assessed using HTRF detection technology in biochemical assay. Biotinylated H4R3 (residues 1-21) was used as a substrate. Compounds were pre-incubated with 15-25 ng PRMT5:MEP50 per well of a 384-well plate for 30 min at room temperature in the assay buffer containing 20 mM Bicine, pH 7.6, 25 mM NaCl, 2 mM DTT, 0.01% Chicken albumin and 0.01% Tween-20. Reaction was initiated by adding 1 µM of SAM and 50 nM biotinylated H4R3. Total assay volume was 15 µL. Reaction was continued for 120 min at room temperature. Then detection solution containing Streptavidin-Eu cryptate, anti-rabbit IgG-XL-665, Histone H4R3 Dimethyl Symmetric (H4R3me2s) Polyclonal Antibody, all prepared in HTRF detection buffer was added and further incubated for 30 min at room temperature. HTRF signal was recorded in PHERAStar microplate reader. Ratio of signal obtained at 665 nm and 620 nm was used to compute the percent inhibition of compound as follows % Inhibition=100−((Test Ratio−Negative control Ratio)/(Positive control Ratio−Negative control Ratio)*100) where Positive control=*PRMT5+SAM+H4R3*

Negative control=*PRMT5+H4R3*

Biochemical Assay Protocol 2

Inhibitory effect of compounds on PRMT5 was assessed using HTRF detection technology in biochemical assay. Biotinylated H4R3 (residues 1-21) was used as a substrate. Compounds were pre-incubated with 2.5 ng PRMT5:MEP50 per well of a 384-well plate for 30 min at room temperature in the assay buffer containing 20 mM Bicine, pH 7.6, 25 mM NaCl, 2 mM DTT, 0.01% Chicken albumin and 0.01% Tween-20. Reaction was initiated by adding 1 µM of SAM and 50 nM biotinylated H4R3. Total assay volume was 15 µL. Reaction was continued for 4 h at room temperature. Then detection solution containing Streptavidin-Eu cryptate, anti-rabbit IgG-XL-665, Histone H4R3 Dimethyl Symmetric (H4R3me2s) Polyclonal Antibody, all prepared in HTRF detection buffer was added and further incubated for 30 min at room temperature. HTRF signal was recorded in PHERAStar microplate reader. Ratio of signal obtained at 665 nm and 620 nm was used to compute the percent inhibition of compound as follows % Inhibition=100−((Test Ratio−Negative control Ratio)/(Positive control Ratio−Negative control Ratio)*100) where Positive control=*PRMT5+SAM+H4R3*

Negative control=*PRMT5+H4R3*

| Activity Range | Compound numbers |
| --- | --- |
| $IC_{50}$ 300 pM to 950 pM | 43, 26, 35b, 47, 21, 38, 34b, 34a, 7a, 13, 37, 18, 33b, 33a, 76a, 23, 25, 24, 48, 1, 61, 73, 44, 2, 15, 36a, 45a, 45b, 35a |

SDMA Inhibition Assay

Protocol

Z-138 cells (ATCC, CRL-3001™) were seeded at a density of 1 million cells/well in transparent, flat bottomed tissue culture grade 48-well plates. Cells were treated with various concentration of test compounds for a period of 48 h. Cell lysate was prepared using 1×CST Lysis buffer (Cell Signaling Technology, USA) and 500 ng/well/50 µL of lysate in pH 9.6 carbonate buffer was coated on 96-well Maxisorb plate and incubated overnight at 4° C. The plate was washed twice in 1×PBS containing 0.05% Tween 20 and blocked in 1% BSA for 1 h at ambient temperature. Further, the plate was incubated first with primary antibody (anti-SDMA antibody; CST #13222s) at ambient temperature for 2 h and then with HRP-conjugated secondary antibody at ambient temperature for 1 h with 2 intermittent washing steps in between.

For luminiscence based detection, HRP substrates (substrate A+substrate B in a 1:1 proportion) were added followed by luminescence reading after 30 min in Synergy™ 2 reader (Biotek, USA).

For absorbance based detection, TMB substrate was added followed by addition of STOP solution (2N $H_2SO_4$) post colour development and absorbance (excitation 450 nm and emission 540 nm) was measured in Synergy™ 2 reader (Biotek, USA).

% inhibition of SDMA was calculated relative to the vehicle control samples containing media with 0.1% DMSO alone as per the formula below.

(Avg. of Untreated Control−Avg. of Test)×100

Avg. of Untreated control

The $IC_{50}$ values of individual compounds were calculated with Non Linear Regression Analysis using Graph Pad Prism (Graph Pad software, Inc, USA).

| Activity Range | Compound numbers |
| --- | --- |
| $IC_{50}$ 1 pM to 1 nM | 7b, 13, 37, 33b, 46, 76b, 23, 24, 2, 48, 1, 61, 73, 47, 38, 34b, 30, 41, 31, 72, 29, 34a, 21, 35a, 26, 43. |
| $IC_{50}$ 1.1 nM to 50 nM | 32, 64, 33a, 76a, 25, 62, 35b. |

Anticancer Activity Assay

Z-138 cells were seeded at a density of 2000-3000 cells per well in culture media (IMDM+10% FBS). PANC-1 (ATCC, CRL-1469™) and MIA PaCa-2 (ATCC, CRL-1420™) cells were seeded at a density of 200-300 cells per well in culture media (DMEM+10% FBS). Cells were seeded in opaque, flat bottomed tissue culture grade 96-well plates and Z-138 cells (suspension) were seeded and treated on the same day with various concentrations of test compounds. PANC-1 and MIA PaCa-2 cells, being adherent, were kept for overnight settlement at standard cell culture conditions (37° C., 5% $CO_2$). On the following day, cells were treated with various concentrations of test compounds. Cells were treated with test compounds for a period of 96 h, 7 days and 10 days, for Z-138 cells, PANC-1 cells and MIA PaCa-2 cells, respectively. Cell viability was assessed using CellTiterGlo™ (Promega, USA) as per manufacturer's instructions. Relative Light Units (RLU) were read in Synergy™ 2 reader (Biotek, USA). The assay measures cellular ATP as an indicator of cell viability. RLU is proportional to the number of viable cells in the respective well.

% inhibition of cell viability was calculated relative to the vehicle control samples containing media with 0.1% DMSO alone as per the formula below.

(Avg. of Untreated Control−Avg. of Test)×100

Avg. of Untreated control

The $IC_{50}$ values of individual compounds were calculated with Non Linear Regression Analysis using Graph Pad Prism (Graph Pad software, Inc, USA).

| Anti-cancer Assay (Z-138) | |
|---|---|
| Activity Range | Compound numbers |
| $IC_{50}$ 0.1 pM to 100 pM | 43, 35a, 47, 21, 40, 38, 34a, 13, 37, 18, 33b, 46, 76b, 24, 2, 48, 1, 54, 61, 73, 34b, 7a, 25, 33a, 44, 72. |
| $IC_{50}$ 101 pM to 1 nM | 26, 64, 39, 7b, 76a, 62, 20b |

| Anti-cancer assay (Panc-1) | |
|---|---|
| Activity Range | Compound numbers |
| $IC_{50}$ 300 pM to 20 nM | 41, 47, 64, 40, 21, 38, 34b, 34a, 7b, 13, 37, 33b, 46, 25, 24, 48, 61, 73, 18, 30, 7a, 2, 1, 54, 35a, 43 |
| $IC_{50}$ 20 nM to 100 nM | 39, 29, 33a, 76b, 62 |

| Anti-cancer assay (MiaPaCa-2) | |
|---|---|
| Activity Range | Compound numbers |
| $IC_{50}$ 1 pM to 40 nM | 21, 38, 34b, 34a, 13, 37, 33b, 25, 24, 2, 48, 1, 61, 73, 18, 30, 40, 64, 62, 33a, 35a, 43, 26 |

In Vivo Efficacy Experiments

Tumor xenograft for mantle cell lymphoma was established by injection of cells into the right flank of female NOD.CB17-Prkdc<scid>/J mice with an age between 7-11 weeks purchased from The Jackson Laboratory, USA. All animal study proposals were reviewed and approved by the Institutional Animal Ethics Committee (IAEC) prior to initiation of experimentation.

Z-138 Xenograft

For Z-138 xenograft mouse model, Z-138 cells (ATCC® CRL-3001™) were grown in IMDM medium supplemented with 10% FBS. Cells were incubated under standard conditions at 37° C. and 5% $CO_2$. For generating tumors, Z-138 cells in IMDM medium were mixed with Matrigel (Corning® Matrigel® Basement Membrane Matrix) in a ratio of 1:1.10×10⁶ cells) in a volume of 200 µL were injected subcutaneously in each mouse to establish tumors. Mice were randomized into treatment groups of 8-10 mice, once tumors reached an average volume between 100 to 120 mm³. Treatment was initiated on day of randomization and continued until end of the study. The Vehicle and test compound treatment groups were administered respective treatments orally, using gavage tubing, at an application volume of 10 mL/kg per mouse twice a day.

Mice were housed in individually ventilated cages (IVC) at room temperature of 22+3° C., humidity 50+20% and 12/12 h light/dark cycle. All the experimental activities were carried-out inside the biosafety cabinets to ensure sterility.

Tumor size was measured with Digimatic Vernier caliper (Mitutoyo, Japan) when the tumors became palpable. Tumor volume (T. V.) is calculated by using the formula:

Tumor volume (mm3)=$(L \times W2)/2$

Where, L: Length of tumor, W: Width of tumor in millimeter

Percent tumor growth inhibition (% TGI) is calculated using the formula:

% TGI=$[1-(Tf-Ti)/(Cf-Ci)] \times 100$

Where, Tf and Ti, are the final and initial tumor volumes (test compound), and Cf and Ci are the final and initial mean tumor volumes (vehicle group), respectively.

Percent tumor regression is calculated as:

% TR: $(Ti-Tf)/(Ti) \times 100$

Where, Tf and Ti, are the final and initial tumor volumes, respectively.

The compounds 24, 33b, and 13 were tested for tumor growth inhibition in Z-138 xenograft model using assay procedure given above; the % of tumor growth inhibition after 38 days at 1 mg/kg dose was found to be 100% and tumor regression was 67-74%. The compound-48 was tested at 5 mg/kg dose, it showed 100% tumor growth inhibition and 63% tumor regression.

The invention claimed is:

1. A method for treating the diseases, disorders, syndromes or conditions associated by inhibition of PRMT5 enzyme to a subject in need thereof, comprising administering to the subject an effective amount of a compound of formula (I), a stereoisomer thereof, or a pharmaceutically acceptable salt thereof, wherein the said diseases, disorders, syndromes or conditions associated by inhibition of PRMT5 enzyme is cancer,

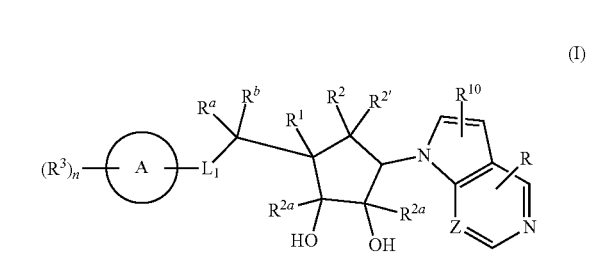

wherein,
$L_1$ is selected from —$CR^aR^b$—, —$NR^a$—, S, and O;
Z is selected from CH and N;
$R^a$ and $R^b$ are independently selected at each occurrence from hydrogen, substituted or unsubstituted alkyl, and substituted or unsubstituted cycloalkyl;
ring A is selected from,

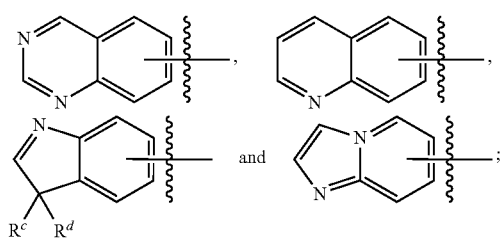

$R^c$ and $R^d$ are selected from substituted or unsubstituted alkyl or together with the carbon atoms to which they are attached form a $C_3$-$C_6$ cycloalkyl ring;

R is selected from —NR⁴R⁵, hydrogen, halogen, substituted or unsubstituted alkyl, substituted or unsubstituted alkoxy, substituted or unsubstituted heteroaryl and substituted or unsubstituted cycloalkyl;

R¹ and R² together with the carbon atoms to which they are attached form a bond in order to form a —C=C—; or R¹ and R² together with the carbon atoms to which they are attached form a cyclopropane ring;

R²' and R²ᵃ which may be same or different and are independently selected from hydrogen and substituted or unsubstituted alkyl;

R³ is independently selected at each occurrence from halogen, cyano, nitro, substituted or unsubstituted alkyl, —OR, —NR⁷R⁸, substituted or unsubstituted cycloalkyl, —C(O)OH, —C(O)O-alkyl, —C(O)R⁹, —C(O)NR⁷R⁸, —NR⁷C(O)R⁹, substituted or unsubstituted aryl, substituted or unsubstituted heteroaryl, and substituted or unsubstituted heterocyclyl;

R⁴ and R⁵ are independently selected from hydrogen, substituted or unsubstituted alkyl, and substituted or unsubstituted cycloalkyl;

R⁶ is selected from hydrogen, substituted or unsubstituted alkyl, and substituted or unsubstituted cycloalkyl;

R⁷ and R⁸ are independently selected from hydrogen, substituted or unsubstituted alkyl, and substituted or unsubstituted cycloalkyl;

R⁹ is selected from substituted or unsubstituted alkyl and substituted or unsubstituted cycloalkyl;

R¹⁰ is selected from hydrogen, halogen, and substituted or unsubstituted alkyl;

'n' is an integer ranging from 0 to 4, both inclusive;

when an alkyl group is substituted, it is substituted with 1 to 4 substituents independently selected from oxo (=O), halogen, cyano, cycloalkyl, aryl, heteroaryl, heterocyclyl, —OR⁷ᵃ, —C(=O)OH, —C(=O)O(alkyl), —NR⁸ᵃR⁸ᵇ, —NR⁸ᵃC(=O)R⁹ᵃ, and —C(=O)NR⁸ᵃR⁸ᵇ;

when the heteroaryl group is substituted, it is substituted with 1 to 4 substituents independently selected from halogen, nitro, cyano, alkyl, haloalkyl, perhaloalkyl, cycloalkyl, heterocyclyl, aryl, heteroaryl, —OR⁷ᵃ, —NR⁸ᵃR⁸ᵇ, —NR⁷ᵃC(=O)R⁹ᵃ, —C(=O)R⁹ᵃ, —C(=O)NR⁸ᵃR⁸ᵇ, —SO₂-alkyl, —C(=O)OH, and —C(=O)O-alkyl;

when the heterocycle group is substituted, it is substituted either on a ring carbon atom or on a ring hetero atom, and when it is substituted on a ring carbon atom, it is substituted with 1 to 4 substituents independently selected from oxo (=O), halogen, cyano, alkyl, cycloalkyl, perhaloalkyl, —OR⁷ᵃ, —C(=O)NR⁸ᵃR⁸ᵇ, —C(=O)OH, —C(=O)O-alkyl, —N(H)C(=O)(alkyl), —N(H)R⁸ᵃ, and —N(alkyl)₂; and when the heterocycle group is substituted on a ring nitrogen, it is substituted with substituents independently selected from alkyl, cycloalkyl, aryl, heteroaryl, —SO₂(alkyl), —C(=O)R⁹ᵃ, and —C(=O)O(alkyl); when the heterocycle group is substituted on a ring sulfur, it is substituted with 1 or 2 oxo (=O) group(s);

R⁷ᵃ is selected from hydrogen, alkyl, perhaloalkyl, and cycloalkyl;

R⁸ᵃ and R⁸ᵇ are each independently selected from hydrogen, alkyl, and cycloalkyl; and R⁹ᵃ is selected from alkyl and cycloalkyl.

2. A method as claimed in claim 1, wherein the said diseases, disorders, syndromes or conditions associated by inhibition of PRMT5 enzyme is glioblastoma multiforme, prostate cancer, pancreatic cancer, mantle cell lymphoma, non-Hodgkin's lymphomas and diffuse large B-cell lymphoma, acute myeloid leukemia, acute lymphoblastic leukemia, multiple myeloma, non-small cell lung cancer, small cell lung cancer, breast cancer, triple negative breast cancer, gastric cancer, colorectal cancer, ovarian cancer, bladder cancer, hepatocellular cancer, melanoma, sarcoma, oropharyngeal squamous cell carcinoma, chronic myelogenous leukemia, epidermal squamous cell carcinoma, nasopharyngeal carcinoma, neuroblastoma, endometrial carcinoma, and cervical cancer.

3. The method of claim 1, wherein the compound has the structure of Formula (II), a stereoisomer thereof, or a pharmaceutically acceptable salt thereof,

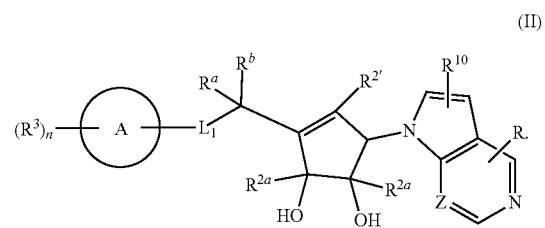

(II)

4. The method of claim 1, wherein the compound has the structure of Formula (III), a stereoisomer thereof, or a pharmaceutically acceptable salt thereof,

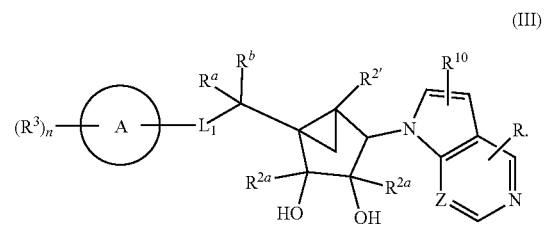

(III)

5. The method of claim 1, wherein the compound has the structure of Formula (IV), a stereoisomer thereof, or a pharmaceutically acceptable salt thereof,

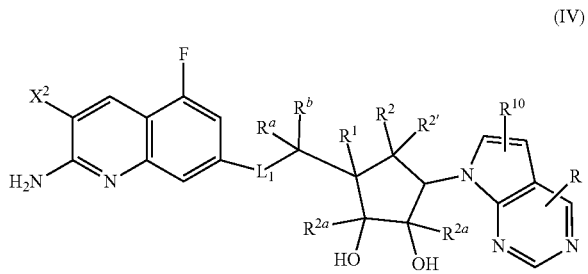

(IV)

wherein,

X² is Br or Cl.

6. The method of claim 1, wherein L₁ is selected from —CH₂—, —CH(CH₃)—, —NH—, —N(CH₃)—, S, and O.

7. The method of claim 1, wherein R³ is selected from F, Cl, Br, CN, —NH₂, —NH(CH₃), —NHCH(CH₃)₂, —CH₃, cyclopropyl, —CH(CH₃)₂, —CF₂CH₃, —OCH₃, CF₃,

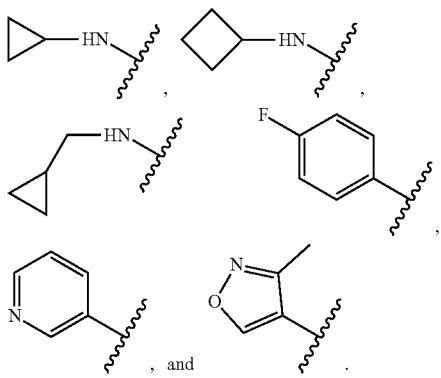

, and

.

8. The method of claim 1, wherein R is selected from hydrogen, —NH₂, Cl, —CH(CH₃)₂, methyl, ethyl, cyclopropyl and

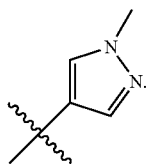 [SMILES: *c1cnn(C)c1]

9. The method of claim 1, wherein $R^a$ and $R^b$ are independently selected from hydrogen, methyl, and cyclopropyl.

10. The method of claim 1, wherein $R^{2'}$ and $R^{2a}$ are independently selected from hydrogen and methyl.

11. The method of claim 1, wherein $R^{10}$ is selected from hydrogen, —F, and methyl.

12. The method of claim 1, wherein ring A is selected from

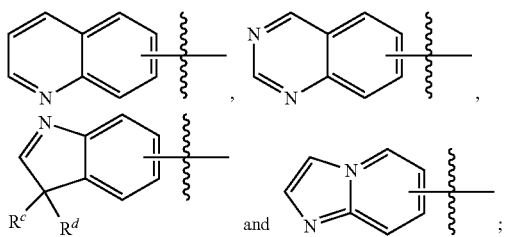

L1 is selected from —CH2-, —CH(CH3)-, —NH—, —N(CH3)-, S, and O; $R^3$ is selected from F, Cl, Br, CN, —NH₂, —NH(CH₃), —NHCH(CH₃)₂, —CH₃, cyclopropyl, —CH(CH₃)₂, —CF₂CH₃, —OCH₃, CF₃,

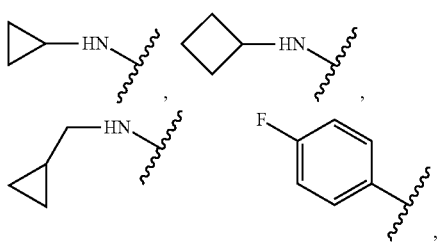

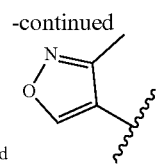

, and

R is selected from hydrogen, —NH₂, Cl, —CH(CH₃)₂, methyl, ethyl, cyclopropyl and $R^a$ and $R^b$ are independently selected from hydrogen, methyl, and cyclopropyl; $R^{2'}$ and $R^{2a}$ are independently selected from hydrogen and methyl; $R^{10}$ is selected from hydrogen, —F, and methyl.

13. The method of claim 1, wherein the compound is selected from:
(1S,2R,5R)-3-(2-(2-Amino-3-bromoquinolin-7-yl)ethyl)-5-(4-amino-7H-pyrrolo[2,3-d]pyrimidin-7-yl)cyclopent-3-ene-1,2-diol;
(1S,2R,5R)-3-(((2-amino-3-chloroquinolin-7-yl)thio)methyl)-5-(4-amino-7H-pyrrolo[2,3-d]pyrimidin-7-yl)cyclopent-3-ene-1,2-diol;
(1S,2R,5R)-3-(1-(2-Amino-3-bromoquinolin-7-yl)propan-2-yl)-5-(4-amino-7H-pyrrolo[2,3-d]pyrimidin-7-yl)cyclopent-3-ene-1,2-diol;
(1S,2R,5R)-3-(((2-amino-3-chloro-5-fluoroquinolin-7-yl)oxy)methyl)-5-(4-amino-7H-pyrrolo[2,3-d]pyrimidin-7-yl)-2-methylcyclopent-3-ene-1,2-diol (Compound-9);
(1S,2R,5R)-3-(1-(2-Amino-3-chloro-5-fluoroquinolin-7-yl)propan-2-yl)-5-(4-methyl-7H-pyrrolo[2,3-d]pyrimidin-7-yl)cyclopent-3-ene-1,2-diol;
(1S,2R,5R)-3-(2-(2-amino-3-chloro-5-fluoroquinolin-7-yl)ethyl)-5-(4-methyl-7H-pyrrolo[2,3-d]pyrimidin-7-yl)cyclopent-3-ene-1,2-diol;
(1S,2R,5R)-3-(1-((2-amino-3-chloro-5-fluoroquinolin-7-yl)oxy)ethyl)-5-(4-amino-7H-pyrrolo[2,3-d]pyrimidin-7-yl)cyclopent-3-ene-1,2-diol;
(1S,2R,5R)-3-(2-(2-amino-3-chloroquinolin-7-yl)ethyl)-5-(4-methyl-7H-pyrrolo[2,3-d]pyrimidin-7-yl)cyclopent-3-ene-1,2-diol;
(2-(2-Amino-3-fluoroquinolin-7-yl)ethyl)-5-(4-amino-7H-pyrrolo[2,3-d]pyrimidin-7-yl)cyclopent-3-ene-1,2-diol;
(1S,2R,5R)-3-(2-(2-amino-3-chloro-5-fluoroquinolin-7-yl)ethyl)-5-(4-amino-7H-pyrrolo[2,3-d]pyrimidin-7-yl)cyclopent-3-ene-1,2-diol;
(1S,2R,5R)-3-(2-(2-amino-3-chloro-6-fluoroquinolin-7-yl)ethyl)-5-(4-amino-7H-pyrrolo[2,3-d]pyrimidin-7-yl)cyclopent-3-ene-1,2-diol;
(1S,2R,5R)-3-(2-(2-amino-3-chloro-8-fluoroquinolin-7-yl)ethyl)-5-(4-amino-7H-pyrrolo[2,3-d]pyrimidin-7-yl)cyclopent-3-ene-1,2-diol;
(1S,2R,5R)-3-(2-(2-amino-3,5-dichloroquinolin-7-yl)ethyl)-5-(4-amino-7H-pyrrolo[2,3-d]pyrimidin-7-yl)cyclopent-3-ene-1,2-diol;

(1S,2R,5R)-3-(((2-amino-3-chloro-5-fluoroquinolin-7-yl)oxy)methyl)-5-(4-amino-7H-pyrrolo[2,3-d]pyrimidin-7-yl)cyclopent-3-ene-1,2-diol;

(1S,2R,5R)-3-(2-(2-amino-3-chloro-5-fluoroquinolin-7-yl)ethyl)-5-(4-isopropyl-7H-pyrrolo[2,3-d]pyrimidin-7-yl)cyclopent-3-ene-1,2-diol;

(1S,2R,5R)-3-(2-(2-amino-3-chloro-5-fluoroquinolin-7-yl)ethyl)-5-(4-(1-methyl-1H-pyrazol-4-yl)-7H-pyrrolo[2,3-d]pyrimidin-7-yl)cyclopent-3-ene-1,2-diol;

(1S,2R,5R)-3-(1-(2-amino-3-chloro-5-fluoroquinolin-7-yl)propan-2-yl)-5-(4-amino-7H-pyrrolo[2,3-d]pyrimidin-7-yl)cyclopent-3-ene-1,2-diol;

(1S,2R,5R)-3-(1-(2-amino-3-chloroquinolin-7-yl)propan-2-yl)-5-(4-amino-7H-pyrrolo[2,3-d]pyrimidin-7-yl)cyclopent-3-ene-1,2-diol;

(1S,2R,5R)-3-(2-(2-amino-3-chloro-5-fluoroquinolin-7-yl)ethyl)-5-(4-amino-7H-pyrrolo[2,3-d]pyrimidin-7-yl)-2-methylcyclopent-3-ene-1,2-diol;

(1S,2R,5R)-3-(1-(2-amino-3-chloro-5-fluoroquinolin-7-yl)propan-2-yl)-5-(4-amino-7H-pyrrolo[2,3-d]pyrimidin-7-yl)-2-methylcyclopent-3-ene-1,2-diol;

(1S,2R,5R)-3-(2-(2-amino-3-chloro-5-fluoroquinolin-7-yl)ethyl)-5-(4-amino-7H-pyrrolo[2,3-d]pyrimidin-7-yl)-2-ethylcyclopent-3-ene-1,2-diol;

(1S,2R,5R)-3-(2-(2-amino-3-chloro-5-fluoroquinolin-7-yl)ethyl)-5-(4-ethyl-7H-pyrrolo[2,3-d]pyrimidin-7-yl)cyclopent-3-ene-1,2-diol;

(1S,2R,5R)-3-(2-(2-amino-3-chloro-5-fluoroquinolin-7-yl)ethyl)-5-(4-cyclopropyl-7H-pyrrolo[2,3-d]pyrimidin-7-yl)cyclopent-3-ene-1,2-diol;

(1S,2R,5R)-3-(2-(2-Amino-3-bromo-5-fluoroquinolin-7-yl)ethyl)-5-(4-amino-7H-pyrrolo[2,3-d]pyrimidin-7-yl)cyclopent-3-ene-1,2-diol;

(1S,2R,5R)-3-(2-(2-Amino-3-bromo-5-fluoroquinolin-7-yl)ethyl)-5-(4-methyl-7H-pyrrolo[2,3-d]pyrimidin-7-yl)cyclopent-3-ene-1,2-diol;

(1S,2R,5R)-3-(1-(2-Amino-3-bromo-5-fluoro quinolin-7-yl)propan-2-yl)-5-(4-amino-7H-pyrrolo[2,3-d]pyrimidin-7-yl)cyclopent-3-ene-1,2-diol;

(1S,2R,5R)-3-(2-(2-Amino-3-chloro-5-fluoro quinolin-7-yl)ethyl)-5-(4-methyl-1H-pyrrolo[3,2-c]pyridin-1-yl)cyclopent-3-ene-1,2-diol;

(1S,2R,5R)-3-(2-(2-Amino-6-fluoroquinolin-7-yl)ethyl)-5-(4-amino-7H-pyrrolo[2,3-d]pyrimidin-7-yl)cyclopent-3-ene-1,2-diol;

(1S,2R,5R)-3-(2-(2-amino-5-fluoroquinolin-7-yl)ethyl)-5-(4-amino-7H-pyrrolo[2,3-d]pyrimidin-7-yl)cyclopent-3-ene-1,2-diol;

(1R,2R,3S,4R,5S)-1-(2-(2-Amino-3-methylquinolin-7-yl)ethyl)-4-(4-amino-7H-pyrrolo[2,3-d]pyrimidin-7-yl) bicyclo[3.1.0]hexane-2,3-diol;

(1R,2R,3S,4R,5S)-1-(2-(2-Amino-3-chloroquinolin-7-yl)ethyl)-4-(4-amino-7H-pyrrolo[2,3-d]pyrimidin-7-yl)bicyclo[3.1.0]hexane-2,3-diol;

(1R,2R,3S,4R,5S)-1-(2-(2-Amino-3-chloro-5-fluoroquinolin-7-yl)ethyl)-4-(4-amino-7H-pyrrolo[2,3-d]pyrimidin-7-yl) bicyclo[3.1.0]hexane-2,3-diol;

(1R,2R,3S,4R,5S)-1-(2-(2-Amino-3-chloro-6-fluoroquinolin-7-yl)ethyl)-4-(4-amino-7H-pyrrolo[2,3-d]pyrimidin-7-yl) bicyclo[3.1.0]hexane-2,3-diol;

(1R,2R,3S,4R,5S)-1-(2-(2-amino-3-bromo-6-fluoroquinolin-7-yl)ethyl)-4-(4-amino-7H-pyrrolo[2,3-d]pyrimidin-7-yl)bicyclo[3.1.0]hexane-2,3-diol;

(1R,2R,3S,4R,5S)-1-(2-(2-Amino-3-bromo-5-fluoroquinolin-7-yl)ethyl)-4-(4-amino-7H-pyrrolo[2,3-d]pyrimidin-7-yl)bicyclo[3.1.0]hexane-2,3-diol; and (1R,2R,3S,4R,5S)-1-(2-(2-Amino-3-bromoquinolin-7-yl)ethyl)-4-(4-amino-7H-pyrrolo [2,3-d]pyrimidin-7-yl) bicyclo [3.1.0]hexane-2,3-diol.

14. The method of claim 1, wherein the compound is selected from:

(1S,2R,5R)-3-(2-(2-amino-3-chloro-5-fluoroquinolin-7-yl)ethyl)-5-(4-methyl-7H-pyrrolo[2,3-d]pyrimidin-7-yl)cyclopent-3-ene-1,2-diol;

(1S,2R,5R)-3-(2-(2-amino-3-chloro-5-fluoroquinolin-7-yl)ethyl)-5-(4-amino-7H-pyrrolo[2,3-d]pyrimidin-7-yl)cyclopent-3-ene-1,2-diol;

(1S,2R,5R)-3-(1-(2-amino-3-chloro-5-fluoroquinolin-7-yl)propan-2-yl)-5-(4-amino-7H-pyrrolo[2,3-d]pyrimidin-7-yl)cyclopent-3-ene-1,2-diol;

(1S,2R,5R)-3-(2-(2-amino-3-chloro-5-fluoroquinolin-7-yl)ethyl)-5-(4-amino-7H-pyrrolo[2,3-d]pyrimidin-7-yl)-2-methylcyclopent-3-ene-1,2-diol;

(1R,2R,3S,4R,5S)-1-(2-(2-Amino-3-chloro-5-fluoroquinolin-7-yl)ethyl)-4-(4-amino-7H-pyrrolo[2,3-d]pyrimidin-7-yl) bicyclo[3.1.0]hexane-2,3-diol;

(1R,2R,3S,4R,5S)-1-(2-(2-Amino-3-chloro-6-fluoroquinolin-7-yl)ethyl)-4-(4-amino-7H-pyrrolo[2,3-d]pyrimidin-7-yl) bicyclo[3.1.0]hexane-2,3-diol;

(1R,2R,3S,4R,5S)-1-(2-(2-Amino-3-bromoquinolin-7-yl)ethyl)-4-(4-amino-7H-pyrrolo [2,3-d]pyrimidin-7-yl) bicyclo [3.1.0]hexane-2,3-diol;

(1S,2R,5R)-3-(2-(2-Amino-3-bromoquinolin-7-yl)ethyl)-5-(4-amino-7H-pyrrolo[2,3-d]pyrimidin-7-yl)cyclopent-3-ene-1,2-diol;

(1S,2R,5R)-3-(2-(2-amino-3-chloro-6-fluoroquinolin-7-yl)ethyl)-5-(4-amino-7H-pyrrolo[2,3-d]pyrimidin-7-yl)cyclopent-3-ene-1,2-diol;

(1S,2R,5R)-3-(((2-amino-3-chloro-5-fluoroquinolin-7-yl)oxy)methyl)-5-(4-amino-7H-pyrrolo[2,3-d]pyrimidin-7-yl)cyclopent-3-ene-1,2-diol;

(1S,2R,5R)-3-(1-(2-amino-3-chloroquinolin-7-yl)propan-2-yl)-5-(4-amino-7H-pyrrolo[2,3-d]pyrimidin-7-yl)cyclopent-3-ene-1,2-diol;

(1S,2R,5R)-3-(1-(2-amino-3-chloro-5-fluoroquinolin-7-yl)propan-2-yl)-5-(4-amino-7H-pyrrolo[2,3-d]pyrimidin-7-yl)cyclopent-3-ene-1,2-diol;

(1S,2R,5R)-3-(1-(2-amino-3-chloro-5-fluoroquinolin-7-yl)propan-2-yl)-5-(4-amino-7H-pyrrolo[2,3-d]pyrimidin-7-yl)-2-methylcyclopent-3-ene-1,2-diol;

(1R,2R,3S,4R,5S)-1-(2-(2-Amino-3-chloroquinolin-7-yl)ethyl)-4-(4-amino-7H-pyrrolo[2,3-d]pyrimidin-7-yl)bicyclo[3.1.0]hexane-2,3-diol;

(1S,2R,5R)-3-(2-(2-Amino-3-bromo-5-fluoroquinolin-7-yl)ethyl)-5-(4-amino-7H-pyrrolo[2,3-d]pyrimidin-7-yl)cyclopent-3-ene-1,2-diol;

(1S,2R,5R)-3-(1-(2-Amino-3-bromo-5-fluoro quinolin-7-yl)propan-2-yl)-5-(4-amino-7H-pyrrolo[2,3-d]pyrimidin-7-yl)cyclopent-3-ene-1,2-diol;

(1S,2R,5R)-3-(2-(2-Amino-3-bromo-5-fluoroquinolin-7-yl)ethyl)-5-(4-methyl-7H-pyrrolo[2,3-d]pyrimidin-7-yl)cyclopent-3-ene-1,2-diol;

(1R,2R,3S,4R,5S)-1-(2-(2-Amino-3-bromo-5-fluoroquinolin-7-yl)ethyl)-4-(4-amino-7H-pyrrolo[2,3-d]pyrimidin-7-yl)bicyclo[3.1.0]hexane-2,3-diol; and (1R,2R,3S,4R,5S)-1-(2-(2-amino-3-bromo-6-fluoroquinolin-7-yl)ethyl)-4-(4-amino-7H-pyrrolo[2,3-d]pyrimidin-7-yl)bicyclo[3.1.0]hexane-2,3-diol.

15. The method of claim 1, wherein the compound is selected from:

(1S,2R,5R)-3-(2-(2-Amino-3-bromo-5-fluoroquinolin-7-yl)ethyl)-5-(4-amino-7H-pyrrolo[2,3-d]pyrimidin-7-yl)cyclopent-3-ene-1,2-diol (Compound-43);

(1S,2R,5R)-3-(2-(2-amino-3-chloro-8-fluoroquinolin-7-yl)ethyl)-5-(4-amino-7H-pyrrolo[2,3-d]pyrimidin-7-yl)cyclopent-3-ene-1,2-diol (Compound-26);

(1S,2R,5R)-3-(1-(2-Amino-3-chloro-5-fluoroquinolin-7-yl)propan-2-yl)-5-(4-methyl-7H-pyrrolo[2,3-d]pyrimidin-7-yl)cyclopent-3-ene-1,2-diol (Compound-35b);

(1S,2R,5R)-3-(2-(2-amino-5-fluoroquinolin-7-yl)ethyl)-5-(4-amino-7H-pyrrolo[2,3-d]pyrimidin-7-yl)cyclopent-3-ene-1,2-diol (Compound-47);

(1S,2R,5R)-3-(2-(2-amino-3-chloroquinolin-7-yl)ethyl)-5-(4-methyl-7H-pyrrolo[2,3-d]pyrimidin-7-yl)cyclopent-3-ene-1,2-diol (Compound-21);

(1S,2R,5R)-3-(1-(2-amino-3-chloro-5-fluoroquinolin-7-yl)propan-2-yl)-5-(4-amino-7H-pyrrolo[2,3-d]pyrimidin-7-yl)-2-methylcyclopent-3-ene-1,2-diol (Compound-38);

(1S,2R,5R)-3-(1-(2-amino-3-chloroquinolin-7-yl)propan-2-yl)-5-(4-amino-7H-pyrrolo[2,3-d]pyrimidin-7-yl)cyclopent-3-ene-1,2-diol (Compound-34a and 34b);

(1S,2R,5R)-3-(1-(2-Amino-3-bromoquinolin-7-yl)propan-2-yl)-5-(4-amino-7H-pyrrolo[2,3-d]pyrimidin-7-yl)cyclopent-3-ene-1,2-diol (Compound-7a);

(1S,2R,5R)-3-(2-(2-amino-3-chloro-5-fluoroquinolin-7-yl)ethyl)-5-(4-methyl-7H-pyrrolo[2,3-d]pyrimidin-7-yl)cyclopent-3-ene-1,2-diol (Compound-13);

(1S,2R,5R)-3-(2-(2-amino-3-chloro-5-fluoroquinolin-7-yl)ethyl)-5-(4-amino-7H-pyrrolo[2,3-d]pyrimidin-7-yl)-2-methylcyclopent-3-ene-1,2-diol (Compound-37);

(1S,2R,5R)-3-(((2-amino-3-chloro-5-fluoroquinolin-7-yl)oxy)methyl)-5-(4-amino-7H-pyrrolo[2,3-d]pyrimidin-7-yl)cyclopent-3-ene-1,2-diol (Compound-18);

(1S,2R,5R)-3-(1-(2-amino-3-chloro-5-fluoroquinolin-7-yl)propan-2-yl)-5-(4-amino-7H-pyrrolo[2,3-d]pyrimidin-7-yl)cyclopent-3-ene-1,2-diol (Compound-33a and 33b);

(1S,2R,3S,4R,5S)-1-((S)-1-(2-Amino-3-bromoquinolin-7-yl)propan-2-yl)-4-(4-amino-7H-pyrrolo[2,3-d]pyrimidin-7-yl)bicyclo[3.1.0]hexane-2,3-diol (Compound-76a);

(1S,2R,5R)-3-(2-(2-Amino-3-fluoroquinolin-7-yl)ethyl)-5-(4-amino-7H-pyrrolo[2,3-d]pyrimidin-7-yl)cyclopent-3-ene-1,2-diol (Compound-23);

(1S,2R,5R)-3-(2-(2-amino-3-chloro-6-fluoroquinolin-7-yl)ethyl)-5-(4-amino-7H-pyrrolo[2,3-d]pyrimidin-7-yl)cyclopent-3-ene-1,2-diol (Compound-25);

(1S,2R,5R)-3-(2-(2-amino-3-chloro-5-fluoroquinolin-7-yl)ethyl)-5-(4-amino-7H-pyrrolo[2,3-d]pyrimidin-7-yl)cyclopent-3-ene-1,2-diol (Compound-24);

(1R,2R,3S,4R,5S)-1-(2-(2-Amino-3-chloro-5-fluoroquinolin-7-yl)ethyl)-4-(4-amino-7H-pyrrolo[2,3-d]pyrimidin-7-yl)bicyclo[3.1.0]hexane-2,3-diol (Compound-48);

(1S,2R,5R)-3-(2-(2-Amino-3-bromoquinolin-7-yl)ethyl)-5-(4-amino-7H pyrrolo[2,3-d]pyrimidin-7-yl)cyclopent-3-ene-1,2-diol (Compound-1);

(1R,2R,3S,4R,5S)-1-(2-(2-Amino-3-chloroquinolin-7-yl)ethyl)-4-(4-amino-7H-pyrrolo[2,3-d]pyrimidin-7-yl)bicyclo[3.1.0]hexane-2,3-diol (Compound-61);

(1R,2R,3S,4R,5S)-1-(2-(2-Amino-3-bromoquinolin-7-yl)ethyl)-4-(4-amino-7H-pyrrolo [2,3-d]pyrimidin-7-yl)bicyclo[3.1.0]hexane-2,3-diol (Compound-73);

(1S,2R,5R)-3-(2-(2-Amino-3-bromo-5-fluoroquinolin-7-yl)ethyl)-5-(4-methyl-7H-pyrrolo[2,3-d]pyrimidin-7-yl)cyclopent-3-ene-1,2-diol (Compound-44);

(1S,2R,5R)-3-(2-(2-amino-3-chloroquinolin-7-yl)ethyl)-5-(4-amino-7H-pyrrolo[2,3-d]pyrimidin-7-yl)cyclopent-3-ene-1,2-diol (Compound-2);

(1S,2R,5R)-3-(2-(2-Amino-3-chloro-5-fluoroquinolin-7-yl)ethyl)-5-(1H-pyrrolo[3,2-c]pyridin-1-yl)cyclopent-3-ene-1,2-diol (Compound-15);

(1S,2R,5R)-3-(1-(2-amino-3-chloro-5-fluoroquinolin-7-yl)propan-2-yl)-2-methyl-5-(4-methyl-7H-pyrrolo[2,3-d]pyrimidin-7-yl)cyclopent-3-ene-1,2-diol (Compound-36a);

(1S,2R,5R)-3-(1-(2-Amino-3-bromo-5-fluoro quinolin-7-yl)propan-2-yl)-5-(4-amino-7H-pyrrolo[2,3-d]pyrimidin-7-yl)cyclopent-3-ene-1,2-diol (Compound-45a and 45b); and (1S,2R,5R)-3-(1-(2-Amino-3-chloro-5-fluoroquinolin-7-yl)propan-2-yl)-5-(4-methyl-7H-pyrrolo[2,3-d]pyrimidin-7-yl)cyclopent-3-ene-1,2-diol (Compound-35a).

16. The method of claim 1, wherein the compound is selected from:

(1S,2R,5R)-3-(1-(2-Amino-3-bromoquinolin-7-yl)propan-2-yl)-5-(4-amino-7H-pyrrolo[2,3-d]pyrimidin-7-yl)cyclopent-3-ene-1,2-diol (Compound-7b);

(1S,2R,5R)-3-(2-(2-amino-3,5-dichloroquinolin-7-yl)ethyl)-5-(4-amino-7H-pyrrolo[2,3-d]pyrimidin-7-yl)cyclopent-3-ene-1,2-diol (Compound-29);

(1S,2R,5R)-3-(2-(2-amino-3-chloroquinolin-7-yl)ethyl)-5-(2-amino-7H-pyrrolo[2,3-d]pyrimidin-7-yl)cyclopent-3-ene-1,2-diol (Compound-30);

(1S,2R,5R)-3-(2-(2-amino-3-chloro-5-fluoroquinolin-7-yl)ethyl)-5-(4-isopropyl-7H-pyrrolo[2,3-d]pyrimidin-7-yl)cyclopent-3-ene-1,2-diol (Compound-31);

(1S,2R,5R)-3-(1-(2-amino-3-chloroquinolin-7-yl)propan-2-yl)-5-(4-amino-7H-pyrrolo[2,3-d]pyrimidin-7-yl)cyclopent-3-ene-1,2-diol (Compound-34b);

(1S,2R,5R)-3-(2-(2-Amino-6-fluoroquinolin-7-yl)ethyl)-5-(4-amino-7H-pyrrolo[2,3-d]pyrimidin-7-yl)cyclopent-3-ene-1,2-diol (Compound-46);

(1S,2R,5R)-3-(2-(2-amino-3-chloro-5-fluoroquinolin-7-yl)ethyl)-5-(4-ethyl-7H-pyrrolo[2,3-d]pyrimidin-7-yl)cyclopent-3-ene-1,2-diol (Compound-41);

(1R,2R,3S,4R,5S)-1-(2-(2-Amino-3-bromo-5-fluoroquinolin-7-yl)ethyl)-4-(4-amino-7H-pyrrolo[2,3-d]pyrimidin-7-yl)bicyclo[3.1.0]hexane-2,3-diol (Compound-72); and (1S,2R,3S,4R,5S)-1-((S)-1-(2-Amino-3-bromoquinolin-7-yl)propan-2-yl)-4-(4-amino-7H-pyrrolo[2,3-d]pyrimidin-7-yl)bicyclo[3.1.0]hexane-2,3-diol (Compound-76b).

17. The method of claim 1, wherein the compound is selected from:

(1S,2R,5R)-3-(2-(2-amino-3-chloro-5-fluoroquinolin-7-yl)ethyl)-5-(4-(1-methyl-1H-pyrazol-4-yl)-7H-pyrrolo[2,3-d]pyrimidin-7-yl)cyclopent-3-ene-1,2-diol (Compound-32); and (1R,2R,3S,4R,5S)-1-(2-(2-Amino-3-chloro-6-fluoroquinolin-7-yl)ethyl)-4-(4-amino-7H-pyrrolo[2,3-d]pyrimidin-7-yl) bicyclo[3.1.0]hexane-2,3-diol (Compound-62).

18. The method of claim 1, wherein the compound is selected from:

(1S,2R,5R)-3-(2-(2-amino-3-chloro-5-fluoroquinolin-7-yl)ethyl)-5-(4-amino-7H-pyrrolo[2,3-d]pyrimidin-7-yl)-2-ethylcyclopent-3-ene-1,2-diol (Compound-40); and (1R,2R,3S,4R,5S)-1-(2-(2-Amino-3-methylquinolin-7-yl)ethyl)-4-(4-amino-7H-pyrrolo[2,3-d]pyrimidin-7-yl) bicyclo[3.1.0]hexane-2,3-diol (Compound-54).

19. The method of claim 1, wherein the compound is (1S,2R,5R)-3-(2-(2-amino-3-chloro-5-fluoroquinolin-7-yl)ethyl)-2-methyl-5-(4-methyl-7H-pyrrolo[2,3-d]pyrimidin-7-yl)cyclopent-3-ene-1,2-diol (Compound-39).

20. A method for treating lymphocytic leukemia in a subject in need thereof, comprising administering to the subject an effective amount of a compound selected from:
(1S,2R,5R)-3-(2-(2-amino-3-chloro-5-fluoroquinolin-7-yl)ethyl)-5-(4-methyl-7H-pyrrolo[2,3-d]pyrimidin-7-yl)cyclopent-3-ene-1,2-diol (Compound-13);
(1S,2R,5R)-3-(2-(2-amino-3-chloro-5-fluoroquinolin-7-yl)ethyl)-5-(4-amino-7H-pyrrolo[2,3-d]pyrimidin-7-yl)cyclopent-3-ene-1,2-diol (Compound-24);
(1S,2R,5R)-3-(1-(2-amino-3-chloro-5-fluoroquinolin-7-yl)propan-2-yl)-5-(4-amino-7H-pyrrolo[2,3-d]pyrimidin-7-yl)cyclopent-3-ene-1,2-diol (Compound-33b); and
(1R,2R,3S,4R,5S)-1-(2-(2-Amino-3-chloro-5-fluoroquinolin-7-yl)ethyl)-4-(4-amino-7H-pyrrolo[2,3-d]pyrimidin-7-yl)bicyclo[3.1.0]hexane-2,3-diol (Compound-48).

* * * * *